US007029848B2

(12) United States Patent
Vogels et al.

(10) Patent No.: US 7,029,848 B2
(45) Date of Patent: Apr. 18, 2006

(54) HIGH THROUGHPUT SCREENING OF GENE FUNCTION USING LIBRARIES FOR FUNCTIONAL GENOMICS APPLICATIONS

(75) Inventors: Ronald Vogels, Linschoten (NL); Abraham Bout, Moerkapelle (NL); Helmuth van Es, Hoofddorp (NL); Govert Schouten, Leiden (NL)

(73) Assignee: Galapagos Genomics N.V., Mechelen (BE)

( * ) Notice: Subject to any disclaimer, the term of this patent is extended or adjusted under 35 U.S.C. 154(b) by 483 days.

(21) Appl. No.: 10/036,949

(22) Filed: Dec. 21, 2001

(65) Prior Publication Data

US 2003/0027170 A1 Feb. 6, 2003

Related U.S. Application Data

(60) Division of application No. 09/358,036, filed on Jul. 21, 1999, now Pat. No. 6,340,595, which is a continuation-in-part of application No. 09/097,239, filed on Jun. 12, 1998, now Pat. No. 6,413,776.

(51) Int. Cl.
*C12Q 1/68* (2006.01)
(52) U.S. Cl. ........................................ 435/6; 435/235.1
(58) Field of Classification Search ..................... None
See application file for complete search history.

(56) References Cited

U.S. PATENT DOCUMENTS

| | | | |
|---|---|---|---|
| 4,405,712 A | 9/1983 | Vande Woude et al. | |
| 4,497,796 A | 2/1985 | Salser et al. | |
| 4,727,028 A | 2/1988 | Santerre et al. | |
| 4,740,463 A | 4/1988 | Weinberg et al. | |
| 5,190,931 A | 3/1993 | Inouye | |
| 5,208,149 A | 5/1993 | Inouye | |
| 5,518,913 A | 5/1996 | Massie et al. | |
| 5,837,511 A | 11/1998 | Falck-Pedersen et al. | |
| 5,994,106 A | 11/1999 | Kovesdi et al. | |
| 5,994,128 A | 11/1999 | Fallaux et al. | |
| 6,033,908 A | 3/2000 | Bout et al. | |
| 6,040,174 A | 3/2000 | Imler et al. | |
| 6,057,427 A | 5/2000 | Smith et al. | 530/388.23 |
| 6,110,735 A | 8/2000 | Chartier et al. | 435/320.1 |
| 6,197,502 B1 | 3/2001 | Renner et al. | 435/6 |

FOREIGN PATENT DOCUMENTS

| | | |
|---|---|---|
| AU | A-28533/95 | 3/1996 |
| CA | 2053187 | 4/1993 |
| CA | 2117668 | 9/1995 |
| CA | 2117669 | 9/1995 |
| EP | 0 707 071 A1 | 4/1996 |
| EP | 0 955 373 A2 | 11/1999 |
| EP | 0 955 373 A3 | 11/1999 |
| FR | 2 707 664 | 1/1995 |
| WO | WO 94/12648 | 6/1984 |
| WO | WO 94/12649 | 8/1994 |
| WO | WO 94/28152 | 12/1994 |
| WO | WO 95/02697 | 1/1995 |
| WO | WO 95/34671 | 12/1995 |
| WO | WO 96/17070 | 6/1996 |
| WO | WO 97/00326 | 1/1997 |
| WO | WO97/27212 | 7/1997 |
| WO | WO97/27213 | 7/1997 |
| WO | WO 97/27213 | 7/1997 |
| WO | WO99/32618 | 7/1999 |

OTHER PUBLICATIONS

"Restricted Changes in the Adenovirus DNA-Binding Protein That Lead to Extended Host Range or Temperature-Sensitive Phenotypes" by D.E. Brough, S.A. Rice, S. Sell and D.F. Kelessig—Journal of Virology, Jul. 1985, pp. 206-212.
"Multiplication of Viruses—An Overview" by B. Rolzman—Virology, Second Edition 1990—pp. 28, 29, 87, & 88.
"Ablation of E2A in Recombinant Adenoviruses Improves Transgene Persistence and Decreases Inflammatory Response in Mouse Liver" by J.F. Engelhard, X. Ye, B. Doranz and J.M. Wilson—Proc. Nat. Acad. Sci. USA vol. 91, pp. 6196-6200.
Hall et al., *Genome Research* (1996) 6: 781-790.
Jayawickreme and Kost, *Current Opinion in Biotechnology* (1997) 8: 629-634.
Stein et al., *Nucleic Acids Research* (1997) 25: 2598-2602.
Hall et al., "An Approach to High-throughput Genotyping", *Genome Research*, 6:781-790, 1996.
Jayawickreme et al., "Gene expression systems in the development of high-throughput screens", *Current Opinion in Biotechnology*, 8:629-634, 1997.
von Steih et al., "A high throughput screening for rarely transcribed differentially expressed genes", *lNucleic Acids Research*, vol. 25, No. 13, pp. 2598-2602, 1997.
D.E. Brough, S.A. Rice, S. Sell and D.F. Kelessig. Restricted Changes in the Adenovirus DNA-Binding Protein That Lead to Extended Host Range of Temperature-Sensitive Phenotypes. (Jul. 1985),*Journal of Virology*, 206-212.
B. Roizman. Multiplication of Viruses—An Overview, (1990),*Virology*, Second Edition pp. 28, 29, 87, & 89.
J.F. Engelhard, X. Ya, B. Doranz and J.M. Wilson. Ablution of E2A in Recombinant Adenoviruses Improves Transgene Persistence and Decreases Inflammatory Responses In Mouse Liver. (1994) *Proc. Nat. Acad. Sci. USA 91*, 6196-6200.

(Continued)

*Primary Examiner*—James Ketter
(74) *Attorney, Agent, or Firm*—Synnestvedt & Lechner LLP

(57) ABSTRACT

Novel means and methods for their use are provided to determine the function of the product(s) of one or more sample nucleic acids. The sample nucleic acids are synthetic oligonucleotides, DNA, or cDNA and encode polypeptides, antisense nucleic acids, or GSEs. The sample nucleic acids are expressed in a host by a vehicle to alter at least one phenotype of the host. The altered phenotype(s) is/are identified as a means to assign a biological function to the product(s) encoded by the sample nucleic acid(s).

56 Claims, 61 Drawing Sheets

OTHER PUBLICATIONS

Shepherd et al., "Preparation and screening of an arrayed human genomic library generated with the P1 cloning system," *Proc. Natl. Acad. Sci. USA*, vol. 91, pp. 2629-2633 (Mar. 1994)†.

Woon et al., "Construction and characterization of a 10-fold genome equivalent Rat P1-derived artificial chromosome library," *Genomics*, vol. 50, pp. 306-316 (1998)†.

Crouzet et al., *Proc. Natl. Acad. Sci. USA*, vol. 94, pp. 1414-1419 (1997).

Vogelstein et al., *Proc. Natl. Acad. Sci. USA*, vol. 95, pp. 2509-2514 (1998).

Davis et al., *Gene Therapy*, vol. 5, pp. 1148-1152 (1998).

Ketner et al., *Proc. Natl. Acad. Sci. USA*, vol. 91, pp. 6186-6190 (1994).

Okada et al., *Nucleic Acids Research*, vol. 26, No. 8, pp. 1947-1950 (1998).

Chartier et al., *J. Virology*, vol. 70, pp. 4805-4810 (1996).

Fu et al., *Human Gene Therapy*, vol. 8, pp. 1321-1330 (1997).

Tashiro et al., *Human Gene Therapy*, vol. 10, pp. 1845-1852 (1999).

Bett et al., *Proc. Natl. Acad. Sci. USA*, vol. 91, pp. 8802-8806 (1994).

IIe et al., *Proc. Natl. Acad. Sci. USA*, vol. 95, pp. 2509-2514 (1998).

Vollmer et al., "Efficient cloning of genes of Neurospora crassa," *Proc. Natl. Acad. Sci. USA*, vol. 83, pp. 4869-4873 (Jul. 1986).

Western blotting analysis of A549 clones transfected with pIG.E1A.NEO and PER clones (HER cells transfected with pIG.E1A.E1B)

Transfection efficiency of PER.C3, PER.C5, PER.C6 and 911 cells. Cells were cultured in 6-well plates and transfected (n=2) with 5 μg pRSV.lasZ by calcium-phosphate co-precipitation. Forty-eight hours later the cells were stained with X-GAL. The mean percentage of blue cells is shown.

Packaging system based on primary cells

Packaging system based on established cell lines: transfection with E1a and selection with G418

The potential hairpin conformation of a single-stranded DNA molecule that contains the HP/asp sequences used in these studies. Restriction with the restriction endonucleases *Asp718I* of plasid pICLHa, containing the annealed oligonucleotide pair HP/asp1 en HP/asp2 will yield a linear double-stranded DNA fragment. In cells in which the required adenovirus genes are present, replication can initiate at the terminus that contains the ITR sequence. During the chain elongation, the one of the strands will be displaced. The terminus of the single-stranded displaced-strand molecule can adopt the conformation depicted above. In this conformation the free 3'-terminus can serve as a primer for the cellular and/or adenovirus DNA polymerase, resulting in conversion of the displaced strand in a double-stranded form.

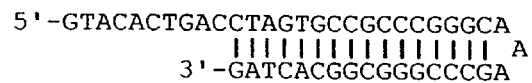

FIG. 15

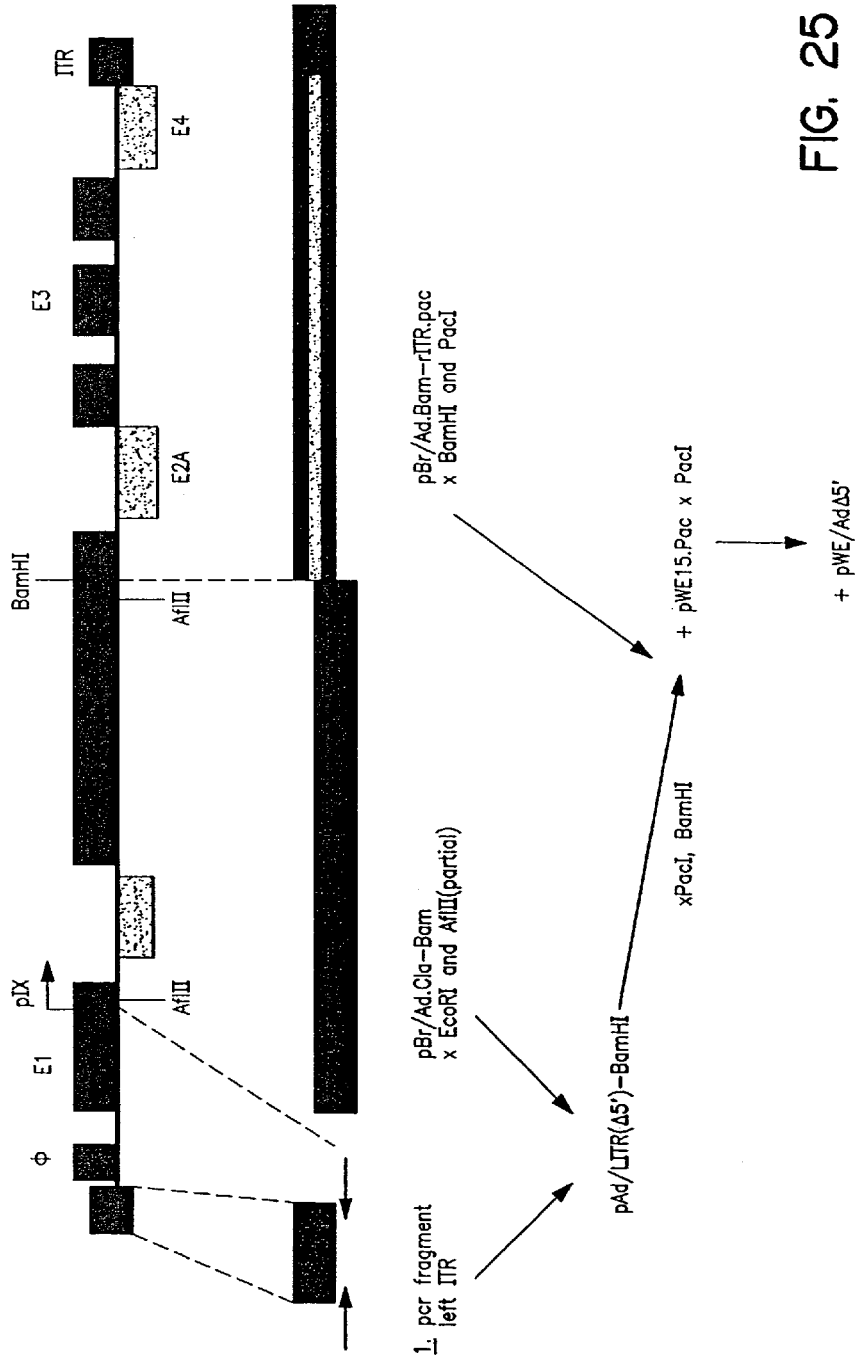

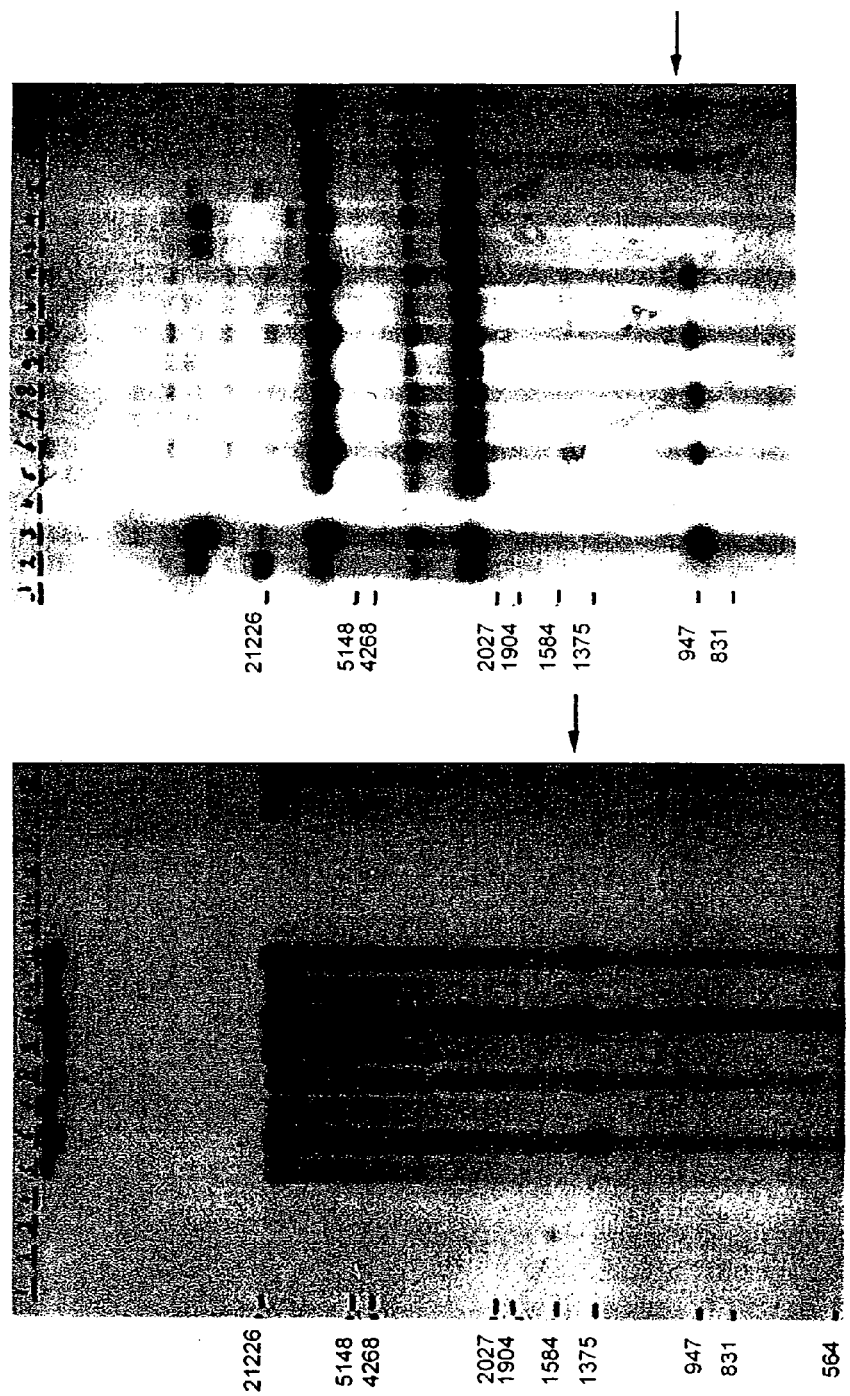

| Gene | Insert kb | |
|---|---|---|
| ceNOS | 3.6 | |
| hTERT | 3.5 | |
| hTERT D712A | 3.5 | |
| lacZ | 3.2 | |
| hCAT1 | 2.2 | |
| GLVR2 | 2.0 | Average titer |
| Luc | 1.7 | $0.8 \pm 0.7 \times 10^9$ pfu/ml |
| SOD3 | 1.4 | |
| MAX1 | .550 | |
| hVEGF121 | .511 | |
| hIL3 | .434 | |
| UBC9 | .412 | |
| ANG1-7 | .104 | |

FIG. 28

EXAMPLE 21 384 WELL PLATE IN PROGRESS

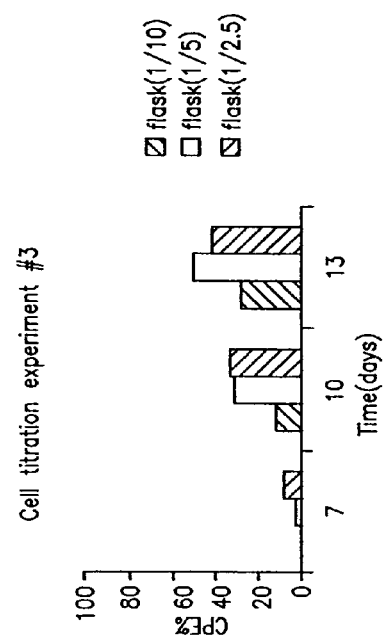
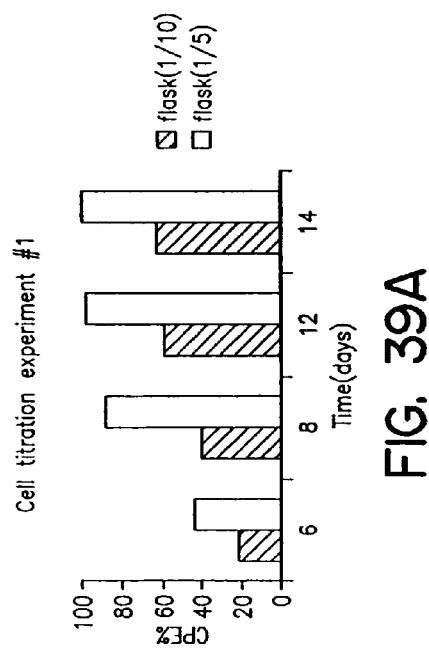
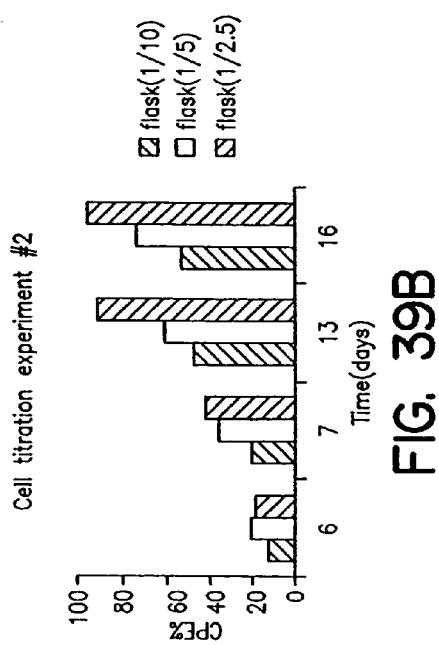

HIGH THROUGHPUT SCREENING OF GENE FUNCTION USING LIBRARIES FOR FUNCTIONAL GENOMICS APPLICATIONS

CROSS-REFERENCE TO RELATED APPLICATION

This application is a division of U.S. application Ser. No. 09/358,036, filed on Jul. 21, 1999, which is a continuation-in-part of U.S. patent application Ser. No. 09/097,239, filed on Jun. 12, 1998, the contents of the entirety of both applications are hereby incorporated by reference.

TECHNICAL FIELD

The invention relates to high throughput methods for identifying the function of sample nucleic acids and their products. The invention is exemplified by the use of the E1-complementing adenoviral packaging cell line PER.C6 in combination with an E1-deleted plasmid-based generation system to produce recombinant adenoviral vectors in a high throughput setting to functionate the product of a sample nucleic acid.

BACKGROUND

The ultimate goal of the Human Genome Project is to sequence the entire human genome. The expected outcome of this effort is a precise map of the 70,000–100,000 genes that are expressed in man. However, a fairly complete inventory of human coding sequences will most likely be publicly available sooner. Since the early 1980s, a large number of Expressed Sequence Tags (ESTs), which are partial DNA sequences read from the ends of complementary DNA (cDNA) molecules, have been obtained by both government and private research organizations. A hallmark of these endeavors, carried out by a collaboration between Washington University Genome Sequencing Center and members of the IMAGE (Integrated Molecular Analysis of Gene Expression) consortium (http:/www-bio.llnl.gov/bbrp/image/image.html), has been the rapid deposition of the sequences into the public domain and the concomitant availability of the sequence-tagged cDNA clones from several distributors (Marra, et al. (1998) *Trends Genet.* 14 (1):4–7). At present, the collection of cDNAs is believed to represent approximately 50,000 different human genes expressed in a variety of tissues including liver, brain, spleen, B-cells, kidney, muscle, heart, alimentary tract, retina, and hypothalamus, and the number is growing daily.

Recent initiatives like that of the Cancer Genome Anatomy project support an effort to obtain full-length sequences of clones in the Unigene set (a set of cDNA clones that is publicly available) by the year 1999. At the same time, commercial entities propose to validate 40,000 full-length cDNA clones by 1999. These individual clones will then be available to any interested party. The speed by which the coding sequences of novel genes are identified is in sharp contrast to the rate by which the function of these genes is elucidated. Assigning functions to the cDNAs in the databases, or functional genomics, is a major challenge in biotechnology today.

For decades, novel genes were identified as a result of research designed to explain a biological process or hereditary disease and the function of the gene preceded its identification. In functional genomics, coding sequences of genes are first cloned and sequenced and the sequences are then used to find functions. Although other organisms such as *Drosophila, C. elegans,* and Zebrafish are highly useful for the analysis of fundamental genes, animal model systems are inevitable for complex mammalian physiological traits (blood glucose, cardiovascular disease, inflammation). However, the slow rate of reproduction and the high housing costs of the animal models are a major limitation to high throughput functional analysis of genes. Although labor intensive efforts are made to establish libraries of mouse strains with chemically or genetically mutated genes in a search for phenotypes that allow the elucidation of gene function or that are related to human diseases, a systematic analysis of the complete spectrum of mammalian genes, be it human or animal, is a significant task.

In order to keep pace with the volume of sequence data, the field of functional genomics needs the ability to perform high throughput analysis of true gene function. Recently, a number of techniques have been developed that are designed to link tissue and cell specific gene expression to gene function. These include cDNA microarraying and gene chip technology and differential display messenger RNA (mRNA). Serial Analysis of Gene Expression (SAGE) or differential display of mRNA can identify genes that are expressed in tumor tissue but are absent in the respective normal or healthy tissue. In this way, potential genes with regulatory functions can be separated from the excess of ubiquitously expressed genes that have a less likely chance to be useful for small drug screening or gene therapy projects. Gene chip technology has the potential to allow the monitoring of gene expression through the measurement of mRNA expression levels in cells of a large number of genes in only a few hours. Cells cultured under a variety of conditions can be analyzed for their mRNA expression patterns and compared. Currently, DNA microarray chips with 40,000 non-redundant human genes are produced and are planned to be on the market in 1999 (Editorial (1998) *Nat. Genet.* 18(3):195–7.). However, these techniques are primarily designed for screening cancer cells and not for screening for specific gene functions.

Double or triple hybrid systems also are used to add functional data to the genomic databases. These techniques assay for protein-protein, protein-RNA, or protein-DNA interactions in yeast or mammalian cells (Brent and Finley (1997) *Annu. Rev. Genet.* 31:663–704). However, this technology does not provide a means to assay for a large number of other gene functions such as differentiation, motility, signal transduction, and enzyme and transport activity. Yeast expression systems have been developed which are used to screen for naturally secreted and membrane proteins of mammalian origin (Klein, et al. (1996) *Proc. Natl. Acad. Sci. USA* 93 (14):7108–13). This system also allows for collapsing of large libraries into libraries with certain characteristics that aid in the identification of specific genes and gene products. One disadvantage of this system is that genes encoding secreted proteins are primarily selected. A second disadvantage is that the library may be biased because the technology is based on yeast as a heterologous expression system and there will be gene products that are not appropriately folded.

Other current strategies include the creation of transgenic mice or knockout mice. A successful example of gene discovery by such an approach is the identification of the osteoprotegerin gene. DNA databases were screened to select ESTs with features suggesting that the cognate genes encoded secreted proteins. The biological functions of the genes were assessed by placing the corresponding full-length cDNAs under the control of a liver-specific promoter. Transgenic mice created with each of these constructs consequently have high plasma levels of the relevant protein. Subsequently, the transgenic animals were subjected to a battery of qualitative and quantitative phenotypic investigations. One of the genes that was transfected into mice produced mice with an increased bone density, which led subsequently to the discovery of a potent anti-osteoporosis factor (Simonet, et al. (1997) *Cell.* 89(2):309–19). The disadvantages of this method are that the method is costly and highly time consuming.

The challenge in functional genomics is to develop and refine all the above-described techniques and integrate their results with existing data in a well-developed database that provides for the development of a picture of how gene function constitutes cellular metabolism and a means for this knowledge to be put to use in the development of novel medicinal products. The current technologies have limitations and do not necessarily result in true functional data. Therefore, there is a need for a method that allows for direct measurement of the function of a single gene from a collection of genes (gene pools or individual clones) in a high throughput setting in appropriate in vitro assay systems and animal models.

The development of high throughput screens is discussed in Jayawickreme and Kost, (1997) *Curr. Opin. Biotechnol.* 8:629–634. A high throughput screen for rarely transcribed differentially expressed genes is described in von Stein et al., (1997) *Nucleic Acids Res.* 35: 2598–2602. High throughput genotyping is disclosed in Hall et al., (1996) *Genome Res.* 6:781–790. Methods for screening transdominant intracellular effector peptides and RNA molecules are disclosed in Nolan, WO97/27212 and WO/9727213.

DISCLOSURE OF THE INVENTION

The invention includes methods, and compositions for use therein, for directly, rapidly, and unambiguously measuring the function of sample nucleic acids of unknown function in a high throughput setting, using a plasmid-based E1-deleted adenoviral vector system and an E1-complementing host cell. The method includes constructing a set of adapter plasmids by inserting a set of cDNAs, DNAs, ESTs, genes, synthetic oligonucleotides, or a library of nucleic acids into E1-deleted adapter plasmids; cotransfecting an E1-complementing cell line with the set or library of adapter plasmids and at least one plasmid having sequences homologous to sequences in the set of adapter plasmids and which also includes all adenoviral genes not provided by the complementing cell line or adapter plasmids necessary for replication and packaging to produce a set or library of recombinant adenoviral vectors preferably in a miniaturized, high throughput setting. To identify and assign a function to product(s) encoded by the sample nucleic acids, a host is transduced in a high throughput setting with the recombinant adenoviral vectors, which express the product(s) of the sample nucleic acids and thereby alter a phenotype of a host. The altered phenotype is identified and used as the basis to assign a function to the product(s) encoded by the sample nucleic acids. The plasmid-based system is used to rapidly produce adenoviral vector libraries that are preferably replications competent adenovirus ("RCA")-free for high throughput screening. Each step of the method can be performed in a multiwell format and automated to further increase the capacity of the system. This high throughput system facilitates expression analysis of a large number of sample nucleic acids from human and other organisms both in vitro and in vivo and is a significant improvement over other available techniques in the field.

BRIEF DESCRIPTION OF THE DRAWINGS

FIG. 11B: New adenoviral packaging construct pIG.E1A.NEO, does not have sequence overlap with new adenoviral vector pMLPI.TK. There are no regions of sequence overlap between the new packaging construct pIG.E1A.NEO and the new adenoviral vector pMLPI.TK that can result in homologous recombination and the formation of RCA.

FIG. 15: Potential hairpin conformation of a single-stranded DNA molecule that contains the HP/asp sequence (SEQ ID NO:47). Asp718I digestion of pICLha, containing the cloned oligonucleotides HP/asp1 and HP/asp2, yields a linear double-stranded DNA with an Ad5 ITR at one terminus and the HP/asp sequence at the other terminus. In cells expressing the adenoviral E2 region, a single-stranded DNA is produced with an Ad5 ITR at the 5'-terminus and the hairpin conformation at the 3'-terminus. Once formed, the hairpin can serve as a primer for cellular and/or adenoviral DNA polymerase to convert the single stranded DNA to double stranded DNA.

FIG. 25: Helper construct for replication and packaging of minimal adenoviral vectors. Schematic representation of the cloning steps for the generation of the helper construct pWE/AdΔ5'.

FIG. 26: Evidence for SV40-LargeT/ori mediated replication of large adenoviral constructs in COS-1 cells. FIG. 26B shows an autoradiogram of the Southern blot hybridized to the adenoviral probe. FIG. 26C shows an autoradiogram of the Southern blot hybridized to the pWE probe. Lane 1, marker lane: λ DNA digested with EcoRI and HindIII. Lane 4 is empty. Lanes 2, 5, 7, 9, 11, 13, 15, and 17 contain undigested DNA and Lanes 3, 6, 8, 10, 12, 14, 16 and 18 contain MboI digested DNA. All lanes contain DNA from COS-1 cells transfected with pWE.pac (lanes 2 and 3), pWE/Ad.Δ5' construct #1 (lanes 5 and 6), #5 (lanes 7 and 8) and #9 (lanes 9 and 10), pWE/Ad.AflII-rITR (lanes 11 and 12), pMV/CMV-LacZ (lanes 13 and 14), pWE.pac digested with PacI (lanes 15 and 16), or pWE/Ad.AflII-rITR digested with PacI (lanes 17 and 18) as described in the text. Arrows point to the expected positive signal of 1416 bp (FIG. 26B) and 887 bp (FIG. 26C).

FIG. 28: Average titers produced in a 96-well plate as measured using a PER.C6/E2A based plaque assay (Example 11).

FIGS. 34A–M: Plasmid maps of adenoviral adapter plasmids (Example 17). These adenoviral adapter plasmids are particularly useful for the construction of expression libraries in adenoviral vectors such as the subject of this application. They have very rare restriction sites for the linearization of adapters and libraries of adapters (with transgenes inserted) and will not inactivate the adapter by digestion of the inserts. In FIG. 34M, the cosmid containing pIPsp-Adapt5- or pCLIP-IppoI-polynew-derived adenoviral DNA can be used for in vitro ligations. Double stranded oligonucleotides containing compatible overhangs are ligated between the I-CeuI and PI-SceI sites, between I-CeuI and I-PpoI, between I-SceI and PI-SceI, and between I-SceI and I-PpoI. The PacI restriction endonuclease is subsequently used not only to linearize the construct after ligation and liberate the left- and right ITRs, but also to eliminate non-recombinants.

FIG. 39 (A, B, and C) (Example 23): The percentage of virus producing cells (CPE positive) scored after propagation of the freeze/thawed transfected cells to new PER.C6/E2A cells, in three different experiments using PER.C6/E2A cells for transfections with indicated confluency at time of transfection. The figure legend refers to Table 9 where the absolute cell numbers from each flask in each experiment were counted. The cells from these flasks were used to seed 96-well plates for transfection with adenoviral adapter and helper DNA molecules.

BEST MODE FOR CARRYING OUT THE INVENTION

Figure 1:
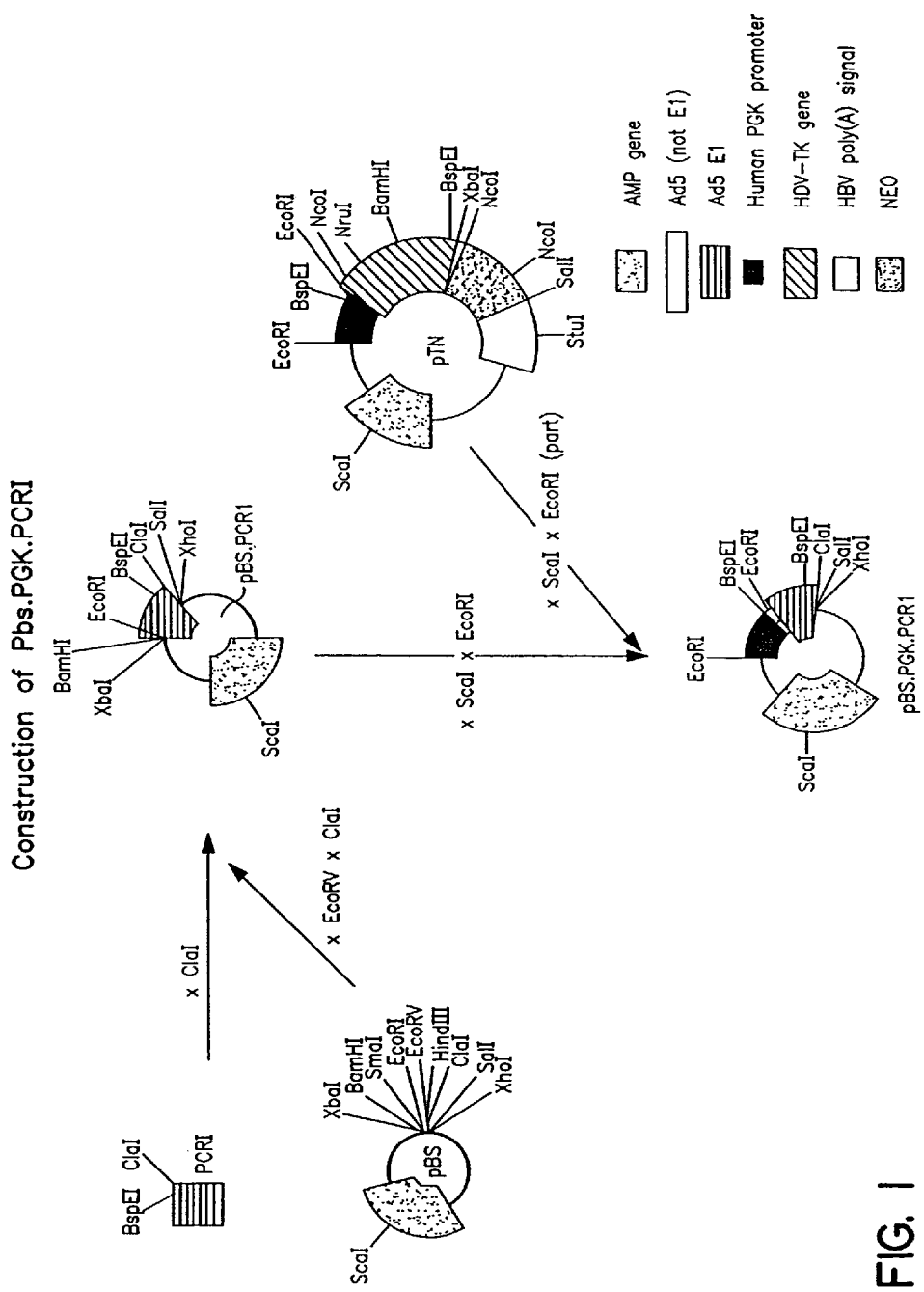
FIG. 1. Make "HBV poly (A) signal" region in pTN plasmid sequence more visible by changing border color to black. Support for this revision is found in the specification on page 40, lines 8 to 9, which describes the pTN plasmid sequence. Change border to black for figure legend as well.

In one aspect, the invention provides for a library of expressible nucleic acids comprising a multiplicity of compartments. Each compartment comprises at least one vehicle including at least one nucleic acid of the library, whereby the vehicle is capable of very efficiently introducing at least one nucleic acid into a cell such that it can be expressed. One advantage of the library is that the library may be introduced into cells very efficiently. Another advantage of the library is that it includes a multiplicity of compartments each including at least one nucleic acid. The library may be favorably used to study the effect of expressed nucleic acid in a cell. A library with this architecture may be favorably used to rapidly select those compartments including at least one nucleic acid which, when expressed in a cell, exerts a certain effect. When a compartment includes only one nucleic acid, then it is known that the nucleic acid exerts the effect. When a compartment includes more than one nucleic acid, it is known that at least one of the nucleic acids exerts the effect. The advantage of knowing which compartment includes nucleic acid which can exert a certain effect is greater when the compartment includes relatively few different nucleic acids and is highest when the compartment includes only one nucleic acid. It is also advantageous to precisely know the number of different nucleic acids per compartment, particularly in larger libraries.

An expressible nucleic acid may be any expressible nucleic acid such as a nucleic acid coding for a proteinaceous molecule, an RNA molecule, or a DNA molecule.

In a preferred embodiment, the vehicle includes a viral element or a functional part, derivative and/or analogue thereof. A viral element may include a virus particle such as, but not limited to, an enveloped retrovirus particle or a virus capsid of a non-enveloped virus such as, but not limited to, an adenovirus. A virus particle is favorable since it allows the efficient introduction of at least one nucleic acid into a cell. A viral element may also include a viral nucleic acid allowing the amplification of the library in cells. A viral element may include a viral nucleic acid allowing the packaging of at least one nucleic acid into a vehicle, where the vehicle is a virus particle.

In a preferred embodiment, the viral element is derived from an adenovirus. Preferably, the vehicle includes an adenoviral vector packaged into an adenoviral capsid.

A cell may be any kind of cell. Preferably, when the library is screened for the presence of nucleic acids with potential therapeutic values, the cell is a eukaryotic cell, especially a mammalian cell.

In one embodiment, at least one compartment includes at least two vehicles. Especially with, but not limited to, large libraries, it becomes advantageous to reduce the number of compartments to reduce the number of screening assays that need to be performed. In such cases, libraries may be provided that include more than one vehicle. If after screening, a certain effect is correlated to a certain compartment, the vehicles in the compartment may be analysed separately in an additional screening assay to select the vehicle including the nucleic acid the expression of which exerts the effect. In addition, the presence of more than one vehicle in a compartment may be advantageous when a library containing one vehicle per compartment is screened for a nucleic acid capable of exerting an effect in combination with one particular other nucleic acid. The other nucleic acid may then be provided to the cell by adding a vehicle including the particular other nucleic acid to all compartments prior to performing the screening assay. Similarly, the vehicle may include at least two nucleic acids.

In a preferred embodiment, the nucleic acid derived from an adenovirus includes the nucleic acid encoding an adenoviral late protein or a functional part, derivative, and/or analogue thereof. An adenoviral late protein, for instance an adenoviral fiber protein, may be favorably used to target the vehicle to a certain cell or to induce enhanced delivery of the vehicle to the cell. Preferably, the nucleic acid derived from an adenovirus encodes for essentially all adenoviral late proteins, enabling the formation of entire adenoviral capsids or functional parts, analogues, and/or derivatives thereof. Preferably, the nucleic acid derived from an adenovirus includes the nucleic acid encoding adenovirus E2A or a functional part, derivative, and/or analogue thereof. Preferably, the nucleic acid derived from an adenovirus includes the nucleic acid encoding at least one E4-region protein or a functional part, derivative, and/or analogue thereof, which facilitates, at least in part, replication of an adenoviral derived nucleic acid in a cell.

In one embodiment, the nucleic acid derived from an adenovirus includes the nucleic acid encoding at least one E1-region protein or a functional part, derivative, and/or analogue thereof. The presence of the adenoviral nucleic acid encoding an E1-region protein facilitates, at least in part, replication of the nucleic acid in a cell. The replication capacity is favored in certain applications when screening is done for expressible nucleic acids capable of irradiating tumor cells. In such cases, replication of an adenoviral nucleic acid leading to the amplification of the vehicle in a mammal including tumor cells may lead to the irradiation of metastasised tumor cells. On the other hand, the presence of an adenoviral nucleic acid encoding an E1-region protein may facilitate, at least in part, amplification of the nucleic acid in a cell for the amplification of vehicles including the adenoviral nucleic acid.

In one embodiment, the vehicle further includes a nucleic acid including an adeno-associated virus terminal repeat or a functional part, derivative, and/or analogue thereof which allows the integration of at least one nucleic acid in a cell.

In one embodiment, the viral element derived from an adenovirus includes an adenoviral capsid or a functional part, derivative, and/or analogue thereof. Adenovirus biology is also comparatively well known on the molecular level. Many tools for adenoviral vectors have been and continue to be developed, thus making an adenoviral capsid a preferred vehicle for incorporating in a library of the invention. An adenovirus is capable of infecting a wide variety of cells. However, different adenoviral serotypes have different preferences for cells. To combine and widen the target cell population that an adenoviral capsid of the invention can enter in a preferred embodiment, the vehicle includes adenoviral fiber proteins from at least two adenoviruses.

Another aspect of the invention provides a method for determining at least one function of at least one nucleic acid present in a library according to the invention. This method includes transducing a multiplicity of cells with at least one vehicle including at least one nucleic acid from the library, culturing the cells while allowing for expression of the nucleic acid, and determining the expressed function. Currently, large numbers of nucleic acids are being sequenced and cloned. In fact, cloning and sequencing of nucleic acid proceeds at such a rate that most of the functions of newly cloned and sequenced nucleic acids are not known. Also, of the nucleic acids with a known function, not all of the functions are known. The current invention provides a method for determining the function of a nucleic acid. In one aspect, the invention provides a method for screening a library of the invention in a screening assay wherein a function of a nucleic acid can be assessed. In such an assay, the function is central. A library of the invention is screened for the presence of expressible nucleic acids capable of influencing, at least in part, the function.

In a preferred embodiment, the multiplicity of cells is divided over a number of compartments each including at least one vehicle including at least one nucleic acid from the library. The number of compartments preferably corresponds to the multiplicity of compartments of the library. In a preferred embodiment, the method further includes selecting the vehicle including a desired function.

In another aspect, the invention provides a method for obtaining an expressible nucleic acid having a desired function when expressed in a cell, determining at least one function of at least one nucleic acid present in a library according to the invention. The method includes transducing a multiplicity of cells with at least one vehicle including at least one nucleic acid from the library, culturing the cell while allowing for expression of at least one nucleic acid, and determining the expressed function.

In another aspect, the invention provides a method for producing a library including a multiplicity of compartments each including at least one nucleic acid delivery vehicle and each including at least one nucleic acid. The method includes recombining the vehicle nucleic acid with at least one nucleic acid, thereby producing a vehicle capable of delivering at least one nucleic acid to a cell in an expressible manner. For expression of a nucleic acid, a number of molecular elements well known in the field such as, but not limited to, promoters, enhancers, poly-adenylation signals, translation start and stop signals etc., are required and/or may be used.

Recombination may be performed through any means such as through means of molecular cloning and/or polymerase mediated amplification techniques such as PCR and NASBA (Organon Teknika). However, recombining preferably includes homologous recombination between at least partially overlapping sequences in the vehicle nucleic acid and at least one nucleic acid. Especially for the generation of large viral derived nucleic acids, homologous recombination is preferred. Preferably, the vehicle nucleic acid and/or at least one nucleic acid includes an adenoviral nucleic acid or a functional part, derivative, and/or analogue thereof. In one example, the adenoviral nucleic acid includes a host range mutation that enables the adenovirus to replicate in non-human primate cells.

In one aspect the invention provides a library obtainable by a method of the invention.

The invention further provides the use of a library obtainable by a method of the invention for determining at least one function of at least one nucleic acid present in a library of the invention.

The invention further provides a method for amplifying a vehicle present in a library of the invention including providing a cell with the vehicle, culturing the cell, allowing the amplification of the vehicle, and harvesting vehicles amplified by the cell. Preferably, the cell is a primate cell thereby enabling the amplification of vehicles including viral elements that allow replication of the vehicle nucleic acid. Preferably, the cell includes a nucleic acid encoding an adenoviral E1-region protein thereby allowing, among other things, the amplification of vehicles including viral elements derived from adenovirus including adenoviral nucleic acids including a functional deletion of at least part of the E1-region. Preferably, the cell is a PER.C6 cell (ECACC deposit number 96022940) or a functional derivative and/or analogue thereof. A PER.C6 cell (or a functional derivative and/or analogue thereof) allows the replication of adenoviral nucleic acid with a deletion of the E1-coding region without concomitant production of RCA in instances wherein the adenoviral nucleic acid and chromosomal nucleic acid in the PER.C6 cell or functional derivative and/or analogue thereof do not include sequence overlap that allows for homologous recombination between the adenoviral and chromosomal nucleic acid leading to the formation of RCA. Preferably, the cell further includes nucleic acid encoding adenovirus E2A and/or an adenoviral E4-region protein or a functional part, derivative, and/or analogue thereof. This allows the replication of adenoviral nucleic acid with functional deletions of nucleic acid encoding adenovirus E2A and/or an adenoviral E4-region protein, thereby inhibiting replication of the adenoviral nucleic acid in a cell not including nucleic acid encoding adenovirus E2A and/or an adenoviral E4-region protein or a functional part, derivative and/or analogue thereof, for instance a cell capable of displaying a certain function.

In one example, the vehicle nucleic acid does not include sequence overlap with other nucleic acids present in the cell, leading to the formation of vehicle nucleic acid capable of replicating in the absence of E1-region encoded proteins.

The invention further provides a library according to the invention or a method according to the invention, wherein the multiplicity of compartments includes a multiwell format. A multiwell format is very suited for automated execution of at least part of the methods of the invention.

In one aspect the invention provides a library wherein at least one nucleic acid encodes a product of unknown function.

The library of the invention and/or the methods of the invention are preferably used or performed in an at least substantially automated setting.

The invention further provides a multiplicity of cells including a library according to the invention.

The present invention uses high throughput generation of recombinant adenoviral vector libraries containing one or more sample nucleic acids, followed by high throughput screening of the adenoviral vector libraries in a host to alter the phenotype of the host as a means of assigning a function to expression product(s) of the sample nucleic acids. Libraries of E1-deleted adenoviruses are generated in a high throughput setting using nucleic acid constructs and transcomplementary packaging cells. The sample nucleic acid libraries can be a set of distinct defined or undefined sequences or can be a pool of undefined or defined sequences. The first nucleic acid construct is a relatively small and easy to manipulate adapter plasmid containing, in an operable configuration, at least a left ITR, a packaging signal, and an expression cassette with the sample nucleic acids. The second nucleic acid construct contains one or more nucleic acid molecules that partially overlap with each other and/or with sequences in the first construct. The second construct also contains at least all adenovirus sequences necessary for replication and packaging of a recombinant adenovirus not provided by the adapter plasmid or packaging cells. The second nucleic acid construct is deleted in E1-region sequences and optionally E2B region sequences other than those required for virus generation and/or E2A, E3 and/or E4 region sequences. Cotransfection of the first and second nucleic acid constructs into the packaging cells leads to homologous recombination between overlapping sequences in the first and second nucleic acid constructs and among the second nucleic acid constructs when it is made up of more than one nucleic acid molecule. Generally, the overlapping sequences are no more than 5000 bp and encompass E2B region sequences essential for virus production. Recombinant viral DNA is generated with an E1-deletion that is able to replicate and propagate in the E1-complementing packaging cells to produce a recombinant adenoviral vector library. The adenoviral vector library is introduced in a high throughput setting into a host which is grown to allow sufficient expression of the product(s) encoded by the sample nucleic acids to permit detection and analysis of its biological activity. The host can be cultured cells in vitro or an animal or plant model. Sufficient expression of the product(s) encoded by the sample nucleic acids alters the phenotype of the host. Using any of a variety of in vitro and/or in vivo assays for biological activity, the altered phenotype is analyzed and identified and a function is thereby assigned to the product(s) of the sample nucleic acids. The plasmid-based adenoviral vector systems described here provide for the creation of large gene-transfer libraries that can be used to screen for novel genes applicable to human diseases. Identification of a useful or beneficial biological effect of a particular adenoviral mediated transduction can result in a useful gene therapeutic product or a target for a small molecule drug for treatment of human diseases.

There are several advantages to the subject invention over currently available techniques. The entire process lends itself to automation especially when implemented in a 96-well or other multi-well format. The high throughput screening, using a number of different in vitro assays, provides a means of efficiently obtaining functional information in a relatively short period of time. The member(s) of the recombinant adenoviral libraries that exhibit or induce a desired phenotype in a host in vitro or in situ are identified to reduce the libraries to a manageable number of recombinant adenoviral vectors or clones which can be tested in vitro in an animal model.

Another distinct advantage of the subject invention is that the methods produce RCA-free adenoviral libraries. RCA contamination throughout the libraries could become a major obstacle, especially if libraries are continuously amplified for use in multiple screening programs. A further advantage of the subject invention is minimization of the number of steps involved in the process. The methods of the subject invention do not require cloning of each individual adenovirus before use in a high throughput screening program. Other systems include one or more steps in *E. coli* to achieve homologous recombination for the various adenoviral plasmids necessary for vector generation (Chartier et al, (1996) *J. Virol.* 70(7):4805–4810; Crouzet et al., (1997) *Proc. Natl. Acad. Sci* 94(4):1414–1419; He et al., (1998) *Proc. Natl. Acad. Sci.* 95(5):2509–2514). Another plasmid system that has been used for adenoviral recombination and adenoviral vector generation, and which is based on homologous recombination in human cells, is the pBHG series of plasmids. However, if this plasmid is used in 293 cells, the plasmid can become unstable because the plasmid pBHG contains two ITRs close together and also can overlap with E1 sequences. All these features are undesirable and lead to RCA production or otherwise erroneous adenoviral vector production (Bett et al., (1994) *Proc. Natl. Acad. Sci. USA* 91(19):8802–8806). The recombinant nucleic acids of the subject invention have been designed to avoid constructions with these undesirable features.

A further advantage of the subject invention is the ability of recombinant adenoviruses to efficiently transfer and express recombinant genes in a variety of mammalian cells and tissues in vitro and in vivo, resulting in the high expression of the transferred sample nucleic acids. The ability to productively infect quiescent cells, further expands the utility of the recombinant adenoviral libraries. In addition, high expression levels ensure that the product(s) of the sample nucleic acids will be expressed to sufficient levels to induce a change that can be detected in the phenotype of a host and allow the function of the product(s) encoded by the sample nucleic to be determined.

The sample nucleic acids can be genomic DNA, cDNA, previously cloned DNA, genes, ESTs, synthetic double stranded oligonucleotides, or randomized sequences derived from one or multiple related or unrelated sequences. The sample nucleic acids can also be directly expressed as polypeptides, antisense nucleic acids, or genetic suppressor elements (GSE). The sample nucleic acid sequences can be obtained from any organism including mammals (for example, man, monkey, mouse), fish (for example, zebrafish, pufferfish, salmon), nematodes (for example, *C. elegans*), insects (for example, *Drosophila*), yeasts, fungi, bacteria, and plants. Alternatively, the sample nucleic acids are prepared as synthetic oligonucleotides using commercially available DNA synthesizers and kits. The strand coding the open reading frame of the polypeptide or product of the sample nucleic acid and the complementary strand are prepared individually and annealed to form double-stranded DNA. Special annealing conditions are not required. The sequences of the sample nucleic acids can be randomized or not through mutagenizing or methodologies promoting recombination. The sample nucleic acids code for a product(s) for which a biological activity is unknown. The phrase biological activity is intended to mean an activity that is detectable or measurable either in situ, in vivo, or in vitro. Examples of a biological activity include but are not limited to altered viability, morphologic changes, apoptosis induction, DNA synthesis, tumorigenesis, disease or drug susceptibility, chemical responsiveness or secretion, and protein expression.

The sample nucleic acids preferably contain compatible ends to facilitate ligation to the vector in the correct orientation and to operatively link the sample nucleic acids to a promoter. For synthetic double-stranded oligonucleotide ligation, the ends compatible to the vector can be designed into the oligonucleotides. When the sample nucleic acid is an EST, genomic DNA, cDNA, gene, or previously-cloned DNA, the compatible ends can be formed by restriction enzyme digestion or the ligation of linkers to the DNA containing the appropriate restriction enzyme sites. Alternatively, the vector can be modified by the use of linkers. The restriction enzyme sites are chosen so that transcription of the sample nucleic acid from the vector produces the desired product, i.e., polypeptide, antisense nucleic acid, or GSE.

The vector into which the sample nucleic acids are preferably introduced contains, in an operable configuration, an ITR, at least one cloning site or preferably a multiple cloning site for insertion of a library of sample nucleic acids, and transcriptional regulatory elements for delivery and expression of the sample nucleic acids in a host. It generally does not contain E1 region sequences, E2B region sequences (other than those required for late gene expression), E2A region sequences, E3 region sequences, or E4 region sequences. The E1-deleted delivery vector or adapter plasmid is digested with the appropriate restriction enzymes, either simultaneously or sequentially, to produce the appropriate ends for directional cloning of the sample nucleic acid whether it be synthetic double-stranded oligonucleotides, genomic DNA, cDNA, ESTs, or a previously-cloned DNA. Restriction enzyme digestion is routinely performed using commercially available reagents according to the manufacturer's recommendations and varies according to the restriction enzymes chosen. A distinct set or pool of sample nucleic acids is inserted into E1-deleted adapter plasmids to produce a corresponding set or library of plasmids for the production of adenoviral vectors. An example of an adapter plasmid is pMLPI.TK, which is made up of adenoviral nucleotides 1–458 followed by the adenoviral major late promoter, functionally linked to the herpes simplex virus thymidine kinase gene, and followed by adenoviral nucleotides 3511–6095. Other examples of adapter plasmids are pAd/L420-HSA (FIG. 21) and pAd/Clip (FIG. 22). pAd/L420-HSA contains adenoviral nucleotides 1–454, the L420 promoter linked to the murine HSA gene, a poly-A signal, and adenoviral nucleotides 3511–6095. pAd/CLIP was made from pAd/L420-HSA by replacement of the expression cassette (L420-HSA) with the CMV promoter, a multiple cloning site, an intron, and a poly-A signal.

Once digested, the vector and sample nucleic acids are purified by gel electrophoresis. The nucleic acids can be extracted from various gel matrices by, for example, agarase digestion, electroelution, melting, or high salt extraction. In combination with these methods or alternatively, the digested nucleic acids can be purified by chromatography (e.g., Qiagen or equivalent DNA binding resins) or phenol-chloroform extraction followed by ethanol precipitation. The optimal purification method depends on the size and type of the vector and sample nucleic acids. Both can be used without purification. Generally, the sample nucleic acids contain 5'-phosphate groups and the vector is treated with alkaline phosphatase to promote nucleic acid-vector ligation and prevent vector-vector ligation. If the sample nucleic acid is a synthetic oligonucleotide, 5'-phosphate groups are added by chemical or enzymatic means. For ligation, molar ratios of sample nucleic acids (insert) to vector DNA range from approximately 10:1 to 0.1:1. The ligation reaction is performed using T4 DNA ligase or any other enzyme that catalyzes double-stranded DNA ligation. Reaction times and temperature can vary from about 5 minutes to 18 hours, and from about 15° to room temperature, respectively.

The magnitude of expression can be modulated using promoters (CMV immediately early, promoter, SV40 promoter, or retrovirus LTRs) that differ in their transcriptional activity. Operatively linking the sample nucleic acid to a strong promoter such as the CMV immediate early promoter and optionally one or more enhancer element(s) results in higher expression allowing the use of a lower multiplicity of infection to alter the phenotype of a host. The option of using a lower multiplicity of infection increases the number of times a library can be used in situ, in vitro, and in vivo. Moreover, the lower the multiplicity of infection and dosages used in screening programs, assays, and animal models decreases the chance of eliciting toxic effects in the transduced host, which increases the reliability of the subject of this invention. Another way to reduce possible toxic effects relating to expression of the library is to use a regulatable promoter, particularly one which is repressed during virus production but can be turned on or is active during functional screenings with the adenoviral library, to provide temporal and/or cell type specific control throughout the screening assay. In this way, sample nucleic acids that are members of the library and are toxic, inhibitory, or in any other way interfere with adenoviral replication and production, can still be produced as an adenoviral vector (see International Patent Appl'n WO 97/20943). Examples of this type of promoter are the AP1-dependent promoters which are repressed by adenoviral E1 gene products, resulting in shut off of sample nucleic acid expression during adenoviral library production (see van Dam et al., (1990) *Mol. Cell. Biol.* 10(11):5857–5864). Such a promoter can be made using combinatorial techniques or natural or adapted forms of promoters can be included. Examples of AP1-dependent promoters are promoters from the collagenase, c-myc, monocyte chemoattractant protein (JE or mcp-1/JE), and stromelysin genes (Hagmeyer et al., (1993) EMBO J. 12(9);3559–3572; Offringa et al., (1990) Cell 62(23):527–538; Offringa et al., (1988) *Nucleic Acids Res.* 16(23):10973–10984; van Dam et al., (1989) *Oncogene* 4(10):1207–1212). Alternatively, other more specific but stronger promoters can be used especially when complex in vitro screenings or in vivo models are employed and tissue-regulated expression is desired. Any promoter/enhancer system functional in the chosen host can be used. Examples of tissue-regulated promoters include promoters with specific activity or enhanced activity in the liver, such as the albumin promoter (Tronche et al., (1990) *Mol. Biol. Med.* 7(2):173–185). Another approach to enhanced expression is to increase the half-life of the mRNA transcribed from the sample nucleic acids by including stabilizing sequences in the 3' untranslated region. A second nucleic acid construct, a helper plasmid having sequences homologous to sequences in the E1-deleted adapter plasmids, which carries all necessary adenoviral genes necessary for replication and packaging, also is prepared. Preferably, the helper plasmid has no complementing sequences that are expressed by the packaging cells that would lead to production of RCA. In addition, preferably the helper plasmids, adapter plasmid, and packaging cell have no sequence overlap that would lead to homologous recombination and RCA formation. The region of sequence overlap shared between the adapter plasmid and the helper plasmid allows homologous recombination and the formation of an E1-deleted, replication-defective recombinant adenoviral genome. Generally, the region of overlap encompasses E2B region sequences that are required for late gene expression. The amount of overlap that provides for the best efficiency without appreciably decreasing the size of the library insert can be determined empirically. The sequence overlap is generally 10 bp to 5000 bp, more preferably 2000 to 3000 bp.

The size of the sample nucleic acids or DNA inserts in a desired adenoviral library can vary from several hundred base pairs (e.g., sequences encoding neuropeptides) to more than 30 Kbp (e.g., titin). The cloning capacity of the adenoviral vectors produced using adapter plasmids can be increased by deletion of additional adenoviral gene(s) that are then easily complemented by a derivative of an E1-complementing cell line. As an example, candidate genes for deletion include E2, E3, and/or E4. For example, regions essential for adenoviral replication and packaging are deleted from the adapter and helper plasmids and expressed, for example, by the complementing cell line. For E3 deletions, genes in this region do not need to be complemented in the packaging cell for in vitro models; in in vivo models, the impact upon immunogenicity of the recombinant virus can be assessed on an ad hoc basis.

The set or library of specific adapter plasmids or pool(s) of adapter plasmids is converted to a set or library of adenoviral vectors. The adapter plasmids containing the sample nucleic acids are linearized and transfected into an E1-complementing cell line. The adapter plasmids are preferably seeded in microtiter tissue culture plates with 96, 384, 1,536 or more wells per plate, together with helper plasmids having sequences homologous to sequences in the adapter plasmid and containing all adenoviral genes necessary for replication and packaging. Recombination occurs between the homologous sequences shared by adapter and helper plasmids to generate an E1-deleted, replication-defective adenoviral genome that is replicated and packaged, preferably, in an E1-complementing cell line. If more than one helper plasmid is used, recombination between homologous regions shared among the helper plasmids and recombination between the helper plasmids and adapter plasmid results in the formation of a replication-defective recombinant adenoviral genome. The regions of sequence overlap between the adapter and helper plasmids are at least about a few hundred nucleotides or greater. Recombination efficiency will increase by increasing the size of the overlap.

The E1-functions provided by the trans complementing packaging cell permit the replication and packaging of the E1-deleted recombinant adenoviral genome. The adapter and/or helper plasmids preferably have no sequence overlap amongst themselves or with the complementing sequences in the packaging cells that can lead to the formation of RCA. Preferably, at least one of the ITRs on the adapter and helper plasmids is flanked by a restriction enzyme recognition site not present in the adenoviral sequences or expression cassette so that the ITR is freed from vector sequences by digestion of the DNA with that restriction enzyme. In this way, initiation of replication occurs more efficiently. In order to increase the efficiency of recombinant adenoviral generation, higher throughput can be obtained by using microtiter tissue culture plates with 96, 384, or 1,536 wells per plate instead of using large tissue culture vials or flasks. E1-complementing cell lines are grown in microtiter plates and cotransfected with the libraries of adapter plasmids and a helper plasmid(s). Automation of the method using, for example, robotics can further increase the number of adenoviral vectors that can be produced (Hawkins et al., (1997) Science 276(5320): 1887–9, Houston, (1997) Methods Find. Exp. Clin. Pharmacol. 19 Suppl. A:43–5).

As an alternative to the adapter plasmids, the sample nucleic acids can be ligated to "minimal" adenoviral vector plasmids. The so-called "minimal" adenoviral vectors, according to the present invention, retain at least a portion of the viral genome that is required for encapsidation of the genome into virus particles (the encapsidation signal). The minimal vectors also retain at least one copy of at least a functional part or a derivative of the ITR, that is DNA sequences derived from the termini of the linear adenoviral genome that are required for replication. The minimal vectors preferably are used for the generation and production of helper- and RCA-free stocks of recombinant adenoviral vectors and can accommodate up to 38 kb of foreign DNA. The helper functions of the minimal adenoviral vectors are preferably provided in trans by encapsidation-defective, replication-competent DNA molecules that contain all the viral genes encoding the required gene products, with the exception of those genes that are present in the complementing cell or genes that reside in the vector genome.

Packaging of the "minimal" adenoviral vector is achieved by cotransfection of an E1-complementing cell line with a helper virus or, alternatively, with a packaging deficient replicating helper system. Preferably, the packaging deficient replicating helper is amplified following transfection and expresses the sequences required for replication and packaging of the minimal adenoviral vectors that are not expressed by the packaging cell line. The packaging deficient replicating helper is not packaged into adenoviral particles because its size exceeds the capacity of the adenoviral virion and/or because it lacks a functional encapsidation signal. The packaging deficient replicating helper, the minimal adenoviral vector, and the complementing cell line, preferably, have no region of sequence overlap that permits RCA formation.

The replicating, packaging deficient helper molecule always contains all adenoviral coding sequences that produce proteins necessary for replication and packaging, with or without the coding sequences provided by the packaging cell line. Replication of the helper molecule itself may or may not be mediated by adenoviral proteins and ITRs. Helper molecules that replicate through the activity of adenoviral proteins (for example, E2-gene products acting together with cellular proteins) contain at least one ITR derived from adenovirus. The E2-gene products can be expressed by an E1-dependent or an E1-independent promoter. Where only one ITR is derived from an adenovirus, the helper molecule also preferably contains a sequence that anneals in an intramolecular fashion to form a hairpin-like structure.

Figure 13:
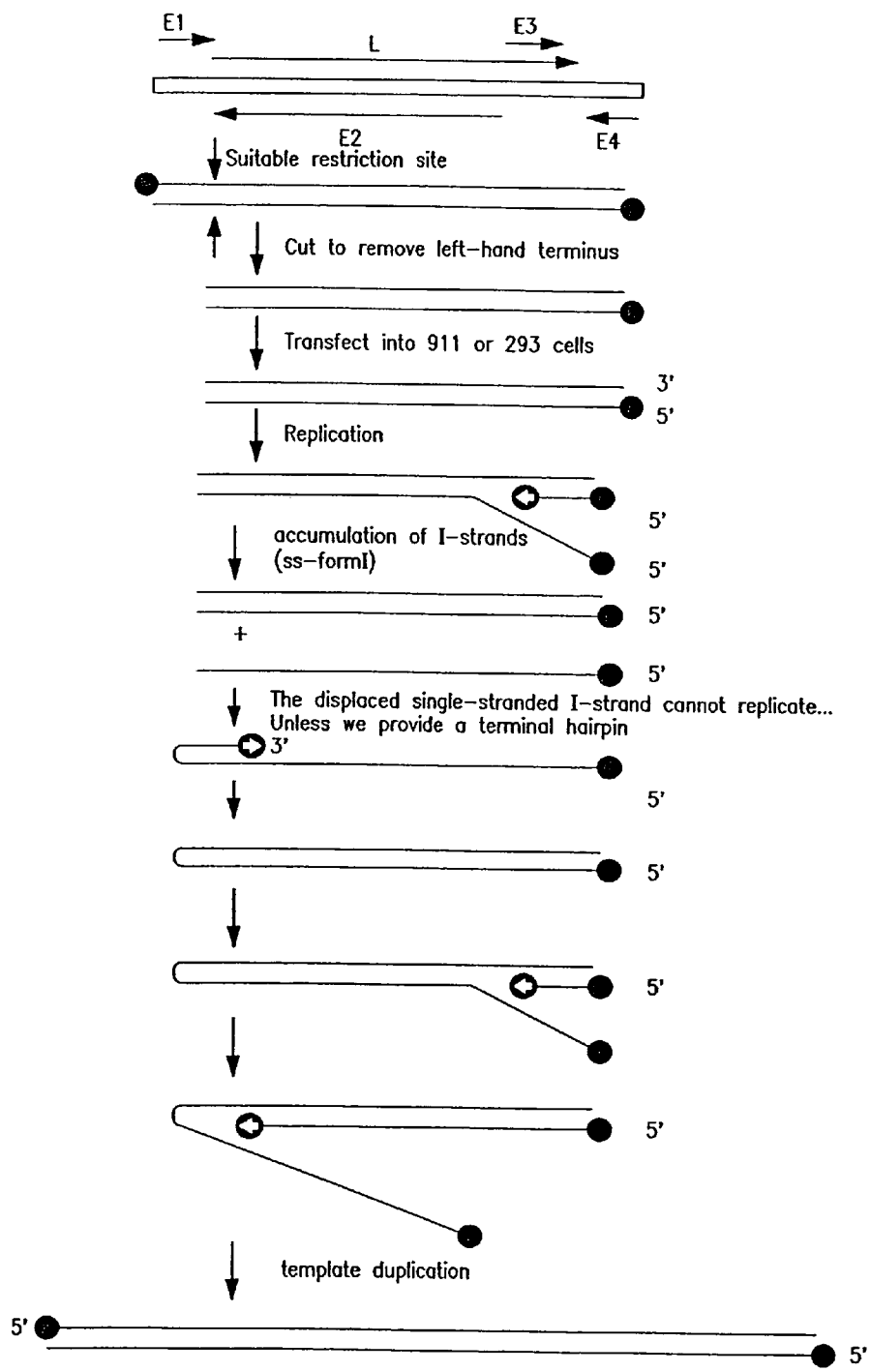
FIG. 13: Rationale for the design of adenoviral-derived recombinant DNA molecules that duplicate and replicate in cells expressing adenoviral replication proteins. A diagram of the adenoviral double-stranded DNA genome indicating the approximate locations of E1, E2, E3, E4, and L regions is shown. The terminal polypeptide (TP) attached to the 5'-terminus is indicated by closed circles. The right arm of the adenoviral genome can be purified by removal of the left arm by restriction enzyme digestion. Following transfection of the right arm into 293 or 911 cells, adenoviral DNA polymerase (white arrow) encoded on the right arm will produce only single-stranded forms. Neither the double-stranded or single-stranded DNA can replicate because they lack an inverted terminal repeat (ITR) at one terminus. Providing the single-stranded DNA with a sequence that can form a hairpin structure at the 3'-terminus, which serves as a substrate for DNA polymerase, will extend the hairpin structure along the entire length of the molecule. This molecule can also serve as a substrate for a DNA polymerase, but the product is a duplicated molecule with ITRs at both termini that can replicate in the presence of adenoviral proteins.
Figure 14:
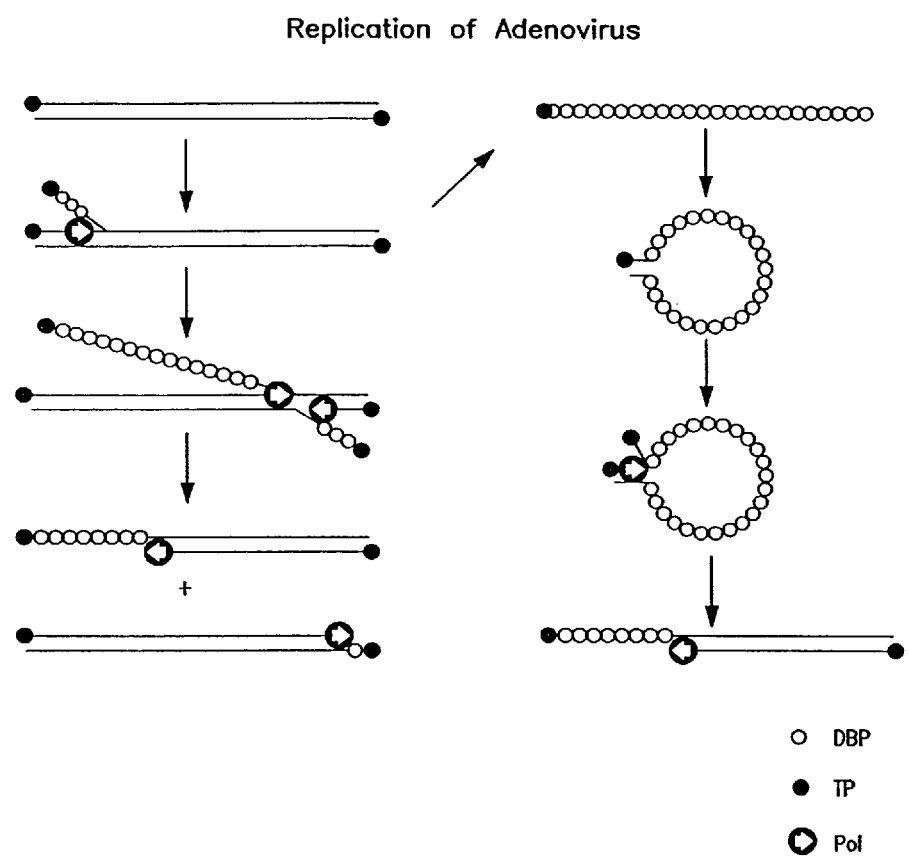
FIG. 14: Adenoviral genome replication. The adenoviral genome is shown in the top left panel. The origins or replication are located within the left and right ITRs at the genome ends. DNA replication occurs in two stages. Replication proceeds from one ITR, generating a daughter duplex and a displaced parental single-strand that is coated with adenoviral DNA binding protein (DBP, open circles) and can form a panhandle structure by annealing of the ITR sequences at both termini. The panhandle is a substrate for DNA polymerase (Pol: white arrows) to produce double-stranded genomic DNA. Alternatively, replication proceeds from both ITRs, generating two daughter molecules, thereby obviating the requirement for a panhandle structure.

Following E2-gene product expression, the adenoviral DNA polymerase recognizes the ITR on the helper molecule and produces a single-stranded copy. Then, the 3'-terminus intramolecularly anneals, forming a hairpin-like structure that serves as a primer for reverse strand synthesis. The product of reverse strand synthesis is a double-strand hairpin with an ITR at one end. This ITR is recognized by adenoviral DNA polymerase that produces a double-stranded molecule with an ITR at both termini (see e.g., FIG. 13) and becomes twice as long as the transfected molecule (in our example it duplicates from 35 Kb to 70 Kb). Duplication of the helper DNA enhances the production of sufficient levels of adenoviral proteins. Preferably, the size of the duplicated molecule exceeds the packaging capacity of the adenoviral virion and is, therefore, not packaged into adenoviral particles. The absence of a functional encapsidation signal in the helper molecule further ensures that the helper molecule is packaging deficient. The produced adenoviral proteins mediate replication and packaging of the cotransfected or co-infected minimal vectors.

When the replication of the helper molecule is independent of adenoviral E2-proteins, the helper construct preferably contains an origin of replication derived from SV40. Transfection of this DNA, together with the minimal adenoviral vector in an E1-containing packaging cell line that also inducibly expresses the SV40 Large T protein or as much SV40 derived proteins as necessary for efficient replication, leads to replication of the helper construct and expression of adenoviral proteins. The adenoviral proteins then initiate replication and packaging of the co-transfected or co-infected minimal adenoviral vectors. Preferably, there are no regions of sequence overlap shared by the replication-deficient packaging constructs, the minimal adenoviral vectors, and the complementing cell lines that may lead to the generation of RCA.

It is to be understood that during propagation of the minimal adenoviral vectors, each amplification step on E1-complementing cells is preceded by transfection of any of the described helper molecules since minimal vectors by themselves can not replicate on E1-complementing cells. Alternatively, a cell line that contains all the adenoviral genes necessary for replication and packaging, which are stably integrated in the genome and can be excised and replicated conditionally, can be used. (Valerio and Einerhand International patent Appl'n PCT/NL9800061).

Transfection of nucleic acid into cells is required for packaging of recombinant vectors into virus particles and can be mediated by a variety of chemicals including liposomes, DEAE-dextran, polybrene, and phosphazenes or phosphazene derivatives (WO97/07226). Liposomes are available from a variety of commercial suppliers and include DOTAP® (Boehringer-Mannheim), Tfx®-50, Transfectam®, ProFection® (Promega, Madison, Wis.), and LipofectAmin®, Lipofectin®, LipofectAce® (GibcoBRL, Gaithersburg, Md.). In solution, the lipids form vesicles that associate with the nucleic acid and facilitate its transfer into cells by fusion of the vesicles with cell membranes or by endocytosis. Other transfection methods include electroporation, calcium phosphate coprecipitation, and microinjection. If transfection conditions for a given cell line have not been established or are unknown, they can be determined empirically (Maniatis et al., Molecular Cloning, pages 16.30–16.55).

The yield of recombinant adenoviral virus vectors can be increased by denaturing the double stranded plasmid DNA before transfection into an E1 complementing cell line. Denaturing can occur by heating double-stranded DNA at, for example, 95–100° C., followed by rapid cooling using various ratios of the adapter and helper plasmids that have overlapping sequences. Also, a PER.C6 derivative that stably or transiently expresses E2A (DNA binding protein) and/or E2B gene (pTP-Pol) could be used to increase the adenoviral production per well by increasing the replication rate per cell. Alternatively, cotransfection of recombinase protein(s), recombinase DNA expression construct(s), i.e. recombinase from *Kluyveromyces waltii* (Ringrose et al., (1997) *Eur. J. Biochem.* 248(3):903–912), or any other gene or genes encoding factors that can increase homologous recombination efficiency can be used. The inclusion of 0.1–100 mM sodium butyrate during transfection and/or replication of the packaging cells can increase viral production. These improvements will result in improved viral yields per microtiter well. Therefore, the number and type of assays that can be done with one library will increase and may overcome variability between the various genes or sample nucleic acids in a library.

The cell lines used for the production of adenoviral vectors that express E1 region products includes, for example, 293 cells, PER.C6 (ECACC 96022940), or 911 cells. Each of these cell lines has been transfected with nucleic acids that encode for the adenoviral E1 region. These cells stably express E1 region gene products and have been shown to package E1-deleted recombinant adenoviral vectors. Yields of recombinant adenovirus obtained on PER.C6 cells are higher than obtained on 293 cells.

Each of these cell lines provides the basis for introduction of E2B, E2A, or E4 constructs (e.g., ts125E2A and/or hrE2A) that permit the propagation of adenoviral vectors that have mutations, deletions, or insertions in the corresponding genes. These cells can be modified to express additional adenoviral gene products by the introduction of recombinant nucleic acids that stably express the appropriate adenoviral genes or recombinant nucleic acids and that transiently express the appropriate gene(s), for example, the packaging deficient replicating helper molecules or the helper plasmids.

All (or nearly all) trans complementing cells grown in microtiter plate wells (96, 384, or more than 1,536 wells) produce recombinant adenovirus following transfection with either the adapter plasmid or the minimal adenoviral plasmid library and the appropriate helper molecule(s). A large number of adenoviral gene transfer vectors or a library, each expressing a unique gene, can thus be conveniently produced on a scale that allows analysis of the biological activity of the particular gene products both in vitro and in vivo. Due to the wide tissue tropism of adenoviral vectors, a large number of cell and tissue types are transducable with an adenoviral library.

Libraries of genes or sample nucleic acids preferably are converted to RCA free adenoviral libraries using the above methods. The adenoviral libraries with unknown function are then used to perform high throughput screening involving a number of in vitro assays, such as immunological assays including ELISAs, proliferation assays, drug resistance assays, enzyme activity assays, organ cultures, differentiation assays, and cytotoxicity assays. Adenoviral libraries can be tested on tissues, tissue sections, or tissue derived primary short-lived cell cultures including primary endothelial and smooth muscle cell cultures (Wijnberg et al., (1997) *Thromb Haemost* 78(2), 880–6), coronary artery bypass graft libraries (Vassalli et al., (1997) *Cardiovasc Res.* 35(3), 459–69; Fuster and Chesebro, (1985) *Adv. Prostaglandin Thromboxane Leukot Res.* 13, 285–99), umbilical cord tissue including HUVEC (Gimbrone, (1976) *Prog. Hemost. Thromb.* 3, 1– 28; Striker et al., (1980) *Methods Cell. Biol.* 21A, 135–51), couplet hepatocytes (Graf et al., (1984) *Proc. Natl. Acad. Sci. USA* 81(20), 6516–20), and epidermal cultures (Fabre, (1991) *Immunol. Lett.* 29(1–2), 161–5; Phillips, (1991) *Transplantation* 51(5), 937–41). Plant cell cultures, including suspension cultures, can also be used as host cells for the adenoviral libraries carrying any DNA sequence, including human derived DNA sequences and plant derived sequences. (de Vries et al., (1994) *Biochem. Soc. Symp.* 60, 43–50; Fukada et al., (1994) *Int. J. Devel. Biol.* 38(2), 287–99; Jones, (1983) *Biochem. Soc. Symp.* 48, 221–32; Kieran et al., (1997) *J. Biotechnol.* 59(1–2), 39–52; Stanley, (1993) *Curr. Opin. Genet. Dev.* 3(1), 91–6; Taticek et al., (1994) *Curr. Opin. Biotechnol.* 5(2), 165–74.

Depending on the size of the initial unselected library, once an adenoviral library of genes has been reduced to a reasonable number of candidates by in vitro assays, the adenoviruses can be tested in appropriate animal models. Examples of animal models that can be used include models for Alzheimer's disease, arteriosclerosis, cancer metastasis, and Parkinson's disease. In addition, transgenic animals which have altered expression of endogenous or exogenous genes including mice with gene(s) that have been inactivated, animals with cancers implanted at specific sites, human bone marrow chimeric mice such as NOD-SCID mice, and the like can be used. As additional testing is required, the stocks of candidate adenoviruses can be increased by passaging the adenoviruses under the appropriate transcomplementing conditions.

Depending on the animal model used, adenoviral vectors or mixtures of pre-selected pools of adenoviral vectors can be applied or administered at appropriate sites such as lung in non-human primates (Sene et al., (1995) *Hum. Gene Ther.* 6(12):1587–93) and brain of normal and apoE deficient mice (Robertson et al., (1998) *Neuroscience* 25 82(1):171–80.) for Alzheimer's disease (Walker et al., (1997) *Brain Res. Brain Res. Rev.* 25(1):70–84) and Parkinson disease models (Hockman et al., (1971) *Brain Res.* 35(2):613–8.; Zigmond and Stricker, (1984) *Life Sci.* 35(1):5–18.). The adenoviral vectors or mixtures of pre-selected pools of adenoviral vectors can also be injected in the blood stream for liver disease models including liver failure and Wilson disease (Cuthbert, (1995) *J. Investig. Med.* 43(4):323–36; Karrer et al., (1984) *Curr. Surg.* 41(6):464–7) and tumor models including metastases models (Esandi et al., (1997) *Gene Ther.* 4(4):280–7; Vincent et al., (1996) *J. Neurosug.* 85(4): 648–54; Vincent et al., (1996) *Hum. Gene Ther.* 7(2): 197–205). In addition, selected adenoviral vectors can be injected directly into the bone marrow of human chimeric NOD-SCID mice (Dick et al., (1997) *Stem Cells* 15 Suppl. 1: 199–203; Mosier et al., (1988) *Nature* 335(6187):256–9). Finally, selected adenovirus can be applied locally, for example, in vascular tissue of restenosis animal models (Karas et al., (1992) *J. Am. Coll. Cardiol.* 20(2):467–74).

In addition, in vitro assays can be complemented by using an electronic version of the sequence database on which the adenoviral library is built. This allows, for example, protein motif searching whereby new members of a family can be linked to known members of the same family with known functions. The use of Hidden Markow Models (HMMs) (Eddy (1996) *Proc. Natl. Acad. Sci. USA* 94(4):1414–1419) allows the establishment of novel families by identifying essential features of a family and building a model of what the members should look like. This can be combined with structural data by using the threading approach which uses a known structure as the thread and tries to find a putative structure without having determined the actual structure of the novel protein (Rastan and Beeley (1997) *Curr. Opin. Genet. Dev.* 7 (6):777–83). The functional data, which is obtained using adenoviral libraries made in accordance with the methods disclosed in this application, is the foundation of the endeavor to find novel genes with expected or desired functions and will be the core of functional genomics. Finally, once the number of adenoviral vectors has reached a level at which animal experiments can be performed, another addition to the method is to produce the selection of candidate adenoviral vectors carrying the candidate genes. Then, the clones can be purified by, for example, using adenovirus tagged in the Hi loop of the knob domain of the fiber. Alternatively, large scale HPLC analysis can be used in a semipreparative fashion to yield partially purified adenoviral samples for in vivo or in vitro experiments when more purified adenoviral preparations are desired. Therefore, the described method and reagents allow rapid transfer of a collection of genes in in vivo studies of a limited number of animals, which otherwise would be unfeasible. The automation of the steps of the procedure using robotics will further enhance the number of genes and sample nucleic acids that can be functionated.

In one aspect, the invention provides a method of producing a recombinant adenoviral vector library. The method includes growing a cell culture containing a plurality of cells including adenoviral E1-complementing sequences with i) an adapter plasmid library including an adapter plasmid based on or derived from an adenovirus having no E1 region sequences which overlap with E1 region sequences in the plurality of cells or a recombinant nucleic acid to be inserted into the packaging cell and would lead to generation of RCA in the plurality of cells, and no E2B region sequences other than essential E2B sequences, no E2A region sequences, no E3 region sequences and no E4 region sequences and having in operable configuration a functional ITR, a functional encapsidation signal, and sufficient adenoviral sequences which allow for homologous recombination with the recombinant nucleic acid, and a library of sample nucleic acids inserted into the adapter plasmid operatively linked to a promoter; and ii) a recombinant nucleic acid based on or derived from an adenovirus, wherein the recombinant nucleic acid includes in operable configuration a functional ITR and sufficient adenoviral sequences for replication, wherein the recombinant nucleic acid partially overlaps with the adapter plasmid library which allow for homologous recombination leading to replication-defective, recombinant adenovirus; under conditions whereby a recombinant adenoviral vector library is produced. Preferably, at least one of the adapter plasmid library and the recombinant nucleic acid are heat denatured prior to transfecting the plurality of cells or ancestors of the plurality of cells.

Preferably, the adenoviral E1-complementing sequences, the adapter plasmid library and the recombinant nucleic acid have no overlapping sequences which allow for homologous recombination leading to replication competent virus in a cell into which they are transferred.

In another aspect, the invention provides a method of producing a recombinant adenoviral vector library. The method includes growing a cell culture containing a plurality of cells including adenoviral E1 complementing sequences with i) a recombinant nucleic acid library including a first recombinant nucleic acid based on or derived from an adenovirus, including in operable configuration two functional ITRs, one functional encapsidation signal, and having no functional adenoviral genes and a library of sample nucleic acids inserted into the first recombinant nucleic acid operatively linked to a promoter; and ii) a second recombinant nucleic acid based on or derived from an adenovirus including in operable configuration two functional ITRs, and sufficient adenoviral sequences for replication, wherein the second recombinant nucleic acid includes a deletion of at least the E1 region and encapsidation signal of the adenovirus; under conditions whereby a recombinant adenoviral vector library is produced. Preferably, the cell culture is in a multiwell format.

Furthermore, the adenoviral E1-complementing sequences, the first recombinant nucleic acid and the second recombinant nucleic acid preferably have no overlapping sequences which allow for homologous recombination leading to replication competent virus in a cell into which they are transferred. Preferably, the cell culture is a PER.C6 cell culture.

In one example, growth medium of the cell culture contains sodium butyrate in an amount sufficient to enhance production of the recombinant adenoviral vector library.

Preferably, the plurality of cells further includes at least one of an adenoviral preterminal protein and a polymerase complementing sequence. Preferably, the plurality of cells further includes an adenoviral E2 complementing sequence. Preferably, the E2 complementing sequence is an E2A complementing sequence or an E2B complementing sequence. In one aspect, the plurality of cells further includes a recombinase protein, whereby the homologous recombination leading to replication-defective, recombinant adenovirus is enhanced. Preferably, the recombinase protein is a *Kluyveromyces waltii* recombinase.

In another aspect, the plurality of cells further includes a nucleotide sequence coding for a recombinase protein. Preferably, the recombinase protein is *Kluyveromyces waltii* recombinase.

In one aspect, the members of the recombinant adenoviral vector library are identical.

In one aspect, the promoter is an inducible promoter. Preferably, the promoter is repressed or down modulated by an adenoviral E1 gene product. In one aspect, the promoter includes an AP1 dependent promoter. Preferably, the AP1 dependent promoter is derived from a collagenase, a c-myc, a monocyte chemoattractant protein or a stromelysin gene.

In one aspect, the sample nucleic acids encode a product of unknown function. In another aspect, the sample nucleic acids are selected from the group consisting of synthetic oligonucleotides, DNAs, cDNAs, genes, ESTs, antisense nucleic acids, or genetic suppressor elements.

In another aspect, the invention provides a method for assigning a function to products encoded by sample nucleic acids. The method includes growing a host cell containing a recombinant adenoviral vector library produced according to the method of the invention, whereby products encoded by the sample nucleic acids are expressed to produce at least one altered phenotype in the host cell; and identifying the at least one altered phenotype, whereby a function is assigned to the products encoded by the sample nucleic acids. Preferably, the host cell is a plant cell or an animal cell. Preferably, the animal cell is a human cell. In one aspect, the host cell is a member of a cell culture. Preferably, the cell culture is in a multiwell format. Preferably, a method of the invention is automated.

The invention further provides a non-human host cell containing a recombinant replication-defective adenoviral vector library. The invention further provides a non-human host cell containing a recombinant replication-defective adenoviral vector library, wherein the replication-defective adenoviral vector library is produced by the method according to a method of the invetion.

The invention further provides an isolated host cell containing a replication-defective adenoviral vector library, such as one wherein the replication-defective adenoviral vector library is produced by the method according to the invention. Preferably, the host cell is a human cell.

The invention further provides a method of producing a recombinant adenoviral vector library. This method includes growing a cell culture containing a plurality of cells expressing adenoviral E1-region sequences and expressing one or more functional gene products encoded by at least one adenoviral region selected from an E2A region and an E4 region with i) an adapter plasmid library including an adapter plasmid based on or derived from an adenovirus having no E1 region sequences which overlap with E1 region sequences in the plurality of cells or a recombinant nucleic acid to be inserted into the packaging cell, and no E2B region sequences other than essential E2B sequences, no E2A region sequences, no E3 region sequences and no E4 region sequences and having in operable configuration a functional ITR, a functional encapsidation signal, and sufficient adenoviral sequences which allow for homologous recombination with the recombinant nucleic acid, and a library of sample nucleic acids inserted into the adapter plasmid operatively linked to a promoter; and ii) a recombinant nucleic acid based on or derived from an adenovirus having no E1 region sequences which overlap with E1 sequences in the plurality of cells, and having no E2A region sequences or E4 region sequences expressed in the plurality of cells which would lead to production of RCA and having in operable configuration a functional adenoviral ITR and sufficient adenoviral sequences for replication in the plurality of cells, wherein the recombinant nucleic acid has sufficient overlap with the adapter plasmid to provide for homologous recombination leading to production of recombinant adenovirus in the packaging cell.; under conditions whereby a recombinant adenoviral vector library is produced in the plurality of cells.

Preferably, the recombinant nucleic acid further has no E3 region sequences. Preferably, the plurality of cells expresses at least one functional E2A gene product. Preferably, the at least one functional E2A gene product is a mutated gene product. Preferably, the mutated gene product is temperature sensitive.

Preferably, at least one of the adapter plasmid library and the recombinant nucleic acid are heat denatured prior to transfecting the plurality of cells or ancestors of the plurality of cells.

Preferably, the plurality of cells expresses one or more functional gene product encoded by E2B region sequences and wherein E2B region sequences for the functional E2B region gene products, other than those required for virus generation, are deleted from the recombinant nucleic acid, and optionally up to all E2B gene region sequences are deleted from the adapter plasmid.

Preferably, the plurality of cells expresses all gene products encoded by E2B region sequences, and wherein E2B region sequences for the functional E2B region gene products, other than those required for virus generation, are deleted from the recombinant nucleic acid, and optionally up to all E2B gene region sequences are deleted from the adapter plasmid. Preferably, the cell culture is a PER.C6 cell culture. Preferably, the promoter is an inducible promoter.

In one aspect, the invention provides a plurality of cells containing a recombinant replication-defective adenoviral vector library, wherein the recombinant replication-defective adenoviral vector library is produced according to a method of the invention. Preferably, the plurality of cells are PER.C6 cells.

The invention further provides a recombinant nucleic acid including: a nucleic acid based on or derived from an adenovirus having no E1 region sequences, which would lead to production of RCA in a packaging cell, into which it is introduced and having in operable configuration a functional adenoviral ITR and sufficient adenoviral sequences for replication in the packaging cell, wherein the nucleic acid has sufficient overlap with an adapter plasmid to provide for homologous recombination leading to production of recombinant adenovirus in the packaging cell. Preferably, the recombinant nucleic acid has at least one of no E2A region sequences or no E4 region sequences that are expressed in the packaging cell and would lead to production of recombinant adenovirus in the packaging cell. Preferably, the recombinant nucleic acid has no E2B region sequences, other than essential E2B region sequences for virus generation, which are expressed in the packaging cell. Preferably, the recombinant nucleic acid has no E3 region sequences. Preferably, the sufficient overlap is about 10 bp to about 5000 bp. Preferably, the sufficient overlap is about 2000 bp to about 3000 bp. Preferably, the sufficient overlap includes E2B region sequences essential for virus generation.

The invention further provides an adapter plasmid including a nucleic acid based on or derived from an adenovirus having no E1 region sequences which overlap with E1 region sequences in a packaging cell into which it is introduced and would lead to production of RCA and no E2B region sequences other than essential E2B sequences, no E2A region sequences, no E3 region sequences and no E4 region sequences which overlap with other nucleic acid to be inserted into the packaging cell or contained in the packaging cell, and having in operable configuration a functional ITR, a functional encapsidation signal, and sufficient adenoviral sequences which allow for homologous recombination with the other nucleic acid leading to replication-defective, recombinant adenovirus, and a cloning site or a multiple cloning site.

Preferably, the cloning site or the multiple cloning site is operably linked to a promoter.

Preferably, the promoter is an inducible promoter. Preferably, the promoter is repressed or down modulated by an adenoviral E1 gene product. Preferably, the promoter includes an AP1 dependent promoter. Preferably, the AP1 dependent promoter is derived from a collagenase gene, a c-myc gene, a monocyte chemoattractant protein gene or a stromelysin gene.

Preferably, a library of sample nucleic acids is inserted into the multiple cloning site. Preferably, a method of the invention is automated.

The invention is further explained through use of the following illustrative Examples.

EXAMPLES

Example 1

Generation of Cell Lines Able to Transcomplement E1 Defective Recombinant Adenoviral Vectors 911 Cell Line A cell line that harbors E1 sequences of adenovirus type 5, able to transcomplement E1 deleted recombinant adenovirus, has been generated (Fallaux et al, (1996) *Hum. Gene Ther.* 7: 215–222). This cell line was obtained by transfection of human diploid human embryonic retinoblasts (HER) with pAd5XhoIC that contains nt. 80–5788 of Ad5. One of the resulting transformants was designated 911. This cell line has been shown to be useful in the propagation of E1 defective recombinant adenovirus and has been found to be superior to 293 cells. Unlike 293 cells, 911 cells lack a fully transformed phenotype which most likely results in better performance as an adenoviral packaging line. In 911 cells the plaque assays can be performed faster (4–5 days instead of 8–14 days on 293), monolayers of 911 cells survive better under agar overlay as required for plaque assays, and there is higher amplification of E1-deleted vectors.

In addition, unlike 293 cells that were transfected with sheared adenoviral DNA, 911 cells were transfected using a defined construct. Transfection efficiencies of 911 cells are comparable to those of 293.

New Packaging Constructs

Source of Adenoviral Sequences

Adenoviral sequences are derived either from pAd5.SalB, containing nt. 80–9460 of human adenoviral type 5, (Bernards et al., (1983) *Virology* 127:45–53) or from wild-type Ad5 DNA. pAd5.SalB was digested with SalI and XhoI, the large fragment was religated, and this new clone was named pAd5.X/S. The pTN construct (constructed by Dr. R. Vogels, IntroGene, NL) was used as a source for the human PGK promoter and the NEO gene.

Human PGK Promoter and NEO$^R$ Gene

Transcription of E1A sequences in the new packaging constructs is driven by the human PGK promoter (Michelson et al, (1983) *Proc. Natl. Acad. Sci. USA* 80:472–476); Singer-Sam et al, (1984) *Gene* 32: 409–417) derived from plasmid pTN (gift of R. Vogels), which uses pUC119 (Vieira et al, (1987) pp. 3–11: *Methods in Enzymology*, Acad. Press Inc.) as a backbone. This plasmid was also used as a source for the NEO gene fused to the Hepatitis B Virus (HBV) poly-adenylation signal.

Fusion of PGK Promoter to E1 Genes (FIG. 1)

In order to replace the E1 sequences of Ad5 (ITR, origin of replication, and packaging signal) with heterologous sequences, E1 sequences (nt.459 to nt.960) of Ad5 were amplified by PCR using primers Ea1 (SEQ ID NO:27) and Ea2 (SEQ ID NO:28) (see Table I). The resulting PCR product was digested with ClaI, ligated into Bluescript (Stratagene), and predigested with ClaI and EcoRV, resulting in construct pBS.PCRI.

Vector pTN was digested with restriction enzymes EcoRI (partially) and ScaI. The DNA fragment containing the PGK promoter sequences was ligated into PBS.PCRI digested with ScaI and EcoRI. The resulting construct, PBS.PGK. PCRI, contains the human PGK promoter operatively linked to Ad5 E1 sequences from nt.459 to nt.916.

Figure 2:
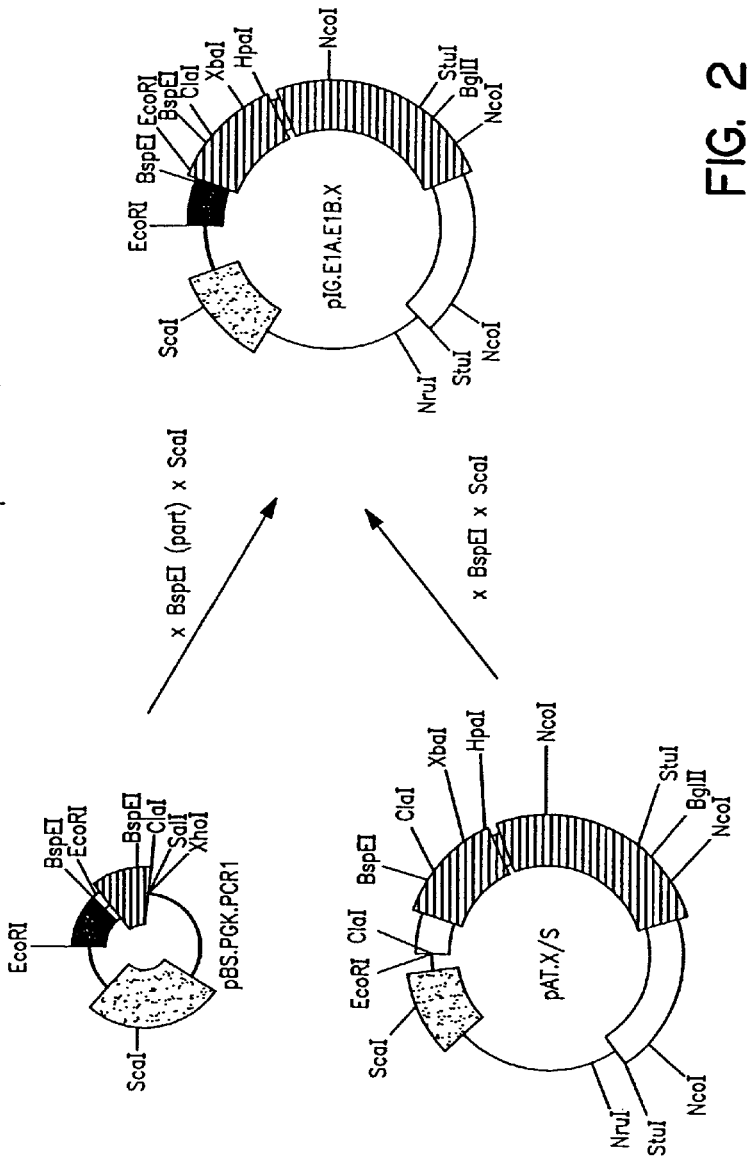
FIG. 2. Close pAT.X/S and pIG.E1a.E1b.X plasmid sequences with a black line. Plasmids pAT.X/S and pIG.E1a.E1b.X are shown in FIGS. 3A and 4 and FIG. 3B respectively.

Construction of pIG.E1A.E1B (FIG. 2)

pIG.E1A.E1B.X contains the E1A and E1B coding sequences under the direction of the PGK promoter. Since Ad5 sequences from nt.459 to nt.5788 are present in this construct, pIX protein of the adenovirus is also encoded by this plasmid. pIG.E1A.E1B.X was made by replacing the ScaI-BspEI fragment of pAT-X/S with the corresponding fragment from PBS.PGK.PCRI (containing the PGK promoter linked to E1A sequences).

Figure 3A:
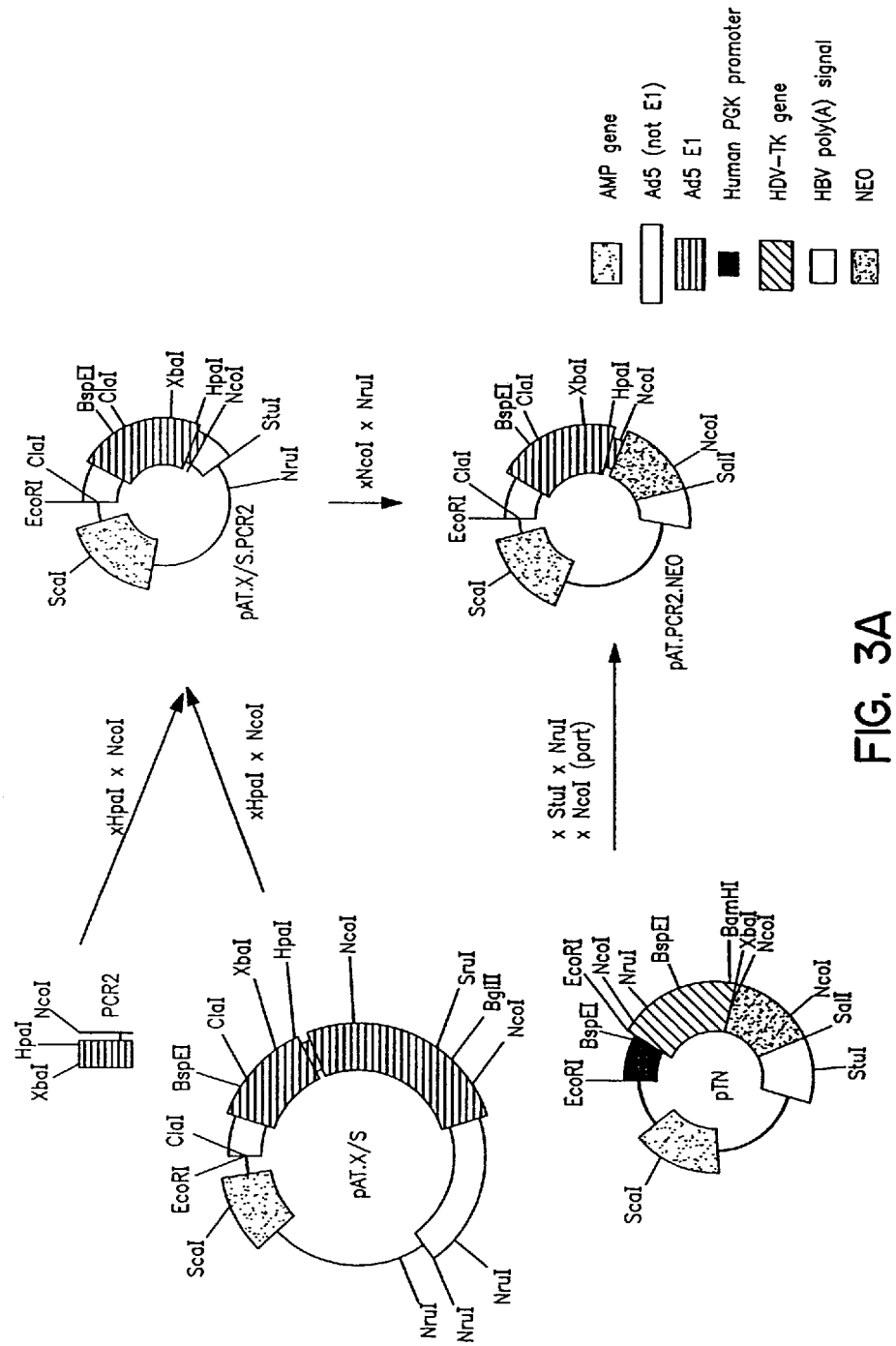
FIG. 3A. Make "HBV poly (A) signal" region in pTN and pAT.PCR2.NEO plasmid sequences more visible by changing border colors to black. Support for this revision is found in the specification on page 40, lines 8 to 9, which describes the pTN plasmid sequence. Change border to black for figure legend as well. See revised figure. Also, the plasmid "pAT PCR2" should include "X/S." inserted into its name to become "pAT.X/S.PCR2". Support for this revision is found Page 40, lines 1 to 16 of the specification, specifically on lines 7 to 8.
Figure 3B:
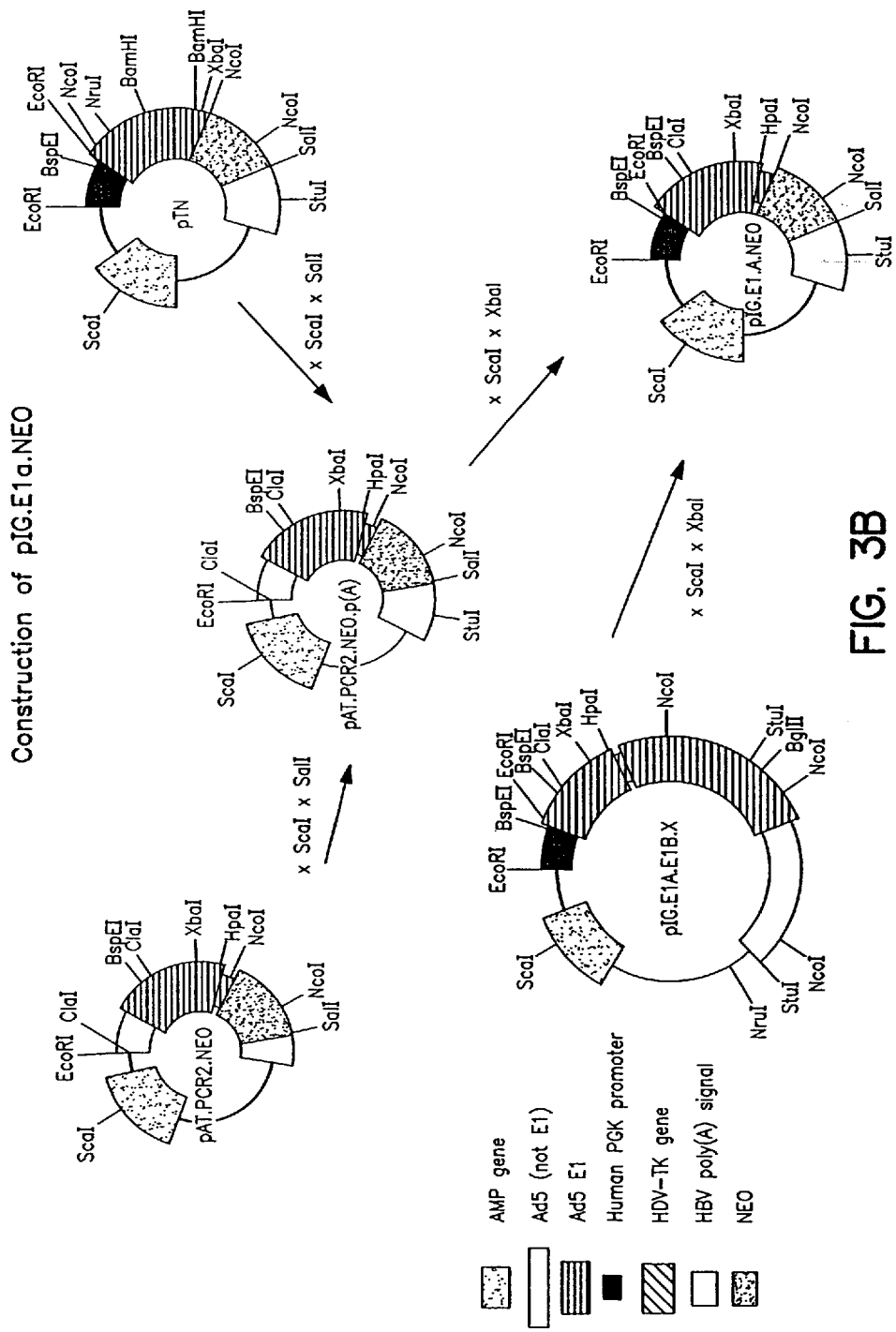
FIG. 3B. Make "HBV poly (A) signal" region in pTN, pAT.PCR2.NEO, pAT. PCR2.NEO.p(A), and pIG.E1A.NEO plasmid sequences more visible by changing border colors to black. Support for this revision is found in the specification on page 40, lines 8 to 9, which describes the pTN plasmid sequence. Change border to black for figure legend as well.

Construction of pIG.E1A.NEO (FIG. 3)

In order to introduce the complete E1B promoter and to fuse this promoter such that the AUG codon of E1B 21 kDa functions exactly as the AUG codon of NEO$^R$, the E1B promoter was amplified using primers Ea3 (SEQ ID NO:29) and Ep2 (SEQ ID NO:30), where primer Ep2 introduces a NcoI site into the PCR fragment. The resulting PCR fragment, named PCRII, was digested with HpaI and NcoI and ligated into pAT-X/S, which was predigested with HpaI and NcoI. The resulting plasmid was designated pAT-X/S-PCR2. The NcoI-StuI fragment of pTN, containing the NEO gene and part of the Hepatitis B Virus (HBV) poly-adenylation signal, was cloned into pAT-X/S-PCR2, which had been digested with NcoI and NruI. The resulting construct was designated pAT-PCR2-NEO. The poly-adenylation signal was completed by replacing the ScaI-SalI fragment of pAT-PCR2.NEO with the corresponding fragment of pTN, resulting in pAT.PCR2.NEO.p (A). The ScaI-XbaI of pAT.PCR2.NEO.p (A) was replaced with the corresponding fragment of pIG.E1A.E1B-X, containing the PGK promoter linked to E1A genes. The resulting construct, named pIG.E1A.NEO, contains Ad5 E1 sequences (nt.459 to nt.1713) under the control of the human PGK promoter.

Figure 4:
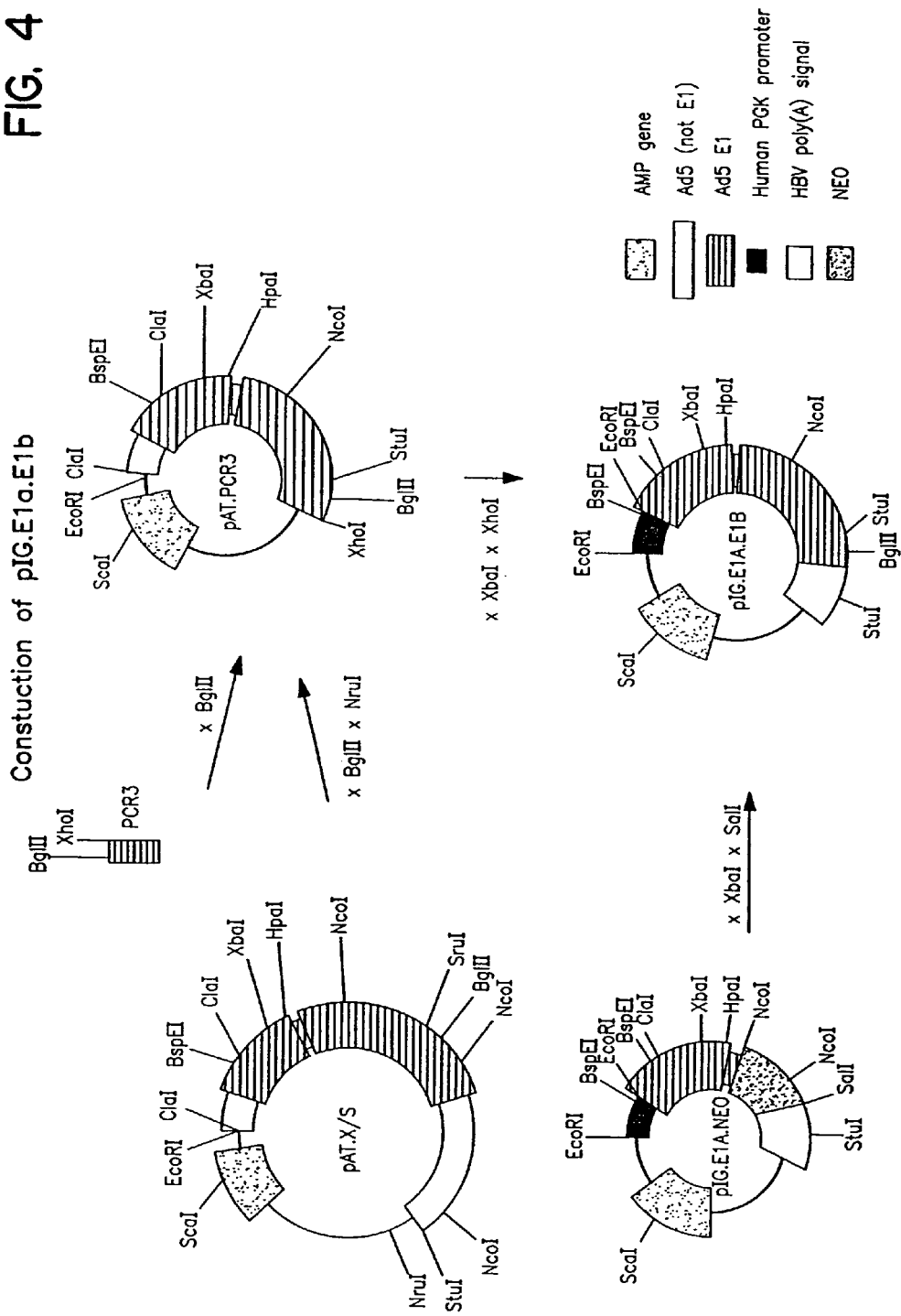
FIG. 4. Make "HBV poly (A) signal" region in pIG.E1A.NEO and pIG.E1A.E1B plasmid sequences more visible by changing border colors to black. Support for this revision is found in the specification on page 40, lines 8 to 9, which describes the pTN plasmid sequence. Change border to black for figure legend as well.

Construction of pIG.E1A.E1B (FIG. 4)

pIG.E1A.E1B contains nt.459 to nt.3510 of Ad5 that encode the E1A and E1B proteins. The E1B sequences are terminated at the splice acceptor at nt.3511. No pIX sequences are present in this construct.

pIG.E1A.E1B was made as follows: The sequences encoding the N-terminal amino acids of E1B 55 kDa were amplified using primers Eb1 (SEQ ID NO:31) and Eb2 (SEQ ID NO:32), which introduces a XhoI site. The resulting PCR fragment was digested with BglII and cloned into BlII/NruI of pAT-X/S, thereby obtaining pAT-PCR3. The HBV poly (A) sequences of pIG.E1A.NEO were introduced downstream of the E1B sequences of pAT-PCR3 by exchange of the Xba-SalI fragment of pIG.E1A.NEO and the XbaI XhoI fragment of pAT.PCR3.

Figure 5:
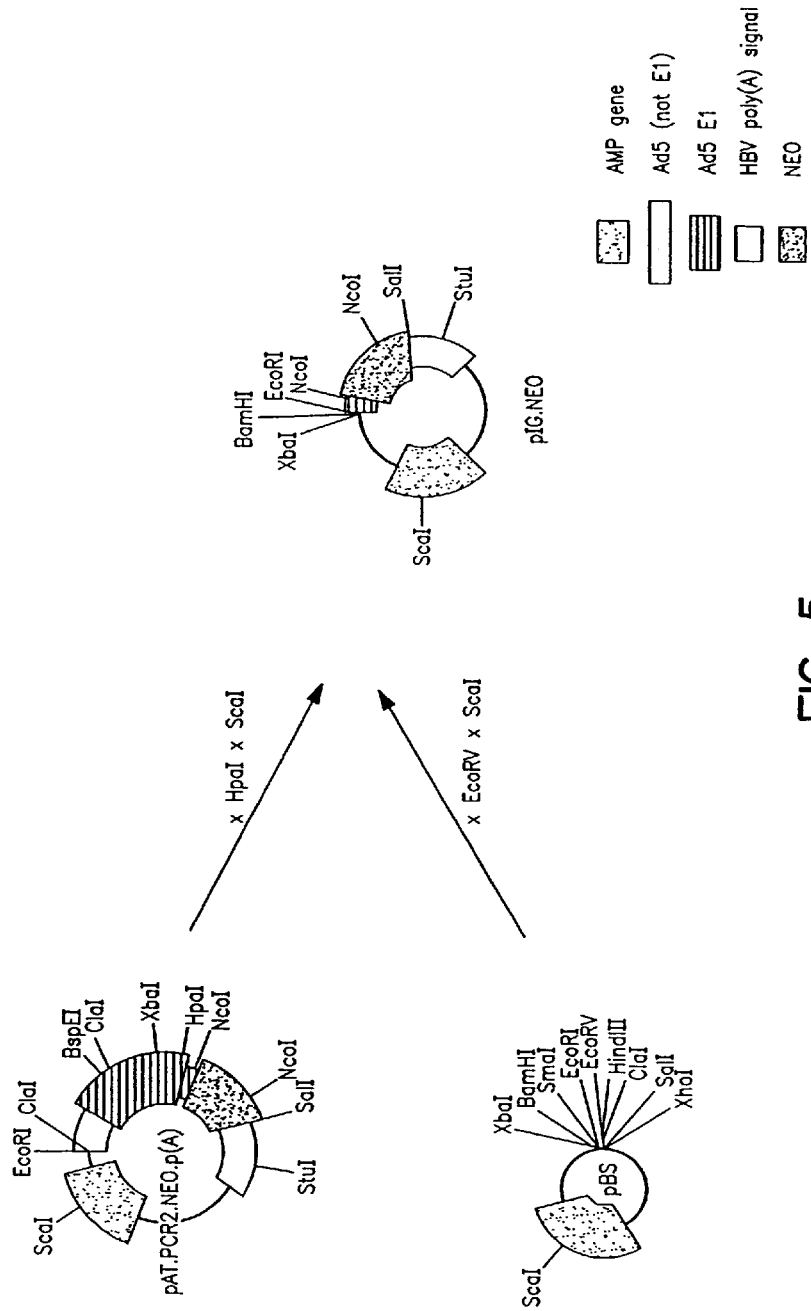
FIG. 5. Make "HBV poly (A) signal" region in pAT.PCR2.NEO.p(A) plasmid sequence more visible by changing border color to black. Support for this revision is found in the specification on page 40, lines 8 to 9, which describes the pTN plasmid sequence. Change border to black for figure legend as well.

Construction of pIG.NEO (FIG. 5)

This construct is of use when established cells are transfected with E1A.E1B constructs and NEO selection is required. Because NEO expression is directed by the E1B promoter, NEO resistant cells are expected to co-express E1A, which also is advantageous for maintaining high levels of expression of E1A during long-term culture of the cells. pIG.NEO was generated by cloning the HpaI-ScaI fragment of pAT.PCR2.NEO.p(A) or pIG.E1A.NEO, containing the NEO gene under the control of the Ad5 E1B promoter, into pBS digested with EcoRV and ScaI.

Testing of Constructs

The integrity of the constructs pIG.E1A.NEO, pIG.E1A.E1B.X, and pIG.E1A.E1B was assessed by restriction enzyme mapping. Furthermore, parts of the constructs that were obtained by PCR analysis were confirmed by sequence analysis. No changes in the nucleotide sequence were found.

The constructs were transfected into primary BRK (Baby Rat Kidney) cells. pIG.E1A.NEO was tested for its ability to immortalize these cells. pAd5.XhoIC, pIG.E1A.E1B.X, and pIG.E1A.E1B were tested for their ability to fully transform these cells. Kidneys of 6-day old WAG-Rij rats were isolated, homogenized, and trypsinized. Subconfluent dishes (diameter 5 cm) of the BRK cell cultures were transfected with 1 or 5 µg of pIG.NEO, pIG.E1A.NEO, pIG.E1A.E1B, pIG/E1A.E1B.X, pAd5XhiIC, or pIG.E1A.NEO together with PDC26 (Elsen et al, (1983) *Virology* 128:377–390) carrying the Ad5.E1B gene under control of the SV40 early promoter. Three weeks post-transfection, when foci were visible, the dishes were fixed, Giemsa stained, and the foci counted.

Figure 6:
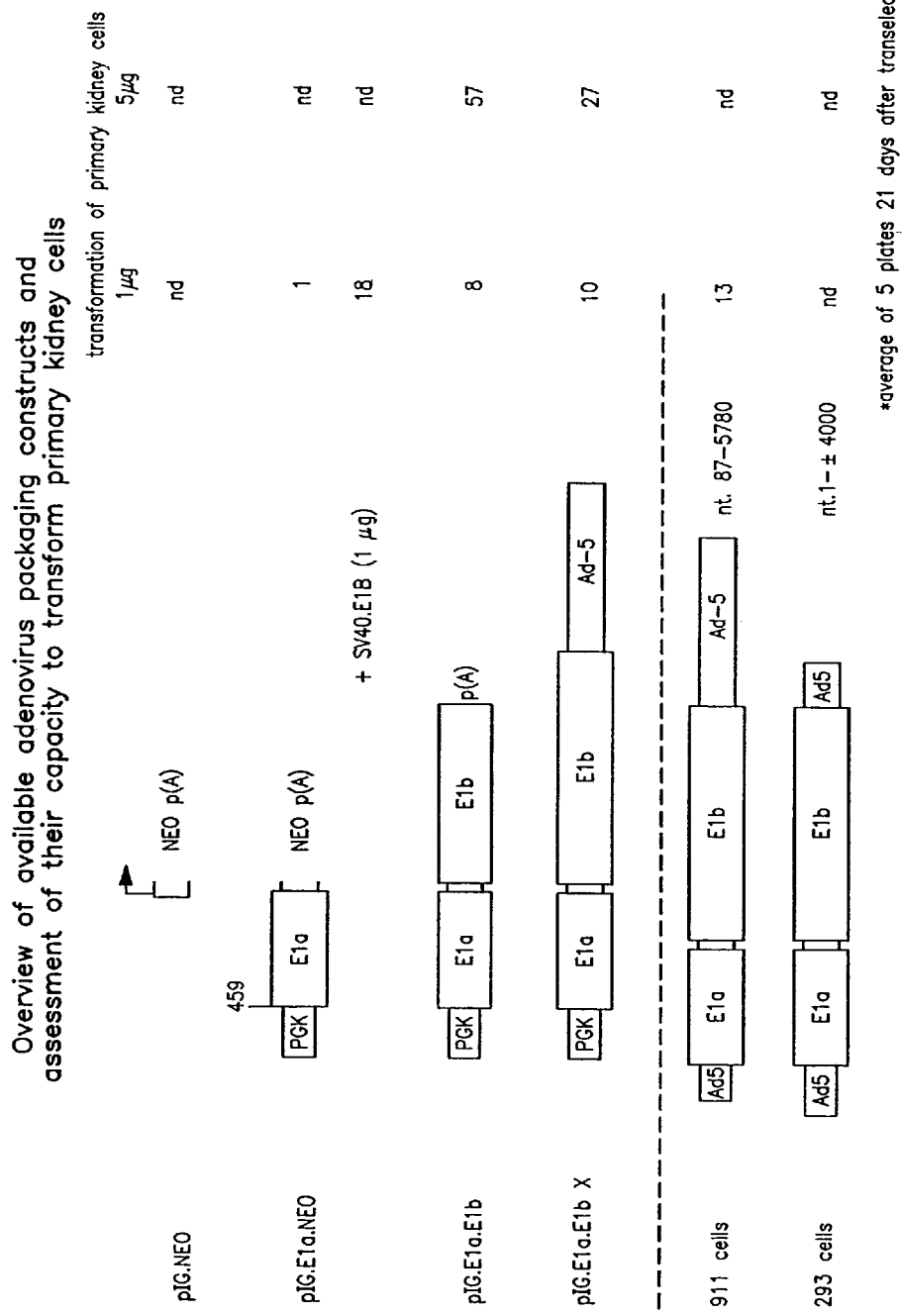
FIG. 6: Transformation of primary baby rat kidney (BRK) cells by adenoviral packaging constructs. Subconfluent dishes of BRK cells were transfected with 1 or 5 μg of either pIG.NEO, pIG.E1A.NEO, pIG.E1A.E1B, pIG.E1A.E1B.X, pAd5XhoIC, or pIG.E1A.NEO plus pDC26, which expresses the Ad5 E1B gene under control of the SV40 early promoter. Three weeks post-transfection, foci were visible, cells were fixed, Giemsa stained and the foci counted. The results shown are the average number of foci per 5 replicate dishes.

An overview of the generated adenoviral packaging constructs, and their ability to transform BRK, is presented in FIG. 6. The results indicate that the constructs pIG.E1A.E1B and pIG.E1A.E1B.X are able to transform BRK cells in a dose-dependent manner. The efficiency of transformation is similar for both constructs and is comparable to what was found with the construct, pAd5.XhoIC, that was used to make 911 cells.

As expected, pIG.E1A.NEO was hardly able to immortalize BRK. However, co-transfection of an E1B expression construct (PDC26) resulted in a significant increase of the number of transformants (18 versus 1), indicating that the E1A encoded by pIG.E1A.NEO is functional. Therefore, it was concluded that the newly generated packaging constructs are suitable for the generation of new adenoviral packaging lines.

Generation of Cell Lines with New Packaging Constructs

Cell Lines and Cell Culture

Human A549 bronchial carcinoma cells (Shapiro et al, (1978) *Biochem. Biophys. Acta* 530:197–207), human embryonic retinoblasts (HER), Ad5-E1-transformed human embryonic kidney (HEK) 293 cells (Graham et al, (1977) *J. Gen. Virol.* 36: 59–72), Ad5-transformed HER 911 cells (Fallaux et al, (1996). *Hum. Gene Ther.* 7: 215–222), and PER cells were grown in Dulbecco's Modified Eagle Medium (DMEM) supplemented with 10% Fetal Calf Serum (FCS) and antibiotics in a 5% $CO_2$ atmosphere at 37° C. Cell culture media, reagents, and sera were purchased from Gibco Laboratories (Grand Island, N.Y.). Culture plastics were purchased from Greiner (N,rtingen, Germany) and Corning (Corning, N.Y.).

Viruses and Virus Techniques

The construction of recombinant adenoviral vectors IG.Ad.MLP.nls.lacZ, IG.Ad.MLP.luc, IG.Ad.MLP.TK, and IG.Ad.CMV.TK is described in detail in patent application EP 95202213. The recombinant adenoviral vector IG.Ad. MLP.nls.lacZ contains the *E. coli* lazZ gene, encoding β-galactosidase, under control of the Ad2 major late promoter (MLP). IG.Ad.MLP.luc contains the firefly luciferase gene driven by the Ad2 MLP and adenoviral vectors. IG.Ad-.MLP.TK and IG.Ad.CMV.TK contain the Herpes Simplex Virus thymidine kinase (TK) gene under the control of the Ad2 MLP and the Cytomegalovirus (CMV) enhancer/promoter, respectively.

Transfections

All transfections were performed by calcium phosphate DNA precipitation (Graham et al., (1973) *Virology* 52: 456–467) with the GIBCO Calcium Phosphate Transfection System (GIBCO BRL Life Technologies, Inc., Gaithersburg, USA), according to the manufacturer's protocol.

Western Blotting

Subconfluent cultures of exponentially growing 293, 911, and Ad5-E1-transformed A549 and PER cells were washed with PBS and scraped in Fos-RIPA buffer (10 mM Tris (pH 7,5), 150 mM NaCl, 1% NP4, 0.01% sodium dodecyl sulfate (SDS), 1% NA-DOC, 0.5 mM phenyl methyl sulfonyl fluoride (PMSF), 0.5 mM trypsin inhibitor, 50 mM NaF and 1 mM sodium vanadate). After 10 min. at room temperature, lysates were cleared by centrifugation. Protein concentrations were measured with the BioRad protein assay kit and 25 µg total cellular protein was loaded on a 12.5% SDS-PAA gel. After electrophoresis, proteins were transferred to nitrocellulose (1 h at 300 mA). Prestained standards (Sigma, USA) were run in parallel. Filters were blocked with 1% bovine serum albumin (BSA) in TBST (10 mM Tris, pH 8, 15 mM NaCl, and 0.05% Tween-20) for 1 hour. First antibodies were the mouse monoclonal anti-Ad5-E1B-55-kDa antibody A1C6 (Zantema et al, unpublished) and the rat monoclonal anti-Ad5-E1B-221-kDa antibody C1G11 (Zantema et al, (1985) *Virology* 142:44–58). The second antibody was a horseradish peroxidase-labelled goat anti-mouse antibody (Promega). Signals were visualized by enhanced chemoluminescence (Amersham Corp. UK).

Southern Blot Analysis

High molecular weight DNA was isolated and then 10 µg of the DNA was digested to completion and fractionated on a 0.7% agarose gel. Southern blot transfer to Hybond $N^+$ (Amersham, UK) was performed with a 0.4 M NaOH, 0.6 M NaCl transfer solution (Church and Gilbert, 1984). Hybridization was performed with a 2463-nt SspI-HindIII fragment from pAd5.SalB (Bernards et al, (1983) *Virology* 127:

45–53). This fragment consisted of Ad5 bp. 342–2805. The fragment was radiolabeled with α-$^{32}$P=dCTP with the use of random hexanucleotide primers and Kelnow DNA polymerase. The southern blots were exposed to a Kodak XAR-5 film at −80° C. and to a Phospho-Imager screen, which was analyzed by B&L systems Molecular Dynamics Software.

A549

Ad5-E1-transformed A549 human bronchial carcinoma cell lines were generated by transfection with pIG.E1A.NEO and selection for G418 resistance. Thirty-one G418 resistant clones were established. Co-transfection of pIG.E1A.E1B with pIG.NEO yielded seven G418 resistant cell lines.

PER

Ad5-E1-transformed human embryonic retina (HER) cells were generated by transfection of primary HER cells with plasmid pIG.E1A.E1B. Transformed cell lines were established from well-separated foci. Seven clonal cell lines, PER.C1, PER.C3, PER.C4, PER.C5, PER.C6, PER.C8, and PER.C9, were established. One of the PER clones, namely PER.C6, has been deposited at the ECACC under number 96022940.

Expression of Ad5 E1A and E1B Genes in Transformed A549 and PER Cells

Figure 7:
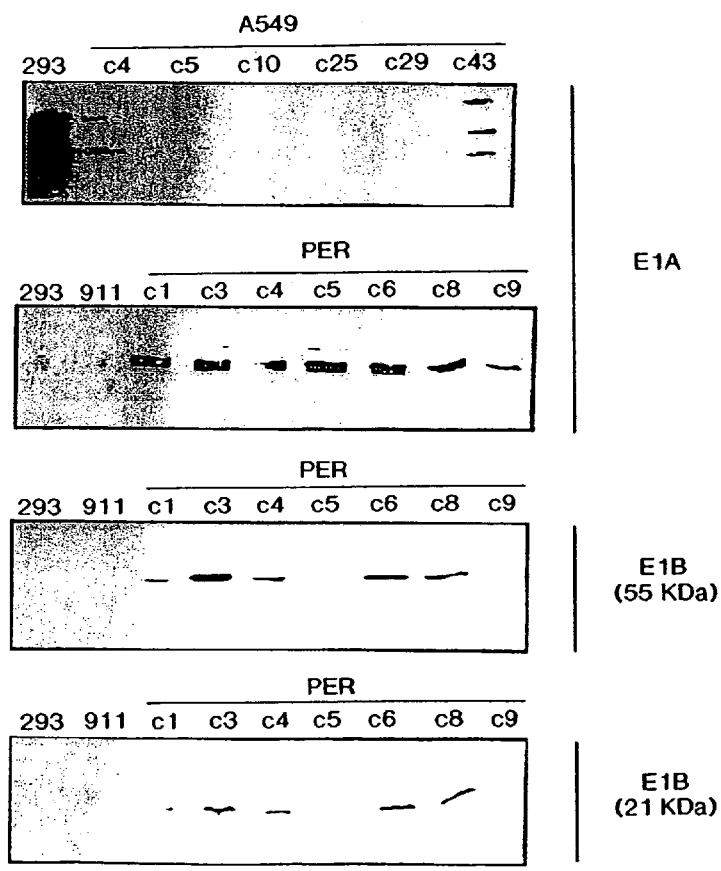
FIG. 7: Western blot analysis of A549 clones transfected with pIG.E1A.NEO and human embryonic retinoblasts (HER) cells transfected with pIG.E1A.E1B (PER clones). Expression of Ad5 E1A and E1B 55 kDa and 21 kDa proteins in transfected A549 cells and PER cells was determined by Western blot with mouse monoclonal antibodies (Mab) M73, which recognizes E1A gene products, and Mabs AIC6 and C1G11, which recognize the E1B 55 kDa and 21 kDa proteins, respectively. Mab binding was visualized using horseradish peroxidase-labelled goat anti-mouse antibody and enhanced chemiluminesence. 293 and 911 cells served as controls.

Expression of the Ad5 E1A and the 55 kDa and 21 kDa E1B proteins in the established A549 and PER cells was analyzed by Western blotting, with the use of monoclonal antibodies (mAb). mAb M73 recognizes the E1A products, whereas mAbs AIC6 and C1G11 are directed against the 55 kDa and 21 kDa E1B proteins, respectively. The antibodies did not recognize proteins in extracts from the parental A549 or the primary HER cells (data not shown). None of the A549 clones that were generated by co-transfection of pIG.NEO and pIG.E1A.E1B expressed detectable levels of E1A or E1B proteins (not shown). Some of the A549 clones that were generated by transfection with pIG.E1A.NEO expressed the Ad5 E1A proteins (FIG. 7), but the levels were much lower than those detected in protein lysates from 293 cells. The steady state E1A levels detected in protein extracts from PER cells were much higher than those detected in extracts from A549-derived cells. All PER cell lines expressed similar levels of E1A proteins (FIG. 7). The expression of the E1B proteins, particularly in the case of E1B 55 kDa, was more variable. Compared to 911 and 293, the majority of the PER clones express high levels of E1B 55 kDa and 2 kDa. The steady state level of E1B 21 kDa was the highest in PER.C3. None of the PER clones lost expression of the Ad5 E1 genes upon serial passage of the cells (not shown). The level of E1 expression in PER cells was found to remain stable for at least 100 population doublings. The PER clones were characterized in more detail.

Southern Analysis of PER Clones

Figure 8:
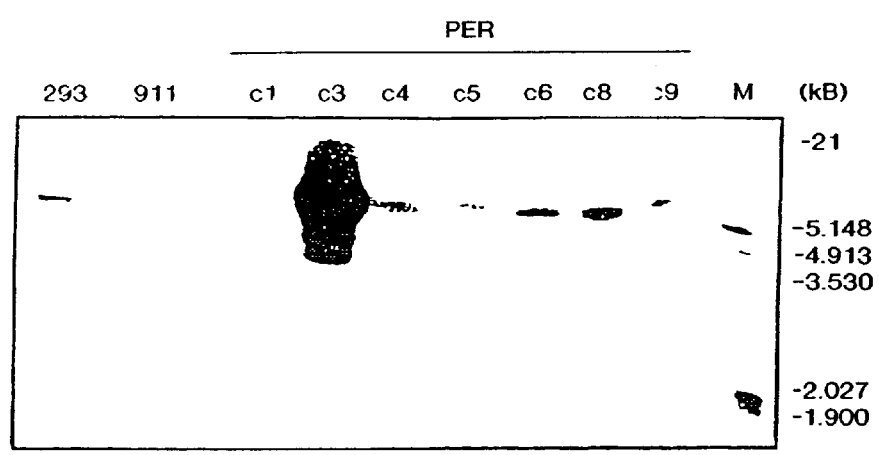
FIG. 8: Southern blot analysis of 293, 911 and PER cell lines. Cellular DNA was extracted, HindIII digested, electrophoresed, and transferred to Hybond N+ membranes (Amersham). Membranes were hybridized to radiolabelled probes generated by random priming of the SspI-HindIII fragment of pAd5.SalB (Ad5 nucleotides 342–2805).

To study the arrangement of the Ad5-E1 encoding sequences in the PER clones Southern analyses were performed. Cellular DNA was extracted from all PER clones, and from 293 and 911 cells. The DNA was digested with HindIII, which cuts once in the Ad5 E1 region. Southern hybridization on HindIII-digested DNA, using a radiolabeled Ad5-E1-specific probe, revealed the presence of several integrated copies of pIG.E1A.E1B in the genome of the PER clones. FIG. 8 shows the distribution pattern of E1 sequences in the high molecular weight DNA of the different PER cell lines. The copies were concentrated in a single band, which suggests that they were integrated as tandem repeats. In the case of PER.C3, C5, C6 and C9, additional hybridizing bands of low molecular weight were found that indicate the presence of truncated copies of pIG.E1A.E1B. The number of copies was determined with the use of a Phospho-Imager. PER.C1, C3, C4, C5, C6, C8 and C9 were estimated to contain 2, 88, 5, 4, 5, 5, and 3 copies of the Ad5 E1 coding region, respectively, and 911 and 293 cells contain 1 and 4 copies of the Ad5 E1 sequences, respectively.

Transfection Efficiency

Figure 9:
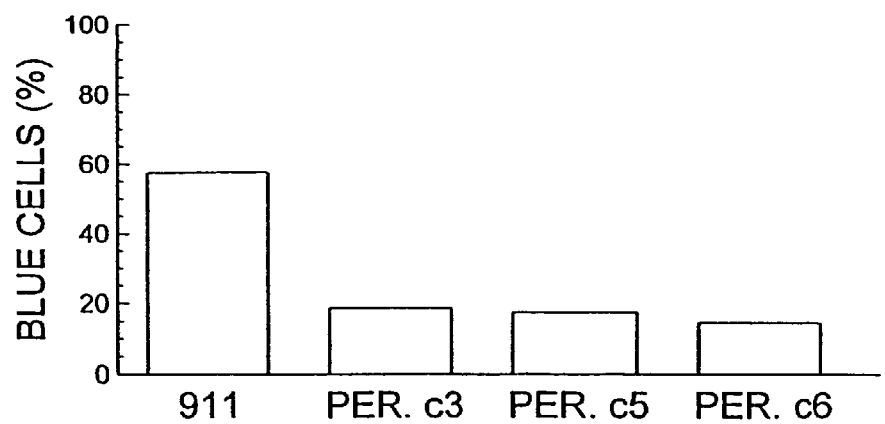
FIG. 9: Transfection efficiency of PER.C3, PER.C5, PER.C6 and 911 cells. Cells were cultured in 6-well plates and transfected in duplicate with 5 μg pRSV.lacZ by calcium-phosphate co-precipitation. Forty-eight hours post-transfection, cells were stained with X-Gal and blue cells were counted. Results shown are the mean percentage of blue cells per well.

Recombinant adenovectors are generated by co-transfection of adaptor plasmids and the large ClaI fragment of Ad5 into 293 cells (EPO patent application 95202213). The recombinant virus DNA is formed by homologous recombination between the homologous viral sequences that are present in the plasmid and the adenoviral DNA. The efficacy of this method, as well as that of alternative strategies, is highly dependent on the transfectability of the helper cells. Therefore, the transfection efficiencies of some of the PER clones were compared with 911 cells, using the *E. coli* β-galactosidase-encoding lacZ gene as a reporter (FIG. 9).

Production of Recombinant Adenovirus

Yields of recombinant adenovirus obtained after inoculation of 293, 911, PER.C3, PER.C5, and PER.C6 with different adenoviral vectors are presented in Table II.

The results indicate that the recombinant adenoviral vector yields obtained with PER cells are at least as high as those obtained with the existing cell lines. In addition, the yields of the novel adenoviral vector IG.Ad.MLPI.TK are similar or higher than the yields obtained for the other viral vectors on all cell lines tested.

Figure 10:
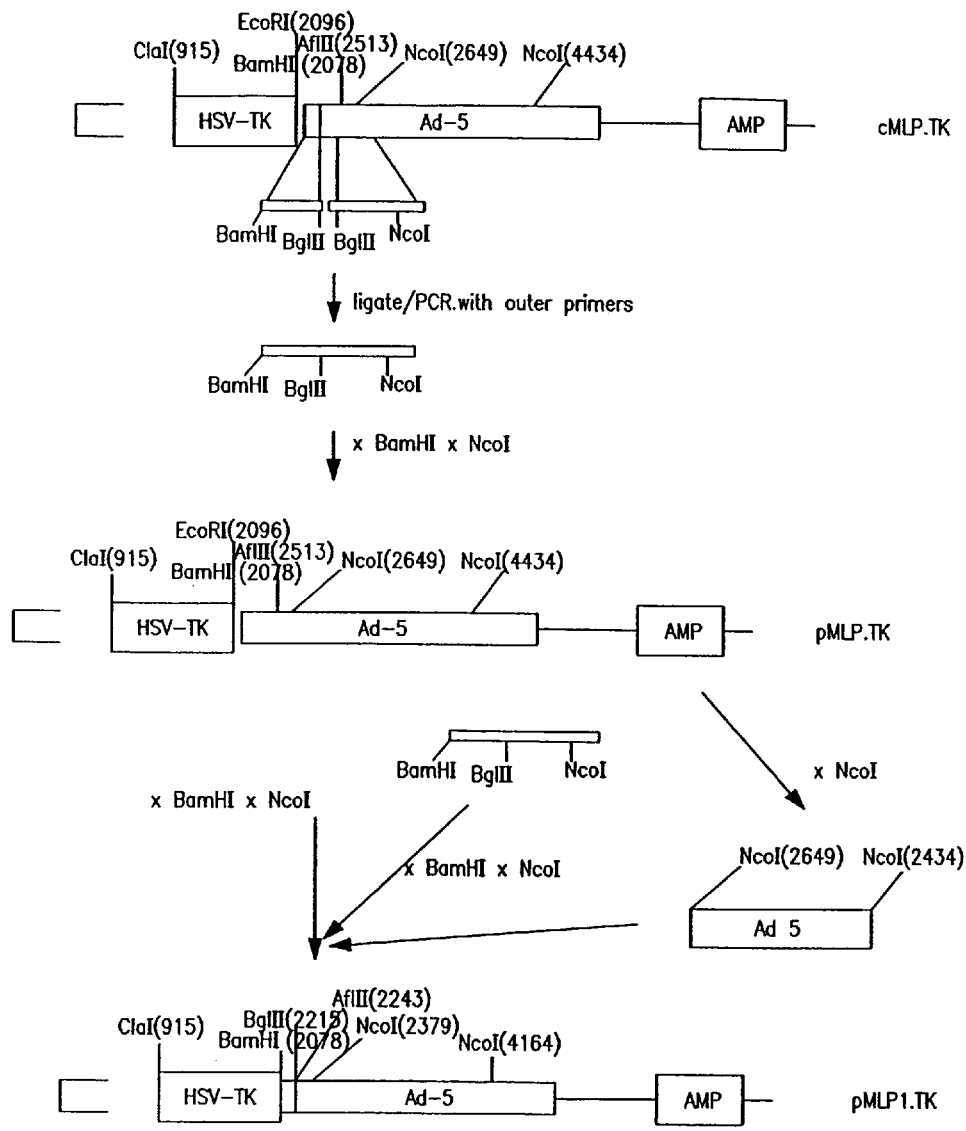
FIG. 10: Construction of adenoviral vector, pMLPI.TK. pMLPI.TK was designed to have no sequence overlap with the packaging construct pIG.E1A.E1B. pMLPI.TK was derived from pMLP.TK by deletion of the region of sequence overlap with pIG.E1A.E1B and deletion of non-coding sequences derived from lacZ. SV40 poly(A) sequences of pMLP.TK were PCR amplified with primers SV40-1 (SEQ ID NO:33), which introduces a BamHI site, and SV40-2 (SEQ ID NO:34), which introduces a BglII site. pMLP.TK Ad5 sequences 2496 to 2779 were PCR amplified with primers Ad5-1 (SEQ ID NO:35), which introduces a BglII site, and Ad5-2 (SEQ ID NO:36). Both PCR products were BglII digested, ligated, and PCR amplified with primers SV40-1 and Ad5-2. This third PCR product was BamHI and AflIII digested and ligated into the corresponding sites of pMLP.TK, producing pMLPI.TK.

Generation of New Adenoviral Vectors (FIG. 10)

The recombinant adenoviral vectors used (see EPO patent application EP 95202213) are deleted for E1 sequences from 459 to nt. 3328. As construct pE1A.E1B contains Ad5 sequences 459 to nt. 3510, there is a sequence overlap of 183 nt. between E1B sequences in the packaging construct pIG.E1A.E1B and recombinant adenoviruses, for example, IG.Ad.MLP.TK. The overlapping sequences were deleted from the new adenoviral vectors. In addition, non-coding sequences derived from lacZ, which are present in the original constructs, were deleted as well. This was achieved (see FIG. 10) by PCR amplification of the SV40 poly (A) sequences from pMLP.TK using primers SV40-1 (SEQ ID NO: 33) and SV40-2 (SEQ ID NO: 34). In addition, Ad5 sequences present in this construct were amplified from nt. 2496 (Ad5, introduces a BglII site) to nt. 2779 (Ad5-2). Both PCR fragments were digested with BglII and were ligated. The ligation product was PCR amplified using primers SV40-1 and Ad5-2 (SEQ ID NO:36). The PCR product obtained was cut with BamHI and AflII and was ligated into pMLP.TK, which was predigested with the same enzymes. The resulting construct, named pMLPI.TK, contains a deletion in adenoviral E1 sequences from nt. 459 to nt. 3510.

Packaging System

Figure 11A:
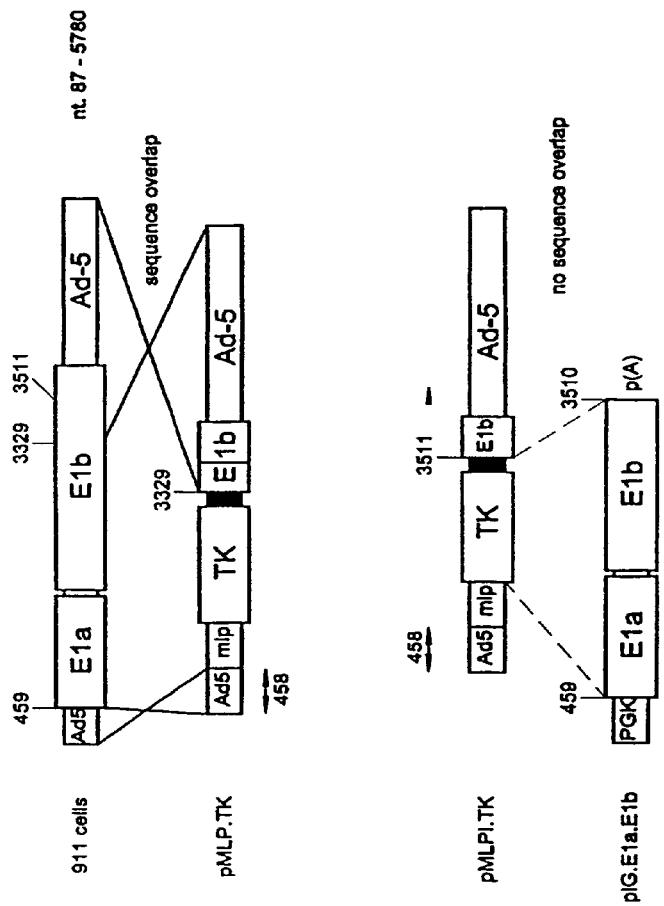
FIG. 11A: New adenoviral packaging construct, pIG.E1A.E1B, does not have sequence overlap with new adenoviral vector, pMLPI.TK. Regions of sequence overlap between the packaging construct pAd5XhoIC, expressed in 911 cells, and adenoviral vector pMLP.TK, that can result in homologous recombination and the formation of RCA are shown. In contrast, there are no regions of sequence overlap between the new packaging construct pIG.E1A.E1B, expressed in PER.C6 cells, and the new adenoviral vector pMLPI.TK.
Figure 1B:
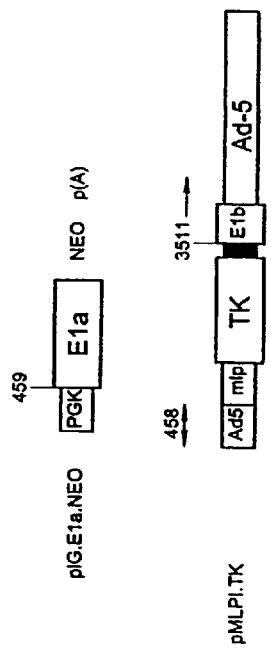

The combination of the new packaging construct pIG.E1A.E1B and the recombinant adenovirus pMLPI.TK, which do not have any sequence overlap, are presented in FIG. 11. In this FIG., the original situation is also presented, where the sequence overlap is indicated. The absence of overlapping sequences between pIG.E1A.E1B and pMLPI.TK (FIG. 11a) excludes the possibility of homologous recombination between the packaging construct and the recombinant virus, and is therefore a significant improvement for production of recombinant adenovirus.

In FIG. 11b the situation is depicted for pIG.E1A.NEO and IG.Ad.MLPI.TK. pIG.E1A.NEO when transfected into established cells, is expected to be sufficient to support propagation of E1-deleted recombinant adenovirus. This combination does not have any sequence overlap, preventing generation of RCA by homologous recombination. In addition, this convenient packaging system allows the propagation of recombinant adenoviruses that are deleted just for E1A sequences and not for E1B sequences.

Recombinant adenoviruses expressing E1B in the absence of E1A are attractive because the E1B protein, in particular E1B 19 kDa, is able to prevent infected human cells from lysis by tumor necrosis factor (TNF). Gooding et al, (1991) *J. Virol.* 65: 3083–3094).

Generation of Recombinant Adenovirus Derived from pMLPI.TK

Figure 12:
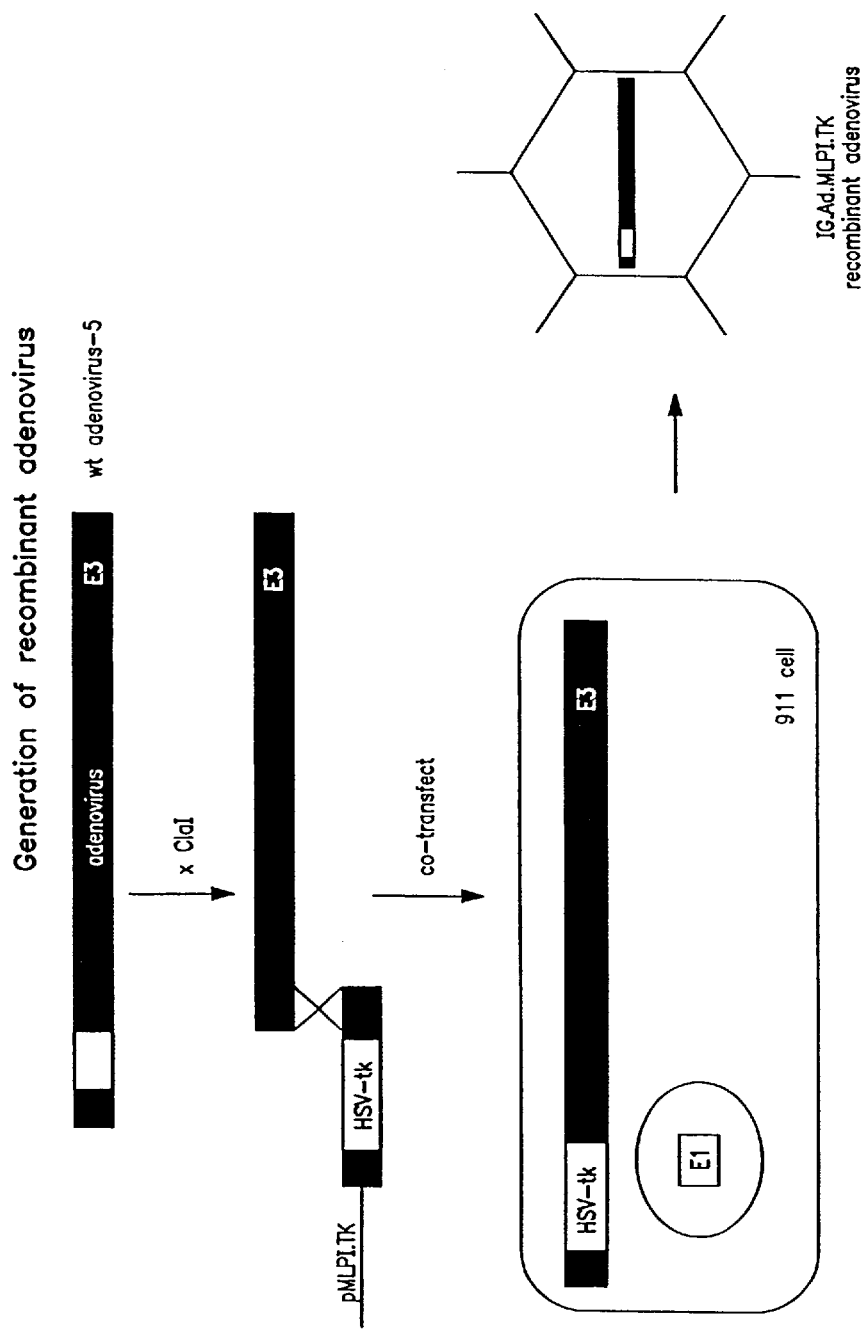
FIG. 12: Generation of recombinant adenovirus, IG.Ad.MLPI.TK. Recombinant adenovirus IG.Ad.MLPI.TK was generated by co-transfection of 293 cells with SalI linearized pMLPI.TK and the right arm of ClaI digested, wild-type Ad5 DNA. Homologous recombination between linearized pMLPI.TK and wild-type Ad5 DNA produces IG.Ad.MLPI.TK DNA, which contains an E1 deletion of nucleotides 459–3510. 293 cells transcomplement the deleted Ad5 genome, thereby permitting replication of the IG.Ad.MLPI.TK DNA and its packaging into virus particles.

Recombinant adenovirus was generated by co-transfection of 293 cells with SalI linearized pMLPI.TK DNA and ClaI linearized Ad5 wt DNA. The procedure is schematically represented in FIG. 12.

Example 2

Plasmid-based System for Rapid RCA-free Generation of Recombinant Adenoviral Vectors Construction of Adenoviral Clones pBr/Ad.Bam-rITR (ECACC Deposit P97082122)

In order to facilitate blunt end cloning of the ITR sequences, wildtype human adenovirus type 5 (Ad5) DNA was treated with Klenow enzyme in the presence of excess dNTPs. After inactivation of the Klenow enzyme, purification by phenol/chloroform extraction, and ethanol precipitation, the DNA was digested with BamHI. This DNA preparation was used without further purification in a ligation reaction with pBr322 derived vector DNA. The pBr322 DNA was prepared as follows: pBr322 DNA was digested with EcoRV and BamHI, dephosphorylated by treatment with TSAP enzyme (Life Technologies), and purified on LMP agarose gel (SeaPlaque GTG). After transformation into competent *E.coli* DH5a (Life Techn.) and analysis of ampicillin resistant colonies, one clone was selected that showed a digestion pattern consistent with an insert extending from the BamHI site in Ad5 to the right ITR. Sequence analysis of the cloning border at the right ITR revealed that the G residue closest to the 3' end of the ITR was missing. However, the remainder of the ITR was found to be correct. The missing G residue is complemented by the other ITR during replication.

pBr/Ad.Sal-rITR (ECACC Deposit P97082119)

pBr/Ad.Bam-rITR was digested with BamHI and SalI. The vector fragment including the adenoviral insert was isolated in LMP agarose (SeaPlaque GTG), ligated to a 4.8 kb SalI-BamHI fragment obtained from wt Ad5 DNA, and purified with the Geneclean II kit (Bio 101, Inc.). One clone was chosen and the integrity of the Ad5 sequences was determined by restriction enzyme analysis. Clone pBr/Ad.Sal-rITR contains adeno type 5 sequences from the SalI site at bp 16746 up to and including the rITR (missing the G residue closest to the 3' end).

pBr/Ad.Cla-Bam (ECACC Deposit P97082117)

Wildtype adeno type 5 DNA was digested with ClaI and BamHI, and the 20.6 kb fragment was isolated from gel by electro-elution. pBr322 was digested with the same enzymes and purified by agarose gel from Geneclean. Both fragments were ligated and transformed into competent DH5α. The resulting clone pBr/Ad.Cla-Bam was analyzed by restriction enzyme digestion and shown to contain an insert with adenoviral sequences from bp 919 to 21566.

pBr/Ad.AflII-Bam (ECACC Deposit P97082114)

Clone pBr/Ad.Cla-Bam was linearized with EcoRI (in pBr322) and partially digested with AflII. After heat inactivation of AflII for 20 minutes at 65° C., the fragment ends were filled in with Klenow enzyme. The DNA was then ligated to a blunt double stranded oligo linker containing a PacI site (5'-AATTGTC<u>TTAATTAA</u>CCGCTTAA-3') (SEQ ID NO:1). This linker was made by annealing the following two oligonucleotides: 5'-AATTGTCTTAATTAACCGC-3' (SEQ ID NO:2) and 5'-AATTGCGGTTAATTAAGAC-3' (SEQ ID NO:3), followed by blunting with Klenow enzyme. After precipitation of the ligated DNA to change buffer, the ligations were digested with an excess PacI enzyme to remove concatameres of the oligo. The 22016 bp partial fragment, containing Ad5 sequences from bp 3534 up to 21566 and the vector sequences, was isolated in LMP agarose (SeaPlaque GTG), religated, and transformed into competent DH5α. One clone that was found to contain the PacI site and that had retained the large adeno fragment was selected and sequenced at the 5' end to verify correct insertion of the PacI linker in the (lost) AflII site.

pBr/Ad.Bam-rITRpac#2 (ECACC Deposit P97082120) and pBr/Ad.Bam-rITR#8 (ECACC Deposit P97082121)

To allow insertion of a PacI site near the ITR of Ad5 in clone pBr/Ad.Bam-rITR, about 190 nucleotides were removed between the ClaI site in the pBr322 backbone and the start of the ITR sequences. pBr/Ad.Bam-rITR was digested with ClaI and treated with nuclease Bal31 for varying lengths of time (2, 5, 10, and 15 minutes). The extent of nucleotide removal was followed by separate reactions on pBr322 DNA (also digested at the ClaI site), using identical buffers and conditions. Bal31 enzyme was inactivated by incubation at 75° C. for 10 minutes, the DNA was precipitated, and then the DNA was resuspended in a smaller volume of TE buffer. To ensure blunt ends, the DNA was further treated with T4 DNA polymerase in the presence of excess dNTPs. After digestion of the (control) pBr322 DNA with SalI, satisfactory degradation (~150 bp) was observed in the samples treated for 10 or 15 minutes. The 10 or 15 minute treated pBr/Ad.Bam-rITR samples were then ligated to the above-described blunted PacI linkers (see pBr/Ad.AflII-Bam). Ligations were purified by precipitation, digested with excess PacI, and separated from the linkers on an LMP agarose gel. After religation, DNAs were transformed into competent DH5α and colonies analyzed. Ten clones that showed a deletion of approximately the desired length were selected and were further analyzed by T-track sequencing (T7 sequencing kit, Pharmacia Biotech). Two clones were found with the PacI linker inserted just downstream of the rITR. After digestion with PacI, clone #2 had 28 bp and clone #8 had 27 bp attached to the ITR.

pWE/Ad.AflII-rITR (ECACC Deposit P97082116)

Cosmid vector pWE15 (Clontech) was used to clone larger Ad5 inserts. First, a linker containing a unique PacI site was inserted in the EcoRI sites of pWE15, creating pWE.pac. The double stranded PacI oligo was used as described for pBr/Ad.AflII-BamHI, except that its EcoRI protuding ends were used. The following fragments were then isolated by electro-elution from an agarose gel: pWE.pac digested with PacI, pBr/AflII-Bam digested with PacI and BamHI, and pBr/Ad.Bam-rITR#2 digested with BamHI and PacI. These fragments were ligated together and packaged using λ phage packaging extracts (Stratagene)

according to the manufacturer's protocol. After infection into host bacteria, colonies were grown on plates and analyzed for presence of the complete insert. pWE/Ad.AflII-rITR contains all adenovirus type 5 sequences from bp 3534 (AflII site) up to and including the right ITR (missing the G residue closest to the 3' end).

Adeno 5 wt DNA was treated with Klenow enzyme in the presence of excess dNTPs and subsequently digested with SalI. Two of the resulting fragments, designated left ITR-Sal(9.4) and Sal(16.7)-right ITR, were isolated in LMP agarose (Seaplaque GTG). pBr322 DNA was digested with EcoRV and SalI and treated with phosphatase (Life Technologies). The vector fragment was isolated using the Geneclean method (BIO 101, Inc.) and ligated to the Ad5 SalI fragments. Only the ligation with the 9.4 kb fragment gave colonies with an insert. After analysis and sequencing of the cloning border, a clone was chosen that contained the full ITR sequence and extended to the SalI site at bp 9462.

pBr/Ad.1ITR-Sal(16.7) (ECACC Deposit P97082118)

pBr/Ad.1ITR-Sal(9.4) is digested with SalI and dephosphorylated (TSAP, Life Technologies). To extend this clone up to the third SalI site in Ad5, pBr/Ad.Cla-Bam was linearized with BamHI and partially digested with SalI. A 7.3 kb SalI fragment containing adenoviral sequences from 9462–16746 was isolated in LMP agarose gel and ligated to the SalI-digested pBr/Ad.1ITR-Sal(9.4) vector fragment.

pWE/Ad.AflII-EcoRI pWE.pac was digested with ClaI and the 5' protruding ends were filled in using Klenow enzyme. The DNA was then digested with PacI and isolated from an agarose gel. pWE/AflII-rITR was digested with EcoRI and after treatment with Klenow enzyme, was digested with PacI. The large 24 kb fragment containing the adenoviral sequences was isolated from an agarose gel and ligated to the ClaI-digested and blunted pWE.pac vector using the Ligation Express™ kit from Clontech. After transformation of Ultracompetent XL10-Gold cells from Stratagene, clones were identified that contained the expected insert. pWE/AflII-EcoRI contains Ad5 sequences from bp 3534–27336.

Construction of New Adapter Plasmids

The absence of sequence overlap between the recombinant adenovirus and E1 sequences in the packaging cell line is essential for safe, RCA-free generation and propagation of new recombinant viruses. The adapter plasmid pMLPI.TK (FIG. 10) is an example of an adapter plasmid designed for use according to the invention in combination with the improved packaging cell lines of the invention. This plasmid was used as the starting material to make a new vector in which nucleic acid molecules including specific promoter and gene sequences can be easily exchanged.

First, a PCR fragment was generated from pZipΔMo+PyF101(N⁻) template DNA (described in PCT/NL96/00195) with the following primers: LTR-1: 5'-CTG TAC GTA CCA GTG CAC TGG CCT AGG CAT GGA AAA ATA CAT AAC TG-3' (SEQ ID NO:4) and LTR-2: 5'-GCG GAT CCT TCG AAC CAT GGT AAG CTT GGT ACC GCT AGC GTT AAC CGG GCG ACT CAG TCA ATC G-3' (SEQ ID NO:5). Pwo DNA polymerase (Boehringer Mannheim) was used according to the manufacturer's protocol with the following temperature cycles: 1 cycle of 5 minutes at 95° C., 3 minutes at 55° C., and 1 minute at 72° C.; followed by 30 cycles of 1 minute at 95° C., 1 minute at 60° C., and 1 minute at 72° C.; followed by 1 cycle of 10 minutes at 72° C. The PCR product was then digested with BamHI and ligated into a pMLP10 vector (Levrero et al, (1991) *Gene* 101:195–202)

digested with PvuII and BamHI, thereby generating vector pLTR10. This vector contains adenoviral sequences from bp 1 up to bp 454, followed by a promoter that includes part of the Mo-MuLV LTR in which the wildtype enhancer sequences are replaced by the enhancer from a mutant polyoma virus (PyF101). The promoter fragment was designated L420.

Next, the coding region of the murine HSA gene was inserted. pLTR10 was digested with BstBI followed by Klenow treatment and digestion with NcoI. The HSA gene was obtained by PCR amplification on pUC18-HSA (Kay et al, (1990) *J. Immunol.* 145:1952–1959) using the following primers: HSA1, 5'-GCG CCA CCA TGG GCA GAG CGA TGG TGG C-3' (SEQ ID NO:6) and HSA2, 5'-GTT AGA TCT AAG CTT GTC GAC ATC GAT CTA CTA ACA GTA GAG ATG TAG AA-3'(SEQ ID NO:7). The 269 bp amplified fragment was subcloned in a shuttle vector using the NcoI and BglII sites. Sequencing confirmed incorporation of the correct coding sequence of the HSA gene, but with an extra TAG insertion directly following the TAG stop codon. The coding region of the HSA gene, including the TAG duplication, was then excised as a NcoI(sticky)-SalI(blunt) fragment and cloned into the 3.5 kb NcoI(sticky)/BstBI (blunt) fragment from pLTR10, resulting in pLTR-HSA10.

Finally, pLTR-HSA10 was digested with EcoRI and BamHI after which the fragment containing the left ITR, packaging signal, L420 promoter, and HSA gene was inserted into vector pMLPI.TK, which was digested with the same enzymes, thereby replacing the promoter and the gene sequences. This resulted in the new adapter plasmid pAd/L420-HSA (FIG. 19) that contains convenient recognition sites for various restriction enzymes around the promoter and gene sequences. SnaBI and AvrII can be combined with HpaI, NheI, KpnI, HindIII to exchange promoter sequences, while the latter sites can be combined with the ClaI or BamHI sites 3' from the HSA coding region to replace genes in this construct.

Figure 20:
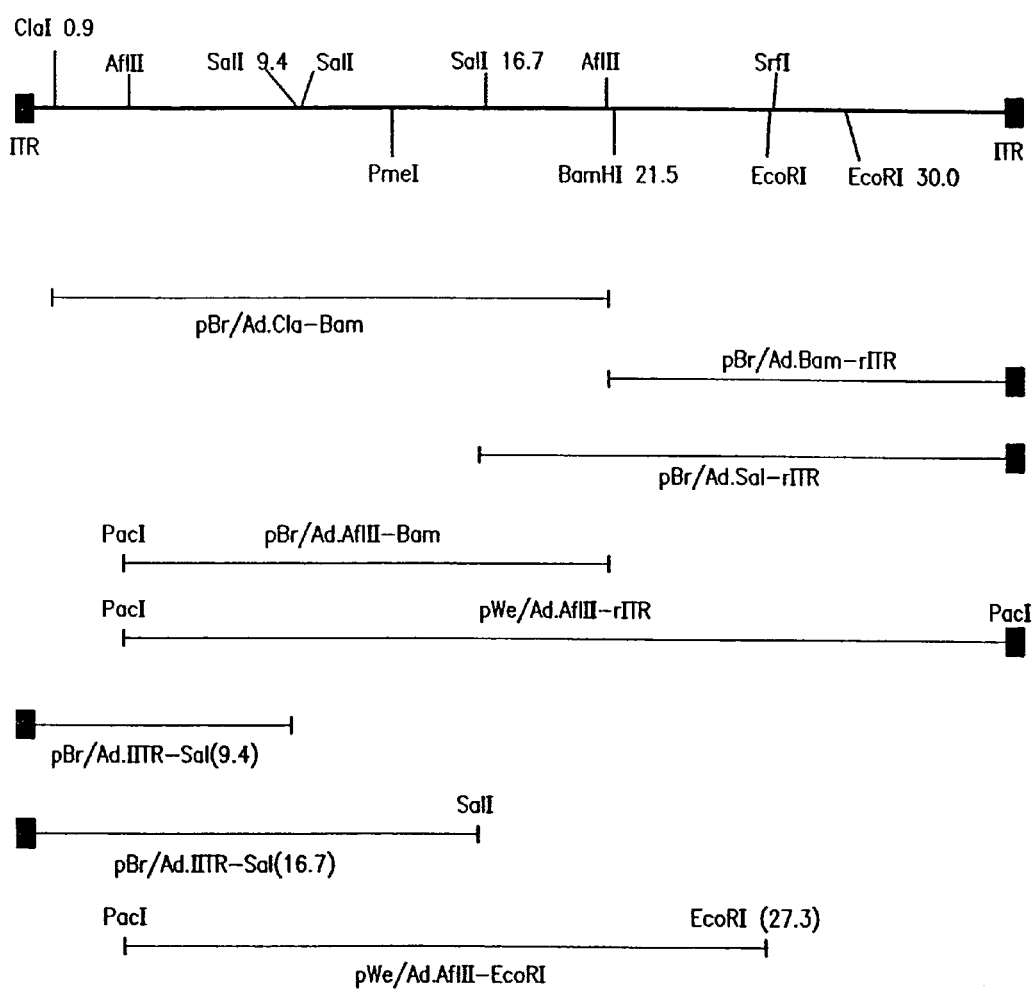
FIG. 20: Shows a schematic overview of the adenoviral fragments cloned in pBr322 (plasmid) or pWE15 (cosmid) derived vectors. The top line depicts the complete adenoviral genome flanked by its ITRs (filled rectangles) and with some restriction sites indicated. Numbers following restriction sites indicate approximate digestion sites (in kb) in the Ad5 genome.

Another adapter plasmid that was designed to allow easy exchange of nucleic acid molecules was made by replacing the promoter, gene, and polyA sequences in pAd/L420-HSA with the CMV promoter, a multiple cloning site, an intron, and a poly-A signal. For this purpose, pAd/L420-HSA was digested with AvrII and BglII, followed by treatment with Klenow to obtain blunt ends. The 5.1 kb fragment with pBr322 vector and adenoviral sequences was isolated and ligated to a blunt 1570 bp fragment from pcDNA1/amp (Invitrogen), which was obtained by digestion with HhaI and AvrII followed by treatment with T4 DNA polymerase. This adapter plasmid was named pCLIP (FIG. 20).

Generation of Recombinant Adenoviruses

E1-deleted Recombinant Adenoviruses with wt E3 Sequences

To generate E1 deleted recombinant adenoviruses with the new plasmid-based system, the following constructs were prepared: an adapter construct containing the expression cassette with the gene of interest linearized with a restriction enzyme that cuts at the 3' side of the overlapping adenoviral genome fragment, preferably not containing any pBr322 vector sequences; and a complementing adenoviral genome construct pWE/Ad.AflII-rITR digested with PacI.

Figure 21:
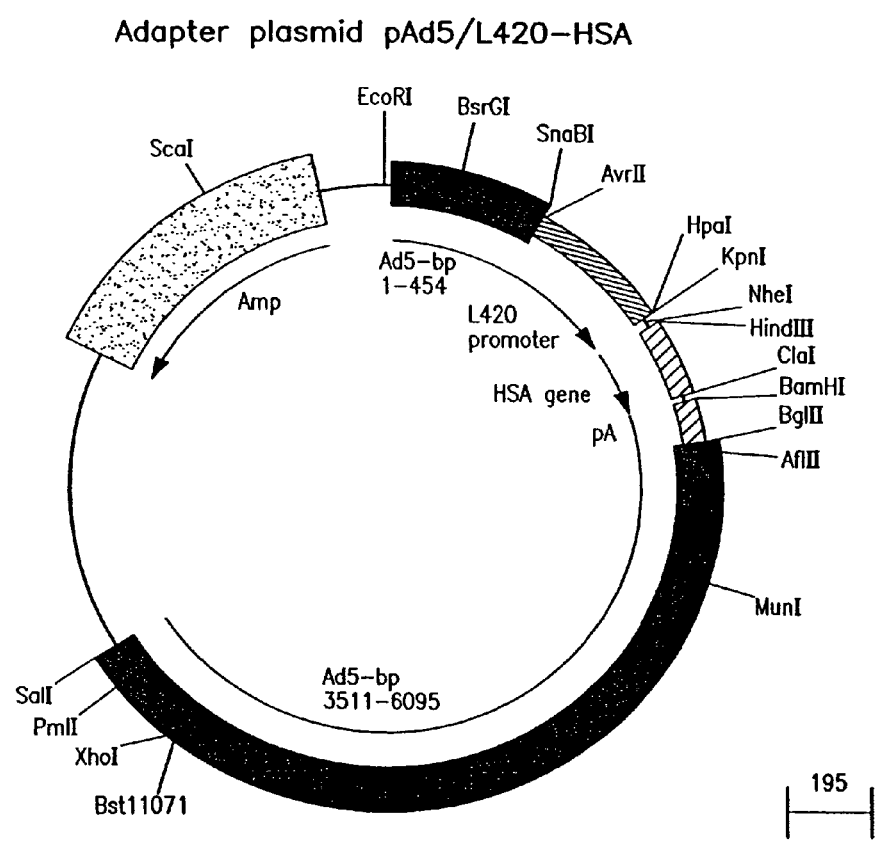
FIG. 21: Drawing of adapter plasmid pAd/L420-HSA
Figure 22:
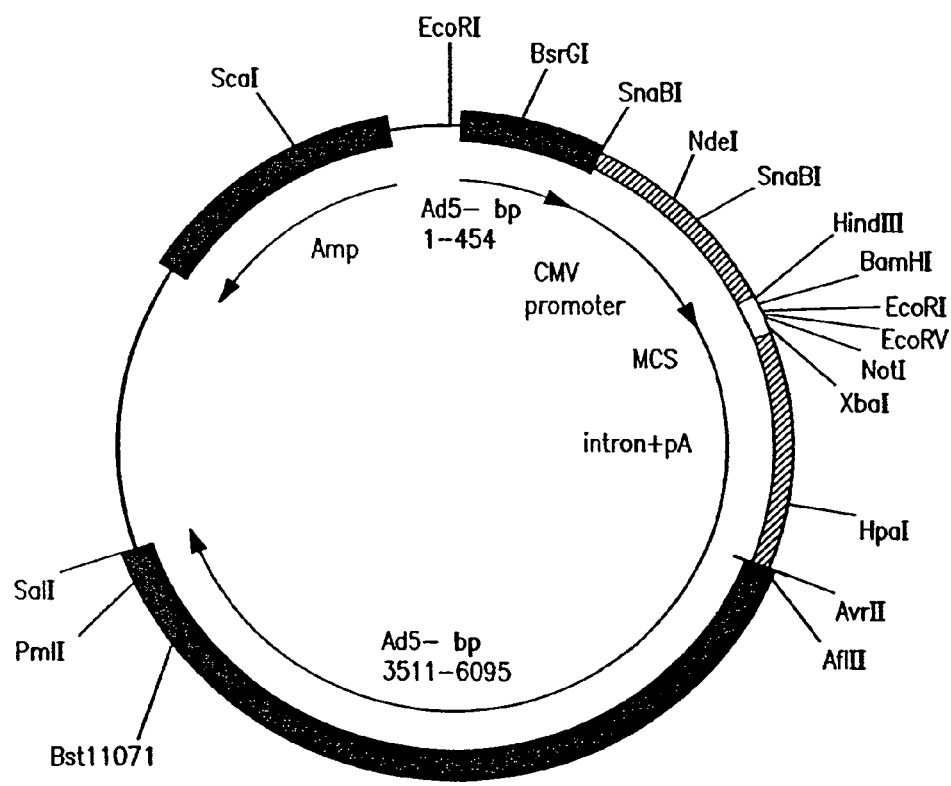
FIG. 22: Drawing of adapter plasmid pAd/Clip

These two DNA molecules were further purified by phenol/chloroform extraction and ethanol precipitation. Co-transfection of these plasmids into an adenoviral packaging cell line, preferably a cell line according to the invention, generates recombinant replication deficient adenoviruses by a one-step homologous recombination between the adapter and the complementing construct (FIG. 21). Alternatively, instead of pWE/Ad.AflII-rITR, other fragments can be used, e.g., pBr/Ad.Cla-Bam digested with EcoRI and BamHI or pBr/Ad.AflII-BamHI digested with PacI and BamHI can be combined with pBr/Ad.Sal-rITR digested with SalI. In this case, three plasmids are combined and two homologous recombinations are needed to obtain a recombinant adenovirus (FIG. 22). It is to be understood that those skilled in the art may use other combinations of adapter and complementing plasmids without departing from the present invention.

A general protocol as outlined below and meant as a non-limiting example of the present invention has been performed to produce several recombinant adenoviruses using various adapter plasmids and the Ad.AflII-rITR fragment. Adenoviral packaging cells (PER.C6) were seeded in ~25 cm² flasks and were transfected with a mixture of DNA and lipofectamine agent (Life Techn.) as described by the manufacturer when they were at about 80% confluency. Routinely, 40 µl lipofectamine, 4 µg adapter plasmid, and 4 µg of the complementing adenoviral genome fragment AflII-rITR (or 2 µg of all three plasmids for the double homologous recombination) were used. Under these conditions, transient transfection efficiencies of approximately 50% (48 hrs post transfection) were obtained as determined with control transfections using a pAd/CMV-LacZ adapter. Two days later, cells were passaged to about 80 cm² flasks and further cultured.

Approximately five (for the single homologous recombination) to eleven days (for the double homologous recombination) later, a cytopathic effect (CPE) was seen, indicating that functional adenovirus had formed. Cells and medium were harvested upon full CPE and recombinant virus was released by freeze/thawing. An extra amplification step in a 80 cm² flask was routinely performed to increase the yield since, at the initial stage, the titers was found to be variable despite the occurrence of full CPE. After amplification, viruses were harvested and plaque purified on PER.C6 cells. Individual plaques were tested for viruses with active transgenes.

Four different recombinant adenoviruses, containing the human interleukin-3 gene (see FIG. 1, WO88/04691), the human endothelial nitric oxide gene (Janssens et al, (1992) *J. Biol. Chem.* 267:14519–14522), the Tc1A transposase gene (Vos et al, (1993) *Genes Dev.* 7:1244–1253), or the bacterial LacZ gene (Kalderon et al, (1984) *Cell* 39:499–509, have been produced using this protocol. In all cases, functional adenovirus was formed and all isolated plaques contained viruses with an active transgene.

E1-deleted Recombinant Adenoviruses with Modifications in the E3 or E4 Regions

Besides replacements in the E1 region, it is possible to delete the E3 region or replace part of the E3 region in the adenovirus because E3 functions are not necessary for the replication, packaging, and infection of a recombinant virus. This creates the opportunity to use a larger insert or to insert more than one gene without exceeding the maximum packagable size (approximately 105% of wt genome length). This can be done, for example, by deleting part of the E3 region in the pBr/Ad.Bam-rITR clone by digestion with XbaI and religation. This removes Ad5 wt sequences 28592–30470 including all known E3 coding regions. Another example is the precise replacement of the coding region of gp19K in the E3 region with a polylinker allowing insertion of new sequences. The replacement leaves all other coding regions intact, obviates the need for a heterologous promoter because the transgene is driven by the E3 promoter and pA sequences which leaves more space for coding sequences, and results in very high transgene expression, at least as good as in a control E1 replacement vector.

For this purpose, the 2.7 kb EcoRI fragment from wt Ad5 containing the 5' part of the E3 region was cloned into the EcoRI site of pBluescript (KS⁻) (Stratagene). Next, the HindIII site in the polylinker was removed by digestion with EcoRV and HincII and subsequent religation. The resulting clone, pBS.Eco-Eco/ad5ΔHIII, was used to delete the gp19K coding region. Primers 1 (5'-GGG TAT TAG GCC AAAGGCGCA-3') (SEQ ID NO:8) and 2 (5'-GAT CCC ATG GAA GCT TGG GTG GCG ACC CCA GCG-3') (SEQ ID NO:9) were used to amplify a sequence from pBS.Eco-Eco/ad5ΔHIII corresponding to sequences 28511 to 28734 in wt Ad5 DNA. Primers 3 (5'-GAT CCC ATG GGG ATC CTT TAC TAA GTT ACA AAG CTA-3') (SEQ ID NO:10) and 4 (5'-GTC GCT GTA GTT GGA CTG G-3') (SEQ ID NO:11) were used on the same DNA to amplify Ad5 sequences from 29217 to 29476. The two resulting PCR fragments were ligated together by virtue of the newly introduced NcoI site and subsequently digested with XbaI and MunI. This fragment was then ligated into a pBS.Eco-Eco/ad5ΔHIII vector that had been partially digested with XbaI and MunI, generating pBS.Eco-Eco/ad5 ΔHIII.Δgp19K.

To allow insertion of foreign genes into the HindIII and BamHI site, an XbaI deletion was made in pBS.Eco-Eco/ad5ΔHIII.Δgp19K to remove the BamHI sites in the Bluescript polylinker. The resulting plasmid pBS.Eco-Eco/ad5ΔHIIIΔgp19KΔXbaI, contained unique HindIII and BamHI sites corresponding to sequences 28733 (HindIII) and 29218 (BamHI) in Ad5. After introduction of a foreign gene into these sites, either the deleted XbaI fragment is reintroduced or the insert is recloned into pBS.Eco-Eco/ad5 ΔHIII.Δgp19K using HindIII and, for example, MunI. Using this procedure, plasmids expressing HSV-TK (McKnight (1980) *Nucl. Acid. Res.* 8:5949–5964 and Vincent et al (1996) *Hum. Gene Ther.* 7:197–205), hIL-1α (Esandi et al, (1998) *Gene Therapy* 5), rat IL-3β (Esandi et al, (1998) *Gene* 11242), luciferase (DeWit et al, (1987) *Mol. Cell Biol.* 7:725–737), or LacZ were generated. The unique SrfI and NotI sites in the pBS.Eco-Eco/ad5ΔHIII.Dgp19K plasmid (with or without an inserted gene of interest) are used to transfer the region containing the gene of interest into the corresponding region of pBr/Ad.Bam-rITR, yielding construct pBr/Ad.Bam-rITRDgp19K (with or without an inserted gene of interest). This construct is used as described supra to produce recombinant adenoviruses. In the viral context, expression of inserted genes is driven by the adenoviral E3 promoter.

Recombinant viruses that are both E1 and E3 deleted are generated by a double homologous recombination procedure as described above for E1-replacement vectors using a plasmid-based system which includes: an adapter plasmid for E1 replacement with or without insertion of a first gene of interest according to the invention, the pWE/Ad.AflII-EcoRI fragment, and the pBr/Ad.Bam-rITRΔgp19K plasmid with or without insertion of a second gene of interest.

In a non-limiting example, the generation and functionality of a recombinant adenovirus containing the murine HSA gene in the E1 region and the firefly luciferase gene in the gp19K region are described. The luciferase gene was excised from pAd/MLP-Luc (described in EPO patent appl'n 0707071) as a HindIII-BamHI construct and cloned into the HindIII-BamHI sites of pBS.Eco-Eco/ad5ΔHIIIΔgp19KΔXbaI. Then, the MscI-MunI fragment containing the luciferse gene was cloned into the corresponding sites of pBS.Eco-Eco/ad5Δgp19K, generating pBS.Eco-Eco/ad5Δgp19K.luc. This restores the Eco-Eco fragment, but now with the luciferase gene in place of gp19K.

To simplify further manipulation, the internal EcoRI sites in the luciferase insert were mutated without making changes to the amino acid sequence of the luciferase gene. One EcoRI site flanked the HindIII site in the 5' non-coding region of the luciferase insert and the other site was located 588 bp 3' from the starting ATG. A 695 bp PCR product was generated with the following primers: 5'-CGA TAA GCT TAA TTC CTT TGT GTT T-3' (SEQ ID NO:12) and 5'-CTT AGG TAA CCC AGT AGA TCC AGA GGA GTT CAT-3' (SEQ ID NO:13) and digested with HindIII and BstEII. This fragment was then ligated to HindIII-BstEII, with pBS.Eco-Eco/ad5Δgp19K.luc replacing the corresponding insert in this vector. The resulting construct is named pBS.Eco-Eco/ad5Δgp19K.luc². The luciferase gene and part of the E3 region were then excised from this clone with SrfI and NotI and introduced in the corresponding sites in pBr/Ad.Bam-rITR, generating clone pBr/Ad.Bam-rITRΔgp19K/luc².

The adapter plasmid pAd5/S1800HSA used for the replacement of E1 in the double insert virus contains the murine HSA gene driven by a retrovirus LTR-based promoter. This adapter plasmid was generated from the pAd5/L420-HSA construct described infra by replacement of the promoter sequence. First, a PCR product was generated on a retroviral vector based on the MFG-S vector described in WO 95/34669 using the same primers as for the amplification of the L420 promoter fragment (described infra). This amplifies the sequences corresponding to bp 453–877 in the MFG-S vector. The L420 promoter in pAd5/IL420-HSA (FIG. 21) was then exchanged for the PCR fragment using the unique AvrII and HindIII sites. The resulting construct, pAd5/S430-HSA, was then digested with NheI and ScaI and the 4504 bp fragment containing the HSA gene, pA sequences, Ad5 sequences, and vector sequences to the ScaI site in the ampicillin gene was isolated.

The construct pAd5/S430-HSA also was digested with XbaI and ScaI and the 1252 bp fragment (containing the remainder of the ampicillin gene, the left ITR and packaging signal from the adenovirus, and the 5' part of the S430 promoter) was isolated. A third fragment of 1576 bp was isolated from the MFG-S-based retroviral vector following a XbaI digestion and contained MFG-S sequences corresponding to bp 695–2271.

The adapter plasmid pAd5/S1800-HSA was constructed by ligating the three isolated fragments. The double insert virus Ad5/S1800-HSA.E31luc was generated (as described above) by transfection of the following DNA fragments into PER.C6 cells: pAd5/S1800-HSA digested with EcoRI and SalI (2 µg). At occurrence of CPE, the virus was harvested and amplified by serial passages of PER.C6 cells. The activity of this HSA-luc virus was compared to single insert ΔE1 viruses containing either the S1800-HSA or the CMV-luc transcription units in the E1 region. A549 cells were seeded at 2×10⁵ cells per well and infected 5 hrs later with different amounts of the virus. Two days later, transgene expression was measured. Luciferase activity was measured using a luciferase assay system (Promega) and expression of the murine HSA gene was measured with an α-HSA antibody (M1/69, Pharmingen). The results are listed in Table III.

This experiment shows that using the plasmid-based recombination system, double insert viruses can be made and that both inserts are functional. Furthermore, the luciferase activity of the double insert viruses is comparable to the CMV-driven luciferase activity of the control virus. Therefore, the E3 promoter was concluded to be highly active in A549 cells, even in the absence of E1A proteins.

In addition to manipulations in the E3 region, changes of the E4 region or parts of the E4 region can be accomplished easily in pBr/Ad.Bam-rITR. Generation and propagation of such a virus, however, in some cases demands complementation in trans.

Example 3

Demonstration of the Competence of a Synthetic DNA Sequence, which is Capable of Forming a Hairpin Structure, to Serve as a Primer for Reverse Strand Synthesis for the Generation of Double-stranded DNA Molecules in Cells that Contain and Express Adenoviral Genes Name convention of the plasmids used:

| | |
|---|---|
| p | plasmid |
| I | ITR (Adenoviral ITR) |
| C | Cytomegalovirus (CMV) Enhancer/Promoter Combination |
| L | Firefly Luciferase Coding Sequence |
| hac, haw | Potential hairpin that can be formed after digestion with restriction endonuclease Asp718 in both the correct and in the reverse orientation, respectively (FIG. 15) |

The naming convention is exemplified as follows. pICLhaw is a plasmid that contains the adenoviral ITR followed by the CMV-driven luciferase gene and the Asp718 hairpin in the reverse (non-functional) orientation.

Plasmids pICLhac, pICLhaw, pICLI, and pICL were generated using standard techniques. The schematic representation of these plasmids is shown in FIGS. 16–19.

Plasmid pICL is derived from the following plasmids:

| | | |
|---|---|---|
| nt.1 | 457 | pMLP10 (Levrero et al, (1991) Gene 101: 195–202) |
| nt.458 | 1218 | pCMVβ (Clontech, EMBL Bank No. U02451) |
| nt.1219 | 3016 | pMLP.luc (IntroGene, unpublished) |
| nt.3017 | 5620 | pBLCAT5 (Stein et al, (1989) Mol. Cell Biol. 9: 4531–4). |

The plasmid has been constructed as follows:

The tet gene of plasmid pMLP10 has been inactivated by deletion of the BamHI-SalI fragment, to generate pBLP10ΔSB. Using primer set PCR/MLP1 (SEQ ID NO:37) and PCR/MLP3 (SEQ ID NO:38), a 210 bp fragment containing the Ad5-ITR, flanked by a synthetic SalI restriction site, was amplified using pMLP10 DNA as the template. The PCR product was digested with the enzymes EcoRI and SgrAI to generate a 196 bp fragment. Plasmid pMLP10ΔSB was digested with EcoRI and SgrAI to remove the ITR. This fragment was replaced by the EcoRI-SgrAI-reated PCR fragment to generate pMLP/SAL.

Figure 19:
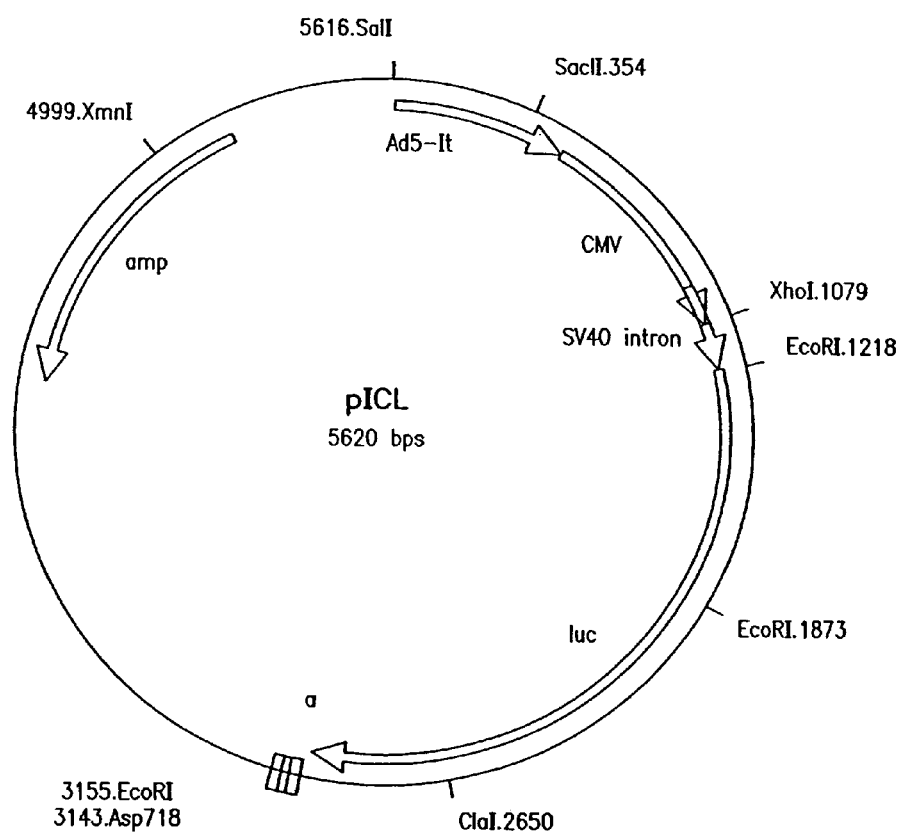
FIG. 19: Diagram of pICL. pICL is derived from the following: (i) nucleotides 1–457, Ad5 nucleotides 1–457 including the left ITR, (ii) nucleotides 458–969, human Cytomegalovirus (CMV) enhancer and immediate early promoter, (iii) nucleotides 970–1204, SV40 19S exon and truncated 16/19S intron, (iv) nucleotides 1218–2987, firefly luciferase gene, (v) nucleotides 3018–3131, SV40 tandem polyadenylation signals from the late transcript, (vi) nucleotides 3132–5620, pUC 12 sequences including an Asp718 site, and (vii) ampicillin resistance gene in reverse orientation.

Plasmid pCMV-Luc was digested to completion with PvuII and recirculated to remove the SV40-derived polyadenylation signal and Ad5 sequences, with the exception of the Ad5 left-terminus. In the resulting plasmid, pCMV-lucΔAd, the Ad5 ITR was replaced by the Sal-site-flanked ITR from plasmid pMLP/SAL by exchanging the XmnI-SacII fragments. The resulting plasmid, pCMV-lucΔAd/SAL, the Ad5 left terminus, and the CMV-driven luciferase gene were isolated as a SalI-SmaI fragment and inserted into the SalI and HpaI digested plasmid pBLCATS, to form plasmid pICL. Plasmid pICL is represented in FIG. 19 and its sequence is presented in FIG. 20.

Plasmid pICL contains the following features:

| | |
|---|---|
| nt.1–457 | Ad5 left terminus (Sequence 1-457 of human adenivorus type 5) |
| nt.458–969 | Human cytomegalovirus enhancer and immediate early promoter (Boshart et al, (1985) Cell 41: 521–530) (from plasmid pCMVβ, Clontech, Palo Alto, USA) |
| nt.970–1204 | SV40 19S exon and truncated 16/19S intron (from plasmid pCMVβ) |
| nt.1218–2987 | Firefly luciferase gene (from pMLP.luc) |
| nt.3018–3131 | SV40 tandem poly-adenylation signals from late transcript, derived from plasmid pBLCAT5) |
| nt.3132–5620 | pUC12 backbone (derived from plasmid pBLCAT5) |
| nt.4337–5191 | β-lactamase gene (Amp-resistance gene, reverse orientation) |

Plasmids pICLhac and pICLhaw

Plasmids pICLhac and pICLhaw were derived from plasmid pICL by digestion of pICL with the restriction enzyme Asp718. The linearized plasmid was treated with Calf-Intestine Alkaline Phosphatase to remove the 51 phosphate groups. The partially complementary synthetic single-stranded oligonucleotides Hp/asp1 (SEQ ID NO:39) and Hp/asp2 (SEQ ID NO:40) were annealed and phosphorylated on their 5' ends using T4-polynucleotide kinase.

Figure 16:
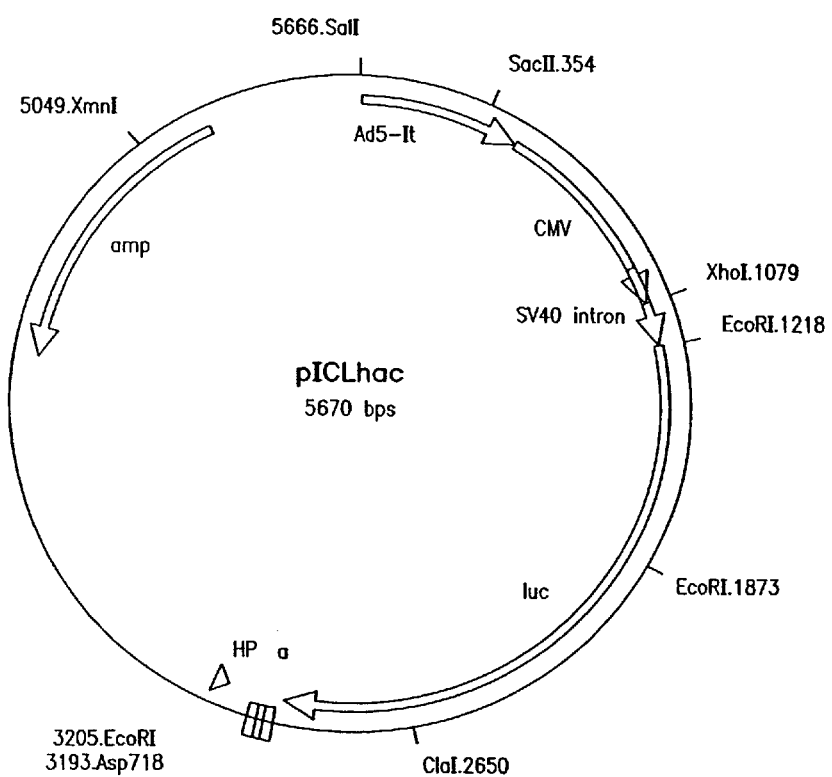
FIG. 16: Diagram of pICLhac. pICLhac contains all the elements of pICL (FIG. 19) but also contains the HP/asp sequence in the Asp718 site in an orientation that will produce the hairpin structure shown in FIG. 15, following linearization by Asp718 digestion and transfection into cells expressing adenoviral E2 proteins.
Figure 17:
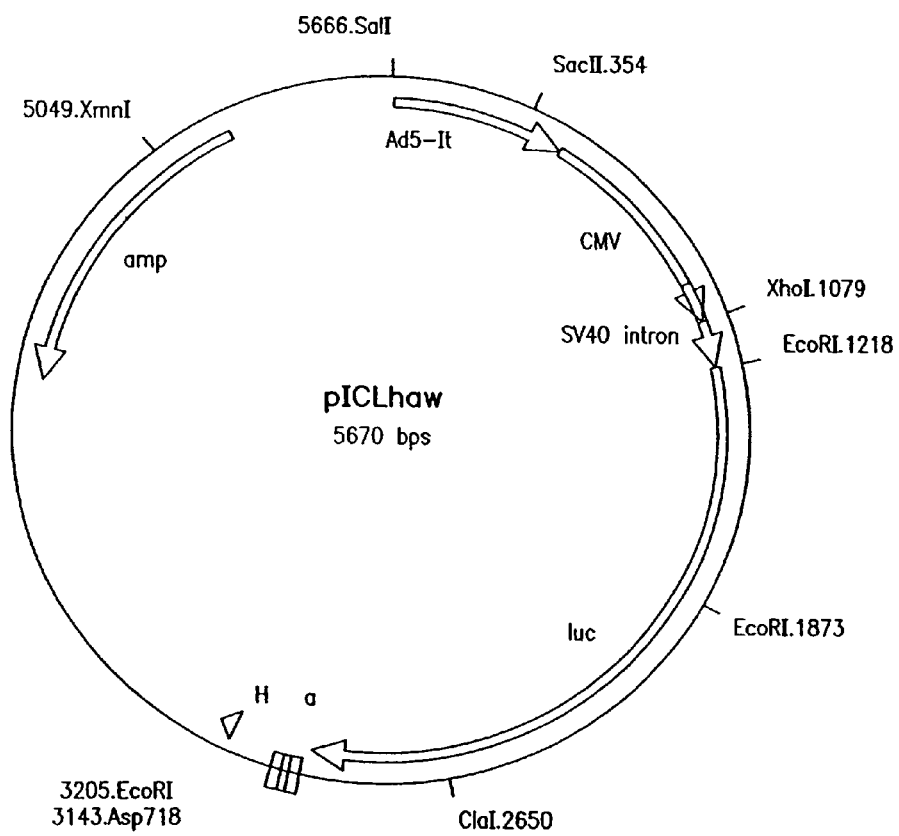
FIG. 17: Diagram of pICLhaw. pICLhaw is identical to pICLhac (FIG. 16) except that the inserted HP/asp sequence is in the opposite orientation.

The phosphorylated double-stranded oligomers were mixed with the dephosphorylated pICL fragment and ligated. Clones containing a single copy of the synthetic oligonucleotide inserted into the plasmid were isolated and characterized using restriction enzyme digests. Insertion of the oligonucleotide into the Asp718 site will at one junction recreate an Asp718 recognition site, whereas at the other junction the recognition site will be disrupted. The orientation and the integrity of the inserted oligonucleotide were verified in selected clones by sequence analyses. A clone containing the oligonucleotide in the correct orientation (the Asp718 site close to the 3205 EcoRI site) was denoted pICLhac. A clone with the oligonucleotide in the reverse orientation (the Asp718 site close to the SV40 derived poly signal) was designated pICLhaw. Plasmids pICLhac and pICLhaw are represented in FIGS. 16 and 17.

Figure 18:
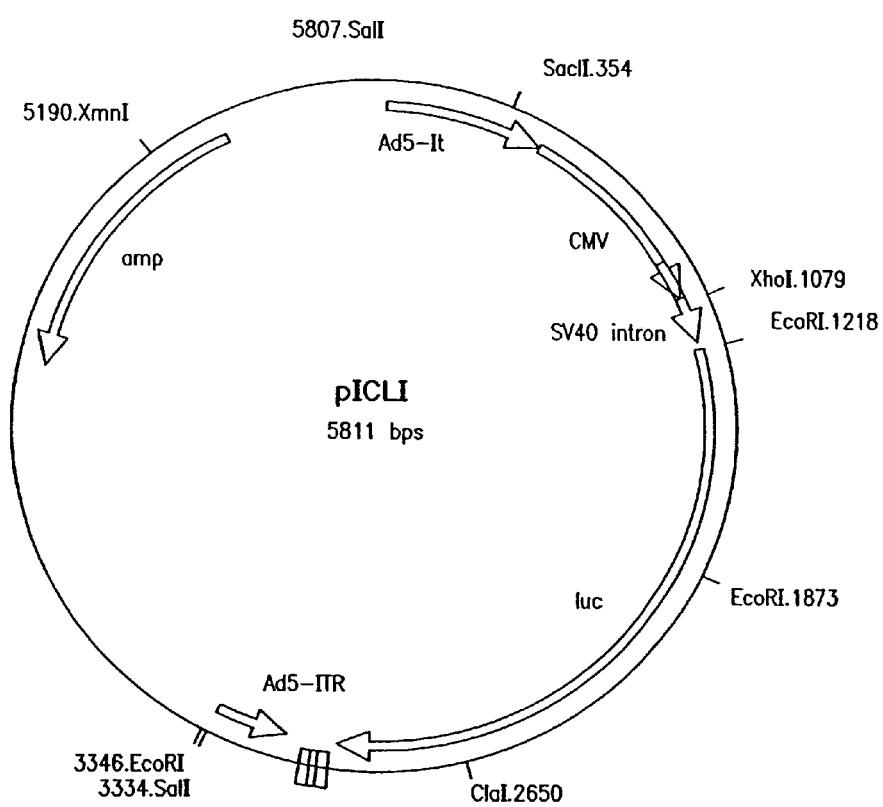
FIG. 18: Schematic representation of pICLI. pICLI contains all the elements of pICL (FIG. 19) but also contains an Ad5 ITR in the Asp718 site.

Plasmid pICLI was created from plasmid pICL by insertion of the SalI-SgrAI fragment from pICL, containing the Ad5-ITR, into the Asp718 site of pICL. The 194 bp SalI-SgrAI fragment was isolated from pICL and the cohesive ends were converted to blunt ends using *E. coli* DNA polymerase I (Klenow fragment) and dNTP's. The Asp718 cohesive ends were converted to blunt ends by treatment with mungbean nuclease. Clones that contained the ITR in the Asp718 site of plasmid pICL were generated by ligation. A clone that contained the ITR fragment in the correct orientation was designated pICLI (FIG. 18).

Recombinant adenovirus Ad-CMV-hcTK was constructed according to the method described in Patent application 95202213. Two components are required to generate a recombinant adenovirus. First, an adaptor-plasmid, which contains the left terminus of the adenoviral genome containing the ITR and the packaging signal, an expression cassette with the gene of interest, and a portion of the adenoviral genome which can be used for homologous recombination, is necessary. In addition, adenoviral DNA is needed for recombination with the aforementioned adaptor plasmid. In the case of Ad-CMV-hcTK, the plasmid pCM-V.TK was used as a basis. This plasmid contains nt.1–455 of the adenovirus type 5 genome, nt. 456–1204 derived from pCMVβ (Clontech, the PstI-StuI fragment that contains the CMV enhancer promoter and the 16S/19S intron from simian Virus 40), the Herpes Simplex Virus thymidine kinase gene (described in EP patent application 95202213.5), the SV40-derived polyadenylation signal (nt. 2533–2668 of the SV40 sequence), and the BglII-ScaI fragment of Ad5 (nt. 3328–6092 of the Ad5 sequence). These fragments are present in a pMLP10-derived (Levrero et al, (1991) *Gene* 101: 195–202) backbone. To generate plasmid pAD-CMVhc-TK, plasmid pCMV.TK was digested with ClaI (the unique ClaI-site is located just upstream of the TK open reading frame) and dephosphorylated with Calf-Intestine Alkaline Phosphate. To generate a hairpin-structure, the synthetic oligonucleotides HP/cla1 (SEQ ID NO:41) and HP/cla2 (SEQ ID NO:42) were annealed and phosphorylated on their 5'-OH groups with T4-polynucleotide kinase and ATP. The double-stranded oligonucleotide was ligated with the linearized vector fragment and used to transform *E. coli* strain Sure. Insertion of the oligonucleotide into the ClaI site will disrupt the ClaI recognition sites. The oligonucleotide contains a new ClaI site near one of its termini. In selected clones, the orientation and the integrity of the inserted oligonucleotide were verified by sequence analyses. A clone containing the oligonucleotide in the correct orientation (the ClaI site at the ITR side) was denoted pAd-CMV-hcTK. This plasmid was co-transfected with ClaI-digested wild-type adenovirus-type5 DNA into 911 cells. A recombinant adenovirus in which the CMV-hcTK expression cassette replaced the E1 sequences was isolated and propagated using standard procedures.

To study whether the hairpin can be used as a primer for reverse strand synthesis on the displaced strand after replication has started at the ITR, the plasmid pICLhac was introduced into 911 cells. The plasmid pICLhaw served as a control: it contains the oligonucleotide pair HP/asp 1 (SEQ ID NO:39) and 2 (SEQ ID NO:40) in the reverse orientation but is otherwise identical to plasmid pICLhac. Also included in these studies were plasmids pICLI and pICL. In pICLI, the hairpin is replaced by an adenoviral ITR. pICL contains neither a hairpin nor an ITR sequence. These plasmids served as controls to determine the efficiency of replication by virtue of the terminal hairpin structure. To provide the viral products other than the E1 proteins (these are produced by the 911 cells) required for DNA replication, the cultures were infected with the virus IG.Ad.MLPI.TK after transfection. Several parameters were studied to demonstrate proper replication of the transfected DNA molecules. First, DNA extracted from the cell cultures transfected with the aforementioned plasmids and infected with IG.Ad.MLPI.TK virus was analyzed by Southern blotting for the presence of the expected replication intermediates, as well as for the presence of the duplicated genomes. Furthermore, from the transfected and IG.Ad.MLPI.TK infected cell populations, virus was isolated that could transfer a luciferase marker gene into luciferase negative cells and express the gene.

Plasmid DNA of pICLhac, pCLhaw, pICLI, and pICL were digested with restriction endonuclease SalI and treated with mungbean nuclease to remove the four nucleotide single-stranded extension of the resulting DNA fragment. In this manner, a natural adenoviral 5' ITR terminus on the DNA fragment was created. Subsequently, both pICLhac and pICLhaw were digested with restriction endonuclease Asp718 to generate the terminus capable of forming a hairpin structure. The digested plasmids were introduced into 911 cells, using the standard calcium phosphate coprecipitation technique. Four dishes for each plasmid were prepared. During the transfection, two of the cultures of each plasmid were infected with the IG.Ad.MLPI.TK virus using five infectious IG.Ad.MLPI.TK particles per cell. At twenty-hours post transfection and forty hours post-transfection, one Ad.TK-virus-infected and one uninfected culture were used to isolate low molecular-weight DNA using the procedure devised by Hirt (as described in Einerhand et al, (1995) *Gene Therapy* 2:336–343). Aliquots of isolated DNA were used for Southern analysis. After digestion of the samples with restriction endonuclease EcoRI using the luciferase gene as a probe, a hybridizing fragment of approximately 2.6 kb was only detected in samples from the adenoviral-infected cells transfected with plasmid pICLhac. The size of this fragment was consistent with the anticipated duplication of the luciferase marker gene. This supports the conclusion that the inserted hairpin is capable of serving as a primer for reverse strand synthesis. The hybridizing fragment would be absent if the IG.Ad.MLPI.TK virus was omitted or if the hairpin oligonucleotide was inserted in the reverse orientation.

The restriction endoculease DpnI recognizes the tetranucleotide sequence 5'-GATC-3' but cleaves only methylated DNA (plasmid DNA propagated in, and derived from, *E. coli*, not DNA that has been replicated in mammalian cells). The restriction endonuclease MboI recognizes the same sequences but cleaves only unmethylated DNA (DNA propagated in mammalian cells). DNA samples isolated from the transfected cells are incubated with MboI and DpnI and analyzed with Southern blots. These results demonstrated that large DpnI-resistant fragments, which were absent in the MboI treated samples, were present only in the cells transfected with pICLhac and the pICLI. These data demonstrate that replication and duplication of the fragments occur only after transfection of pICLI and pICLhac.

These data demonstrate that in adenoviral-infected cells, linear DNA fragments that have an adenoviral-derived ITR at one terminus and a nucleotide sequence that can anneal to sequences on the same strand at the other terminus, when present in single-stranded form, generate a hairpin structure and will be converted to structures that have ITR sequences on both ends. The resulting DNA molecules will replicate by the same mechanism as the wild-type adenoviral genomes.

Example 4

Demonstration that the DNA Molecules that Contain a Luciferase Marker Gene, a Single Copy of the ITR, the Encapsidation Signal, and a Synthetic DNA Sequence that is Capable of Forming a Hairpin Structure are Sufficient to Generate DNA Molecules that Can Be Encapsidated into Virions To demonstrate that the DNA molecules generated in Example 3, which contain two copies of the CMV-luc marker gene, can be encapsidated into virions, virus was harvested from the remaining two cultures via three cycles of freeze/thaw crushing and was used to infect murine fibroblasts. Forty-eight hours after infection, the infected cells were assayed for luciferase activity. To exclude the possibility that the luciferase activity had been induced by transfer of free DNA rather than by virus particles, virus stocks were treated with DNaseI to remove DNA contaminants. Furthermore, as an additional control, aliquots of the virus stocks were incubated for 60 minutes at 56° C. The heat treatment does not affect the contaminating DNA but does inactivate the viruses. Significant luciferase activity was only found in the cells infected with the virus stocks derived from IG.Ad.MLPI.TK-infected cells transfected with pICLhc and pICLI. No significant luciferase activity was found in the non-infected cells or in the infected cells transfected with pICLhw and pICL. Heat inactivation, but not DNaseI treatment, completely eliminated luciferase expression, demonstrating that adenoviral particles, but not free (contaminating) DNA fragments, were responsible for transfer of the luciferase reporter gene.

The results demonstrate that these small viral genomes can be encapsidated into adenoviral particles and suggest that the ITR and the encapsidation signal are sufficient for encapsidation of linear DNA fragments into adenoviral particles. These adenoviral particles can be used for efficient gene transfer. When introduced into cells that contain and express at least some of the adenoviral genes (namely E1, E2, E4, and L, and VA), recombinant DNA molecules that include at least one ITR, at least part of the encapsidation signal, and a synthetic DNA sequence that is capable of forming a hairpin structure have the intrinsic capacity to autonomously generate recombinant genomes that can be encapsidated into virions. Such genomes and vector systems can be used for gene transfer.

Example 5

Demonstration that DNA Molecules, which Contain Nucleotides 3510–35953 of the Adenovirus Type 5 Genome and a Terminal DNA Sequence that is Capable of Forming a Hairpin Structure, Can Replicate in 911 Cells In order to develop a replicating DNA molecule that can provide the adenoviral products necessary to allow the ICLhac vector genome and similar minimal adenovectors to be encapsidated into adenoviral particles by helper cells, the Ad-CMV-hcTK adenoviral vector was developed. The annealed oligonucleotide pair (Table I) HP/cla 1 and 2 was inserted between the CMV enhancer/promoter region and the thymidine kinase gene. The vector Ad-CMV-hcTK was propagated and produced in 911 cell using standard procedures. This vector was grown and propagated exclusively as a source of DNA used for transfection. DNA of the adenoviral Ad-CMV-hcTK was isolated from viral particles that had been purified using CsCl density-gradient centrifugation by standard techniques. The viral DNA was digested with restriction endonuclease ClaI. The digested DNA was size-fractionated on a 0.7% agarose gel and the large fragment was isolated and used for further experiments. Cultures of 911 cells were transfected with the large ClaI-fragment of the Ad-CMV-hcTK DNA using standard calcium phosphate co-precipitation techniques. Similar to the previous experiments with pICLhac, the Ad-CMV-hc replicates starting at the right-hand ITR. Once the 1-strand is displaced, a hairpin can be formed at the left-hand terminus of the fragment. This facilitates DNA polymerase elongation of the chain towards the right-hand side. The process proceeds until the displaced strand is completely converted to its double-stranded form. Finally, the right-hand ITR is recreated and normal adenoviral replication-initiation and elongation occur at this location. The polymerase reads through the hairpin, thereby duplicating the molecule. The input DNA molecule of 33250 bp, which had an adenoviral ITR sequence at one terminus and a DNA sequence that had the capacity to form a hairpin structure on the other terminus, is duplicated so that both ends contain an ITR sequence. The resulting DNA molecule consists of a palindromic structure of approximately 66500 bp.

This structure is detected in low-molecular weight DNA extracted from transfected cells using Southern analysis. The palindromic nature of the DNA fragment can be demonstrated by digestion of the low-molecular weight DNA with suitable restriction endonucleases and Southern blotting with the HSV-TK gene as the probe. This molecule can self-replicate in the transfected cells by virtue of the adenoviral gene products that are present in the cells. In part, the adenoviral genes are expressed from templates that are integrated in the genome of the target cells (namely, the E1 gene products), while the other genes reside in the replicating DNA fragment itself. This linear DNA fragment cannot be encapsidated into virions. Not only does it lack all the DNA sequences required for encapsidation, but its size is much too large to be encapsidated.

Example 6

Demonstration that DNA Molecules, which Contain Nucleotides 3503–35953 of the Adenovirus Type 5 Genome and a Terminal DNA Sequence that is Capable of Forming a Hairpin Structure, Can Replicate in 911 Cells and Can Provide the Helper Functions Required to Encapsidate the pICLI and pICLhac Derived DNA Fragments The purpose of the next series of experiments is to demonstrate that the DNA molecule described in Example 5 can be used to encapsidate the minimal adenovectors described in Examples 3 and 4.

The large fragment isolated after endonuclease ClaI-digestion of Ad-CMV-hcTK DNA was introduced into 911 cells (as described in Example 5) along with endonuclease SalI, mungbean nuclease, endonuclease Asp718-treated plasmid pICLhac, or as a control similarly treated plasmid pICLhaw. After 48 hours, virus was isolated by freeze/thaw crushing of the transfected cell population. The virus preparation was treated with DNaseI to remove contaminating free DNA. The virus was used subsequently to infect Rat2 fibroblasts. Forty-eight hours post infection, the cells were assayed for luciferase activity. Significant luciferase activity was only demonstrated in the cells infected with virus isolated from the cells transfected with pICLhac. No activity was demonstrated in the cells infected with virus isolated from the cells transfected with pICLhaw. Heat inactivation of the virus prior to infection completely abolished the luciferase activity, indicating that the luciferase gene was transferred by a viral particle. Infection of 911 cells with the virus stock did not result in any cytopathological effects, demonstrating that pICLhac was produced without any infectious helper virus being propagated on 911 cells. These results demonstrate that the proposed method can be used to produce stocks of minimal-adenoviral vectors that are completely devoid of infectious helper viruses that are able to replicate autonomously on adenoviral-transformed human cells or on non-adenoviral transformed human cells.

Example 7

Construction of Plasmids for the Generation and Production of Minimal Adenoviral Vectors A minimal adenoviral vector contains, as operably linked components, the adenoviral-derived cis elements necessary for replication and packaging, with or without foreign nucleic acid molecules to be transferred. Recently, the lower limit for efficient packaging of adenoviral vectors has been determined at 75% of the genome length (Parks and Graham, 1997). To allow flexible incorporation of various lengths of stuffer fragments, a multiple cloning site (MCS) was introduced into a minimal adenoviral vector. To obtain a minimal adenoviral vector according to the invention, the following constructs were made: pAd/L420-HSA (FIG. 19) was digested with BglII and SalI and the vector-containing fragment was isolated. This fragment contains the left ITR and packaging signal from Ad5 and the murine HSA gene driven by a modified retroviral LTR. The right adenoviral ITR was amplified by PCR on a pBr/Ad.BamHI-rITR template DNA using the following primers: PolyL-ITR: 5'-AAC-TGC-AGA-TCT-ATC-GAT-ACT-AGT-CAA-TTG-CTC-GAG-TCT-AGA-CTA-CGT-CAC-CCG-CCC-CGT-TCC-3' (SEQ ID NO:14) and ITR-BSN: 5'-CGG-GAT-CCG-TCG-ACG-CGG-CCG-CAT-CAT-CAA-TAA-TAT-ACC-3' (SEQ ID NO:15). The amplified fragment was digested with PstI and BamHI and cloned into pUC119 digested with the same enzymes. After sequence confirmation of correct amplification of the ITR and the MCS, a BglII-SalI fragment was isolated and cloned into the BglII/SalI-digested pAd/L420-HSA fragment described above. The resulting clone was named pAd/L420-HSA.ITR.

Figure 24:
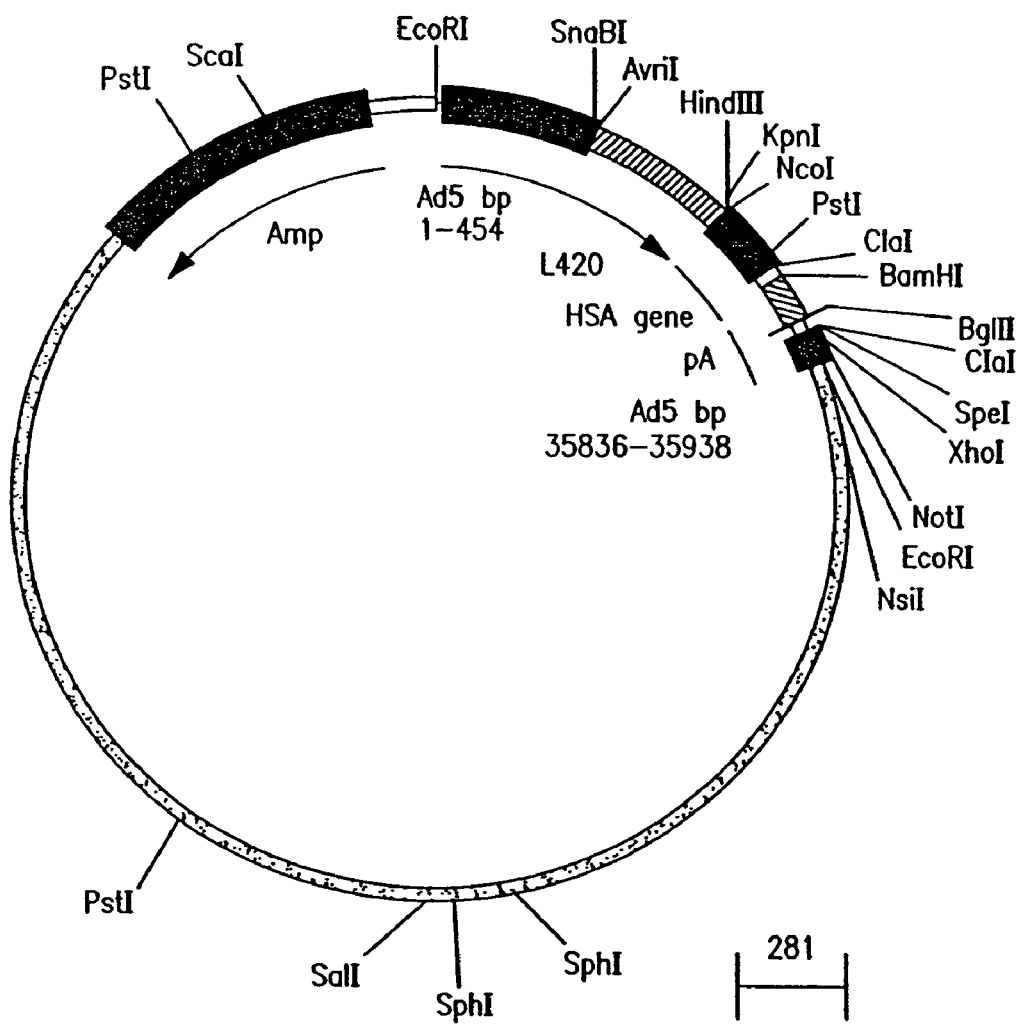
FIG. 24: Drawing of minimal adenoviral vector pMV/L420H

To be able to manipulate constructs of lengths exceeding 30 kb, the minimal adenoviral vector pAd/L420-HSA.ITR was subcloned in a cosmid vector background. For this purpose, the cosmid vector pWE15 was modified to remove restriction sites in the backbone. pWE15 was digested with PstI and fragments of 4 kb and 2.36 kb were isolated from an agarose gel and ligated together. The resulting clone, stripped of the SV40 ori/early promoter and neomycine resistance coding sequence, was named pWE20. Then, pWE20 was digested with ClaI and HindIII and the sticky ends were filled in with Klenow enzyme. A 6354 bp blunt fragment was ligated to a phosphorylated NsiI linker with the following sequence: 5'-CGATGCATCG-3' (SEQ ID NO:16). The ligated DNA was phenol/chloroform extracted, precipitated with EtOH to change buffers, and digested with excess NsiI. Digested DNA was separated from the linkers by electrophoresis, isolated, and then religated. The resulting clone was named pWE25. Correct insertion of the NsiI linker was confirmed by restriction enzyme digestion and sequencing. To construct the minimal adenoviral vector, pAd/L420-HSA.ITR was digested with ScaI and NotI. The resulting 2 kb fragment, containing part of the ampicillin gene and the adeno ITRs, was cloned into pWE25 digested with ScaI and NotI. The resulting clone was named pMV/L420H (FIG. 24). This clone allows easy manipulation to exchange the promoter and/or gene and also allows insertion of DNA fragments of not-easily-cloned lengths into normal plasmid backbones.

Plasmid pMV/CMV-LacZ was made by exchanging the L420-HSA fragment (SnaBI-BamHI) for a fragment from pcDNA3-nlsLacZ (NruI-BamHI) that contains the CMV promoter and LacZ coding sequences. pcDNA3-nlsLacZ was constructed by insertion of a KpnI-BamHI fragment obtained after PCR amplification of the nlsLacZ coding sequences into pcDNA3 (Invitrogen) digested with KpnI and BamHI. The PCR reaction was performed on a pMLP-.nlsLacZ template DNA using the primers 1: 5'-GGG-GTG-GCC-AGG-GTA-CCT-CTA-GGC-TTT-TGC-AA-3' (SEQ ID NO:17) and 2: 5'-GGG-GGG-ATC-CAT-AAA-CAA-GTT-CAG-AAT-CC-3' (SEQ ID NO:18). Correct amplification and cloning were confirmed by assaying P-galactosidase expression in a transient transfection experiment in 911 cells.

The vector pAd/MLPnlsLacZ was made as follows: pMLP10 (Levrero et al, (1991) *Gene* 101: 195–202) was digested with HindIII and BamHI and ligated, in a three-part ligation, to a 3.3 kb AvrII-BamHI fragment from L7RHbgal (Kalderon et al, (1984) *Cell* 499–509), and a synthetic linker with HindIII and XbaI overhang. The linker was made by annealing two oligonucleotides of sequence 5'-AGC TTG AAT TCC CGG GTA CCT-3' (SEQ ID NO:19) and 5'-CTA GAG GTA CCC GGG AAT TCA-3' (SEQ ID NO:20). The resulting clone was named pMLP.nlsLacZ/-Ad. Next, pMLP.nlsLacZ/-Ad was digested with BamHI and NruI and the vector containing fragment was ligated to a 2766 bp BglII-ScaI fragment from pAd5SalB (Bernards et al, (1982) *Virology* 120:422–432). This resulted in the adapter plasmid pMLP.nlsLacZ (described in EP 0 707 071).

Figure 23:
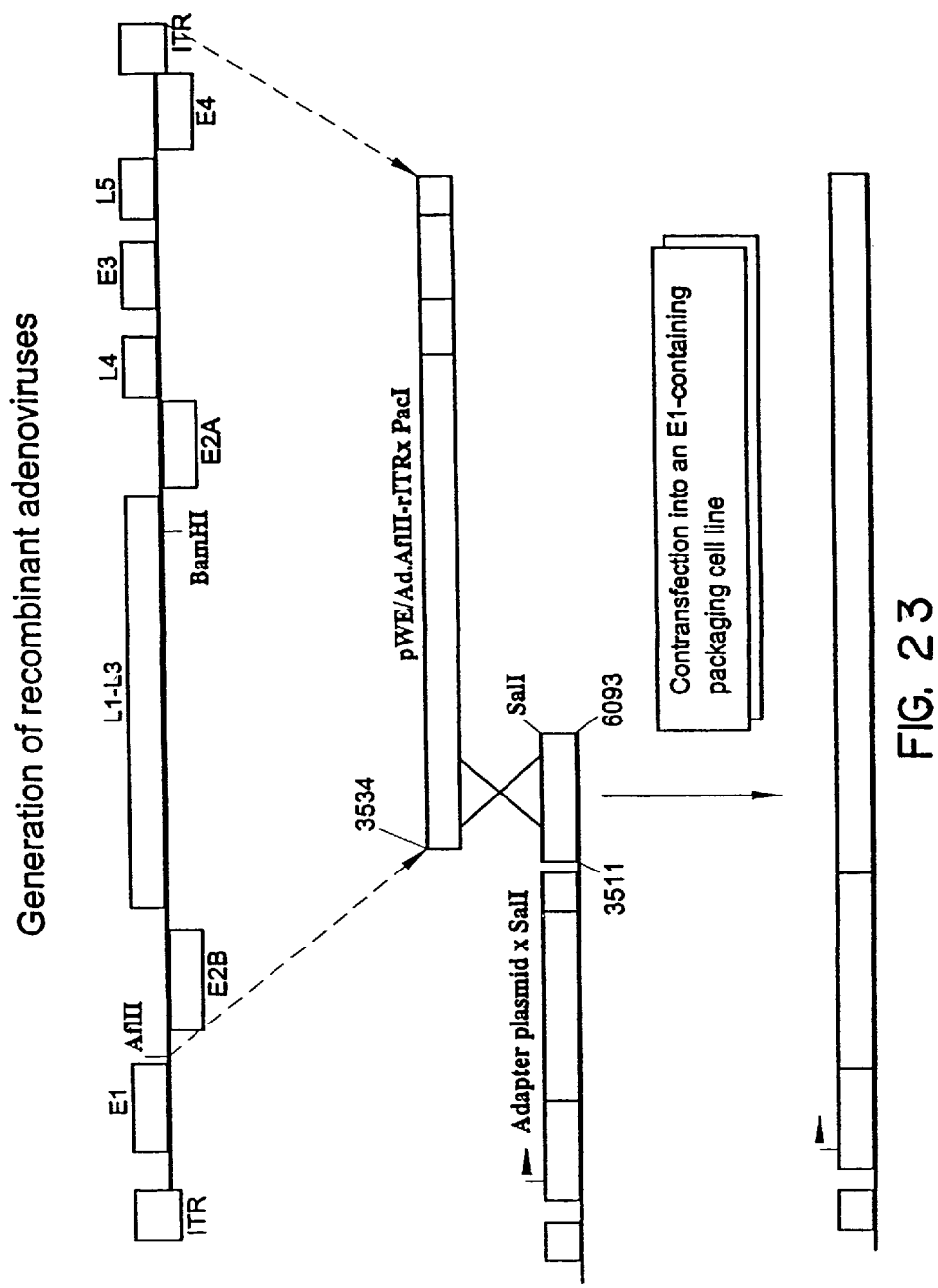
FIG. 23: Schematic representation of the generation of recombinant adenoviruses using a plasmid-based system. In the top of the figure, the genome organization of Ad5 is shown with filled boxes representing the different early and late transcription regions and flanking ITRs. The middle of the figure represents the two DNAs used for a single homologous recombination while the bottom of the figure represents the recombinant virus after transfection into packaging cells.

Propagation of a minimal adenoviral vector can only be achieved by expression of adenoviral gene products. Expression of adenoviral gene products at levels high enough to sustain production of large quantities of virus requires replication of the coding nucleic acid molecule. Usually, replicating helper viruses are used to complement the minimal adenoviral vectors. However, the present invention provides packaging systems for minimal adenoviral vectors without the use of helper viruses. One of the methods of the invention makes use of a replicating DNA molecule that contains the 5'-ITR and all adenoviral sequences between bp 3510 and 35938, i.e., the complete adenoviral genome except for the E1 region and the packaging signal. Construct pWE/Ad.Δ5' (FIG. 23) is an example of a replicating molecule according to the invention that contains two adenoviral ITRs. pWE/Ad.Δ5' as made in a cosmid vector background from three fragments. First, the 5' ITR from Ad5 was amplified using the following primers: ITR-EPH: 5'-CGG-AAT-TCT-TAA-TTA-AGT-TAA-CAT-CAT-CAA-TAA-TAT-ACC-3' (SEQ ID NO:21) and ITR-pIX: 5'-ACG-GCG-CGC-CTT-AAG-CCA-CGC-CCA-CAC-ATT-TCA-GTA-CGT-ACT-AGT-CTA-CGT-CAC-CCG-CCC-CGT-TCC- 3' (SEQ ID NO:22). The resulting PCR fragment was digested with EcoRI and AscI and cloned into vector pNEB193 (New England Biolabs) digested with the same enzymes. The resulting construct was named pNEB/ITR-pIX. Sequencing confirmed correct amplification of the Ad5 sequences in the left ITR (Ad5 sequences 1 to 103) linked to the pIX promoter (Ad5 sequences 3511 to 3538), except for a single mismatch with the expected sequence according to GenBank (Accession no.: M73260/M29978), i.e., an extra C residue was found just upstream of the AflII site. This ITR-pIX fragment was isolated with EcoRI and AflII and ligated to an EcoRI-AflII vector fragment containing Ad5 sequences 3539–21567. The latter fragment was obtained by digestion of pBr/Ad.Cla-Bam (supra) with EcoRI and partially with AflII. The resulting clone was named pAd/LITR(Δ5')-BamHI. The final construct pWE/Ad.Δ5' was made by ligating cosmid vector pWE15.Pac (supra) digested with PacI to pAd/LITR(Δ5')-BamHI digested with PacI/BamHI and pBr/Ad.Bam-rITR.pac#2 (supra) digested with PacI/BamHI (FIG. 23).

An alternative method to produce packaging systems for minimal adenoviral vectors without the use of helper viruses according to the invention is to use a replicating DNA molecule. The replicating DNA molecule must contain the complete adenoviral genome, except for the E1 region and the packaging signal, and also one of the ITRs in the molecule must be replaced by a fragment containing a DNA sequence complementary to a portion of the same strand other than the ITR so that the molecule is able to form a hairpin structure (FIG. 10). In a non-limiting example, the DNA sequence complementary to a portion of the same strand other than the ITR is derived from the adeno-associated virus (AAV) terminal repeat. Such a replicating DNA molecule is made following the same cloning strategy as described for pWE/Ad.Δ5', except that the AAV terminal repeat is linked to part of the adenoviral pIX promoter. To this end, the adenoviral ITR sequences between the HpaI and SpeI sites in construct pNEB/ITR-pIX were exchanged for the AAV ITR by introducing the PvuII/XbaI fragment from psub201(+) containing the AAV ITR (Samulski et al, (1989) *J. Virol.* 63:3822–3828). This results in construct pWE/AAV.Δ5' that replicates in an E1 complementing cell line.

Another alternative packaging system for minimal adenoviral vectors is described infra and makes use of the replication system of SV40. A functional helper molecule according to this method contains at least the adenoviral sequences necessary to sustain packaging of a minimal construct, but does not contain the E1 sequences and packaging signal and preferably also lacks ITRs. This adenoviral-derived entity has to be present on a vector that contains, besides the sequences needed for propagation in bacteria, an origin of replication from SV40 virus. Transfection of this molecule, along with the minimal adenoviral vector described supra, into a packaging cell line (e.g., PER.C6) expressing, besides the E1 proteins, SV40 derived Large T antigen proteins, results in Large T-dependent replication of the adenoviral-derived helper construct. This replication leads to high levels of adenoviral proteins necessary for replication of the minimal adenoviral vector and packaging into virus particles. In this way, there is no sequence overlap that leads to homologous recombination between the minimal adenoviral vector construct and the helper molecule. In addition, there is no sequence overlap that leads to homologous recombination between the helper molecule and minimal adenoviral vector on the one side and the E1 sequence in the packaging cell on the other side.

Figure 26A:
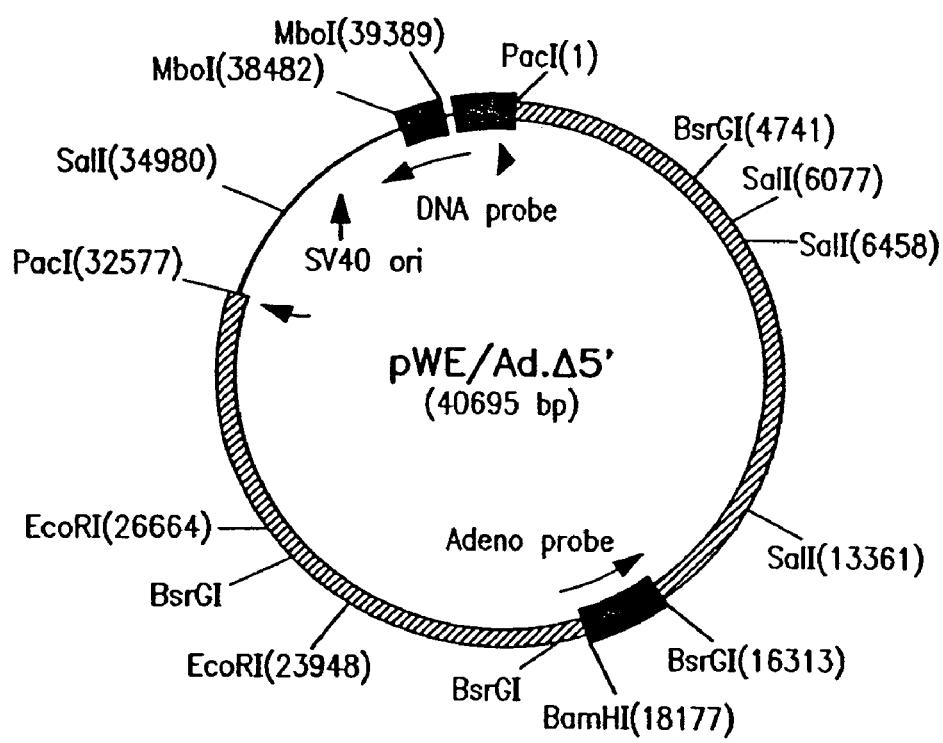
FIG. 26A shows a schematic representation of construct pWE/Ad.Δ5'. The location of the SV40 ori sequence and the fragments used to prepare probes are indicated. Evidence for SV40-LargeT/ori mediated replication of large adenoviral constructs in COS-1 cells.

Replication of a 40 kb adenoviral construct was investigated in cells expressing SV40 Large T proteins. Cells ($2\times10^6$ Cos-1) were transfected in a T25 flask with the following constructs complexed with lipofectamine reagent (Life techn.): the 8 kb cosmid vector pWE.pac, the 40.5 kb construct pWE/Ad.AflII-rITR, and three clones (#1, #5 and #9) of the 40.6 kb construct pWE/Ad.Δ5' (described infra). Control transfections were carried out with the constructs pWE.pac and pWE/Ad.AflII-rITR digested with PacI enzyme and a CMV-LacZ expression vector without the SV40 ori sequence. Transfection efficiency was 50% as determined by a separate transfection using the CMV-LacZ vector and X-gal staining after 48 hrs. All cells were harvested 48 hrs. after transfection and DNA was extracted according to the Hirt procedure (as described in Einerhand et al, (1995) *Gene Therapy* 2:336–343). Final pellets were resuspended in 50 μl TE+RNase (20 μg/ml) and 10 μl samples were digested with MboI (35 units overnight at 37° C.). Undigested samples (5 μl) and MboI digested samples were run on a 0.8% agarose gel, transferred to a nylon filter (Amersham), and hybridized to radioactive probes according to standard procedures. One probe was derived from an 887 bp DpnI fragment from the cosmid vector pWE.pac; the other probe was derived from a 1864 bp BsrGI-BamHI fragment from adenoviral sequences. These probes hybridize to an 887 bp band and a 1416 bp band, respectively, in MboI digested material. Input DNA from bacterial origin is methylated and therefore not digested with MboI. Therefore, it is possible to specifically detect DNA that is replicated in eukaryotic cells. FIG. 26A shows a schematic presentation of the construct pWE/Ad.Δ5' and also shows the locations of the SV40 origin of replication, the pWE-derived probe, and the adenoviral-derived probe. The lower part of the FIG. presents the autoradiograms of the Southern blots hybridized to the adenoviral probe (B) and the pWE probe (C). See legends for explanation of sample loading. These experiments show that all lanes that contain material from Cos-1 cells that were transfected with plasmids harbouring an SV40 ori sequence contain MboI sensitive DNA and show a specific band of the expected length. The bands specific for replication in the lanes with Cos-1 cells transfected with PacI digested material (lanes B 17/18 and C 15–18) probably result from incomplete PacI digestion. From these experiments it can be concluded that large DNA fragments can be replicated with the SV40 LargeT/ori system in eukaryotic cells.

Example 8

A functional adenoviral helper molecule lacking ITR sequences was constructed starting with the clone pWE/Ad.D5' described supra. pWE/Ad.D5' was digested with Bst1107I and the 17.5 kb vector-containing fragment was religated to give pWE/Ad.D5'-Bst1107I. This clone was then used to amplify the 3' part of the adenoviral genome sequences without the right ITR. A 2645 bp PCR fragment was generated using the primers Ad3'/Forw: 5'-CGG AAT TCA TCA GGA TAG GGC GGT GG-3' (SEQ ID NO:23) and Ad3'/Rev: 5'-CGG GAT CCT ATC GAT ATT TAA ATG TTT TAG GGC GGA GTA ACT TG-3' (SEQ ID NO:24). The amplified fragment was digested with EcoRI and BamHI and subcloned into pBr322 digested with the same enzymes. After confirmation of correct amplification by sequencing, the 2558 bp SbfI-ClaI fragment of the clone was recloned into pWE/Ad.D5'-Bst1107I digested with the same enzymes. The resulting construct lacks the right ITR and is named pWE/ΔrI-Bst1107I. Next, the left ITR was replaced by a linker with a PacI and AflII overhang constructed by annealing the following primers: PA-pIX1 5'-TAA GCC ACT AGT ACG TAC TGA AAT GTG TGG GCG TGG C-3' (SEQ ID NO:25) and PA-pIX2 5'-TTA AGC CAC GCC CAC ACA TTT CAG TAC GTA CTA GTG GCT TAA T-3' (SEQ ID NO:26). The removal of the left ITR restored correct sequence of the pIX promoter. This clone is named pWE/ΔITR-Bst1107I. Correct insertion of the double stranded linker was confirmed by sequencing. The deleted Bst1107I fragment was then cloned back into pWE/ΔITR-Bstl 1107I and the correct orientation was checked by restriction digestion. The resulting clone is named pWE/Ad-H. Following transfection of this DNA molecule into packaging cells that express adenoviral E1 proteins and the SV40 Large T antigen, replication of the molecule takes place, resulting in high levels of adenoviral proteins encoded by the adenoviral entity on that molecule.

Example 9

Miniaturized, Multiwell Production of Recombinant Adenoviral Vectors

A 96-well microtiter tissue culture plate (plate 1) (Greiner, NL, catalogue #6555180) was coated with poly-L-lysine (PLL, 0.1 mg/ml) (Sigma) dissolved in sterile water by incubating each well for 20–120 minutes at room temperature. Alternatively, precoated 96-well plates can be used (Becton Dickinson). After the incubation with PLL, each well was washed two times with 100 μl sterile water and dried at room temperature for at least two hours. The day before transfection, PER.C6 cells were harvested using trypsin-EDTA and counted. The cells were then diluted to a suspension of 45,000 cells per 100 μl, followed by seeding 100 μl of cell suspension per well in the PLL coated 96-well plates. The next day, 2.6 μl of SalI linearized pAd/CMV-LacZ (1 μg/μl), 2.6 μl of PacI linearized pWE-Ad.AflII-rITR plasmid DNA (1 μg/μl), and 95 μl serum free Dulbecco's Modified Eagles Medium (DMEM) were mixed with 25.6 μl lipofectamine diluted in 74.4 μl serum free DMEM by adding the lipofectamine to the DNA mix. The DNA/lipofectamine mixture was left at room temperature for 30 minutes after which 1.3 ml serum free medium was added. The latter mixture was then added (30 μl per well) to PER.C6 seeded wells that were washed with 200 μl DMEM prior to transfection. After 3 hours in a humidified $CO_2$ incubator (37° C., 10% $CO_2$), 200 μl DMEM with 10% fetal calf serum and 10 mM $MgCl_2$ was added to each well and the plates were returned to the humidified $CO_2$ incubator (37° C., 10% $CO_2$). The next day, the medium of each well was replaced with 200 μl DMEM, 10% FCS, 10 mM $MgCl_2$. The plates were then left in the humidified $CO_2$ incubator for an additional three days, after which the wells were subjected to freezing at −20° C. for at least 1 hour followed by thawing and resuspension by repeated pipetting. Transfection efficiency was determined using lacZ staining in additional plates and found to be approximately 40% for each transfected well of PER.C6 cells. An aliquot of 100 μl of freeze/thawed transfected cells was transferred to each well of a plate with new PER.C6 cells seeded as described above, except without PLL coated plates (plate 2). The second 96-well plate was checked for CPE. At least 5% of the wells showed clear CPE after 2 days. Four days after infection with the lysate from plate 1, the plate was subjected to one freeze/thaw cycle and 10 μl from each lysed well was added to wells of a plate seeded with A549 cells ($1\times10^4$ cells per well seeded in 100 μl in DMEM, 10% FCS the day before). Two days after infection, the wells were stained for lacZ activity. Of the infected wells, 96% were infected and stained blue. All wells stained and a large number of wells showed 100% blue staining implying transduction of all cells with adenoviral vector carrying lacZ. The adenoviral titer of well-produced virus is around $10^6$–$10^7$ infectious units per ml as determined by extrapolation from MOI experiments in tissue culture flasks.

The subject invention discloses methods and compositions for the high throughput delivery and expression in a host of sample nucleic acid(s) encoding product(s) of unknown function. Methods are described for the construction of complementing cell lines, libraries of adenoviral derived plasmids containing sample nucleic acids, packaging the adenoviral-derived plasmids into adenoviral vectors, infecting a host with the adenoviral vectors that express the product(s) of the sample nucleic acid(s) in the host, identifying an altered phenotype induced in the host by the product(s) of the sample nucleic acids, and thereby assigning a function to the product(s) encoded by the sample nucleic acids. The sample nucleic acids can be, for example, synthetic oligonucleotides, DNAs, or cDNAs and can encode, for example, polypeptides, antisense nucleic acids, or GSEs. The methods can be fully automated and performed in a multiwell format to allow for convenient high throughput analysis of sample nucleic acid libraries.

Example 10

Miniaturized, Multiwell Production of E1 and E2A Deleted Recombinant Adenoviral Vectors Carrying Therapeutic and Marker Transgenes To allow the construction of cDNA libraries with a representative repertoire of cDNA sequences, the cloning capacity of the miniaturized adenoviral production system PER.C6/E2A, a derivative of PER.C6, was used. This cell line allows the production of a vector with three deletions of adenoviral expression cassettes: E1, E2A, and E3. These three deletions allow the theoretical cloning of vectors with transgene sizes of up to about 10.5 kb in length. The production of E1 and E2A deleted vectors carrying a variety of human and mouse cDNAs, as well as additional marker genes, is shown.

Figure 27:
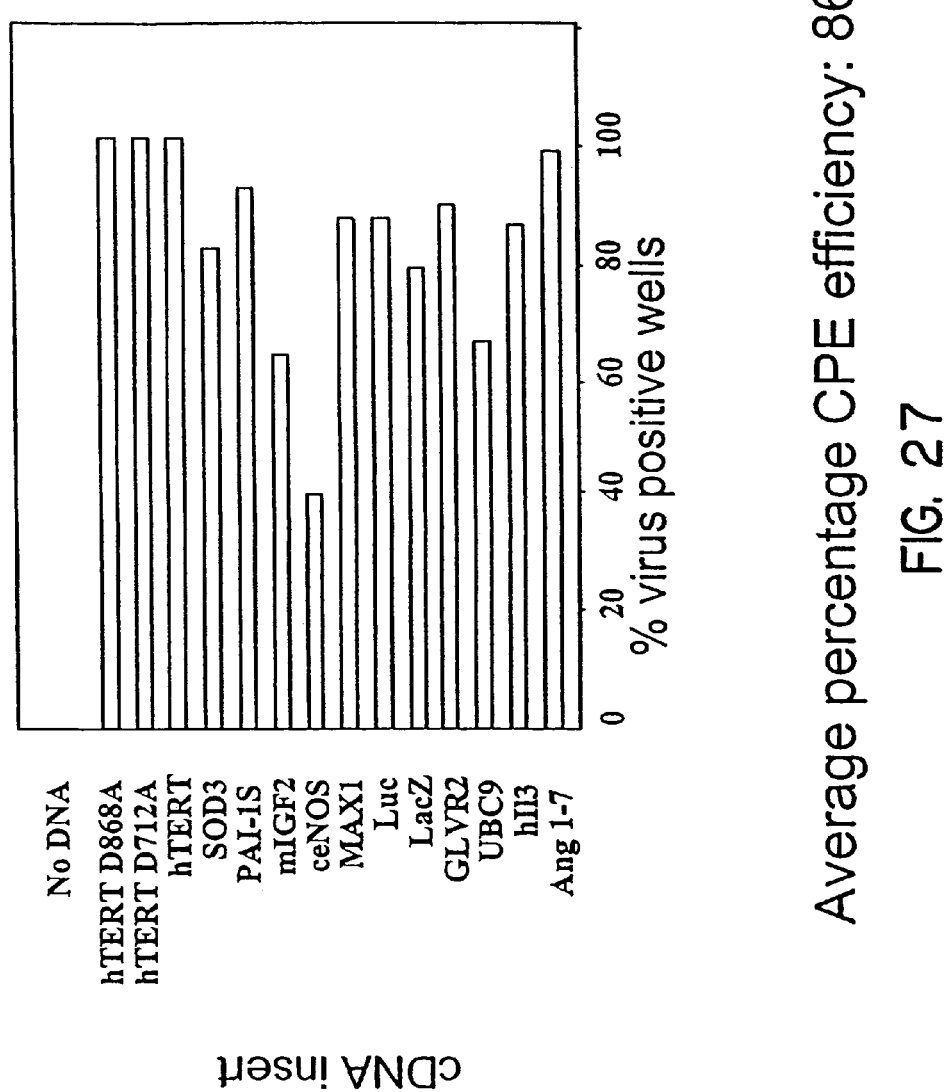
FIG. 27: Production of E1/E2A deleted adenoviral vectors and its efficiency in miniaturized PER.C6/E2A based production system (Example 10).

The day before transfection, PER.C6/E2A cells were harvested using trypsin-EDTA and counted. The cells were then diluted with culture medium (DMEM with 10% fetal bovine serum and 10 mM $MgCl_2$) to a suspension of 22,500 cells per 100 µl followed by seeding 100 µl per well in poly-L-lysine (PLL) coated 96-well plates (Becton Dickinson). The next day, 2.6 µg of the linearized adapter molecules and 2.6 µg of PacI linearized pWE/Ad.AflII-rITR.deltaE2A plasmid DNA (see example 19) in 100 µl serum free Dulbecco's Modified Eagles Medium (DMEM) were mixed with 25.6 µl lipofectamine diluted in 74.4 µl serum free DMEM by adding the lipofectamine mixture to the DNA mix. The DNA/lipofectamine mixture was left at room temperature for 30 minutes, after which 1.3 ml serum free medium was added. The latter mixture (30 µl per well) was then added to PER.C6/E2A seeded wells that were washed with 200 µl DMEM prior to transfection. After 3 hours in a humidified $CO_2$ incubator (39° C., 10% $CO_2$), 200 µl DMEM with 10% fetal bovine serum and 10 MM $MgCl_2$ was added to each well and the plates were returned to the humidified $CO_2$ incubator (39° C., 10% $CO_2$). The next day, the medium of each well was replaced with 200 µl DMEM with 10% fetal bovine serum and 10 mM $MgCl_2$. The plates were then returned to the humidified $CO_2$ incubator (32° C., 10% $CO_2$) for an additional seven days, after which the wells were subjected to freezing at −20° C. overnight followed by thawing and resuspension by repeated pipetting. A 100 µl aliquot of the freeze/thawed transfected cells was transferred to each well of a plate with fresh PER.C6/E2A cells seeded on normal 96-well-tissue culture plates (plate 2) as described above. The second 96-well plate, with PER.C6/E2A cells incubated and thus infected with freeze/thawed cell lysate of the first transfected plate, was checked for CPE formation (see FIG. 27) and stored at −20° C. In FIG. 27, the percentage of virus producing cells (CPE positive wells) scored after propagation of the freeze/thawed transfected cells to new PER.C6/E2A cells is depicted. Clearly, the miniaturized system subject of this application allows the efficient production of deltaE1/E2A double deleted vectors with a variety of transgene inserts.

Example 11

Quantification of Adenoviral Vector Particles Produced in Miniaturized Production System Using PER.C6/E2A Adenoviral plaque assays were performed in order to determine the titer of the adenoviral vectors produced in one well of a 96-well-tissue-culture plate. PER.C6/E2A cells were harvested using trypsin-EDTA and counted. The cells were then diluted with culture medium (DMEM with 10% fetal bovine serum and 10 mM $MgCl_2$) to a suspension of $1.5 \times 10^6$ cells per 2 ml, followed by seeding 2 ml per well on PLL coated 6-well plates (Becton Dickinson). Microtiter plates containing adenoviral vector lysates were thawed and 50 µl of a randomly chosen well of each adenovirus was used to make serial 10-fold dilutions of the adenovirus in culture medium. The medium of the PER.C6/E2A cells, which were seeded the same day, was replaced with 2 ml per well diluted virus and the 50–60% monolayer was infected for approximately 16 hours in a humidified $CO_2$ incubator (32° C., 10% $CO_2$). After infection, the cells were overlayed with 3 ml per well agarose mix (2×MEM, 2% fetal bovine serum, 1 mM $MgCl_2$, PBS, and 1% agarose) and returned to the humidified $CO_2$ incubator (32° C., 10% $CO_2$). After two weeks, nine individual plaques, including one negative control, were transferred to 200 µl of culture medium and stored at −20° C. An aliquot of 25 µl of this material was used to infect PER.C6/E2A cells ($2.25 \times 10^4$ cells per well in 100 µl), seeded in 96-well tissue culture plates one day prior to infections. This was incubated in the humidified $CO_2$ incubator (32° C., 10% $CO_2$) until the presence of full CPE was observed and was subsequently stored at −20° C.

The final titer of the adenoviruses, produced in a well of a 96-well tissue culture plate, was determined one week after picking the individual plaques. In FIG. 28, the titer of adenoviruses, in pfu/ml, produced in a well of a 96-well plate is depicted. Average titers of $0.8 \pm 0.7 \times 10^9$ pfu/ml imply that depending on the MOI needed in a particular cell based assay in a functional genomics screen using 384-well plates, sufficient virus is produced for 400–4000 assays (MOIs of 100–10). This allows multiple screens using one library.

Example 12

The Quality of Adenoviral Vector Produced in a Microtiter Plate on PER.C6/E2A Cells To test for functionality of the produced recombinant adenovirus, the following functional assays were performed on cells infected with the respective adenoviral vectors: β-Galactosidase assay, hIL3 assay, luciferase assay, ceNOS assay, GLVR2 assay, and EGFP assay.

β-Galactosidase Assay

A549 cells were harvested using trypsin-EDTA and counted. The cells were then diluted with culture medium (DMEM with 10% heat-inactivated FBS) to a suspension of 10,000 cells per 100 µl, followed by seeding 100 µl per well of 96-well tissue culture plates. The next day, all CPE-positive PER.C6/E2A wells containing lacZ-transducing adenoviruses, as well as negative controls (both primary wells and plaques amplified on fresh PER.C6/E2A cells), were used to infect the A549 cells. For this purpose, the frozen wells were thawed and 20 µl of each well of the freeze/thawed cell lysate was used to infect one well of the A549 cells. Two days after infection, the medium of the infected A549 cells was removed and each well was washed two times with 100 µl PBS (phosphate-buffered saline). After washing, the cells were fixated for five minutes at room temperature by adding 100 µl fixative (1% formaldehyde, 0.2% glutardialdehyde) per well. After washing the cells two times with PBS, 100 µl X-gal staining solution (0.2 M $K_3Fe(CN)_6$, 0.2 M $K_4Fe(CN)_6$, X-gal in DMSO and 0.1 M $MgCl_2$) was added to each well.

All of the wells that were infected with CPE-positive wells stained blue. A large number of wells showed 100% blue staining implying transduction of all cells with adenoviral vector carrying lacZ (see FIG. 29).

hIL-3 Assay

The day before infection, the A549 cells were seeded as described above. The next day, all CPE-positive PER.C6/E2A wells containing human interleukin-3 (hIL-3) transducing adenoviruses (both primary wells and plaques amplified on fresh PER.C6/E2A cells), as well as positive and negative controls, were used to infect the A549 cells. For this purpose, the frozen wells were thawed and 20 µl of each well of the freeze/thawed cell lysate was used to infect one well of the A549 cells. Three days after infection, the quantity of hIL-3 concentrations in 100 µl of the supernatants of the infected A549 cells was determined using the human IL-3 immunoassay (Quantikine™).

Figure 29:
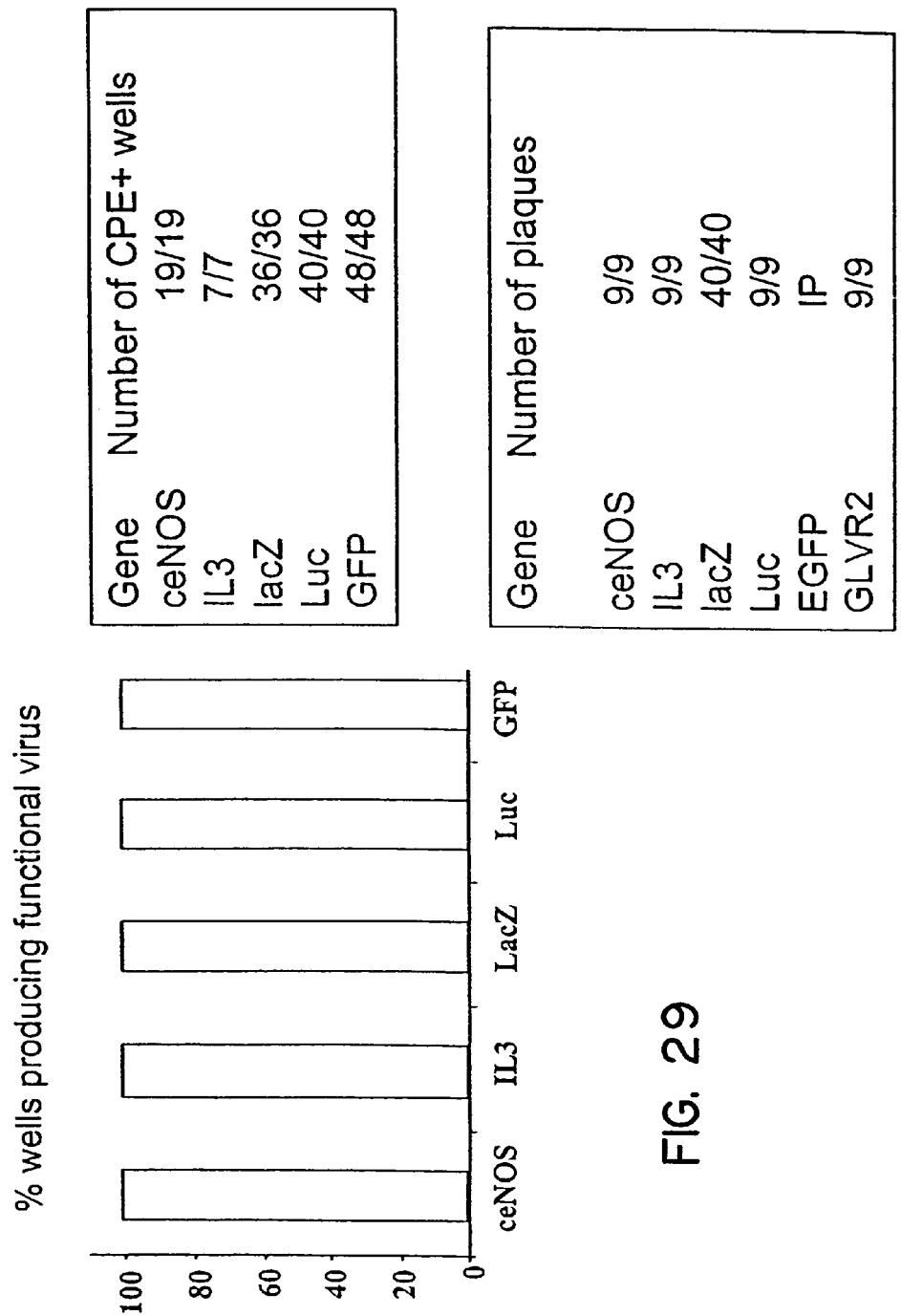
FIG. 29: Fidelity of adenoviral vector production miniaturized PER.C6/E2A based production system for a number of marker and human cDNA transgenes (Example 12).

All of the wells that were infected with CPE-positive wells showed high hIL-3 concentrations (see FIG. 29).

Luciferase Assay

The day before infection, the A549 cells were seeded as described above. The next day, all CPE-positive PER.C6/E2A wells containing luciferase transducing adenoviruses (both primary wells and plaques amplified on fresh PER.C6E2A cells), as well as positive and negative controls, were used to infect the A549 cells. For this purpose, the frozen wells were thawed and 20 µl of each well of the freeze/thawed cell lysate was used to infect one well of the A549 cells. Two days after infection, the medium of the infected A549 cells was removed and each well was washed with 100 µl PBS. After adding 100 µl 1× reporter lysis buffer (Promega), the wells were subjected to freeze/thawing followed by measuring the luciferase activity in 20 µl of the freeze/thawed cell lysates.

All of the wells that were infected with CPE-positive wells showed a high luciferase activity (see FIG. 29).

ceNOS Assay

PER.C6/E2A cells were harvested using trypsin-EDTA and counted. The cells were then diluted with culture medium (DMEM devoid of phenol-red with 10% FBS and 10 mM $MgCl_2$) to a suspension of 22,500 cells per 100 µl, followed by seeding 100 µl per well of 96-well tissue culture plates. The next day, all CPE-positive PER.C6/E2A wells containing ceNOS transducing adenoviruses (both primary wells and plaques amplified on fresh PER.C6/E2A cells), as well as positive and negative controls, were used to infect the PER.C6/E2A cells. For this purpose, the frozen wells were thawed and 20 µl of each well of the freeze/thawed cell lysate was used to infect one well of the PER.C6/E2A cells. Three days after infection, 50 µl color solution [GreissA reagent (0.1% N-(1-Naphthyl)Ethylenediamine) and GreissB reagent (25% Sulfanylamide in 5% phosphoric acid) in a 1:1 ratio] was added to 50 µl of the supernatants of the infected PER.C6E2A cells. After adding the color solution, supernatants with a positive ceNOS activity turned pink.

All of the wells that were infected with CPE-positive wells showed a positive ceNOS activity (see FIG. 29).

GLVR2 Amphotropic Receptor Assay

Adenoviral mediated transduction of GLVR2, the receptor for amphotropic retroviruses, was measured essentially as described (Lieber et al, 1995), except for the use of an amphotropic retroviral supernatant transferring a truncated version of the human nerve growth receptor (NGFR). Retroviral transduction of the CHO cells infected with GLVR2 adenoviral supernatant was detected using anti-NGFR antibodies and a flow cytometer.

All of the wells that were infected with CPE-positive PER.C6/E2A wells containing GLVR2 transducing adenoviruses (plaques amplified on fresh PER.C6/E2A cells) showed a positive GLVR2 activity (see FIG. 29).

EGFP Assay

EGFP expression was measured on a microtiter plate fluorimeter or by flow cytometer.

In conclusion, virus produced from wells as well as virus plaque purified (i.e., cloned) from producing wells showed transduction of their respective transgenes. Therefore, the system shows high fidelity for the production of functional adenoviral vectors and produces no aberrant forms for the transgene inserts tested.

Example 13

DNA Isolation Methods Generating Sufficiently Purified Plasmid DNA for Production of Adenoviral Vectors in PER.C6 and PER.C6-E2A Cells It is well known that plasmid DNA that is used for transfection studies in eukaryotic cells must be of sufficient purity and free of endotoxins to achieve high levels of transfection efficiencies. Conventional methods for purifying plasmid DNA from *E. coli* include an alkaline lysis procedure (Birnboim, H. C. and Doly, J, (1979) and a rapid alkaline lysis procedure for screening recombinant plasmid DNA (Nucleic Acid Res. 7: 1513–1522) followed by either banding of the plasmid DNA on cesium chloride (CsCI) gradients (see Sambrook, J. et al, eds. (1989) Molecular cloning: a laboratory manual, $2^{nd}$ edition, Cold Spring Harbor Laboratory Press) or by binding and elution on an anion-exchange resin (see, for example, Qiagen™ plasmid purification methods of Qiagen Inc.; and Concert™ plasmid purification systems of Life Technologies). However, all of these methods are unsuited for high throughput DNA isolations because they require considerable hands-on time per isolation. Therefore, to reduce the amount of time and costs per isolation, other methods were examined.

Methods that were examined using the SalI linearized adenoviral adapter plasmid pCLIP-SalI LacZ and the E2A deleted helper fragment pWE/Ad.AflII-rITR.deltaE2A: alkaline lysis followed by column based plasmid purification (Qiagen)

1. alkaline lysis followed by isopropanol precipitation, and solubilization in TE buffer
2. alkaline lysis followed by isopropanol precipitation, and solubilization in TE buffer containing RNAse at 10 microgram per ml
3. alkaline lysis followed by isopropanol precipitation, and solubilization in TE buffer containing RNAse at 10 microgram per ml, followed by phenol/chloroform extraction and ethanol precipitation
4. Standard cetyltrimethylammonium bromide (CTAB) plasmid isolation (Nucleic Acids Res, $16^{20}$;1488)
5. Standard CTAB plasmid isolation, but solubilization in TE buffer containing RNAse at 10 microgram per ml, followed by phenol/chloroform extraction Equal volumes of the resulting plasmids were linearized with SalI, followed by phenol/chloroform extraction and ethanol precipitation. Following solubilization in TE buffer and verification on an agarose gel, equal amounts of DNA (as determined by the ethidium bromide staining) were transfected into PER.C6/E2A cells with lipofectamine as described under examples 9 and 10. After propagation, wells were scored for CPE formation as a measure of virus production.

Figure 30:
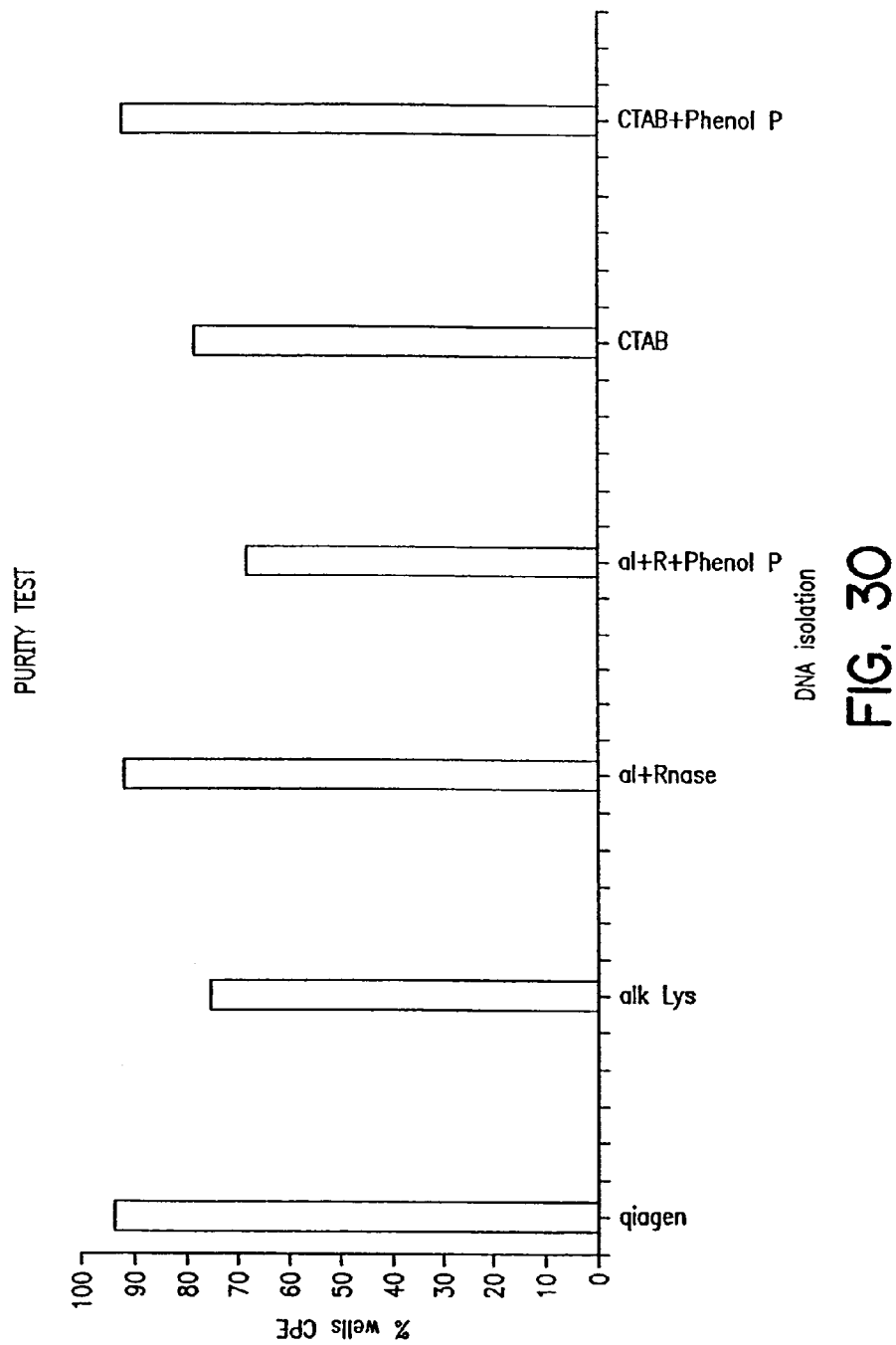
FIG. 30: Percentage of wells showing CPE formation after transfection of PER.C6/E2A cells with pCLIP-LacZ, purified by 6 different protocols (Example 13). Qiagen: standard alkaline lysis followed by Qiagen plasmid purification; AlkLys: alkaline lysis followed by isopropanol precipitation, and solubilization in TE buffer; AL+RNAse: alkaline lysis followed by isopropanol precipitation, and solubilization in TE buffer containing RNase at 10 microgram per ml; AL+R+phenol: alkaline lysis followed by isopropanol precipitation, and solubilization in TE buffer containing RNase at 10 microgram per ml, followed by phenol/chloroform extraction and ethanol precipitation; cetyltrimethylammoniumbromide (CTAB): Standard CTAB plasmid isolation; CTAB+phenol: Standard CTAB plasmid isolation, but solubilization in TE buffer containing RNase at 10 microgram per ml, followed by phenol/chloroform extraction.

In FIG. 30, the percentage of wells showing CPE formation (CPE positive) after transfection of PER.C6/E2A cells transfected with pCLIP-LacZ, purified by 6 different protocols, is represented. Qiagen: standard alkaline lysis followed by Qiagen plasmid purification; AlkLys: alkaline lysis followed by isopropanol precipitation and solubilization in TE buffer; AL+RNAse: alkaline lysis followed by isopropanol precipitation and solubilization in TE buffer containing RNAse at 10 microgram per ml; AL+R+phenol: alkaline lysis followed by isopropanol precipitation and solubilization in TE buffer containing RNAse at 10 microgram per ml, followed by phenol/chloroform extraction and ethanol precipitation; CTAB: standard CTAB plasmid isolation; CTAB+phenol: standard CTAB plasmid isolation, but solubilization in TE buffer containing RNAse at 10 microgram per ml is followed by phenol/chloroform extraction. It is evident that the quality of DNA is not a major determinant for transfection of, and virus production in, PER.C6/E2A cells, as all 6 differently isolated plasmids produced similar numbers of wells with CPE.

In conclusion, for high throughput transfection of, and virus production in, PER.C6/E2A cells, it is sufficient to use plasmid DNA that was precipitated with 0.6 volumes of isopropanol after standard alkaline lysis, followed by solubilization in TE buffer.

Example 14

The Use of Unpurified, Digested Adapter and Helper Adenoviral DNA Molecules for the Generation of Adenoviral Vectors in a Miniaturized Format In order to minimize the overall costs and chances for errors in the procedure, and to maximize the throughput when producing recombinant adenoviruses in a high throughput fashion, it is desirable to eliminate as many steps as possible. Any improvement here is also applicable when generating adenoviral vectors on a smaller, low throughput scale. The most difficult step to automate when producing recombinant adenoviruses is the DNA clean-up step by phenol/chloroform extraction (p/c) prior to transfection of cells with the DNA. DNA is purified after linearization in order to obtain enyzme-free DNA. This is thought to be important to obtain high percentages of viral generation after transfection with the adapter and helper DNA molecules. An additional motivation to eliminate the p/c purification procedure is the risk of traces of phenol and chloroform in the DNA used for transfection, which can have a negative effect on the generation of viruses. Therefore, it was investigated whether the complicated p/c purification step could be omitted from the miniaturized adenoviral vector generation protocol subject of this application. This method forms the basis of high throughput construction of libraries, such as sense or antisense cDNA expression libraries. Several independant experiments were performed in order to test the effect of omitting the p/c step on the efficiency of adenoviral vector generation. The p/c purification was carried out as follows: after digesting the adapter-DNA and rITR-DNA with the appropriate restriction enzymes, an equal volume of phenol and chloroform (1:1) was added, mixed thoroughly, and centrifuged (5 minutes, 14,000 rpm). The aqueous phase was transferred to a new micro-centrifuge tube and an equal volume of chloroform was added. Again, this was mixed thoroughly and centrifuged (5 minutes, 14,000 rpm). The aqueous phase was transferred to a new microcentrifuge tube and 0.1 times the volume of 3 M sodium acetate (pH 5.2) and 2.5 times the volume of absolute ethanol were added. The mixture was kept at −20° C. for at least 20 minutes, subsequently centrifuged (15 minutes, 14,000 rpm), and the pellet was washed with 70% ethanol. The DNA was air-dried and a suitable volume of sterile water was added (in Laminar Airflow Cabinet). Transfection was carried out as described in examples 9 and beyond using PER.C6/E2A cells. All viruses were E1 and E2A deleted and were produced in PER.C6/E2A cells.

Figure 31A:
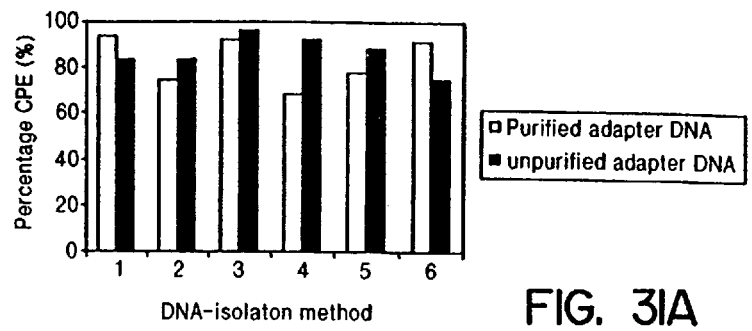
FIG. 31: Effect of using digested plasmid for transfection without phenol-chloroform extraction (Example 14). The results of all experiments are depicted and expressed as percentage of wells showing CPE formation. A) LacZ-adapter DNA was isolated using 6 different isolation methods (see example 13); 1: Qiagen, 2: Alkaline lysis, 3: Alkaline lysis+RNAse treatment, 4: Alkaline lysis+RNAse treatment+p/c purification of DNA before linerization, 5: cetyltrimethylammoniumbromide (CTAB), 6: CTAB+p/c purification of DNA before linerization, rITR was p/c purified, B) Purified and unpurified EGFP- and EYFP-adapter DNA, rITR was p/c purified, C) EGFP-adapter DNA and rITR were tested purified and unpurified; 1: Both adapter and rITR purified (control), 2: rITR purified, adapter DNA unpurified, 3: rITR and adapter unpurified.

In the first experiment, adapter-DNA containing β-galactosidase (pAd5.Clipsal.LacZ) of 6 different DNA isolation protocols (as described in example 13) were analyzed and compared for their efficiency in producing adenoviral vector by monitoring for CPE formation. Half of the DNA samples were p/c purified after linearization using the appropriate restriction enzyme (SalI) while the remaining half of the samples were not purified after linearization. The restriction enzyme was heat inactivated to exclude inadvertant digestion of the helper DNA because a SalI site is present in the rITR delta E2A helper fragment. In this experiment, p/c purified rITR delta E2A helper DNA was used. In all of the DNA isolation methods, CPE was formed efficiently (FIG. 31A). In some cases, elimination of the p/c purification step gave higher CPE efficiencies. In conclusion, adenoviral adapter DNA digested with the linearizing enzyme can be used for transfection without prior purification.

Figure 31B:
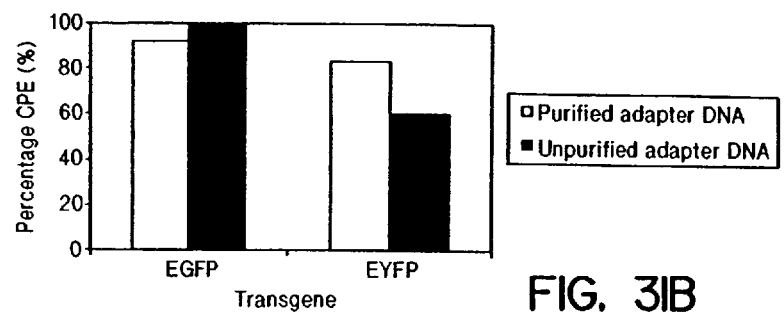
Figure 31C:
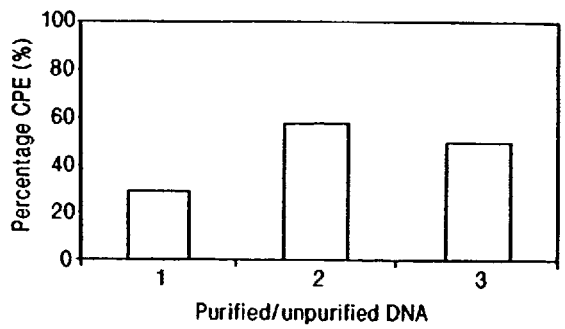

In the second experiment, the difference between using a purification step and not using a purification step were compared using adapter-DNA containing Enhanced Green Fluorescent Protein (EGFP) and Enhanced Yellow Fluorescent Protein (EYFP) (pAd5.Clippac.EGFP and pAd5.Clippac.EYFP). The adapter plasmid-DNA was isolated using the Qiagen isolation method. The rITR delta E2A used was p/c purified. The adapter-DNA was linearized using PacI, which did not have to be heat inactivated before transfection because there is no PacI site in the rITR. No consistent differences were found in the percentages of CPE observed and production of adenoviral vector was efficient (FIG. 31B).

The third experiment tested the need to purify the rITR. The adapter-DNA contained EGFP (pAd5.Clippac.EGFP) and was isolated using the Qiagen isolation method (FIG. 30C). The results after transfection and propagation show that the purification of both adapter and rITR DNA after digestion is not necessary.

Taking all results in account, it is clear that the phenol chloroform purification step is not necessary to obtain high percentages of CPE and for adenoviral vector production. The above described modification of the procedure, as for example described in examples 9 and 10, results in a significant increase in throughput when generating adenoviral vector libraries in an automated setup and when making vectors manually on a smaller scale.

Example 15

Production of Adenoviral Vectors in Relation to Stability of the Produced Vector Generation of recombinant denoviruses, as described in the various examples herein, indicates that a functional adenovirus will be formed approximate five to eleven days after amplification of the virus produced on the transfected PER.C6 cells, and their derivatives, grown in multiwell tissue culture plates. The observation of a cytopathic effect (CPE) indicates that functional adenovirus has been formed and is replicating. The nature of the transgene inserts and variations in the experimental conditions cause the kinetics of virus generation to be variable. In a high throughput setting where large numbers of wells and plates containing adenoviral vector are handled, it is desirable to have a single point in time to harvest the plates and score for adenoviral vector production. The above mentioned variations in adenoviral vector generation may be overcome by postponing the harvest of the plates as long as possible, i.e. until the slower wells also have produced adenoviral vector. For this purpose, the stability of recombinant lacZ adenovirus (pCLIP-lacZ), once it is produced starting from low numbers of virus to higher numbers of virus, was tested. Then, the titers (see example 11) and lacZ transduction-potential of the virus after up to three weeks were determined.

PER.C6/E2A cells were seeded in two rows of 96-well microtiter tissue culture plates using $4 \times 10^4$ cells/well. The plates were incubated overnight at 39° C. The next day, PER.C6/E2A was infected with purified LacZ-adenoviral vector of serotype 5. The infections were done at different MOIs according to the scheme below (21 plates in total).

TABLE 1

| | 1 | 2 | 3 | 4 | 5 | 6 | 7 | 8 | 9 | 10 | 11 | 12 |
|---|---|---|---|---|---|---|---|---|---|---|---|---|
| A | | | | | | | | | | | | |
| B | 0.01 | 0.01 | 0.01 | 0.1 | 0.1 | 0.1 | 1 | 1 | 1 | 10 | 10 | 10 |
| C | 0 | 0 | 0 | 0 | 0 | 0 | 0 | 0 | 0 | 0 | 0 | 0 |

To determine the effect of temperature on stability of adenoviruses produced in wells, seven plates were incubated at 32° C., seven plates at 34° C., and seven plates at 39° C. At days 2, 3, 6, 9, 13, 16, and 21 after infection, one plate corresponding to each incubation temperature was frozen. The cell lysates were used in the following experiments.

In order to determine the transduction potential of the produced adenoviruses, A549 cells were seeded in 96-well microtiter tissue culture plates with $1 \times 10^4$ cells/well and incubated overnight at 37° C. Then, the cells were infected with 50 μl cell lysate and incubated at 37° C. After two days, the cells were screened for toxicity followed by lacZ staining. A clear toxic effect was observed with increasing MOI and increasing time of infection. The table below is a summary of when all cells stained blue in all wells.

TABLE 2

| | moi | # days after infection. |
|---|---|---|
| 32° C. | 0.001 | 9 |
| | 0.01 | 9 |
| | 0.1 | 6 |
| | 1 | 6 |
| 34° C. | 0.001 | 6 |
| | 0.01 | 6 |
| | 0.1 | 6 |
| | 1 | 6 |
| 37° C. | 0.001 | 6 |
| | 0.01 | 6 |
| | 0.1 | 3 |
| | 1 | 3 |

Three weeks after infection, 100% of blue cells/well were still observed and thus all cells with adenoviral vector carrying lacZ. Thus, this showed no decreased infectivity upon incubation up to 3 weeks.

Figure 32:
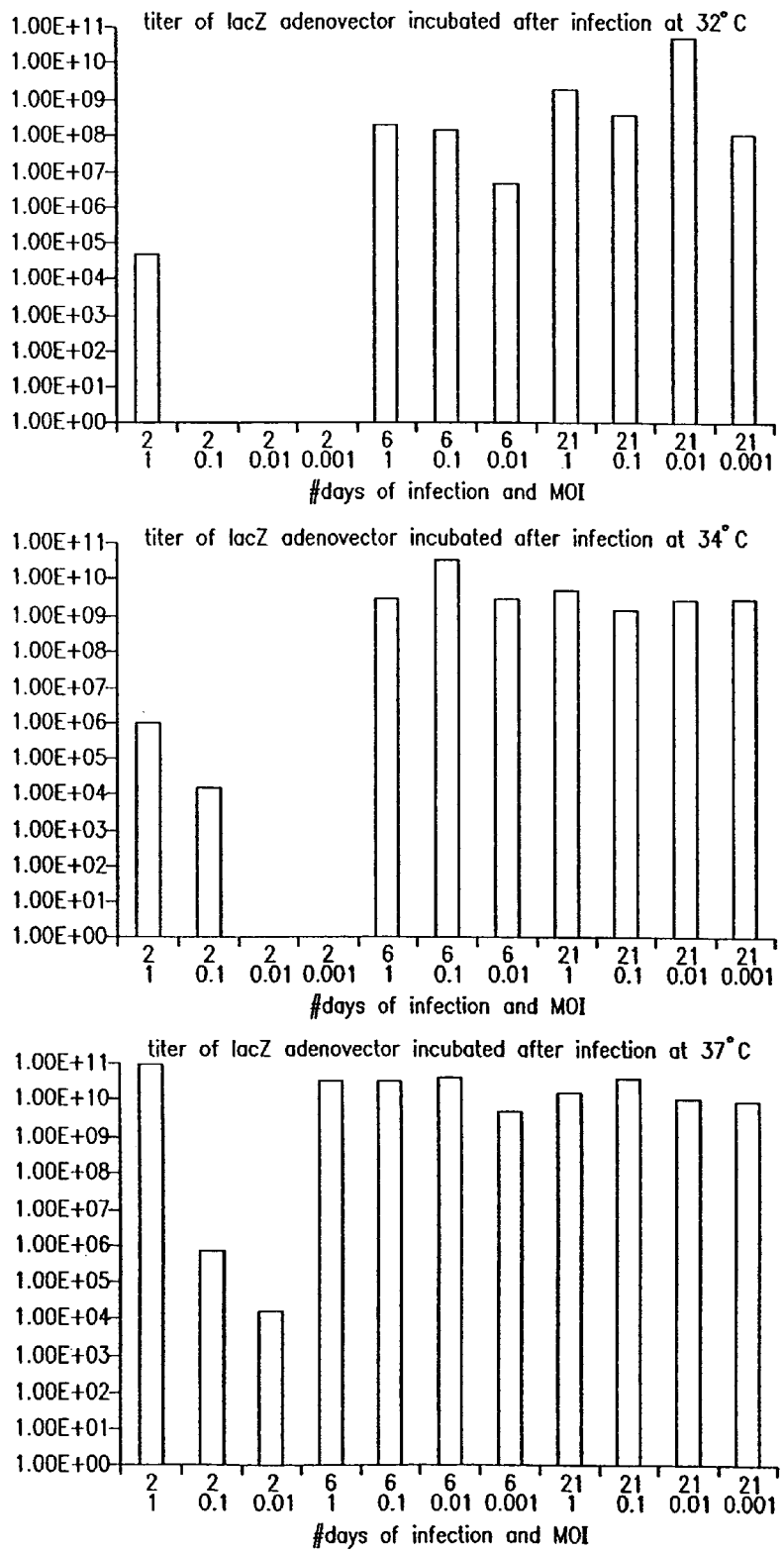
FIG. 32: Stability of adenoviral vectors produced in miniaturized format and incubated for up to three weeks at three different temperatures and measured using a plaque forming assay for adenoviral vectors (Example 15).

In order to determine the number of infectious viral particles in the cell lysate, a titration assay was performed for the samples which were incubated 2, 6, and 21 days after infection corresponding to each incubation temperature and MOI. Three weeks after infection, an average titer of $2 \times 10^{10}$ pfus per ml was observed. An overview of the titers is given in FIG. 32.

The above mentioned experiments indicate that variations in adenoviral vector generation may be overcome by postponing the harvest of the plates as long as possible, i.e. until the slower wells also have produced adenoviral vector. Although a clear toxic effect is seen with increasing MOI and increasing time of infection, there is no decreased infectivity and no decrease in titer of the produced adenoviral vector.

Example 16

Miniaturized Production of Adenoviral Vectors Carrying Antisense DNA Sequences and Expressing Antisense mRNA Sequences Decreasing endogenous gene expression in screens using antisense cDNA expression libraries is very useful in functional genomics programs. Individual antisense adenoviral vectors can also be used for gene validation and the development of an antisense gene therapeutic. An example is the use of antisense-Vascular Endothelial Growth Factor (VEGF). VEGF is a pivotal molecule in tumoral angiogenesis that promotes endothelial cell growth and plays a major role in neovascularization and growth of gliomas. The VEGF-antisense molecule inhibits tumor growth in vivo. (Seock-Ah et al., 1999, Cancer research 59, 895–900). Constructing large, complex antisense libraries in adenoviral vectors are valuable and very useful for Functional Genomics screening programs.

PER.C6/E2A cells were cotransfected with linearized adapter DNA, containing a defined human cDNA sequence in antisense orientation, and linearized rITR delta E2A helper DNA, as described in example 10. The genes cloned in antisense orientation in adapter DNA are described in Table 3. For pCLIP, two variants were used with SalI or PacI as the site to linearize depending on the transgene inserts.

TABLE 3

| Antisense-cDNA | Abbreviation | Adenoviral vector |
|---|---|---|
| constitutive nitric oxide synthase | CeNOS | pClIP, pIPspAdapt |
| lysosomal beta-glucocerebrosidase | hGC | pCLIP |
| Phenol UDP-glucuronosyltransferase | P-UGT | pCLIP, pIPspAdapt |
| Bilirubin 1 UDP-glucuronosyltransferase | B-UGT | pCLIP, pIPspAdapt |
| Plasminogen Activator Inhibitor type-1 | PAI-1 | pCLIP, pIPspAdapt |
| Ribosomal protein L4 | NA | pCLIP |
| Phosphoenolpyruvate carboxykinase | PEPCK | pCLIP |
| β-globin | NA | pCLIP |
| Lysozyme | NA | pCLIP |
| Chrom 1 spec. transcr. KIAA0493 | KIAA | pCLIP |
| snRNP core protein Sm D2 | SnRNP | pCLIP |

Figure 33:
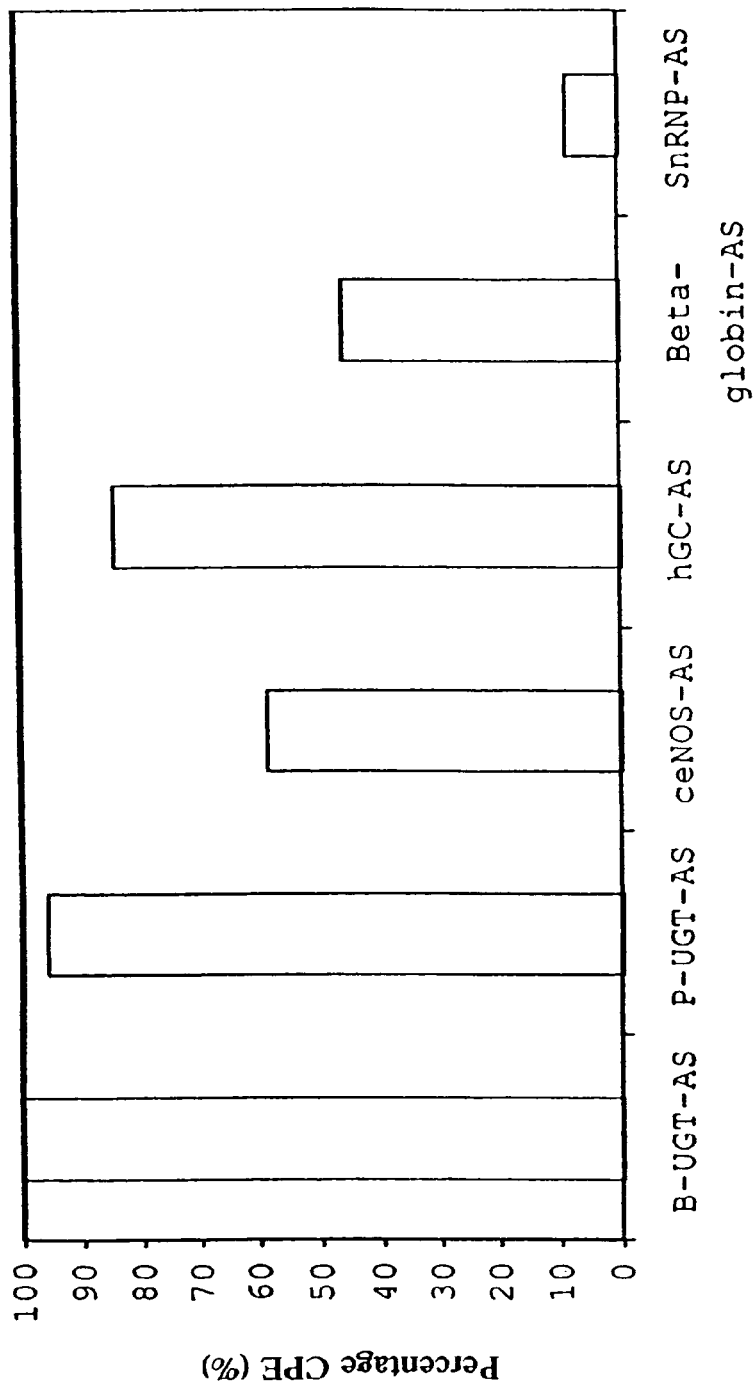
FIG. 33: Efficiencies of virus generation in percentages of CPE after virus generation of several adenoviruses (E1 and E2A deleted) containing cDNAs in antisense (AS) orientation (Example 16).

In FIG. 33, an example is given of some of the above mentioned cDNAs for generation of antisense cDNA adenoviral vectors using the miniaturized production system subject of this invention. These viruses will be used to attempt to lower the endogenous expression of the cells tested.

Example 17

Construction of Adapter Plasmids for the Generation and Production of Recombinant Adenoviruses, in Particular, for the Generation and Production of Adenoviral Expression Libraries Adenoviral adapter plasmids ("adapter") were constructed that contain multiple cloning sites in multiple orientations that allow efficient cloning of sense or antisense cDNA sequences and the generation of libraries of nucleic acids including cDNA libraries in these vectors. Furthermore, these new adapter plasmids contain novel restriction enzyme recognition sequences bordering the left adenoviral ITR and the sequences overlapping with the helper fragment up to nucleotide 6095 of the Ad5 viral genome. These modifications of the adenoviral adapter plasmids significantly enhance the possibility to linearize the adapter plasmids, without digestions of inserted transgenes or transgene libraries. Following cotransfection with pWE/Ad.AflII-rITR.deltaE2A, homologous recombination between the improved adapter plasmids and the adenoviral cosmid results in the generation of functional adenoviruses.

Figure 34A:
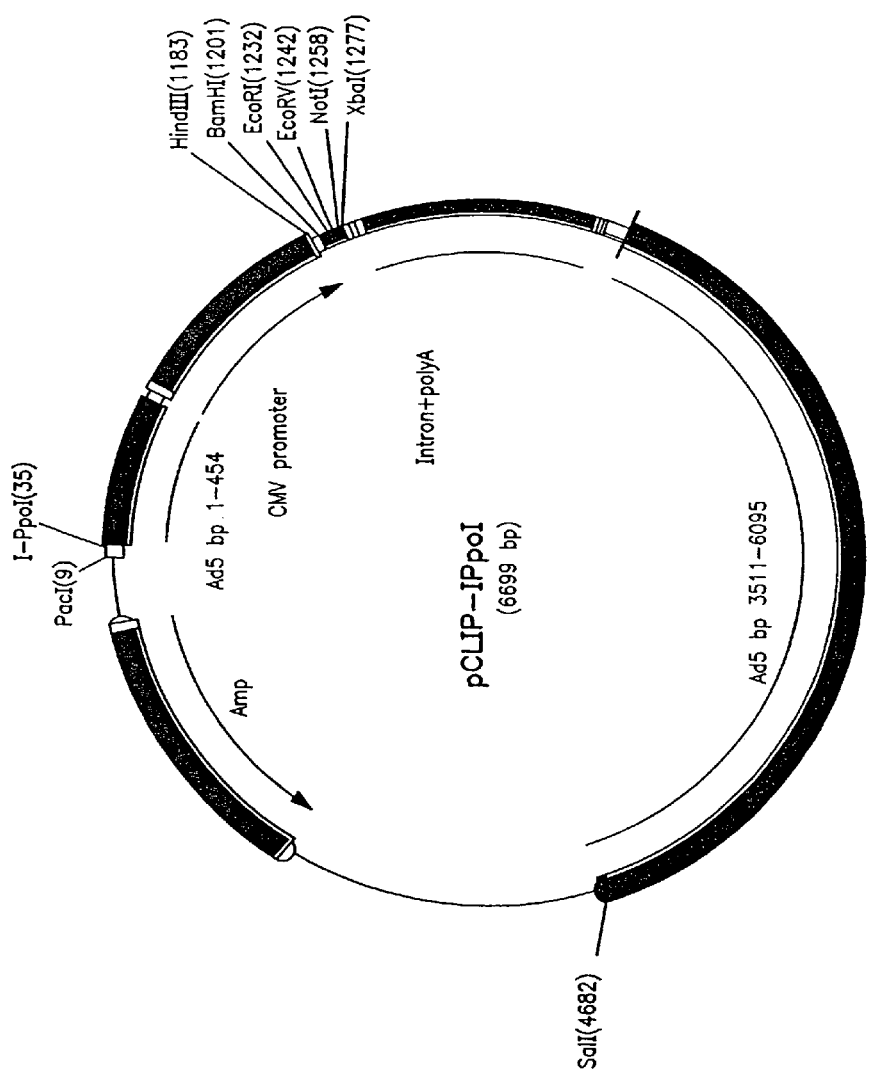
Figure 34B:
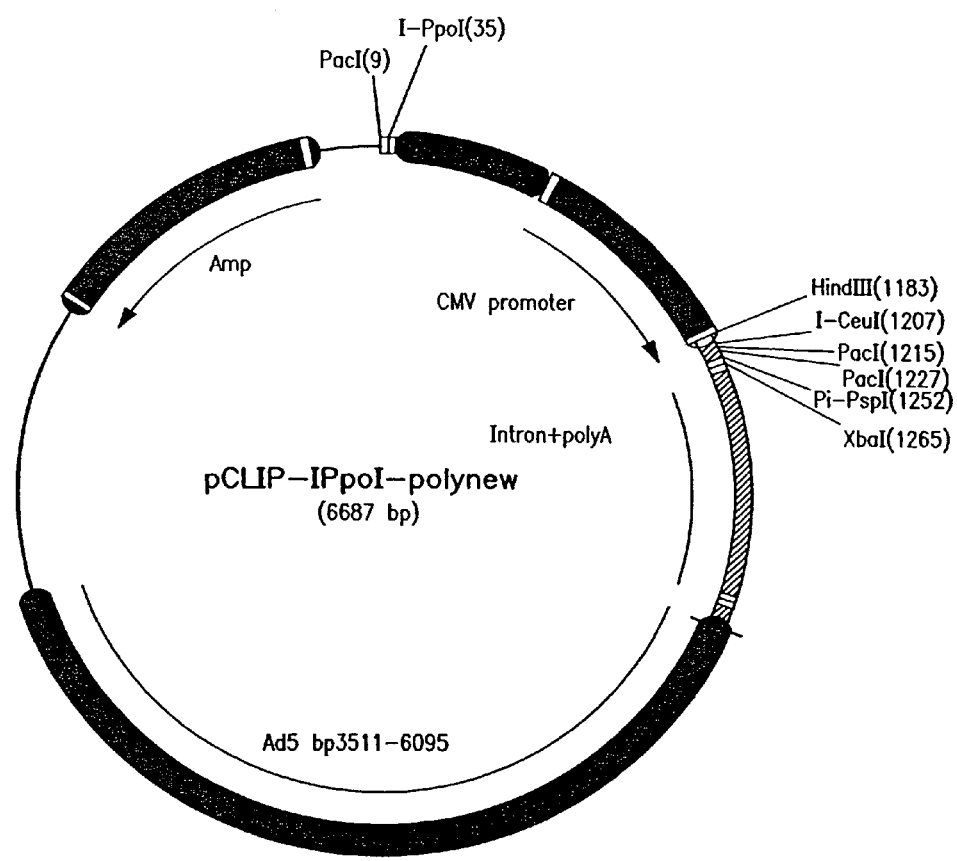

The first adapter constructs, pCLIP-IppoI (FIG. 34A) and pCLIP-IppoI-polynew (FIG. 34B), are derived from pAd5/CLIP-Pac and contain a new I-PpoI linearization site at position −11 bp in front of the left ITR. In addition, pCLIP-IppoI-polynew contains an improved poly-linker sequence downstream of the CMV promoter encompassing restriction enzyme recognition sequences for different, rare-cutting restriction endonucleases and intron-encoded endonucleases. The recognition sequences for intron-encoded endonucleases are extremely rare in genomes, including the human genome, and consist of 11–23 base pairs. As these intron-encoded endonuclease sites are absent in the adenoviral genome, sequences can be directly inserted into a full adenoviral vector genome obtained from an insertless pCLIP-IPpoI (see also below).

To construct this adapter plasmid, part of the left ITR of Ad5 was amplified by PCR on pCLIP-PacI template plasmid DNA using the following primers: PCLIPPACIPPO: 5'-TTT TTA ATT AAT AAC TAT GAC TCT CTT AAG GTA GCC AAA TCA TCA TCA ATA ATA TAC CTT ATT TTG G-3' (SEQ ID NO:48) and PCLIPBSRGI: 5'-GCG AAA ATT GTC ACT TCC TGT G-3' (SEQ ID NO:49) and Elongase polymerase from Life Technologies (LTI; Breda, NL). Primer pCLIP-PacI contains a PacI site 5' from a I-PpoI sequence. The amplified fragment was digested with PacI and BsrGI and the resulting 255 bp fragment cloned into a fragment of 6471 bp, which was obtained from pAd5/CLIP-PacI digested with the same enzymes and isolated on a 1% agarose gel. Nucleotide sequences were confirmed by dideoxynucleotide sequence analysis. This construct, containing PacI and I-PpoI recognition sequences 5' to the left ITR at a distance of 33 nucleotides and 11 nucleotides, respectively, was named pCLIP-I-PpoI (see FIG. 34A). This construct was subsequently digested with XbaI and HindIII, separated on a gel, and used to insert a new synthetic linker sequence. This linker sequence, composed of the two single stranded and the following annealed oligonucleotides LINKERPOLYNEW-S: 5'-AGC TTT AAC TAT AAC GGT CCT AAG GTA GCG ATT AAT TAA CAG TTT AAT TAA TGG CAA ACA GCT ATT ATG GGT ATT ATG GGT T-3' (SEQ ID NO:50); and LINKERPOLYNEW-AS: 5'-CTA GAA CCC ATA ATA CCC ATA ATA GCT GTT TGC CAT TAA TTA AAC TGT TAA TTA ATC GCT ACC TTA GGA CCG TTA TAG TTA A-3' (SEQ ID NO:51), was directly ligated into the digested construct. This adapter construct, termed pCLIP-I-PpoI-polynew, now contains recognition sequences for the restriction enzymes HindIII, I-CeuI, PacI, PI-PspI, and XbaI in the polylinker (see FIG. 34B). Correct insertion of this linker was verified by digestions with the respective enzymes and sequence analysis.

Figure 34C:
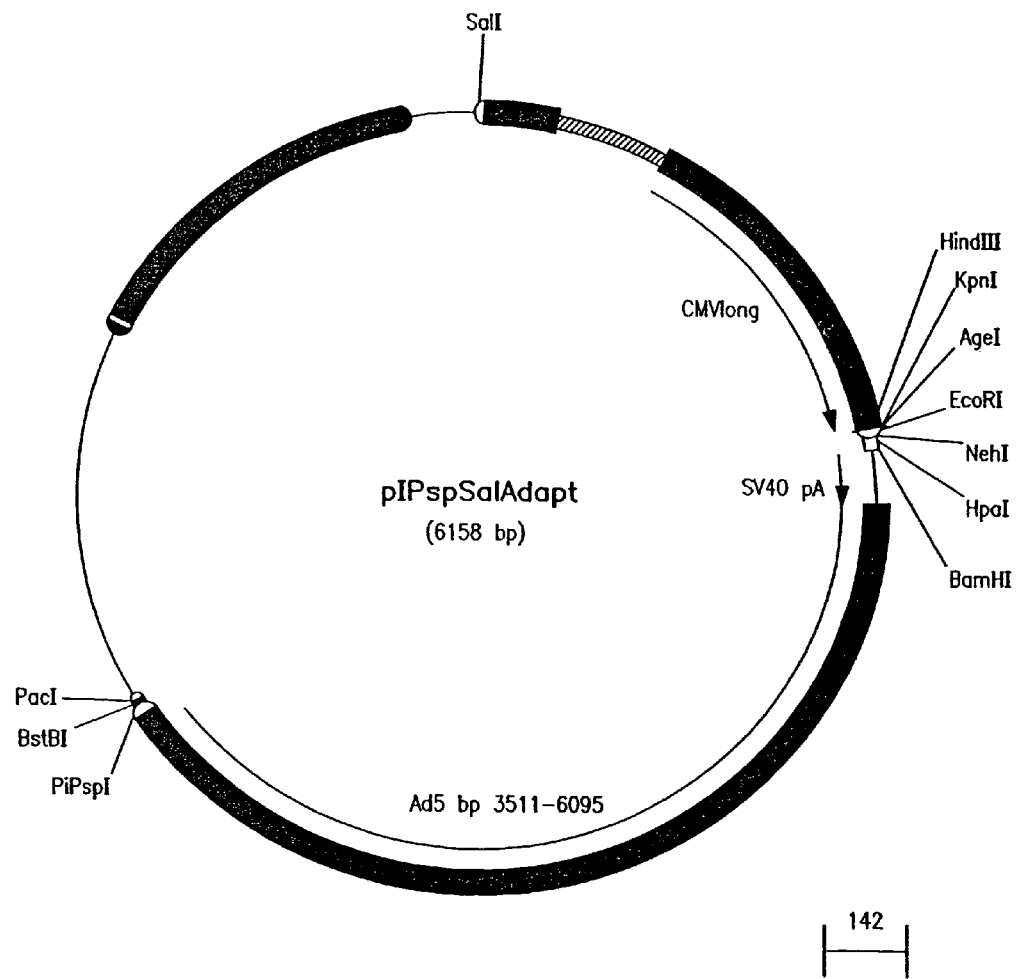
Figure 34D:
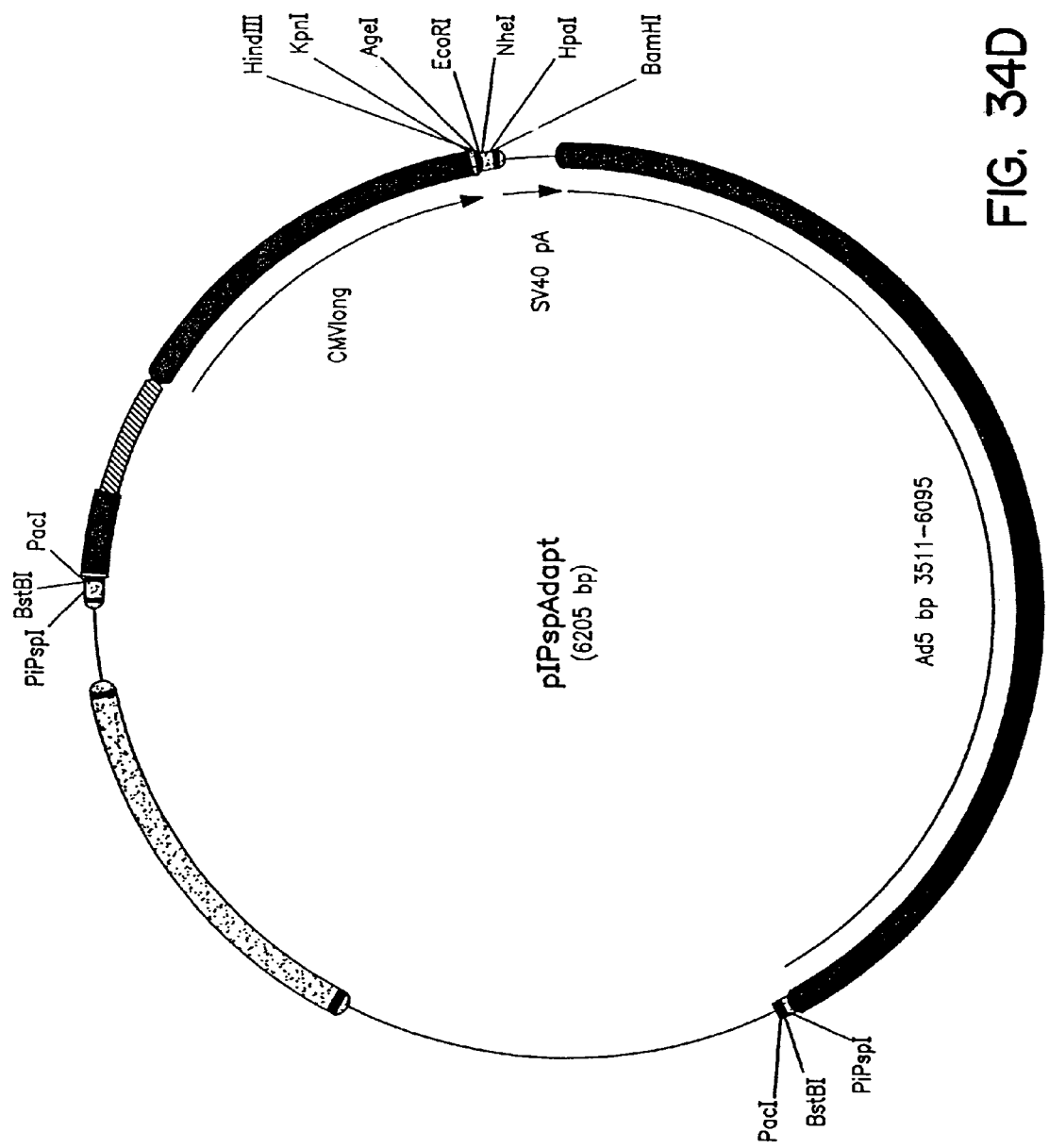

A different adapter construct, pADAPT, which contains a stronger CMV promoter than pCLIP-based adenoviral adapters, as well as a different poly(A) sequence, was used as a backbone to construct another set of adapter plasmids. To enhance the linearization possibilities, a number of pADAPT derivatives were designed and constructed. For this purpose, pADAPT plasmid DNA was digested with SalI and treated with Shrimp Alkaline Phosphatase to reduce religation. A linker, composed of the following two phosphorylated and annealed oligonucleotides ExSalPacF 5'-TCG ATG GCA AAC AGC TAT TAT GGG TAT TAT GGG TTC GAA TTA ATT AA-3' (SEQ ID NO:52) and ExSalPacR 5'-TCG ATT AAT TAA TTC GAA CCC ATA ATA CCC ATA ATA GCT GTT TGC CA-3' (SEQ ID NO:53), was directly ligated into the digested construct, thereby replacing the SalI restriction site with PI-PspI, SwaI, and PacI. Furthermore, part of the left ITR of pADAPT was amplified by PCR using the following primers: PCLIPMSF: 5'-CCC CAA TTG GTC GAC CAT CAT CAA TAA TAT ACC TTA TTT TGG -3' (SEQ ID NO:54) and pCLIPBSRGI (see above). The amplified fragment was digested with MunI and BsrGI and cloned into pCLIP-EcoRI, which was partially digested with EcoRI and after purification digested with BsrGI. After restriction enzyme analysis, the construct was digested with ScaI and SgrAI and an 800 bp fragment was isolated from an agarose gel and ligated into a ScaI/SgrAI digested pADAPT+ExSalPac linker. The resulting construct, named pIPspSalAdapt (see FIG. 34C), was digested with SalI, dephosphorylated, and ligated to the above-mentioned phosphorylated ExSalPacF/ExSalPacR doublestranded linker. A clone in which PacI site was closest to the ITR was identified by restriction analysis and sequences were confirmed by sequence analysis. This novel pADAPT construct, termed pIPspAdapt (see FIG. 34D), thus harbours two ExSalPac linkers containing recognition sequences for PacI, PI-PspI, and BstBI, which surround the adenoviral part of the adenoviral adapter construct and can be used to linearize the plasmid DNA prior to cotransfection with adenoviral helper fragments.

Figure 34E:
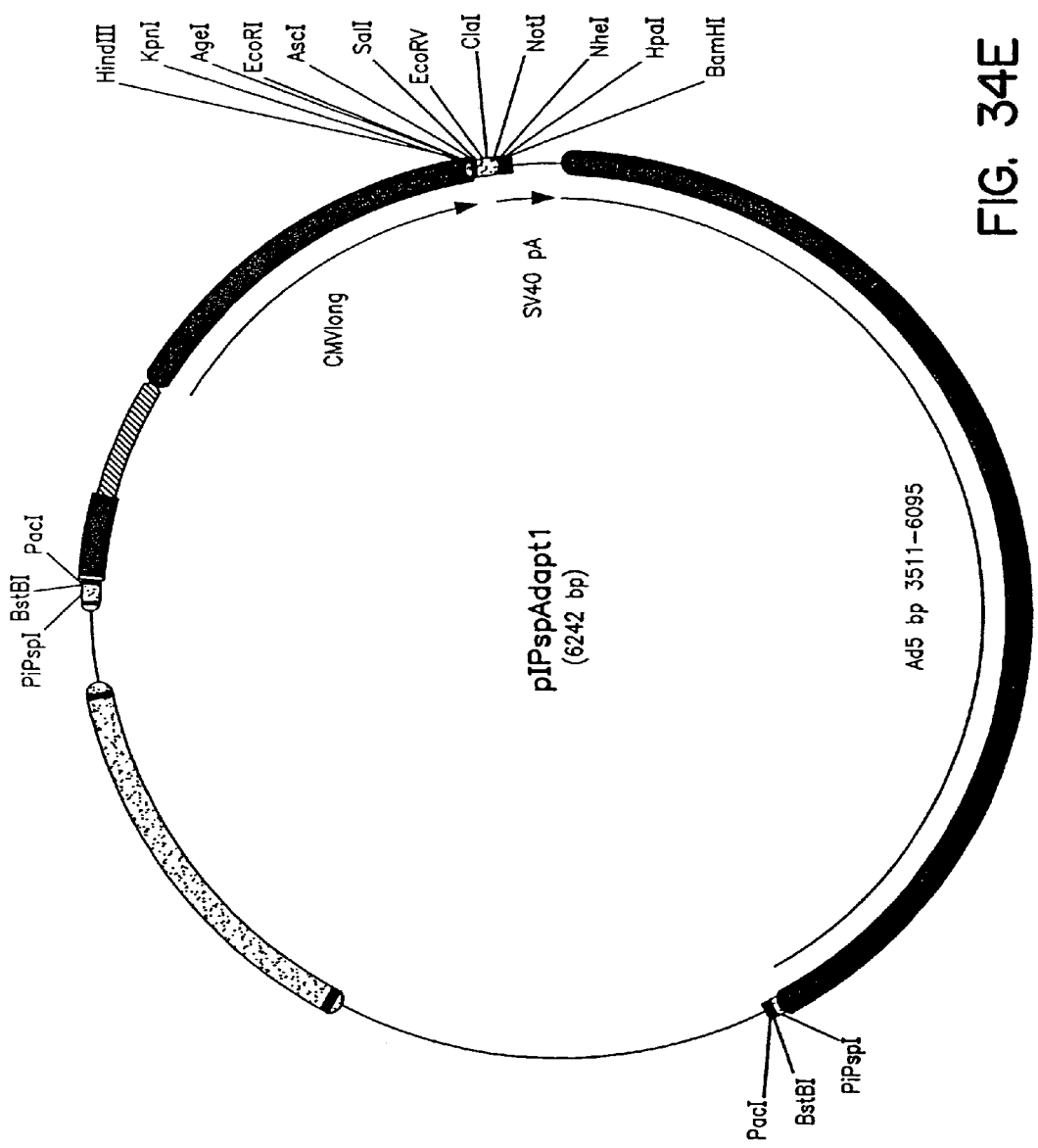
Figure 34F:
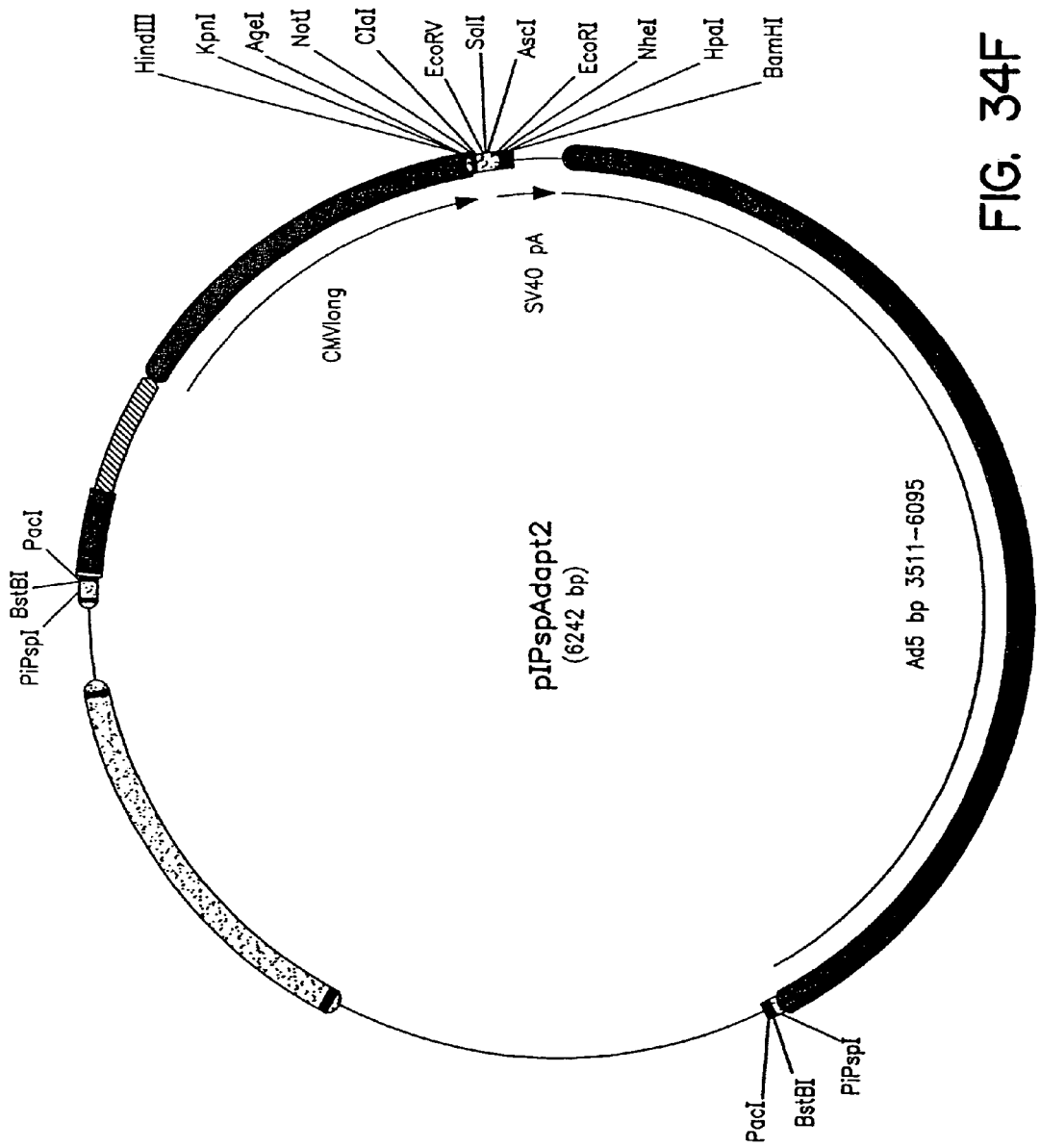

In order to further increase transgene cloning permutations, a number of polylinker variants were constructed based on pIPspAdapt. For this purpose, pIPspAdapt was first digested with EcoRI and dephosphorylated. A linker composed of the following two phosphorylated and annealed oligonucleotides: Ecolinker+: 5'-AAT TCG GCG CGC CGT CGA CGA TAT CGA TAG CGG CCG C 3' (SEQ ID NO:55) and Ecolinker−: 5'-AAT TGC GGC CGC TAT CGA TAT CGT CGA CGG CGC GCC G 3' (SEQ ID NO:56) was ligated into this construct, thereby creating restriction sites for AscI, SalI, EcoRV, ClaI and NotI. Both orientations of this linker were obtained and sequences were confirmed by restriction analysis and sequence analysis. The plasmid containing the polylinker in the order 5' HindIII, KpnI, AgeI, EcoRI, AscI, SalI, EcoRV, ClaI, NotI, NheI, HpaI, BamHI, and XbaI was termed pIPspAdapt1 (see FIG. 34E) while the plasmid containing the polylinker in the order HindIII, KpnI, AgeI, NotI, ClaI, EcoRV, SalI, AscI, EcoRI, NheI, HpaI, BamHI and XbaI was termed pIPspAdapt2 (see FIG. 34F).

Figure 34G:
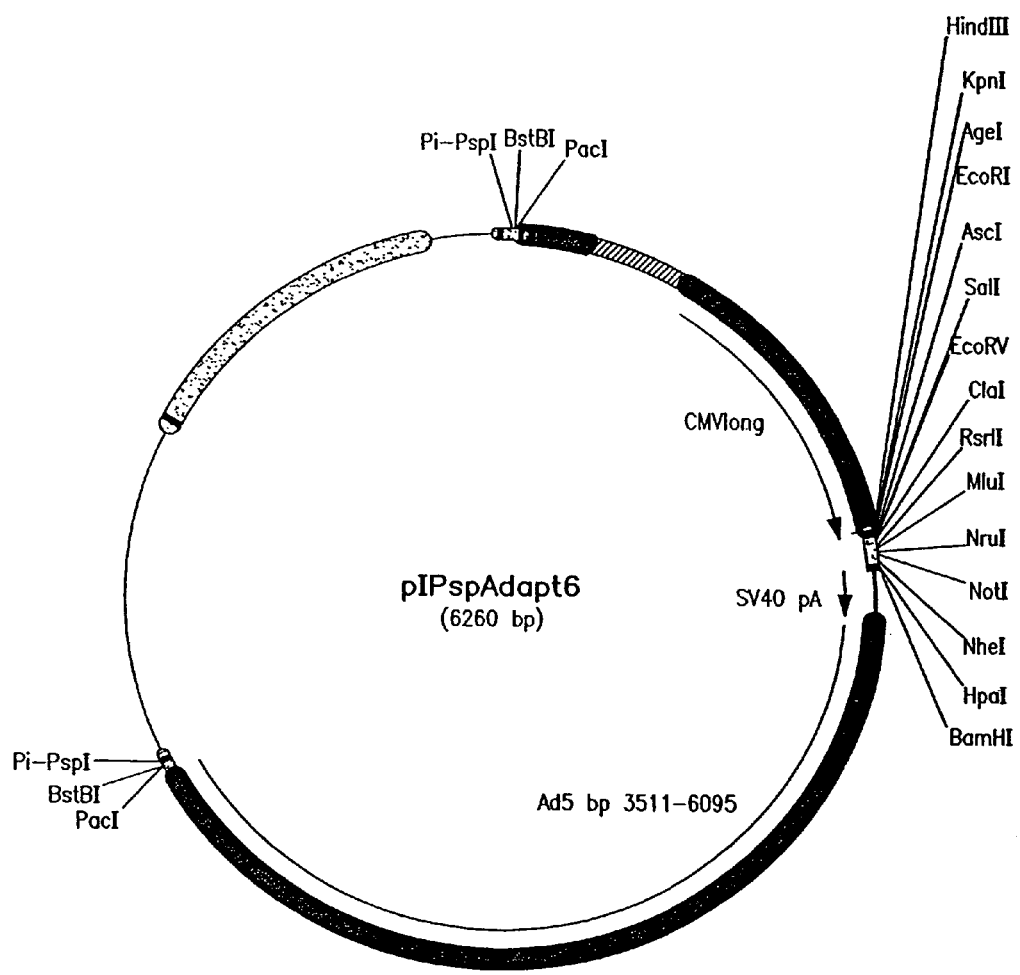
Figure 34H:
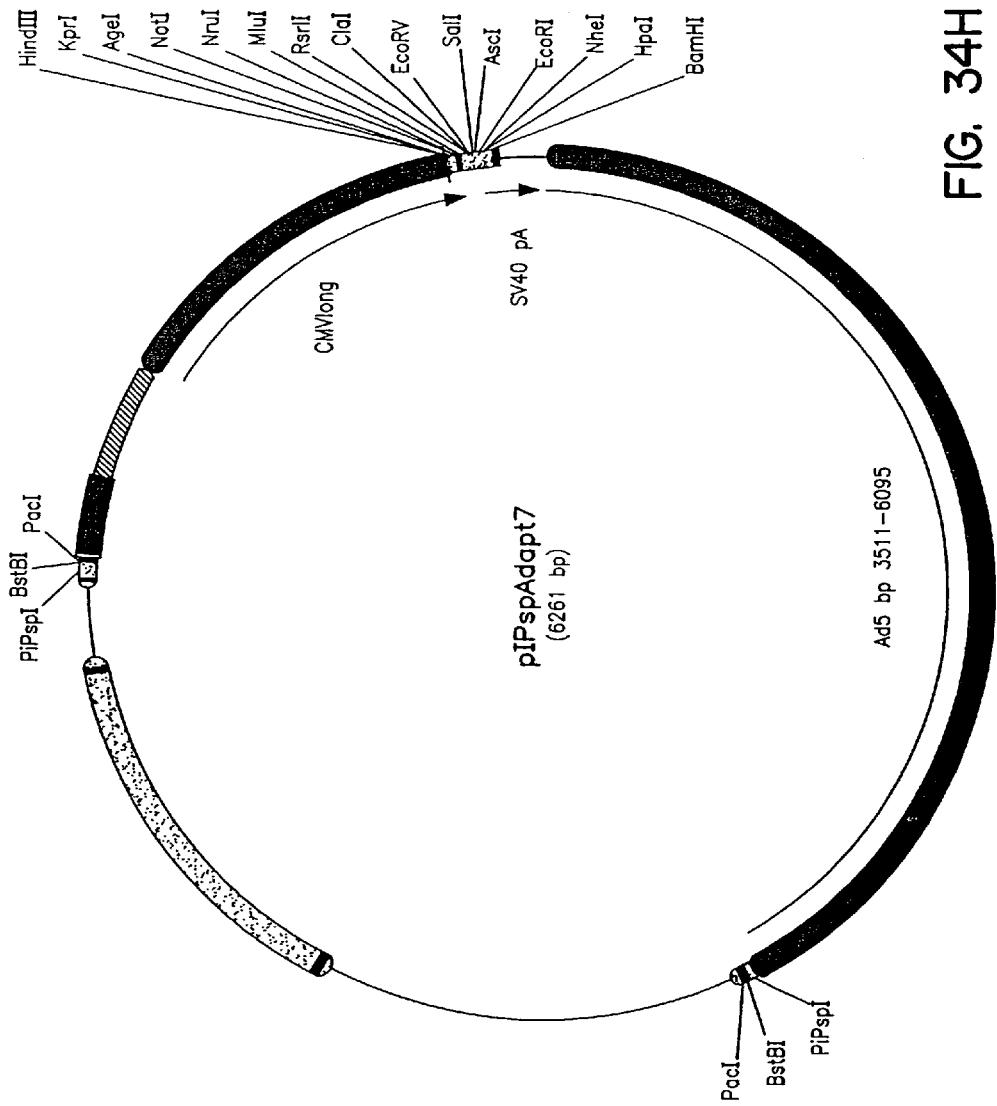
Figure 341:
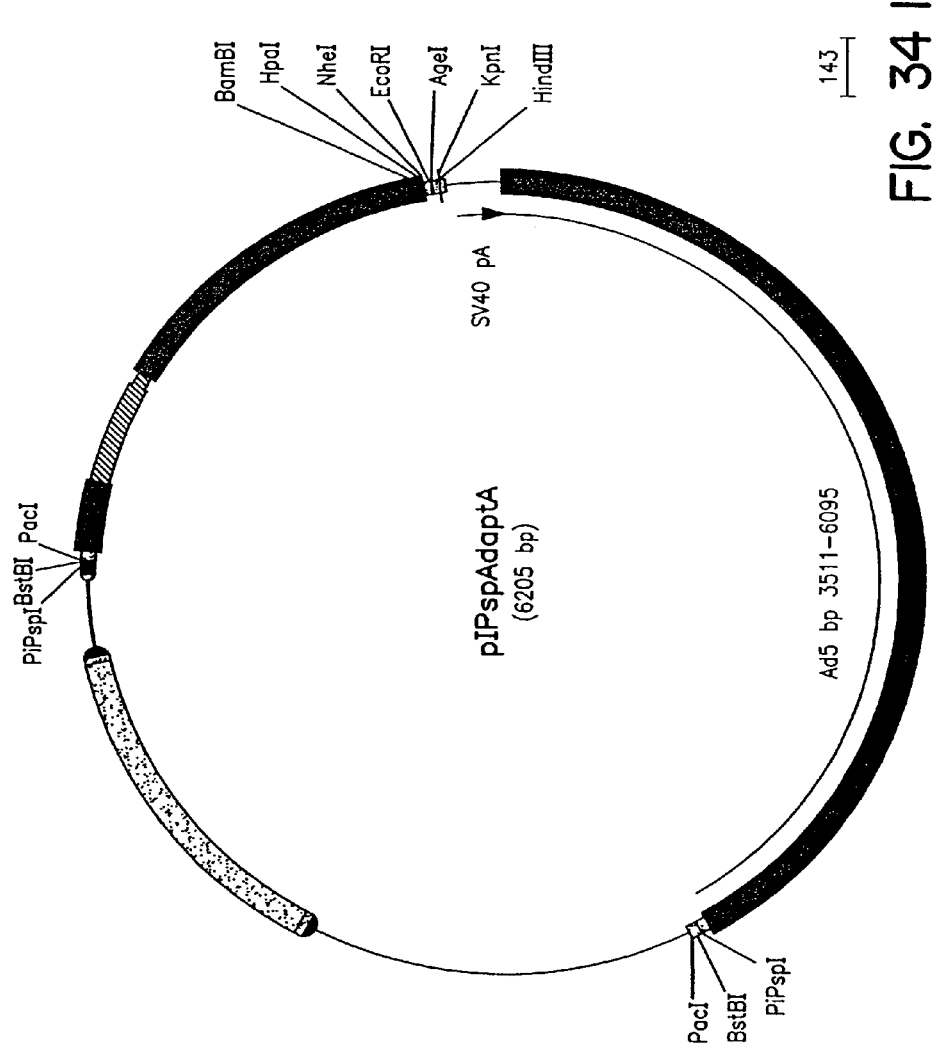

Those skilled in the art of making cDNA libraries will appreciate that an extra polylinker, consisting of the oligonucleotides GalMlu-F: 5'-CGA TCG GAC CGA CGC GTT CGC GAG C-3' (SEQ ID NO:57) and GalMlu-R: 5'-GGC CGC TCG CGA ACG CGT CGG TCC GAT-3' (SEQ ID NO:58), was inserted in between the ClaI and NotI sites of pIPspAdapt1, to generate pIPspAdapt6 (see FIG. 34G). pIPspAdapt6 contains extra restriction sites for RsrII, MluI, and NruI, which were introduced to increase the distance between the SalI and NotI sites in order to improve the digestion of the combination of these enzymes. Furthermore, the enzymes allow the pre-digestion and dephosphorylation of this vector prior to restriction with SalI and NotI, which will reduce background recombinants in the case of cloning individual inserts or libraries with SalI- and NotI-compatible overhangs. The GalMlu oligo was also cloned into pIPsp-Adapt2, leading to pIPspAdapt7 (see FIG. 34H).

Figure 34J:
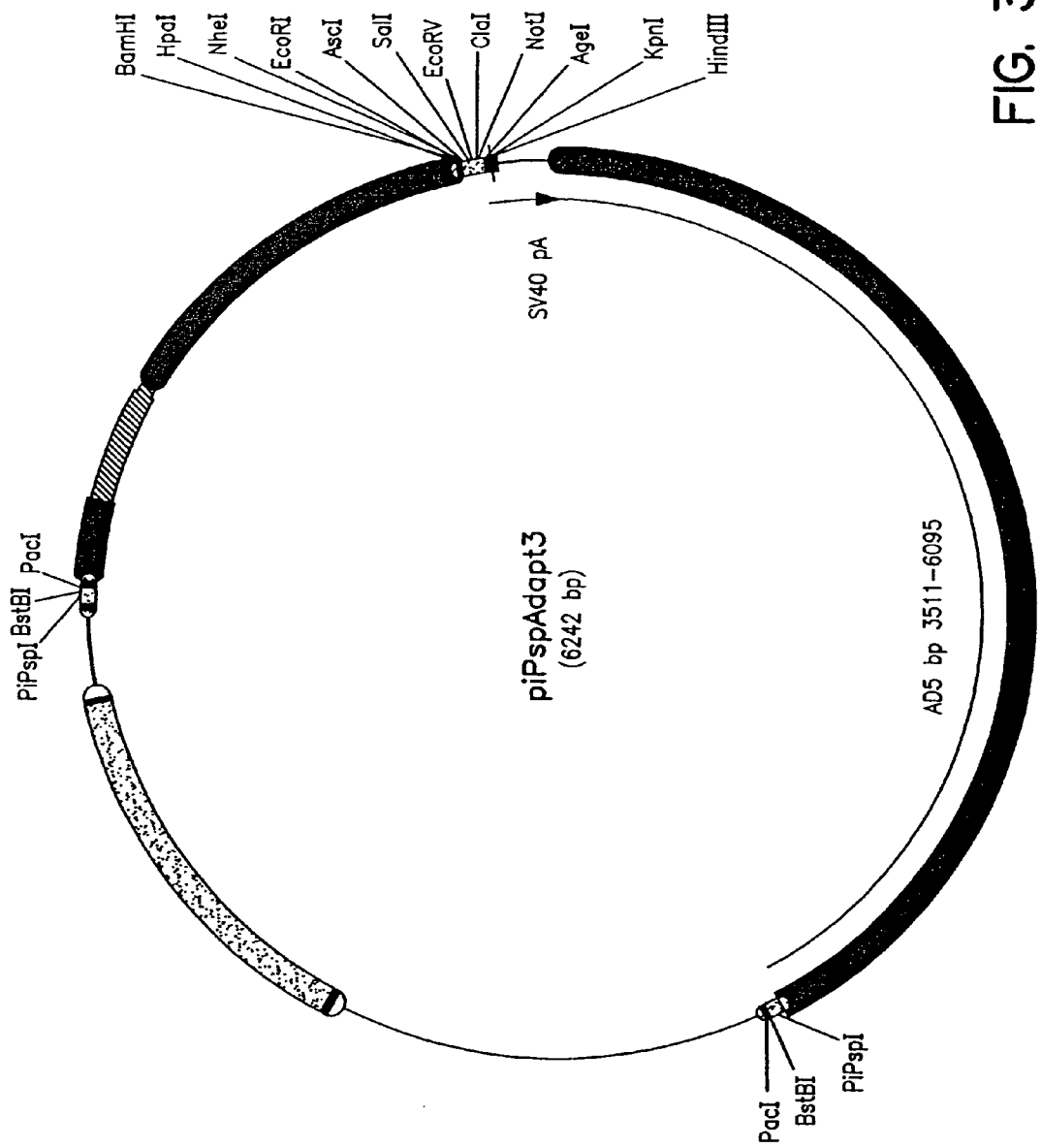
Figure 34K:
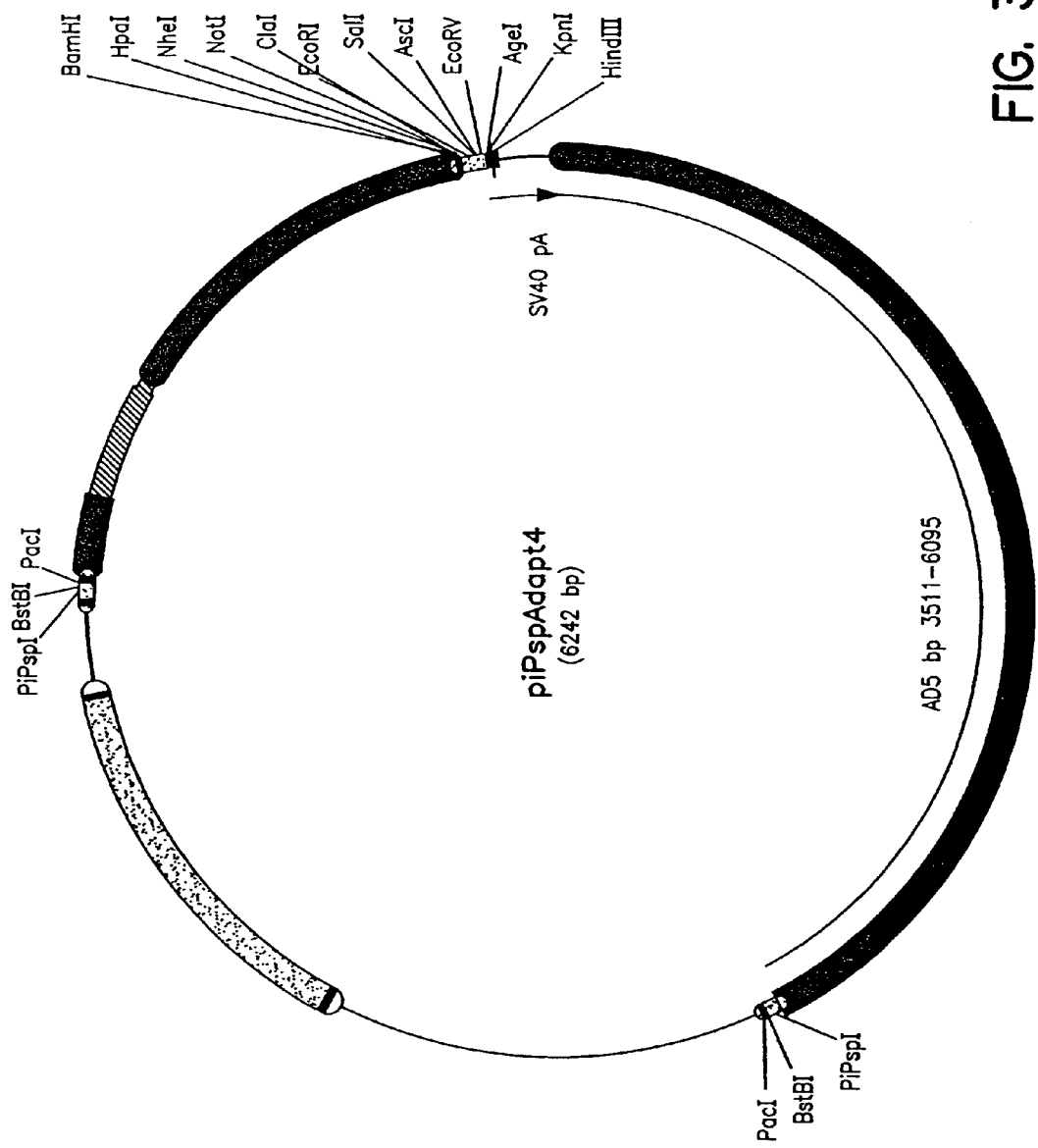

To facilitate the cloning of additional sense or antisense constructs, a linker composed of the following two oligonucleotides was designed to reverse the polylinker of pIPspAdapt: HindXba+ 5'-AGC TCT AGA GGA TCC GTT AAC GCT AGC GAA TTC ACC GGT ACC AAG CTT A-3' (SEQ ID NO:59); HindXba− 5'-CTA GTA AGC TTG GTA CCG GTG AAT TCG CTA GCG TTA ACG GAT CCT CTA G-3' (SEQ ID NO:60). This linker was ligated into HindIII/XbaI digested pIPspAdapt and the correct construct was isolated. Confirmation of the correct construct was done by restriction enzyme analysis and sequencing. This new construct, pIPspAdaptA (see FIG. 34I), was digested with EcoRI and the above mentioned Ecolinker was ligated into this construct. Both orientations of this linker were obtained, resulting in pIPspAdapt3 (see FIG. 34J), which contains the polylinker in the order XbaI, BamHI, HpaI, NheI, EcoRI, AscI, SalI, EcoRV, ClaI, NotI, AgeI, KpnI, and HindIII, and pIPspAdapt4, which contains the polylinker in the order XbaI, BamHI, HpaI, NheI, NotI, ClaI, EcoRV, SalI, AscI, EcoRI, AgeI, KpnI and HindIII (see FIG. 34K). All sequences were confirmed by restriction enzyme analysis and sequencing.

Figure 34L:
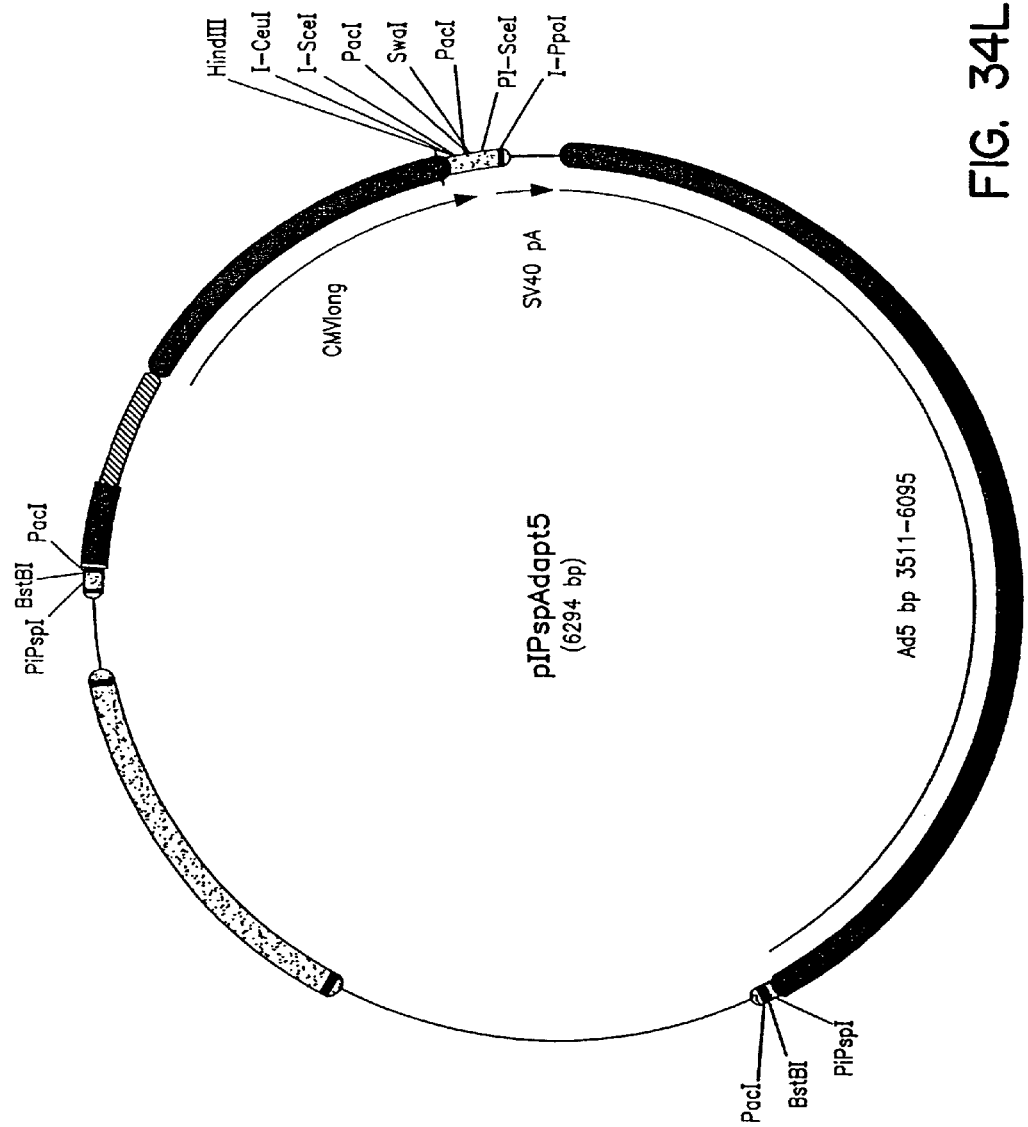

As mentioned above, intron-encoded endonucleases are rare, cutting enzymes and do not digest the adenoviral genome. Those skilled in the art will appreciate that these enzymes allow the direct ligation of sequences in the adenoviral genome, since they do not have a recognition sequence in the adenoviral genome. To obtain a pADAPT version that contains recognition sequences for intron-encoded endonucleases in the polylinker, a linker was ligated into HindIII/XbaI digested pIPspAdapt, consisting of the single stranded sequences: 5'-AGC TTA ACT ATA ACG GTC CTA AGG TAG CGA TAG GGA TAA CAG GGT AAT TAA TTA ATT TAA ATT AAT TAA TCT ATG TCG GGT GCG GAG AAA GAG GTA ACT ATG ACT CTC TTA AGG TAG CCA AAT-3' (SEQ ID NO:61); and 5'-CTA GAT TTG GCT ACC TTA AGA GAG TCA TAG TTA CCT CTT TCT CCG CAC CCG ACA TAG ATT AAT TAA TTT AAA TTA ATT AAT TAC CCT GTT ATC CCT ATC GCT ACC TTA GGA CCG TTA TAG TTA-3' (SEQ ID NO:62). This linker was composed of four oligonucleotides (IntrolinkerF1, IntrolinkerF2, IntrolinkerR1, and IntrolinkerR2) and contains recognition sequences for the intron-encoded endonucleases I-CeuI, I-SceI, PI-SceI, and I-PpoI and the endonucleases PacI and SwaI. The correctness of the construct, termed pIPspAdapt5 (see FIG. 34L), was confirmed by sequence analysis.

Adenoviral DNA from viruses containing pIPspAdapt5 or pCLIPIppoI-polynew was isolated and cloned into the cosmid vector pWE15/SnaB1. pWE15/SnaB1 was created by auto-annealing the phosphorylated oligonucleotide PacSna: 5'-TAA TAC GTA TTA AT-3' (SEQ ID NO:63) and ligating the resulting double stranded sequence in PacI-digested and dephosphorylated pWE15/PAC, a derivative of pWE15 (see Sambrook, J. et al, eds. (1989) Molecular cloning: a laboratory manual, $2^{nd}$ edition, Cold Spring Harbor Laboratory Press). This generates a restriction site for SnaBl, which is flanked by PacI sites. For the generation of adenoviral DNA-containing cosmid, blunt-ended adenoviral DNA was isolated according to standard laboratory procedures using Dnase and Proteinase K, followed by elution on an anion-exchange resin spin column. A molar excess of the resulting purified adenoviral DNA was ligated into SnaB1-restricted pWE15/SnaB1 and the resulting ligation mixture was transfected into *E. coli* Stb12 cells (LTI, Breda).

Figure 34M:
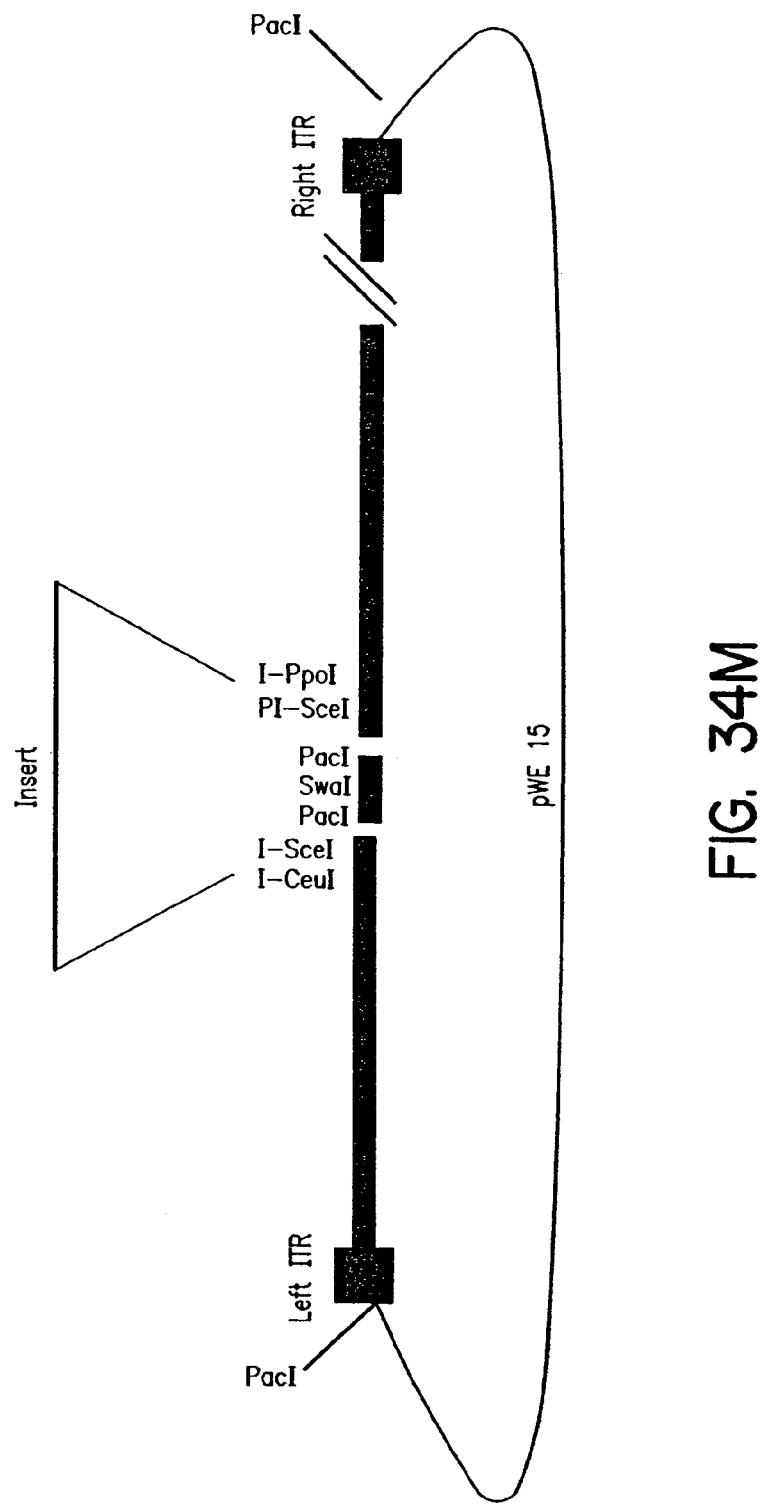

The resulting plasmid DNA was subsequently used for in vitro ligations (see FIG. 34M). The use of pIPspAdapt5-derived cosmid DNA will be used an an example in the following: double stranded oligonucleotides containing compatible overhangs were ligated between the I-CeuI and PI-SceI sites, between I-CeuI and I-PpoI, between I-SceI and PI-SceI, and between I-SceI and I-PpoI. The PacI restriction endonuclease was subsequently used not only to linearize the construct after ligation and thereby to liberate the left- and right ITRs, but also to eliminate non-recombinants. In this case, ligation mixtures can be used directly for transfection in PER.C6/PER.C6/E2A packaging cells or variants thereof, thereby eliminating the need for a cross-over or homologous recombination event to generate functional adenovirus.

As an alternative, adapter plasmids and cosmids containing adenoviral DNA, which was made from pIPspAdapt5 or pCLIP-IppoI-polynew, were used to generate fragments either encompassing the region between the left ITR and the first part of the polylinker or encompassing the second part of the polylinker until the right ITR. Care is taken that the left and right ITR are linearized with distinct and non-compatible restriction enzymes since ligation efficiencies are otherwise strongly reduced. pIPspAdapt5-derived cosmid DNA will be used as an example: plasmid pIPspAdapt5 was cut with either BstBI and I-CeuI or BstBI and I-SceI to generate the adenoviral fragment containing the left ITR. The cosmid containing the pIPspAdapt5-derived adenoviral DNA was restricted with I-PpoI and PacI or PI-SceI and PacI to generate the fragment containing the right ITR. Fragments containing the left and right ITR were isolated on a 0.8% agarose gel and purified using anion exchange resins. Subsequently, double stranded oligonucleotides containing compatible overhangs for either I-CeuI or I-SceI at the 5' end and I-PpoI or PI-SceI at the 3' end were ligated in equimolar amounts with the fragments containing the left and right ITRs. The resulting ligation mixture was used for transfection into PER.C6/PER.C6/E2A packaging cells or variants thereof, again eliminating the need for a cross-over or homologous recombination event to generate functional adenovirus.

The direct transfection of in vitro ligated products benefits from an alternative method of isolating the adenoviral vector DNA. To improve the efficiency of viral production after transfection of in vitro ligation reactions, adenoviral vector DNA can be isolated from purified adenoviral particles (see Pronk, R. et al., Chromosoma 102: S39–S45 (1992)). This virion DNA contains two molecules of Terminal Protein (TP) covalently bound to the ITR sequences. It is known that TP-DNA stimulates adenoviral DNA replication over 20 fold compared to protein-free DNA.

Figure 34N:
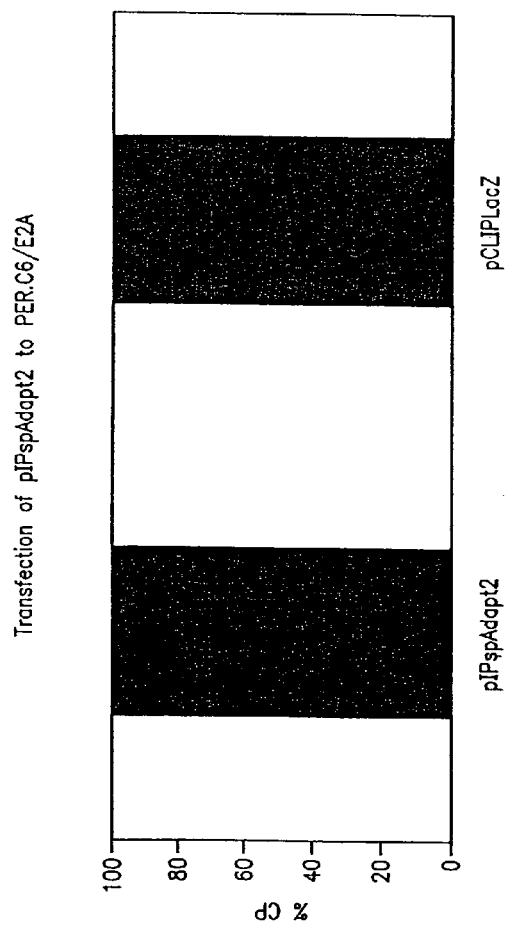
FIG. 34N: Percentage of wells showing CPE formation after transfection of PER.C6/E2A cells with pCLIP-LacZ and the adapter plasmid pIPspAdapt2.

Therefore, pIPspAdapt5- or pCLIP-IppoI-polynew-derived adenoviral DNA can be isolated from virions using guanidinium hydrochloride as described (Van Bergen, B. et al. *Nucleic Acids Res.* 11: 1975–1989 (1983)). This DNA was digested with a suitable combination of intron-encoded restriction endonucleases and used for in vitro ligation reactions. After ligation, non-recombinants were removed by digestion with PacI. Further procedures were as described above and in example 10 and beyond. pIPspAdapt adapter plasmids were co-transfected with pWE/Ad.AflII-rITRDE2A in the PER.C6/E2A packaging cells to generate recombinant adenoviruses, as is shown in FIG. 34N using pIPspAdapt2 as an example.

Example 18

E1-deleted or E1+E2A-deleted Recombinant Adenoviruses with Deletions in the E3 Region for Cloning of Larger DNA Inserts in Miniaturized Adenoviral Vector Production System It is known that none of the E3-encoded proteins is required for adenoviral replication, packaging, and infection in cultured cells. This allows the possible removal of the E3 region from recombinant adenoviruses, creating the opportunity for inserting large genes or complex regulatory elements without exceeding the maximal packaging capacity. For example, part of the E3 region can be removed by deleting a XbaI-XbaI fragment, corresponding to Ad5 wt sequence 28592–30470. Another example is an expanded deletion of the E3 region in which sequences between the stop codon of pVIII and the translation initiation codon of fiber, corresponding to Ad5 wt sequence 27865–30995, were removed.

Generation of pWE/Ad.AflII-rITRΔE2A

Deletion of the E2A coding sequences from pWE/Ad.AflII-rITR (ECACC deposit P97082116) has been accomplished as follows: the adenoviral sequences flanking the E2A coding region at the left and the right sites were amplified from the plasmid pBr/Ad.Sal.rITR (ECACC deposit P97082119) in a PCR reaction with the Expand PCR system (Boehringer) according to the manufacturer's protocol. The following primers were used:

coding sequences were left intact. This ensures proper expression of the L3-genes and the gene encoding the 100K L4-protein during the adenoviral life cycle.

Next, the plasmid pWE/Ad.AflII-rITRΔE2A was generated. The plasmid pBr/Ad.Sal-rITRΔE2A was digested with BamHI and SpeI. The 3.9 kb fragment in which the E2A coding region was replaced by the unique NsiI site was isolated. The pWE/Ad.AflII-rITR was digested with BanHI and SpeI. The 35 kb DNA fragment, from which the BamHI/SpeI fragment containing the E2A coding sequence was removed, was isolated. The fragments were ligated and packaged using λ phage-packaging extracts according to the manufacturer's protocol (Stratagene), yielding the plasmid pWE/Ad.AflII-rITRΔE2A.

This cosmid clone can be used to generate adenoviral vectors that are deleted for E2A by cotransfection of PacI digested DNA along with digested adapter plasmids onto packaging cells that express functional E2A gene product. Examples of E2A complementing cell lines are described below:

Generation of pBr/Ad.Bam-rITRsp and pWE/Ad.AflII-rITRsp

The 3' ITR in the vector pWE/Ad.AflII-rITR does not include the terminal G-nucleotide. Furthermore, the PacI site is located almost 30 bp from the right ITR. Both these characteristics may decrease the efficiency of virus generation due to inefficient initiation of replication at the 3'ITR. Note that during virus generation, the left ITR in the adapter plasmid is intact and enables replication of the viral DNA after homologous recombination.

To improve the efficiency of initiation of replication at the 3'ITR, the pWE/Ad.AflII-rITR was modified as follows: construct pBr/Ad.Bam-rITRpac#2 was first digested with PacI and then partially digested with AvrII. The 17.8 kb vector containing fragment was isolated and dephophorylated using SAP enzyme (Boehringer Mannheim). This fragment lacks the adenoviral sequences from nucleotide

```
Right flanking sequences (corresponding Ad5 nucleotides 24033 to 25180):
ΔE2A.SnaBI:     5'-GGC GTA CGT AGC CCT GTC GAA AG-3'              (SEQ ID NO:64)

ΔE2A.DBP-start: 5'-CCA ATG CAT TCG AAG TAC TTC CTT CTC CTA TAG GC-3' (SEQ ID NO:65)
The amplified DNA fragment was digested with SnaBI and NsiI
(NsiI site is generated in the primer ΔE2A.DBP-start, underlined).

Left flanking sequences (corresponding Ad5 nucleotides 21557 to 22442):
ΔE2A.DBP-stop: 5'-CCA ATG CAT ACG GCG CAG ACG G-3'          (SEQ ID NO:66)

ΔE2A.BamHI:    5'-GAG GTG GAT CCC ATG GAC GAG-3'            (SEQ ID NO:67)
The amplified DNA fragment was digested with BamHI and NsiI
(NsiI site is generated in the primer ΔE2A.DBP-stop, underlined).
```

Subsequently, the digested DNA fragments were ligated into SnaBI/BamHI digested pBr/Ad.Sal-rITR. Sequencing confirmed the exact replacement of the DBP coding region with a unique NsiI site in pBr/Ad.Sal-rITRΔE2A. The unique NsiI site can be used to introduce an expression cassette for a gene to be transduced by the recombinant vector.

The deletion of the E2A coding sequences was performed such that the splice acceptor sites of the 100K encoding L4-gene at position 24048 in the top strand was left intact. In addition, the poly adenylation signals of the original E2A-RNA and L3-RNAs at the lefthand site of the E2A 35464 to the 3' ITR. Using DNA from pWE/Ad.AflII-rITR as a template and the primers ITR-EPH: 5'-CGG AAT TCT TAA TTA AGT TAA CAT CAT CAA TAA TAT ACC-3' (SEQ ID NO:68) and Ad101: 5'-TGA TTC ACA TCG GTC AGT GC-3' (SEQ ID NO:69), a 630 bp PCR fragment was generated corresponding to the 3' Ad5 sequences. This PCR fragment was subsequently cloned into the vector pCR2.1 (Invitrogen) and clones containing the PCR fragment were isolated and sequenced to check correct amplification of the DNA. The PCR clone was then digested with PacI and AvrII. The resulting 0.5 kb adeno insert was ligated to the PacI/partial AvrII digested pBr/Ad.Bam-rITRpac#2 fragment, generating pBr/Ad.Bam-rITRsp. Next, this construct was used to generate a cosmid clone that has an insert corresponding to the adenosequences 3534 to 35938. This clone was named pWE/AflII-rITRsp.

Generation of pBr/Ad.Bam-rITRspΔXba and pWE/Ad.AflII-rITRspΔXba

Plasmid pBr/Ad.Bam-rITRsp was propagated in *E. coli* strain DM1 (dam−; dcm−) (Life Technologies). The plasmid was digested with XbaI, removing the 1.88 kb XbaI-XbaI fragment, and religated. The resulting clone, pBr/Ad.Bam-rITRspΔXba, was used to construct helper cosmid pWE/Ad.AflII-rITRspΔXba as described above. The following fragments were isolated by extraction from an agarose gel (QIAGEN): pWE.pac digested with PacI, pBr/AflII-Bam digested with PacI and BamHI, and pBr/Ad.Bam-rITRΔXba digested with BamHI and PacI. These fragments were ligated together and packaged using lambda phage packaging extracts according to the maufacturer's instructions (Stratagene). After infection of host bacteria assembled phage, the resulting colonies were analyzed for the presence of the intact insert. pWE/Ad.AflII-rITRspΔXba contains sequences identical to that of pWE/Ad.AflII-rITRsp, but with deletion of the XbaI-XbaI fragment.

Generation of pBr/Ad.Bam-rITRspΔE2AΔXba and pWE/Ad.AflII-rITRspΔE2AΔXba

Plasmid pBr/Ad.Bam-rITRspΔE2AΔXba was constructed for the generation of E1-deleted recombinant adenoviruses with dual deletion of E2A and E3. A SpeI-BamHI fragment containing E2A deletion was isolated from plasmid pBr/Ad.Sal-rITRΔE2A and inserted into SpeI-BamHI-digested pBr/Ad.Bam-rITRspΔXba, yielding plasmid pBr/Ad.Bam-rITRspΔE2AΔXba. This plasmid was used to construct helper pWE/Ad.AflII-rITRspΔE2AΔXba, using three fragment ligation as described above. pWE/Ad.AflII-rITRspΔE2AΔXba contains sequences identical to that of pWE/Ad.AflII-rITRsp, but with dual deletions of the E2A region and the XbaI-XbaI fragment.

Generation of pBr/Ad.Bam-rITRspΔE3, pWE/Ad.AflII-rITRspΔE3, pBr/Ad.Bam-rITRspΔE2AΔE3, and pWE/Ad.AflII-rITRspΔE2AΔE3

To allow insertion of larger DNA fragments, an expanded deletion of the E3 region was constructed in which the complete E3 coding region was removed. Primers 1 (5'-AAA CCG AAT TCT CTT GGA ACA GGC GGC-3')(SEQ ID NO: 1) and 2 (5'-GCT CTA GAC TTA ACT ATC AGT CGT AGC CGT CCG CCG-3')(SEQ ID NO:2) were used to amplify a sequence from pBr/Ad.Bam-rITRsp, corresponding to sequence 27326 to 27857 in wt Ad5 genome. Primers 3 (5'-GCT CTA GAC CTC CTG TTC CTG TCC ATC CGC-3') (SEQ ID NO:3) and 4 (5'-GTA TGT TGT TCT GGA GCG GGA GGG TGC-3') (SEQ ID NO:4) were used to amplify the sequence from the same DNA template, corresponding to sequences 30994 to 35502 in wt Ad5 genome. The amplification products were digested with EcoRI/XbaI and XbaI/AvrII, respectively, and ligated together. The resulting EcoRI-AvrII fragment was cloned into vectors of pBr/Ad.Bam-rITRsp and pBr/Ad.Bam-rITRspΔE2A that had been digested with EcoRI and AvrII, yielding pBr/Ad.Bam-rITRspΔE3 and pBr/Ad.Bam-rITRspΔE2A ΔE3, respectively. These two plasmids were used to construct cosmid helper molecules as described above. pWE/Ad.AflII-rITRspΔE3 contains sequences identical to sequences of pWE/Ad.AflII-rITRsp, but with a deletion of the E3 region corresponding to sequences 27857–30994 in wt Ad5 genome. pWE/Ad.AflII-rITRspΔE2AΔAdE3 is identical to pWE/Ad.AflII-rITRspΔE3, but with an additional deletion of the E2A region.

The above-described cosmids are particularly useful for the production of adenoviral expression libraries, in particular, libraries carrying collections of large inserts. See also Examples 19 and 20.

Example 19

Miniaturized, Multiwell Production of E1, E2A and E3 Deleted Recombinant Adenoviral Vectors Carrying Therapeutic and Marker Transgenes As mentioned in Example 10, a combined deletion of E1, E2A, and E3 will allow cloning of foreign DNA sequences up to approximate 10.5 kb in size. Here, the production of E1, E2A, and E3 deleted vectors carrying human cDNAs is shown, as well as marker genes in PER.C6/E2A cells.

Figure 35:
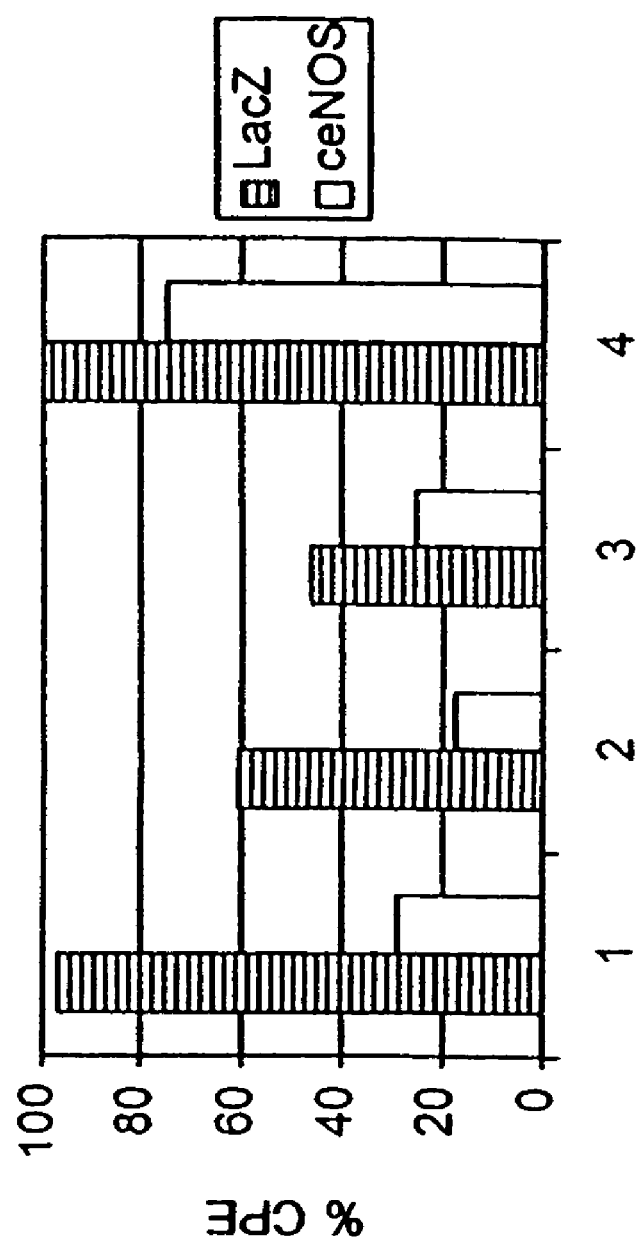
FIG. 35: (Example 19). Percentage of virus producing wells (CPE positive) in a 96-well plate of PER.C6/E2A cell after propagation of the freeze/thawed transfected cell lysates. Helper molecules used for cotransfection were (1) pWE/Ad.AflII-rITRsp, (2) pWE/Ad.AflII-rITRsp.dE2A, (3) pWE/Ad.AflII-rITRsp.dXba, and (4) pWE/Ad.AflII-rITR.

Cell culture conditions were described in Example 10. For DNA transfection, adapter and helper molecules were prepared according to Example 14. Linearized adapter plasmids pAD/CLIP-ceNOS and pAD/CLIP-lacZ were used for transfection in combination with four different PacI-linearized helper cosmids, namely pWE/Ad.AflII-rITRsp, pWE/Ad.AflII-rITRsp.dE2A, pWE/Ad.AflII-rITRsp.dXba, and pWE/Ad.AflII-rITR. The DNA transfection procedure was identical to that described in Example 10. An aliquot of 100 μl of the freeze/thawed lysates was used to infect a second 96-well plate with PER.C6/E2A cells and CPE formation was monitored. FIG. 35 shows the percentage of virus producing wells (CPE positive) in a 96-well plate of PER.C6/E2A cell after propagation of the freeze/thawed transfected cells. Clearly, it is possible to produce E1 and E3 deleted recombinant adenoviral vectors carrying therapeutic and marker transgenes in PER.C6/E2A cells.

Example 20

Construction of a Sense or Antisense, Arrayed Adenoviral Expression Library for Selecting Phenotypes The miniaturization of adenoviral vector production allows the large-scale, high throughput construction, screening of cloned or pooled gene expression libraries.

To construct a cloned and arrayed cDNA expression library in an adenoviral vector format based on the PER.C6 (and derivatives) production system, poly(A+) mRNA of human placenta is isolated using oligo(dT) cellulose and converted into cDNA using materials and reagents supplied by vendors such as Life Technologies Inc. (LTI; Breda, NL). The resulting double stranded cDNA molecules contain a SalI-compatible overhang at the 5' end and a NotI-compatible overhang at the 3' end. The total cDNA was ligated into pIPspAdapt6 (for sense orientation of cDNA inserts ) or pIPspAdapt7 (for antisense orientation of cDNA inserts) (see example 17 for adapter configurations). Then, pIPspAdapt6 and pIPspAdapt7 were digested with the restriction endonuclease MluI, followed by dephosphorylation of the 5' overhangs using thermosensitive alkaline phosphatase (LTI). After digestion with SalI and NotI, the linearized plasmid was isolated on a 0.8% agarose gel and purified by anion exchange chromatography. Following ligation of the cDNA molecules into the plasmids, the resulting library was introduced into *E. coli* DH5a electrocompetent bacteria by electroporation on a BTX 600 electrocell manipulator or equivalent. The unamplified library was aliquoted and frozen as a glycerol stock.

On the day of plating, vials were thawed and plated on large petri dishes containing LB media with 1.5% agar and ampicillin at 50 micrograms per ml. To obtain even distribution of the plated colonies, glass beads were used while plating. After overnight growth at 37° C., the agar-plates were transferred to an automated colony-picking robot (Flexys; Genome solutions). Individual colonies were picked and transferred by the robot to microtiter plates with 300 µl of Terrific Broth media and ampicillin at 50 micrograms per ml. Plates inoculated in this way are then transferred to HiGro incubators (Genemachines) aerated with oxygen and grown according to the manufacturer's manual for 12–16 hours. Thereafter, the individual plasmids were isolated by the conventional alkaline lysis plasmid DNA isolation method as described in Sambrook et al. (Sambrook, J. et al, eds. (1989) Molecular cloning: a laboratory manual, $2^{nd}$ edition, Cold Spring Harbor Laboratory Press). For this, the plates are first transferred to centrifuges (e.g., Eppendorf 5810R or Heraeus Megafuge 2.0) and bacteria are pelleted for 20 minutes at 1500×g. Using robotic liquid handlers, the supernatant in the individual wells of the individual plates is removed and discarded. Bacterial pellets are resuspended in 100 µl 25 mM Tris, pH 8.0 containing 50 mM glucose and 10 mM EDTA, and bacteria are lysed by adding 100 µl of 0.2N NaOH/1% SDS. Following neutralization by adding 100 µl of 5M potassium acetate, a cleared lysate is obtained by filtration over a MultiScreen-NA lysate clearing plate (Millipore B.V., Etten-Leur) or equivalent thereof, using a vacuum manifold. The plasmid DNA in the cleared lysate is subsequently precipitated by adding 200 µl of 2-isopropanol and centrifugation (1500×g, 30 minutes, 4° C.). The precipitate is washed once with 70% ethanol, air dried, and resuspended in 20 µl of TE.

The isolated plasmid DNA in each individual well is quantified using the Picogreen DNA quantification kit (Molecular Probes, Eugene, Oreg. USA) by transferring an aliquot of the plasmid DNA from each well to fresh plates with the appropriate dilution. PER.C6 cells, or derivatives such as PER.C6/E2A, are seeded as described under the other examples for miniaturized adenovirus generation. For each well, 55 nanogram of purified plasmid DNA was transferred into a new plate and linearized with PiPspI for 60 minutes at 65° C. This plasmid is then cotransfected with an appropriate helper DNA molecule (e.g., E2A deleted (such as pWE/Ad.AflII-rITR.deltaE2A), E2A/E3 deleted, or E2A/E3/E4 deleted, see example 18) into PER.C6 or PER.C6/E2A packaging cells. Transfection is similar to the experiments and methods described in examples 9, 10, or 25 for adenovirus generation in microtiter plates. Viral formation in individual wells is quantified using CPE formation, blot based virus assays, or reporter systems. The arrayed adenoviral library is then ready to be used in cell based screens where one can select for a particular phenotype.

Figure 36A:
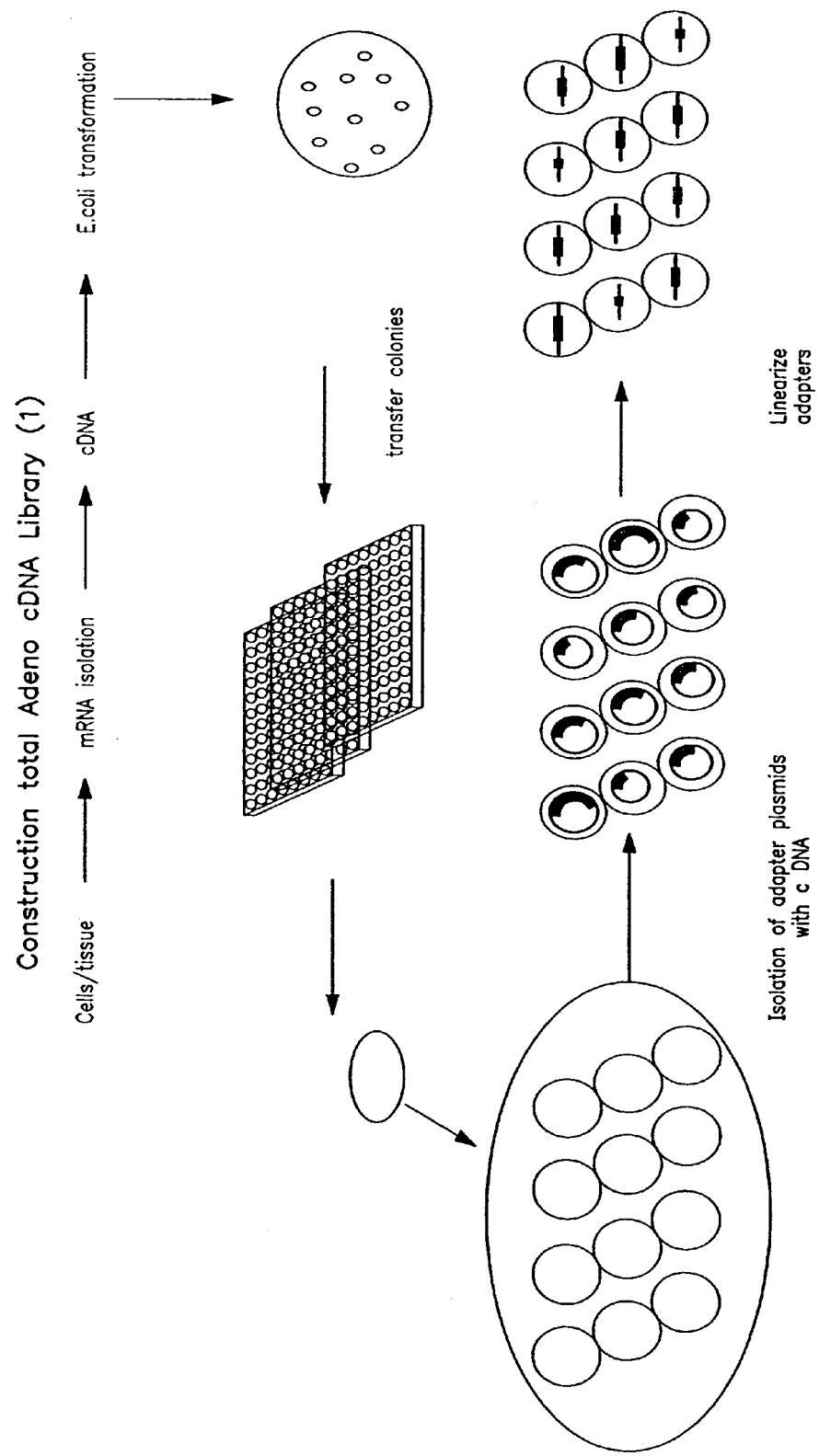
FIG. 36 (A and B) (Example 20): Schematic overview of constructing an arrayed adenoviral cDNA expression library.
Figure 36B:
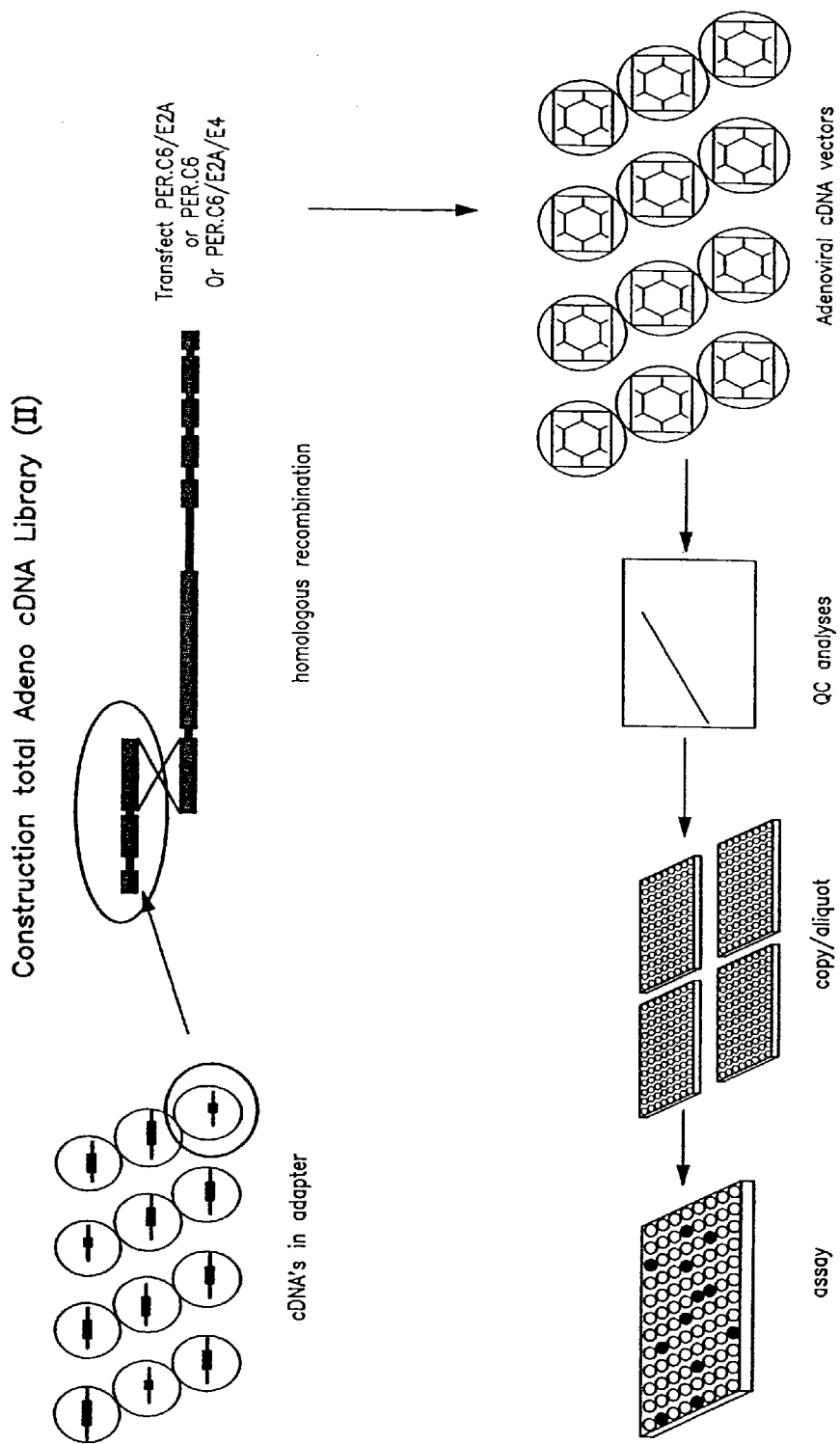
Figures 37A, 37B, 37C, 37D:
FIG. 37 (A, B, C, and D) (Example 21): Comparison of cotransfections of different adapter plasmids and pWE/Ad.AflII-rITRDE2A on 384-well plates with cotransfections on 96-well plates. The percentage of virus producing wells (CPE positive wells) scored at different time points as indicated after propagation of the freeze/thawed transfected cell to new PER.C6/E2A cells 5 days after transfection (upper panel) or 7 days after transfection (lower panel) is shown.

In FIG. 36A and FIG. 36B, an overview is given of the scheme of an adenoviral cDNA expression library constructed and arrayed as described above. This scheme describes the construction of libraries of individually cloned adenoviral vector libraries in a high throughput fashion. The improvement of this strategy over pooled libraries is that no bias for viruses with a growth advantage can occur. This is because individual members of the library are in the format of individual colonies straight after the plating of the library, and are kept individually during all further procedures.

The adenoviral expression library can be used for infection of different cells appropriate for selection of a particular phenotype such as capillary formation, cell proliferation, cell migration, or marker gene expression either in an appropriate unmodified cell type or a reporter cell line designed for this purpose. Detection of these phenotypes can be done, for example, using automated image analysis of morphology changes or changes in intracellular localization of a reporter protein. Once hits have been selected, the cloned bacterial DNA version is available immediately for sequence analysis in the form of pIPspAdapt6 or pIPsp-Adapt7 adapter plasmid as produced in *E. coli*. This means that no rescue is necessary, as is the case with pooled retroviral or plasmid-based expression libraries.

If desired (for example, using robotic liquid handlers or manually), individual wells containing individual adenoviral vectors in one row, one column, one plate, or multiple plates can be pooled before doing assays. This may be advantageous if a desired assay is not amenable to high throughput analyses and the total number of wells needs to be decreased for a primary screen. An additional improvement or advantage of pooled but originally cloned adenoviral vectors is that multi-gene dependant phenotypes are selectable.

Example 21

Viral Production in Wells of a 384-well Tissue Culture Plate

Essentially, this experiment was performed as described in Example 10, except for the following minor changes. The day before transfection, PER.C6/E2A cells were diluted with culture medium (DMEM with 10% fetal bovine serum and 10 mM $MgCl_2$) to a suspension of 11,250 cells per 25 µl, followed by seeding 25 µl per well of a 384-well tissue culture plate using a 16 channel multichannel pipette (Finn). After adding 1.3 ml serum free DMEM to the DNA/lipofectamine mixture, 15 µl of this mixture was then added to each PER.C6/E2A seeded well that had been washed with 25 µl DMEM prior to transfection. After 3 hours in a humidified $CO_2$ incubator (39° C., 10% $CO_2$), 50 µl culture medium was added to each well and the plates were returned to the humidified $CO_2$ incubator (39° C., 10% $CO_2$). The next day, the medium of each well was replaced with 50 µl culture medium. The plates were then returned to a humidified $CO_2$ incubator (32° C., 10% $CO_2$) for an additional 4 days, after which the wells were subjected to freezing at −20° C. overnight followed by thawing and resuspension by repeated pipetting. An aliquot of 25 µl of the freeze/thawed transfected cells was transferred to each well of a plate with fresh PER.C6/E2A cells seeded as described above on 384-well tissue culture plates (plate 2). The second 384-well plate, with PER.C6/E2A cells incubated and thus infected with freeze/thawed cell lysate of the first transfected plate, was checked for CPE formation and stored at −20° C. The experiment mentioned above was performed twice. In FIG. 37A, FIG. 37B, FIG. 37C, and FIG. 37D, the percentage of CPE positive wells scored after propagation of the freeze/thawed transfected cells to new PER.C6/E2A cells is depicted.

Example 22

Figure 38A:
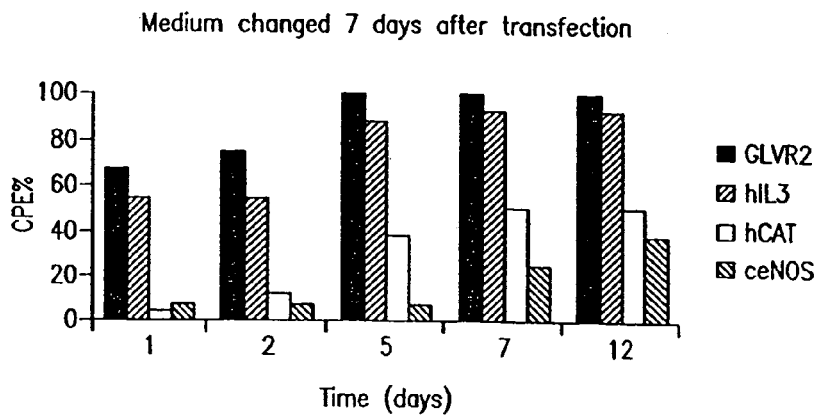
FIG. 38 (Example 22): The percentage of virus producing wells (CPE positive wells) scored at different time points as indicated after changing the medium of the transfected cells 7 days after transfection (A); after no medium change (B); and after standard propagation of the freeze/thawed transfected cells to new PER.C6/E2A cells (C).

The Effect of Omitting Propagation, or Refreshment of Culture Medium Instead of Propagation, on the Speed and Production Efficiency of Virus Formation Making the process of miniaturized adenoviral vector production more amenable to automation calls for a simplification of the whole procedure. One laborious and time consuming step is the propagation of cell lysates from transfected PER.C6/E2A cells on fresh cells, therefore omitting this step is desirable. In order to determine the effect of changing the medium of transfected cells instead of using the freeze/thawed, transfected PER.C6/E2A cells (see example 10 and others) to infect new PER.C6/E2A cells (propagation), or to omit propagation all together, the following experiment was performed. The day before transfection, PER.C6/E2A cells were harvested using trypsin-EDTA and then counted. The cells were then diluted with culture medium (DMEM with 10% fetal bovine serum and 10 mM $MgCl_2$) to a suspension of 22,500 cells per 100 µl, followed by seeding 100 µl per well in the 96-well tissue culture plates. The next day, 2.6 µg of the linearized adapter molecules and 2.6 µg of the PacI linearized pWE-Ad.AflII-rITRdE2A plasmid DNA, in a volume of 100 µl serum free DMEM, were mixed with 26.5 µl lipofectamine diluted in 74.4 µl serum free DMEM by adding the lipofectamine mix to the DNA mix. The DNA/lipofectamine mixture was left at room temperature for 30 minutes, after which 1.3 ml serum free DMEM was added. The mixture was then added (30 µl per well) to PER.C6/E2A seeded wells that had been washed with 200 µl DMEM prior to transfection. All of the transfections were performed in duplicate. After three hours in a humidified $CO_2$ incubator (39° C., 10% $CO_2$), 200 µl culture medium was added to each well and the plates were returned to the humidified $CO_2$ incubator (39° C., 10% $CO_2$). The next day, the medium of each well was replaced with 200 µl culture medium. The plates were then returned to the humidified $CO_2$ incubator (32° C., 10% $CO_2$). After seven days, the medium of one of the two transfected plates was replaced with 200 µl culture medium, returned to the humidified $CO_2$ incubator (32° C., 10% $CO_2$), and the formation of CPE was followed. In FIG. 38A, the percentage of virus producing cells (CPE positive wells) scored after changing the medium of the transfected cells, instead of propagation and amplification fresh PER.C6/E2A cells, is depicted.

Figure 38B:
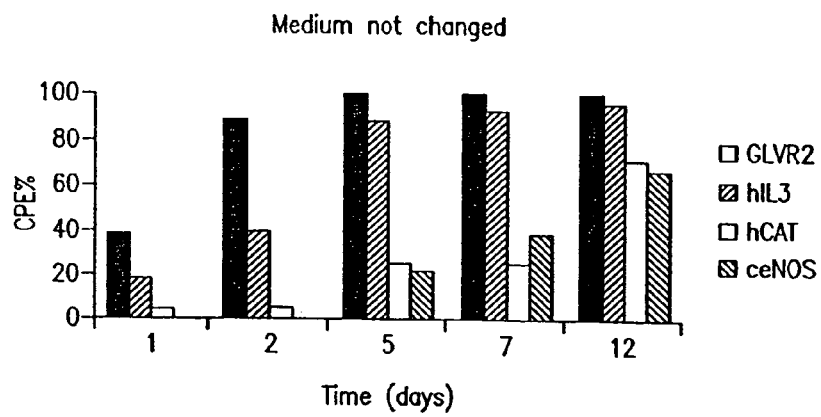
Figure 38C:
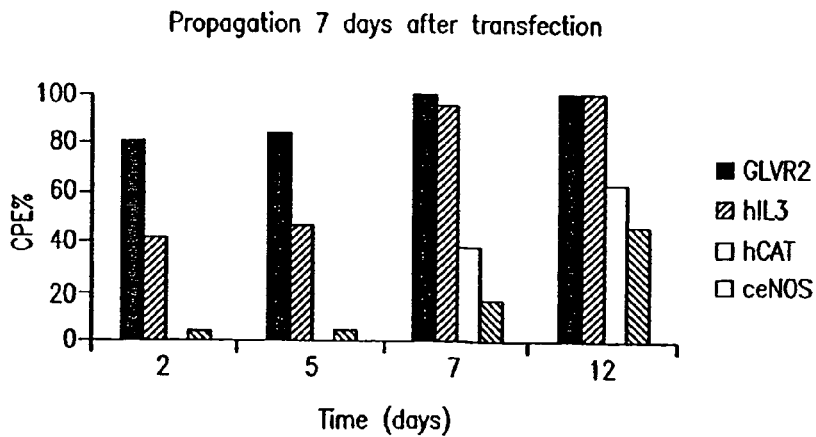

The wells of the second plate were subjected to freezing at −20° C. overnight, followed by thawing and resuspension by repeated pipetting. A 100 µl aliquot of the freeze/thawed transfected cells was transferred to each well of a plate with new PER.C6/E2A cells ($2.25 \times 10^4$ cells per well in 100 µl) that had been seeded in 96-well tissue culture plates one day prior to infections. The plate was incubated in the humidified $CO_2$ incubator (32° C., 10% $CO_2$) until the presence of full CPE was observed. In FIG. 38B, the percentage of virus producing cells (CPE positive wells) scored after propagation on freshPER.C6/E2A cells is depicted. In all experiments, untransfected wells were included for control of cross contamination. All the control wells remained negative for CPE formation. In FIG. 38C, the results of a parallel normal procedure as described under example 10 are shown.

These results show that replacement of medium or completely omitting any handling after transfection can replace reinfection of fresh PER.C6/E2A cells with lysate from the primary transfectant plates.

Example 23

Determination of the Influence of the Cell Growth of PER.C6/E2A Cells on the Speed and Production Efficiency of Virus Formation For construction of adenoviral gene expression libraries, the conditions for miniaturized production of adenoviral vector need to be optimal. Therefore, a number of parameters that may influence virus generation were varied and their effects in adenoviral vector production were measured.

In order to determine whether the cell confluency of the complementing cell line PER.C6/E2A, prior to seeding in microtiter plates, influences the speed and efficiency of virus production, the following experiment was performed. On day one, PER.C6/E2A cells were harvested using trypsin-EDTA and counted. The cells were seeded at 1/10, 1/5, and 1/2.5 of the harvested cells in three different 175 $cm^2$ tissue culture flasks. In table 9, the number of cells that were seeded in each 175 $cm^2$ tissue culture flask in three different experiments are shown. Four days later, the PER.C6/E2A cells from each flask were harvested, counted, and then diluted with culture medium (DMEM with 10% fetal bovine serum and 10 mM $MgCl_2$) to a suspension of 22,500 cells per 100 µl. From each cell suspension, two 96-well tissue culture plates were seeded with 100 µl of cell suspension per well. The next day, 10.6 µg of SalI linearized pAd/Clip-lacZ and 10.6 µg of the PacI linearized pWE-Ad.AflII-rITRdE2A plasmid DNA, in a volume of 600 µl serum free DMEM, were mixed with 153.6 µl lipofectamine diluted in 446.4 µl serum free DMEM by adding the lipofectamine mix to the DNA mix. The DNA/lipofectamine mixture was left at room temperature for 30 minutes, after which 7.8 ml serum free DMEM was added. The latter mixture was then added (30 µl per well) to PER.C6/E2A seeded wells that had been washed with 200 µl DMEM prior to transfection. After three hours in a humidified $CO_2$ incubator (39° C., 10% $CO_2$), 200 µl DMEM with 10% fetal bovine serum and 10 mM $MgCl_2$ was added to each well and the plates were returned to the humidified $CO_2$ incubator (39° C., 10% $CO_2$). The next day, the medium of each well was replaced with 200 µl DMEM with 10% fetal bovine serum and 10 mM $MgCl_2$. The plates were then returned to a humidified $CO_2$ incubator (32° C., 10% $CO_2$). After two days, one of the two transfected plates was used to determine the transfection efficiency using lacZ staining. The transfection efficiency of each 96-well tissue culture plate, scored after lacZ staining in three different experiments, is shown in Table 9.

The second plate of the two transfected plates was used for virus production. Seven days after transfection, the wells of the second plate were subjected to freezing at −20° C. overnight, followed by thawing and resuspension by repeated pipetting. A 100 µl aliquot of the freeze/thawed transfected cells was transferred to each well of a plate with new PER.C6/E2A cells ($2.25 \times 10^4$ cells per well in 100 µl) that were seeded in 96-well tissue culture plates one day prior to infections. The plate was incubated in the humidified $CO_2$ incubator (32°, 10% $CO_2$) until the presence of full CPE was observed. In FIG. 39A, FIG. 39B, and FIG. 39C, the percentage of virus producing cells (CPE positive wells), scored after propagation of the freeze/thawed transfected cells to new PER.C6/E2A cells, is depicted. The data indicate that the level of confluency of the PER.C6/E2A cells, prior to transfection with the adenoviral adapter and helper DNA molecules, influences the final percentage of virus producing wells. The higher confluency was the most optimal for absolute fmal number of wells producing virus and the speed at which the virus generation occurs.

Example 24

Figure 40:
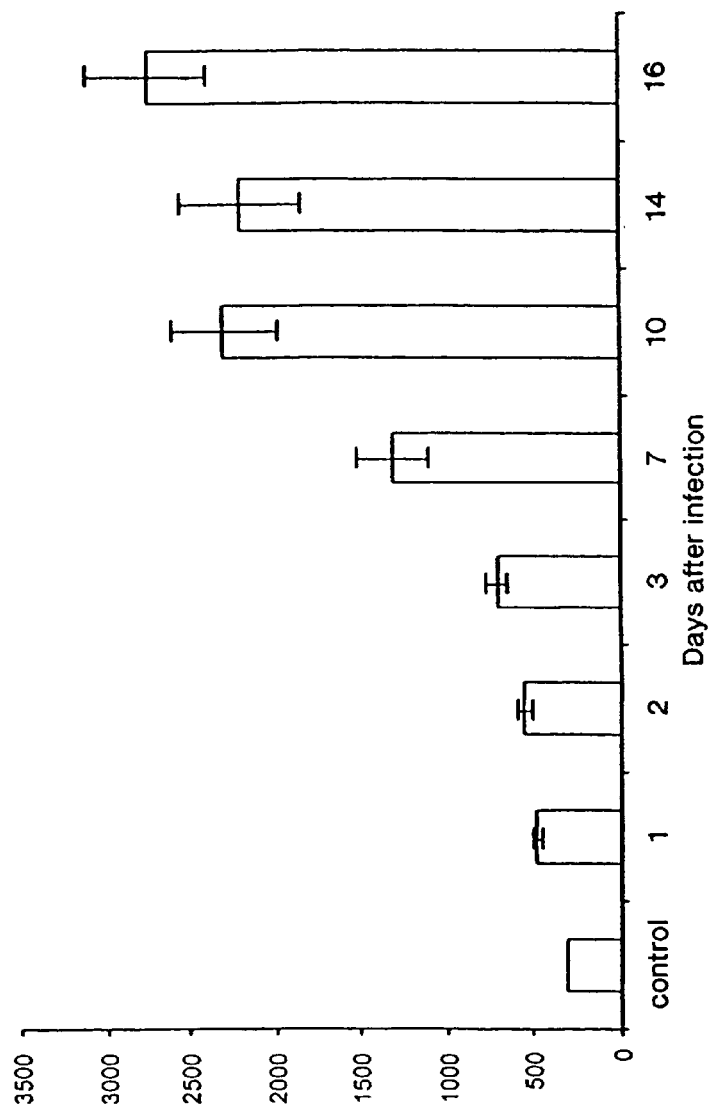
FIG. 40: The use of adenoviral expression vectors as a semi-stable expression system for assays with a delayed readout of phenotype after infection with an adenoviral expression library (Example 24). Transgene used: Green Fluorescent Protein (EGFP, Clontech). A crude PER.C6/E2A production lysate was used at an multiplicity of infection (MOI) of about 500–1000.

Long-term Incubation with Adenoviral Supernatant Allows Detection of Slow Phenotypes The use of adenoviral vector libraries in functional genomics calls for the use of appropriate cell based assays which are amenable to high throughput screening and miniaturization, in addition to a phenotype that is detectable and relevant for the genes one is looking for, such as the ones used in example 12. The time of assaying after infection with an adenoviral expression library, for example as described in Example 20, is variable and dependent on the parameters determined by the phenotype being assayed for. For example, using automated image analysis, the formation of blood capillaries in each well can be assayed simply by detecting the formation of capillaries. Formation of these structures, which are indicative of angiogenesis or blood vessel formation, can be induced by infection of relevant precursor cells. Such cells can be endothelial cells from heart or tumor origin with an adenoviral vector carrying a relevant transgene, for example a vascular endothelial like growth vector (VEGF). However, a complex phenotype such as capillary formation only appears after several days to weeks. Therefore, expression of the library of genes as mediated by the adenoviral expression cassette in some cases needs to be long enough to allow the phenotype to develop. In FIG. 40, the results of an experiment with an EGFP-adenoviral vector that was used to infect A549 cells in 96-well plates are shown. Based on the stability features described in example 15, the adenoviral dilution (in DMEM) was not removed but left for up to 2 weeks and EGFP expression measured at regular intervals. Clearly, these experiments show that adenoviral transduction can be regarded as semi-stable and even increase over time, suggesting that reinfection occurs and/or that newly divided cells are infected. This implies that the transient adenoviral vector system can be used to screen for phenotypes that take 2 weeks or more to develop by leaving the adenoviral supernatant on the cells in the multiwell plates (384-well or smaller).

Example 25

Miniaturized, Multiwell Production of Recombinant Adenoviral Vectors Using Cost Effective Polyethylenimine (PEI) as DNA Transfection Agent For the purpose of cost reduction and variable toxicity reduction, it is desirable to replace the liposomal transfection reagent lipofectamine. The cationic polymer polyethylenimine (PEI) has been tested in the miniaturized, multiwell (96-well) adenoviral vector production system for this purpose. See also Examples 9 and 10. PEI has been tested for transfection of PER.C6 and PER.C6/E2A, with different transgene inserts in the adenoviral helper plasmid: LacZ and EGFP. Different parameters were tested including PEI/DNA ratios, incubation times, and amounts of PEI/DNA complex per single well.

Testing of PEI with Different PEI/DNA Ratios

The 96-well microtiter plates were seeded the day before transfection with PER.C6 or PER.C6/E2A cells as described in example 10. Then, 3 micrograms of SalI linearized pCLIP-LacZ and 3 micrograms PacI linearized pWEAflIIr-ITR for PER.C6 or pWEAflIIrITRdE2A for PER.C6/E2A were diluted in 150 μl 150 mM NaCl and incubated at room temperature for 10 minutes. Also, a 20 mM 25 kDa PEI solution was diluted in 150 μl of 150 mM NaCl at different amounts to obtain different PEI/DNA ratio's and incubated at room temperature for 10 minutes. See table 4. The assays were performed on sixteen wells (8 wells in duplicate on different plates).

The DNA and PEI solutions were mixed by adding PEI dropwise to DNA and then incubated for 10 minutes at room temperature. Cells were washed with 100 μl of serum free DMEM per well. Then, 1.3 ml of DMEM was added to the mixture and 80 μl of the solution was applied to the cells in each well. As a positive control, DNA/lipofectamine complexes were transfected (prepared according to Example 9). Additional control incubations of DMEM, PEI without DNA (ratio 13), and two times the amount of PEI/DNA ratio 13 were included. The transfections were done four hours later. For the PEI transfections, 80 μl of PEIPER.C6 medium (DMEM with 20% v/v fetal calf serum (FCS) 10 mM $MgCl_2$)/well was added to the cells. For the lipofectamine transfections, 180 μl of DMEM, 10% v/v FCS, 10 mM MgCl2 per well was added to the cells. The plates were returned to a humidified $CO_2$ incubator and incubated at 37° C. for PER.C6 and at 39° C. for PER.C6/E2A. The next day, the medium of each well was replaced with 200 μl DMEM, 10% v/v FCS, 10 mM MgCl2. The plates were then left at 37° C. for PER.C6 plates and at 32° C. for PER.C6/E2A plates in a humidified $CO_2$ incubator. After 3 days, one of the duplicate plates was stained with X-gal to determine the transfection efficiency, the results of which are depicted in table 5.

After four days post-transfection, the plates were subjected to freezing at −20° C. for 4 hrs, followed by thawing and resuspension by repeated pipetting. A 100 μl aliquot was transferred to a new plate of PER.C6 or PER.C6/E2A cells seeded a day before as described above. The plates were then placed back into the $CO_2$ incubators. After 14 days post-propagation, virus formation was scored by CPE as an indicator and the plates were subjected to freezing at −20° C. for 4 hrs, followed by thawing and resuspension by repeated pipetting. A 20 μl aliquot was transferred to wells of plates seeded with $1 \times 10^4$ A549 cells per well of a 96-well plate in a volume of 100 μl. Two days after infection, the wells were stained with X-Gal for LacZ activity as described under example 9. The results are summarized in table 6.

Testing of PEI with Different PEI/DNA Ratios in Combination with Different Amounts of Complex Per Well In order to test the optimal amount of PEI/DNA complex that can be applied to the cells without being toxic, the PEI/DNA ratios 5 and 11.7 were tested on PER.C6/E2A. The standard concentration (1X) is the concentration as described in the previous transfection experiment (see Table 4).

To make PEI solutions with amounts of PEI between 0.9 and 42 μl, various amounts of a 150 mM NaCl solution were added to the 20 mM 25 kDa PEI (Fluka cat.nr.03880) solution to a final volume of 300 ul. From this solution, 150 μl was added to the DNA mix (see table 7). DNA (50% pCLIP-LacZ and 50% pWEAflIIrITRdE2A) to 150 microliters with 150 mM NaCl.

Transfections were performed as described above. Lipofectamine was used as a positive control, as well as DNA, PEI, or DMEM without any additives. After three days, a duplicate plate was stained for lacZ expression. These results are given in table 8. First, the cells were checked for toxicity. At ratio 11.7, the double concentration (2X) is more toxic but the transfection efficiency at X is higher. At concentration 0.1X for both ratios, no blue cells were seen after staining, indicating that the cells were not transfected. Processing, CPE monitoring, A549 transduction, and lacZ staining was done as described.

Figure 41:
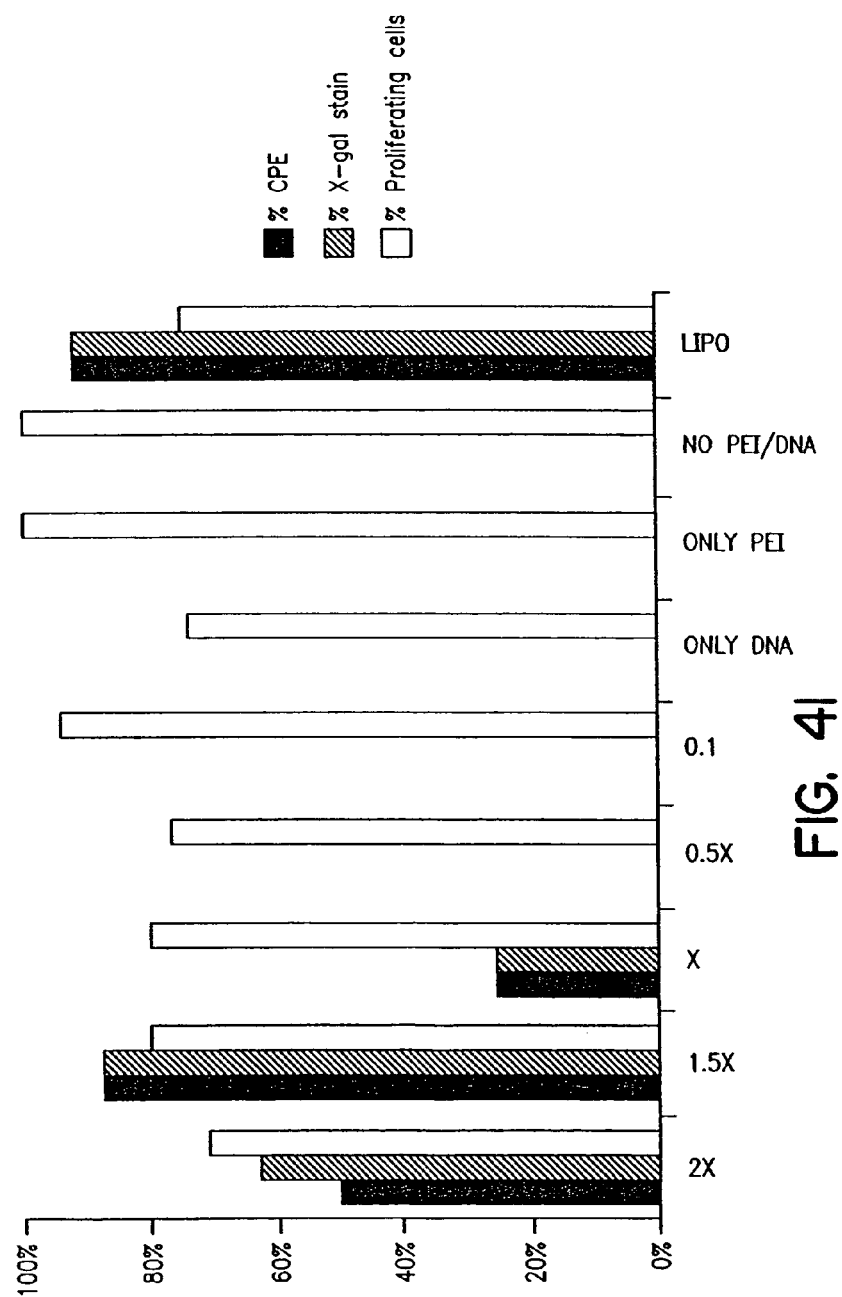
FIG. 41: The use of polyethylenimine (PEI) for generating adenoviral vectors in miniaturized format (Example 25). Transfection efficiency, virus formation (CPE), and proliferation (toxicity) are depicted.

To quantitatively test toxicity, the latter transfections were repeated. Two days after medium replacement, a cell proliferation assay (Promega) was used to determine the number of living cells or toxicity of PEI/DNA complexes. All actions were according to the manufacturer's protocol. After 4 hrs of incubation at 37° C., the plates were read using the microplate manager (Bio-Rad). The results of this experiment for PEI ratio 5 and 11.7 are summarized in FIG. 41. Clearly, toxicity is lowest and virus generation optimal at ratio 5 (1.5 times the standard amount of complex) and at ratio 11.7 (at the standard conditions between 0.5 and 1.5 times the standard amounts).

Figure 42:
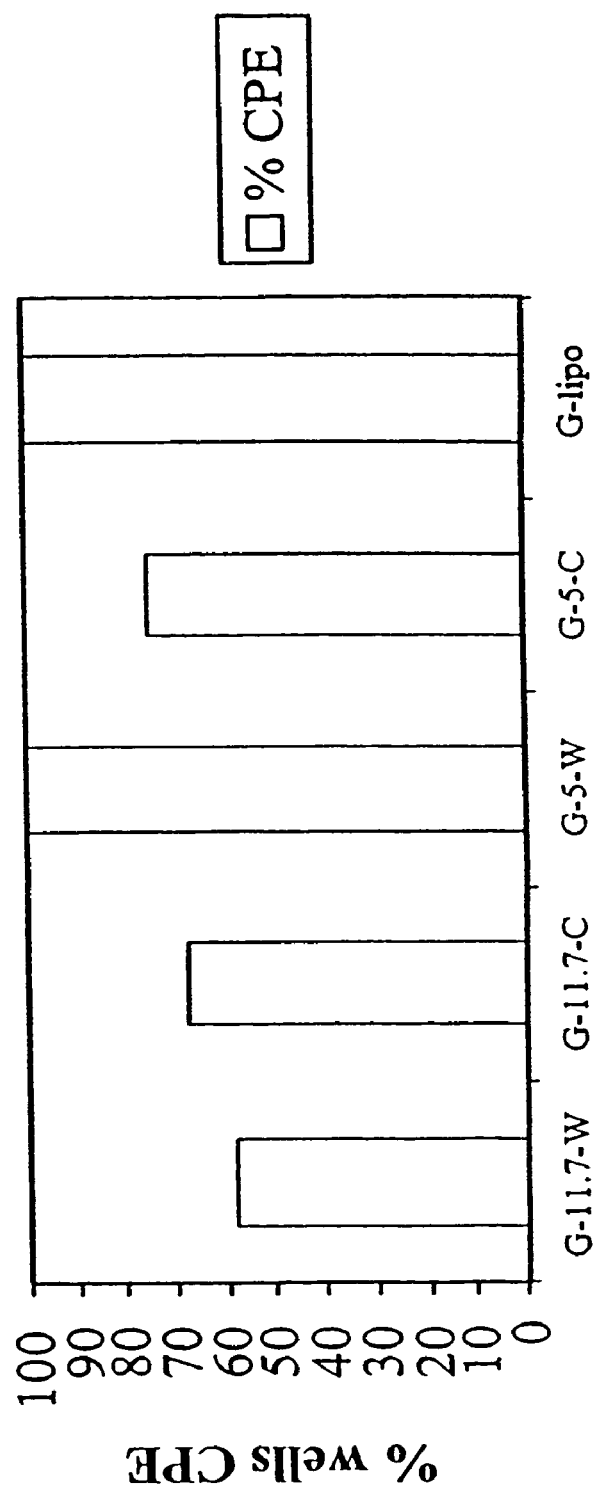
FIG. 42: Effect of temperature PEI at time of transfections on CPE efficiency (Example 25). W: Warm (room temperature) and C: Cold (4° C.).

Testing PEI as a DNA Carrier with Different PEI/DNA Ratios, with a Different Gene, and at Different Temperatures In order to determine if the temperature of PEI influences the complex formation, the above-described protocol was tested with PEI at 4° C. and at room temperature. The best concentrations of the two ratios were used in this transfection experiment (450 ng DNA/well PEI/DNA ratio 5 and 300 ng DNA/well PEI/DNA ratio 11.7). In addition, another transgene insert, EGFP, was tested. Processing, CPE monitoring, A549 transduction, and lacZ staining were performed as described. As can be seen in FIG. 42, there is no significant difference between warm and cold PEI. Virus formation with EGFP and PEI worked very well (PEI ratio 5 warm and the positive control lipofectamine both 100% CPE).

Testing of PEI as DNA Carrier with Different PEI/DNA Complex Volumes Per Well

Figure 43:
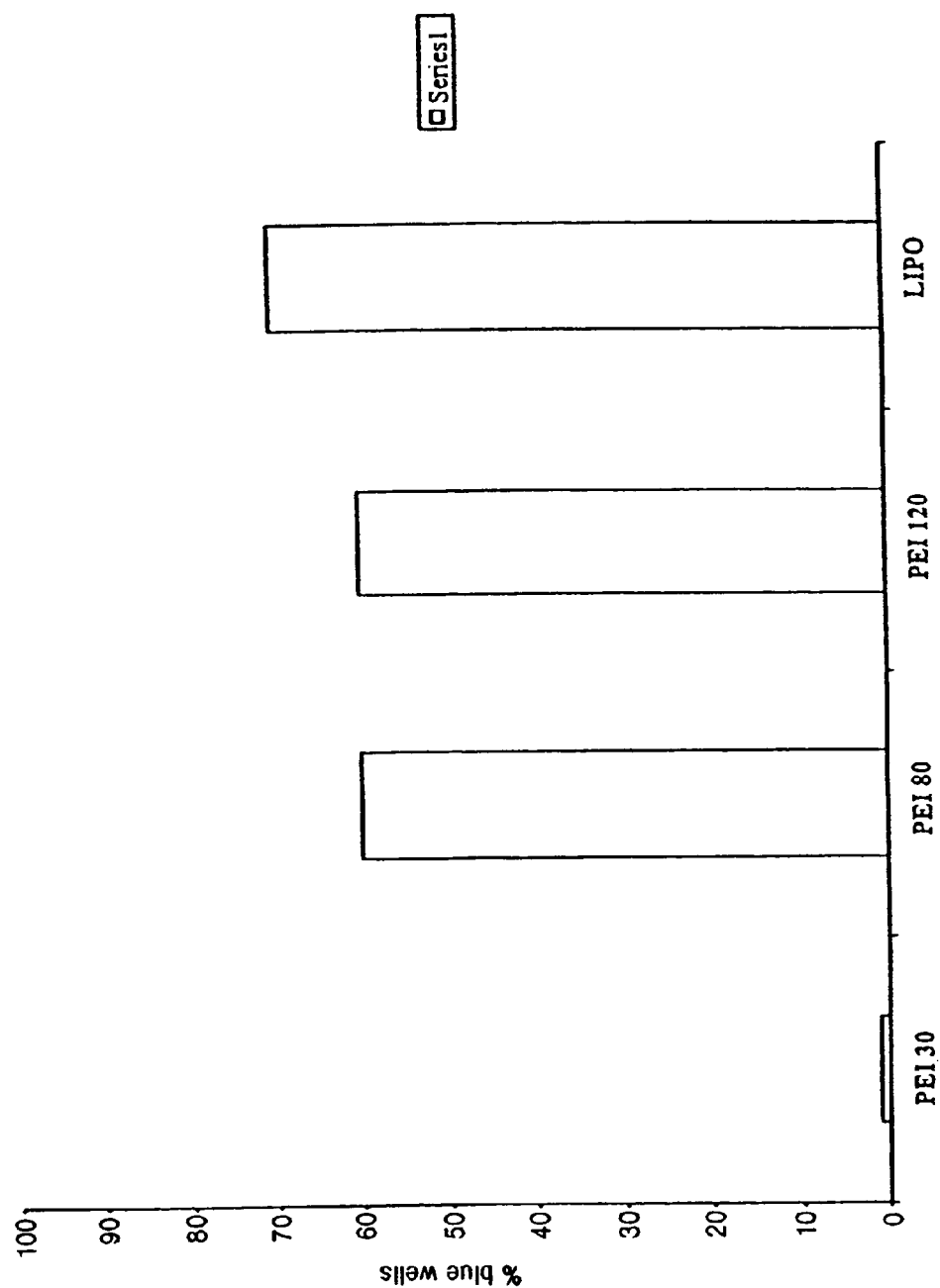
FIG. 43: Effect of PEI transfection volume on transfection efficiencies (Example 25).

In order to test if the volume of DNA/PEI complex influenced the efficiency of virus generation in the above-described protocol, 30, 80, and 120 µl per well of the PEI/DNA complex (ratio 5 450 ng DNA per well, PEI 20 mM 25 kDa, Fluka) were added to the cells. Processing, CPE monitoring, A549 transduction, and lacZ staining were done as described above. As is shown in FIG. 43, there is a significant difference in transfection efficiency between applying 30 µl, 80 µl, and 120 µl. Only 1% of the cells within a well were stained blue with 30 µl, whereas 60% of the cells stained blue with 80 µl. The 120 µl sample showed the same results as applying 80 µl. For virus formation, the same trend was observed: no CPE was found for 30 µl, whereas 80 µl and 120 µl gave similar percentages (not shown). In conclusion, PEI can be used to produce adenoviral vectors in a miniaturized setup.

Example 26

Figure 44:
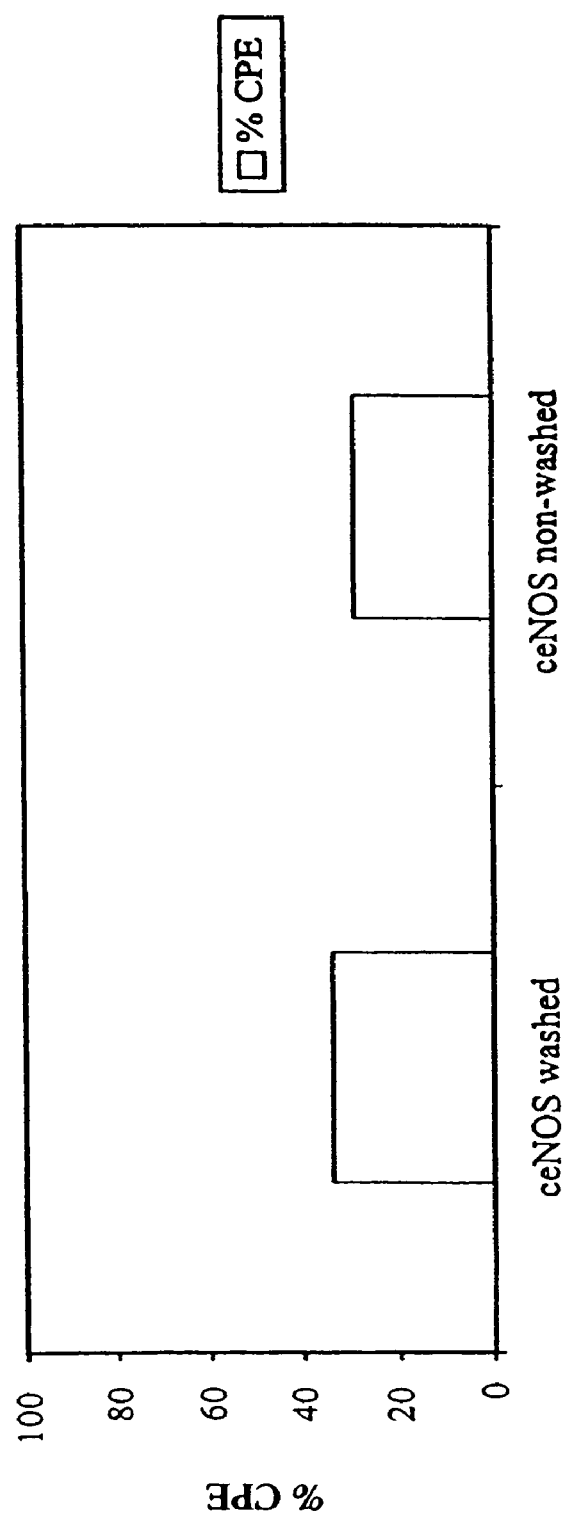
FIG. 44: Washing of PER.C6/E2A cells with serum free medium before applying lipofectamine-DNA complex can be omitted (Example 26).

Miniaturized, Multiwell Production of Recombinant Adenoviral Vectors Without a Cell Washing Step Prior to Transfection In order to reduce steps in automation of the miniaturized, multiwell production of recombinant adenoviral vectors and cost reduction, the serum free medium (SFM) washing step of the PER.C6 or PER.C6/E2A cells or derivatives prior to transfection was removed from the standard protocol. Transfections were performed as described in example 10. The transfections were performed using the human ceNOS as the transgene insert. Removal of the cell washing step was tested and compared to the standard procedure. Processing and CPE monitoring were done as described. As seen in FIG. 44, there is no significant reduction in virus production when the cells were not washed prior to transfection.

In conclusion, removal of the cell washing step, which removes the bulk of serum proteins as part of the standard transfection protocol, is possible without effecting the CPE efficiency. Removal of this step is very useful when reducing the complexity of the whole process is desirable for automating the miniaturized, multiwell production of recombinant adenoviral vectors.

Example 27

The Use of Adenoviral Constructs to Modulate Gene Expression in Zebrafish

Modulation of gene expression by adenoviral constructs in whole animals can give important information about the function of genes. For instance, adenoviral constructs that express a sense cDNA construct encoding a full length protein can be used for overexpression of that protein in animal model systems, while adenoviral constructs that express the antisense cDNA can be used to reduce the expression levels of the endogenous protein. In addition, overexpression of an adenoviral-encoded protein might rescue a mutant phenotype. Adenoviral-mediated modulation of gene expression in animal models can give important information about the function of a gene. In this example, zebrafish, *Danio rerio*, will be discussed as an animal model system to show the feasibility of the approach. Zebrafish cDNA libraries will be screened with cDNAs that are identified and isolated by methods described in this application. The obtained homologous zebrafish cDNAs, encoding full length proteins, will be isolated and cloned in both orientations, sense and antisense, in adapter plasmids of the pIPSPAdapt series (see example 17). These will subsequently be used to generate recombinant adenovirus, which will be used to infect either wildtype or mutant zebrafish embryos (see for instance *Development* 1996 Volume 123, December). Methods for breeding zebrafish are well known to those skilled in the art.

The effect of up- or down-modulation of gene expression can be studied in wildtype or mutant embryos or adult fish. Embryos will be collected as follows: zebrafish are photoperiodic in their breeding and produce embryos every morning shortly after sunrise. For continuous production of a relatively small number of embryos (30–50 per tank per day), an equal number of males and females are used. The day-night cycle is controlled with an automatic timer (14 hr light/10 hr dark). The bottom of the tank is covered with a single layer of marbles to keep the fish from eating the newly spawned eggs. Freshly produced embryos are collected each morning by siphoning the bottom of the tank. The embryos can then be infected with recombinant adenovirus in several ways, as described below. The method of choice depends on the expression pattern of the gene.

Recombinant adenovirus can be injected directly into the chorion fluid, after which the embryos are washed and cultivated further in system water. Similarly, recombinant adenovirus can be deposited at specific sites in embryos or adult fish, for instance, by injection into the blood stream or by oral or rectal administration. Injection can be performed by holding the embryos in wedged-shaped troughs made with a plastic mold in 1.5% agarose, in which case there is no need to remove their chorions. Each trough can hold approximately 35 embryos (with chorions). Embryos can be aligned by gently tapping them down with forceps. Agarose is useful because pipette tips generally will not break if they accidentally touch the surface. As the pipette penetrates the chorion, the embryo is forced against the rear vertical wall of the trough. The exact positioning of the pipette tip within the embryo is achieved by slight movement of the pipette with a micro-manipulator or by movement of the stage. Alternatively, embryos can be dechorionated (see below) and incubated in medium containing recombinant adenovirus.

After injection, 25–30 eggs are deposited into 250 ml beakers. After hatching, larvae are transferred into a new beaker and completely separated from their chorions. Larvae are raised under standard conditions well known to those skilled in the art.

Monitoring changes after adenoviral infection of zebrafish can be done as early as the embryonic stage. Some observations of zebrafish development can be made directly through the chorion. However, for most procedures it is better to remove the chorion, which is easily done with sharp forceps. When raised at 28.5° C., zebrafish develop normally outside their chorions. Embryos removed from their chorions can be transferred from one container to another by gently pipetting them up with a fire-polished Pasteur pipette or by gentle pouring. Small petri dishes (35 mm diameter) are adequate for holding up to 25 embryos during the first few days of development. The embryos can be brought to the center of the dish for viewing by gently swirling the medium in a circular motion. Larvae and adult fish can be monitored without further treatment.

More elaborate analysis methods include the staining of sections by classical histological methods or specific methods such as anti-sense hybridization or incubation with antibodies to look at differences at the molecular level.

The phenotypic changes observed after infection of zebrafish with recombinant adenovirus can give important information about the function of the encoded genes in vivo. The described method can also be applied to other animal models.

TABLE 4

| Ratio | # 20 mM PEI (µl) | # 150 mM NaCl (µl) |
|---|---|---|
| 8.3 | 7.5 | 142.5 |
| 10 | 8 | 142 |
| 11.7 | 10.5 | 139.5 |
| 13 | 12 | 138 |
| 15 | 13.5 | 136.5 |

TABLE 5

Transfection efficiency control. X-gal staining.

| Ratio | % blue cells PER.C6 | % blue cells PER.C6E2A |
|---|---|---|
| 8.3 | 45 | 60 |
| 10 | 45 | 60 |
| 11.7 | 55 | 65 |
| 13 | 55 | 65 |
| 15 | 50 | 40 |
| 2*13 | 10 | 10 |
| Only PEI 13 | 0 | 0 |
| Only DMEM | 0 | 0 |
| LIPO | 65 | 80 |

TABLE 6

| PER.C6 Ratio | # CPE | % CPE | # blue wells after infection A549 | % blue wells after infection A549 |
|---|---|---|---|---|
| 8.3 | 6/8 | 75 | 7/8 | 87.5 |
| 10 | 3/8 | 37.5 | 5/8 | 62.5 |
| 11.7 | 4/7 | 57 | 4/7 | 57 |
| 13 | 4/8 | 50 | 5/8 | 62.5 |
| 15 | 3/7 | 37.5 | 3/7 | 43 |
| 2*13 | 0/8 | 0 | 0/8 | 0 |
| Only PEI 13 | 0/8 | 0 | 0/8 | 0 |
| Only DMEM | 0/8 | 0 | 0/8 | 0 |
| Lipofectamine | 1/16 | 6 | 1/8 | 12.5 |

| PER.C6/E2A Ratio | # CPE | % CPE | # blue wells A549 cells | % blue A549 cells |
|---|---|---|---|---|
| 8.3 | 0/8 | 0 | 0/8 | 0 |
| 10 | 1/8 | 12.5 | 3/8 | 37.5 |
| 11.7 | 3/8 | 37.5 | 6/8 | 75 |
| 13 | 1/8 | 12.5 | 2/8 | 25 |
| 15 | 1/8 | 12.5 | 2/8 | 25 |
| 2*13 | 0/8 | 0 | 0/8 | 0 |
| Only PEI 13 | 0/8 | 0 | 0/8 | 0 |
| Only DMEM | 0/8 | 0 | 0/8 | 0 |
| Lipofectamine | 11/16 | 69 | 13/16 | 81 |

TABLE 7

| Concentration of PEI/DNA complex | Amount of DNA/well (ng/µl) | DNA (µg) | PEI ratio 11.7 (µl) | PEI ratio 5 (µl) |
|---|---|---|---|---|
| 2 X | 600 | 12 | 42 | 18 |
| 1.5 X | 450 | 9 | 31.5 | 13.5 |
| Standard 1 X | 300 | 6 | 21 | 9 |
| 0.5 X | 150 | 3 | 10.5 | 4.5 |
| 0.1 X | 30 | 0.6 | 2.1 | 0.9 |

TABLE 8

| Complex | Amount of DNA (ng) per well | % blue cells PEI ratio 5 | % blue cells PEI ratio 11.7 |
|---|---|---|---|
| PEI 2 X | 600 | 30 | 45 |
| PEI 1.5 X | 450 | 40 | 55 |
| PEI standard X | 300 | 25 | Not determined |
| PEI 0.5 X | 150 | 5 | 40 |
| PEI 0.1 X | 30 | 0 | 0 |
| Lipofectamine | 100 | 65 | 65 |
| –/– | | 0 | 0 |

TABLE 9

| $T_{175}$ flask | Cell # $1^{st}$ exp. | Cell # $2^{nd}$ exp. | Cell # $3^{rd}$ exp. |
|---|---|---|---|

Confluencies of cells harvested for transfection

| 1/10 | $2.3 \times 10^6$ | $1.3 \times 10^6$ | $3.3 \times 10^6$ |
| 1/5 | $4.7 \times 10^6$ | $2.6 \times 10^6$ | $6.7 \times 10^6$ |
| 1/2.5 | — | $5.2 \times 10^6$ | $13.3 \times 10^6$ |

| 96-well-plate | Efficiency $1^{st}$ exp. | Efficiency $2^{nd}$ exp. | Efficiency $3^{rd}$ exp. |
|---|---|---|---|

Transfection efficiencies

| 1/10 | 30–40% | 50–60% | 50–60% |
| 1/5 | 70–80% | 50–60% | 50–60% |
| 1/2.5 | — | 50–60% | 50–60% |

All publications and patent applications mentioned in this specification are indicative of the level of skill of those skilled in the art to which this invention pertains. All

What is claimed is:

1. A method for determining the function of a unique nucleic acid present in a library, said method comprising:
   (a) providing a library of a multitude of unique expressible nucleic acids, said library including a multiplicity of compartments, each of said compartments consisting essentially of one or more adenoviral vector comprising at least one unique nucleic acid of said library in an aqueous medium, wherein said adenoviral vector is capable of introducing said nucleic acid into a host cell, is capable of expressing the product of said nucleic acid in said host cell, and is deleted in a portion of the adenoviral genome necessary for replication thereof in said host cell;
   (b) transducing a multiplicity of host cells with at least one adenoviral vector comprising at least one unique nucleic acid from said library;
   (c) incubating said host cells to allow expression of the product of said nucleic acid; and
   (d) determining the function of said nucleic acid.

2. A method for determining at least one function of at least one nucleic acid present in a library of claim 1, said method comprising:
   transducing a multiplicity of cells with at least one vehicle comprising said at least one nucleic acid from said library, and
   culturing said multiplicity of cells while allowing for expression of said at least one nucleic acid and determining the expressed function thereof.

3. The method of claim 1 wherein step (d) comprises observing said host cell to identify any changes in said host cell relative to a host cell that has not been transduced with an adenoviral vector comprising said nucleic acid.

4. The method of claim 1, wherein the function of the expression product of all of said unique expressible nucleic acids in said library is unknown at the time said library is first made.

5. The method of claim 1, wherein none of said compartments contain any adenoviral vector capable of replication except in a packaging cell containing said deleted portion of adenoviral genome.

6. The method of claim 1, wherein said host cell is a eucaryotic cell.

7. The method of claim 1, wherein at least one compartment comprises at least two adenoviral vectors.

8. The method of claim 1, wherein each of said compartments consists essentially of one said adenoviral vector.

9. The method of claim 5, wherein each of said compartments contains from about $0.01 \times 10^{10}$ to about $10 \times 10^{10}$ pfu of said adenoviral vector per ml of aqueous medium.

10. The method of claim 9, wherein each of said compartments further contains the cellular debris from packaging cell lysate.

11. The method of claim 5, wherein said adenoviral vector is a minimal vector.

12. The method of claim 11, wherein said minimal vector comprises an adenovirus encapsidation signal or a functional part, derivative and/or analogue thereof, and at least one copy of at least a functional part or a derivative of an adenoviral ITR.

13. The method of claim 5, wherein said adenoviral vector comprises adenoviral genomic sequence deleted for sequence encoding the E1-region proteins.

14. The method of claim 12 wherein said minimal vector further comprises an adeno-associated virus terminal repeat or a functional part, derivative and/or analogue thereof.

15. The method of claim 13, wherein said adenoviral vector is further deleted for sequence encoding the E2A-region proteins, or the E2B region proteins or the complete E2 region proteins.

16. The method of claim 1, wherein said adenoviral vector further comprises adenovirus genomic sequence encoding adenoviral fiber proteins from at least two serotypes of adenovirus.

17. The method according to claim 1, wherein said multiplicity of cells is divided over a multiplicity of compartments, each said compartment comprising at least one vector.

18. The method according to claim 1, further comprising selecting at least one vector having a desired function.

19. The method according to claim 1, wherein at least one of said performed steps is automated.

20. A method for obtaining an expressible nucleic acid having a desired function when expressed in a cell, said method comprising:
   (a) performing the method of claim 1;
   (b) determining which compartment in said library contains an adenoviral vector comprising a unique nucleic acid having said desired function; and
   (c) obtaining said vector from said compartment.

21. The method according to claim 1, wherein said multiplicity of compartments comprises a multiwell format of at least 6 wells.

22. The method according to claim 21, wherein substantially each said well consists essentially of one or more said adenoviral vector comprising said unique nucleic acid that encodes a product of unknown function.

23. The method according to claim 21, wherein said library is configured to be made and used in a substantially automated process.

24. The method according to claim 21, wherein said multiplicity of compartments comprises a multiwell format of at least 96 wells.

25. The method according to claim 24, wherein each well contains cellular debris from eucaryotic packaging cell lysate.

26. The method of claim 24, wherein none of said wells contains adenoviral vector capable of replication except in a packaging cell containing said deleted portion of adenoviral genome.

27. The method of claim 26, wherein each of said wells contains from about $0.01 \times 10^{10}$ to about $10 \times 10^{10}$ pfu of said adenoviral vector per ml of aqueous medium.

28. The method of claim 1, wherein each of said unique nucleic acids is derived from a member of a population of nucleic acids, said population selected from the group consisting of naturally occurring populations of messenger RNA, DNAs, cDNAs, genes, ESTs and genetic suppressor elements; synthetic oligonucleotides; and antisense nucleic acids.

29. The method of claim 10, wherein the contents of each said compartment is capable of transfecting said host cell and expressing the product of each said unique nucleic acid in said host cell.

30. The method of claim 29, wherein each said compartment is capable of providing from about 400 to about 4000 aliquots of said adenoviral vector.

31. The method of claim 27, wherein the contents of each said well is capable of transfecting said host cell and expressing the product of each said unique nucleic acid in said host cell.

32. The method of claim 31, wherein each said well is capable of providing from about 400 to about 4000 aliquots of said adenoviral vector.

33. The method of claim 12, wherein said minimal vector comprises an regulatable promoter operably linked to said unique nucleic acid.

34. The method of claim 13, wherein said adenoviral vector comprises an regulatable promoter operably linked to said unique nucleic acid.

35. The method of claim 13, wherein said adenoviral vector is further deleted for the adenoviral E3-region or a functional part thereof.

36. The method of claim 15, wherein said adenoviral vector is further deleted for the adenoviral E3-region or a functional part thereof.

37. The method of claim 35, wherein said adenoviral vector is further deleted for the adenoviral E4-region or a functional part thereof.

38. The method of claim 36, wherein said adenoviral vector is further deleted for the adenoviral E4-region or a functional part thereof.

39. The method of claim 33, wherein said promoter is repressed by an adenoviral E1 gene product.

40. The method of claim 34, wherein said promoter is repressed by an adenoviral E1 gene product.

41. The method of claim 39, wherein said promoter is an AP1 dependent promoter.

42. The method of claim 40, wherein said promoter is an AP1 dependent promoter.

43. A method according to claim 40, wherein said adenoviral vector is packaged into an adenoviral capsid.

44. The method of claim 1 wherein said function comprises a biological activity.

45. The method of claim 44 wherein said biological activity is selected from the group consisting of altered viability, morphologic changes, apoptosis, DNA synthesis, tumorigenesis, disease or drug susceptibility, chemical responsiveness, chemical secretion and protein expression.

46. The method of claim 1 wherein said unique expressible nucleic acid is derived from the group consisting of mammals, fish, nemotodes, insects, yeasts, fungi, bacteria and plants.

47. The method of claim 46 wherein said library of unique nucleic acid is derived from human placenta mRNA.

48. The method of claim 46 wherein said library of unique nucleic acid is derived from zebrafish mRNAs.

49. The method of claim 46 wherein said host cells are present in zebrafish embryos.

50. The method of claim 46 wherein said host cells are present in zebrafish adults.

51. A method for determining the function of a unique nucleic acid present in a library, said method comprising:

(a) growing a plurality of cell cultures containing at least one cell, said one cell expressing adenoviral sequence consisting essentially of E1-region sequences and expressing one or more functional gene products encoded by at least one adenoviral region selected from an E2A region and an E4 region; and (b) transfecting, under conditions whereby said recombinant adenovirus vector library is produced, said at least one cell in each of said plurality of cell cultures with i) an adapter plasmid comprising adenoviral sequence coding, in operable configuration, for a functional Inverted Terminal Repeat, a functional encapsidation signal, and sequences sufficient to allow for homologous recombination with a first recombinant nucleic acid, and not coding for E1 region sequences which overlap with E1 region sequences in said at least one cell, for E1 region sequences which overlap with E1 region sequences in a first recombinant nucleic acid, for E2B region sequences other than essential E2B sequences, for E2A region sequences, for E3 region sequences and for E4 region sequences, and further comprises a unique nucleic acid sequence and promoter operatively linked to said unique nucleic acid sequence; and ii) a first recombinant nucleic acid comprising adenoviral sequence coding, in operable configuration, for a functional adenoviral Inverted Terminal Repeat and for sequences sufficient for replication in said at least one cell, but not comprising adenoviral E1 region sequences which overlap with E1 sequences in said at least one cell, and not comprising E2A region sequences or E4 region sequences expressed in said plurality of cells which would otherwise lead to production of replication competent adenovirus wherein said first recombinant nucleic acid has sufficient overlap with said adapter plasmid to provide for homologous recombination resulting in production of recombinant adenoviral vectors in said at least one cell;

(c) incubating said plurality of cells under conditions which result in the lysis of said plurality of cells facilitating the release of said recombinant adenoviral vectors containing said unique nucleic acid; and (d) transferring an aliquot of said adenoviral vectors into a corresponding plurality of host cell cultures consisting of cells in which said vectors do not replicate, but in which said nucleic acids are expressible;

(e) incubating said host cells to allow expression of the product of said nucleic acid; and (f) observing said host cell for changes in said host cell.

52. A method according to claim 51, further comprising (g) assigning a function to said nucleic acids, for which the expressed product thereof results in observed changes in said host cells.

53. A method according to claim 52, wherein said biological function comprises apoptosis, DNA synthesis, tumorigenesis, disease or drug susceptibility, chemical responsiveness, chemical secretion, protein expression, cell differentiation, proliferation, drug resistance, capillary formation, or cell migration.

54. A method according to claim 52, wherein said observing uses an assay selected from the group consisting of a beta-galactosidase assay, hIL3 assay, Luciferase assay, ceNOS assay, GLVR2 assay and EGFP assay.

55. A method according to claim 52 wherein said zebrafish host cells comprise embryos.

56. The method of claim 52 said zebrafish host cells comprise adult cells.

* * * * *

SEQUENCE LISTING

<160> NUMBER OF SEQ ID NOS: 69

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 1
aattgtctta attaaccgct taa                                            23

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence:oligo-
      nucleotide

<400> SEQUENCE: 2
aattgtctta attaaccgc                                                 19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:oligo-
      nucleotide

<400> SEQUENCE: 3
aattgcggtt aattaagac                                                 19

<210> SEQ ID NO 4
<211> LENGTH: 47
<212> TYPE: DNA
<213> ORGANISM: Artificial Sequence
<220> FEATURE:
<223> OTHER INFORMATION: Description of Artificial Sequence:primer

<400> SEQUENCE: 4
ctgtacgtac cagtgcactg gcctaggcat ggaaaaatac ataactg                  47

<210> SEQ ID NO 5
<211> LENGTH: 60
<212> TYPE: DNA
<213> ORGANISM: Artificial Sequence
<220> FEATURE:
<223> OTHER INFORMATION: Description of Artificial Sequence:primer

<400> SEQUENCE: 5
gcggatcctt cgaaccatgg taagcttggt accgctagcg ttaaccgggc gactcagtca    60

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence:primer

```
<400> SEQUENCE: 6
gcgccaccat gggcagagcg atggtggc                                      28

<210> SEQ ID NO 7
<211> LENGTH: 50
<212> TYPE: DNA
<213> ORGANISM: Artificial Sequence
<220> FEATURE:
<223> OTHER INFORMATION: Description of Artificial Sequence:primer

<400> SEQUENCE: 7
gttagatcta agcttgtcga catcgatcta ctaacagtag agatgtagaa              50

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 8
gggtattagg ccaaaggcgc a                                             21

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 9
gatcccatgg aagcttgggt ggcgacccca gcg                                33

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence:primer

<400> SEQUENCE: 10
gatcccatgg ggatccttta ctaagttaca aagcta                             36

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence:primer

<400> SEQUENCE: 11
gtcgctgtag ttggactgg                                                19

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 12
cgataagctt aattcctttg tgttt                                         25

<210> SEQ ID NO 13
```

```
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 13
cttaggtaac ccagtagatc cagaggagtt cat                          33

<210> SEQ ID NO 14
<211> LENGTH: 60
<212> TYPE: DNA
<213> ORGANISM: Artificial Sequence
<220> FEATURE:
<223> OTHER INFORMATION: Description of Artificial Sequence:primer

<400> SEQUENCE: 14
aactgcagat ctatcgatac tagtcaattg ctcgagtcta gactacgtca cccgccccgt    60

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence:primer

<400> SEQUENCE: 15
cgggatccgt cgacgcggcc gcatcatcaa taatatacc                    39

<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence:linker

<400> SEQUENCE: 16
cgatgcatcg                                                    10

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 17
ggggtggcca gggtacctct aggcttttgc aa                           32

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 18 gggggggatcc ataaacaagt tcagaatcc                              29

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:oligo-
      nucleotide
```

<400> SEQUENCE: 19
agcttgaatt cccgggtacc t                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:oligo-
      nucleotide

<400> SEQUENCE: 20
ctagaggtac ccgggaattc a                                              21

<210> SEQ ID NO 21
<211> LENGTH: 39
<212> TYPE: DNA
<213> ORGANISM: Artificial Sequence
<220> FEATURE:
<223> OTHER INFORMATION: Description of Artificial Sequence:primer

<400> SEQUENCE: 21
cggaattctt aattaagtta acatcatcaa taatatacc                           39

<210> SEQ ID NO 22
<211> LENGTH: 66
<212> TYPE: DNA
<213> ORGANISM: Artificial Sequence
<220> FEATURE:
<223> OTHER INFORMATION: Description of Artificial Sequence:primer

<400> SEQUENCE: 22
acggcgcgcc ttaagccacg cccacacatt tcagtacgta ctagtctacg tcacccgccc    60
cgttcc                                                               66

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 23
cggaattcat caggataggg cggtgg                                         26

<210> SEQ ID NO 24
<211> LENGTH: 44
<212> TYPE: DNA
<213> ORGANISM: Artificial Sequence
<220> FEATURE:
<223> OTHER INFORMATION: Description of Artificial Sequence:primer

<400> SEQUENCE: 24
cgggatccta tcgatattta aatgttttag ggcggagtaa cttg                     44

<210> SEQ ID NO 25
<211> LENGTH: 37
<212> TYPE: DNA
<213> ORGANISM: Artificial Sequence
<220> FEATURE:
<223> OTHER INFORMATION: Description of Artificial Sequence:primer

<400> SEQUENCE: 25
taagccacta gtacgtactg aaatgtgtgg gcgtggc                             37

<210> SEQ ID NO 26
<211> LENGTH: 43
<212> TYPE: DNA
<213> ORGANISM: Artificial Sequence
<220> FEATURE:
<223> OTHER INFORMATION: Description of Artificial Sequence:primer

<400> SEQUENCE: 26
ttaagccacg cccacacatt tcagtacgta ctagtggctt aat          43

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 27
cgtgtagtgt atttataccc g                                   21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 28
tcgtcactgg gtggaaagcc a                                   21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 29
tacccgccgt cctaaaatgg c                                   21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 30
gcctccatgg aggtcagatg t                                   21

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 31
gcttgagccc gagacatgtc                                     20

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence:primer

```
<400> SEQUENCE: 32 ccccctcgagc tcaatctgta tctt                                          24

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 33
gggggatccg aacttgttta ttgcagc                                        27

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 34
gggagatcta gacatgataa gatac                                          25

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 35
gggagatctg tactgaaatg tgtgggc                                        27

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 36
ggaggctgca gtctccaacg gcgt                                           24

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence:primer set

<400> SEQUENCE: 37
ggcgaattcg tcgacatcat caataatata cc                                  32

<210> SEQ ID NO 38
<211> LENGTH: 17
<212> TYPE: DNA
<213> ORGANISM: Artificial Sequence
<220> FEATURE:
<223> OTHER INFORMATION: Description of Artificial Sequence:primer set

<400> SEQUENCE: 38
ctgtgtacac cggcgca                                                   17

<210> SEQ ID NO 39
```

```
<211> LENGTH: 50
<212> TYPE: DNA
<213> ORGANISM: Artificial Sequence
<220> FEATURE:
<223> OTHER INFORMATION: Description of Artificial Sequence:oligo-
      nucleotide

<400> SEQUENCE: 39
gtacactgac ctagtgccgc ccgggcaaag cccgggcggc actaggtcag            50

<210> SEQ ID NO 40
<211> LENGTH: 50
<212> TYPE: DNA
<213> ORGANISM: Artificial Sequence
<220> FEATURE:
<223> OTHER INFORMATION: Description of Artificial Sequence:oligo-
      nucleotide

<400> SEQUENCE: 40
gtacctgacc tagtgccgcc cgggctttgc ccgggcggca ctaggtcagt            50

<210> SEQ ID NO 41
<211> LENGTH: 55
<212> TYPE: DNA
<213> ORGANISM: Artificial Sequence
<220> FEATURE:
<223> OTHER INFORMATION: Description of Artificial Sequence:oligo-
      nucleotide

<400> SEQUENCE: 41
gtacattgac ctagtgccgc ccgggcaaag cccgggcggc actaggtcaa tcgat      55

<210> SEQ ID NO 42
<211> LENGTH: 55
<212> TYPE: DNA
<213> ORGANISM: Artificial Sequence
<220> FEATURE:
<223> OTHER INFORMATION: Description of Artificial Sequence:oligo-
      nucleotide

<400> SEQUENCE: 42
gtacatcgat tgacctagtg ccgcccgggc tttgcccggg cggcactagg tcaat      55

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 43
tggacttgag ctgtaaacgc                                             20

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 44
gggggatcct caaatcgtca cttccgt                                     27

<210> SEQ ID NO 45
<211> LENGTH: 27
<212> TYPE: DNA
<213> ORGANISM: Artificial Sequence
```

```
<220> FEATURE:
<223> OTHER INFORMATION: Description of Artificial Sequence:primer

<400> SEQUENCE: 45
ggggtctaga catcatcaat aatatac                                        27

<210> SEQ ID NO 46
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 46
ggcgaattcg gtaccatcat caataatata cc                                  32

<210> SEQ ID NO 47
<211> LENGTH: 45
<212> TYPE: DNA
<213> ORGANISM: Artificial Sequence
<220> FEATURE:
<223> OTHER INFORMATION: Description of Artificial Sequence:primer

<400> SEQUENCE: 47
gtacactgac ctagtgccgc ccgggcaaag cccgggcggc actag                    45

<210> SEQ ID NO 48
<211> LENGTH: 67
<212> TYPE: DNA
<213> ORGANISM: Artificial Sequence
<220> FEATURE:
<223> OTHER INFORMATION: Description of Artificial Sequence:primer

<400> SEQUENCE: 48
tttttaatta ataactatga ctctcttaag gtagccaaat catcatcaat aatatacctt    60
attttgg                                                              67

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 49
gcgaaaattg tcacttcctg tg                                             22

<210> SEQ ID NO 50
<211> LENGTH: 82
<212> TYPE: DNA
<213> ORGANISM: Artificial Sequence
<220> FEATURE:
<223> OTHER INFORMATION: Description of Artificial Sequence:oligo-
     nucleotide

<400> SEQUENCE: 50
agctttaact ataacggtcc taaggtagcg attaattaac agtttaatta atggcaaaca    60
gctattatgg gtattatggg tt                                             82

<210> SEQ ID NO 51
<211> LENGTH: 82
<212> TYPE: DNA
<213> ORGANISM: Artificial Sequence
<220> FEATURE:
<223> OTHER INFORMATION: Description of Artificial Sequence:oligo-
``` nucleotide

<400> SEQUENCE: 51
ctagaaccca taatacccat aatagctgtt tgccattaat taaactgtta attaatcgct    60
accttaggac cgttatagtt aa                                              82

<210> SEQ ID NO 52
<211> LENGTH: 47
<212> TYPE: DNA
<213> ORGANISM: Artificial Sequence
<220> FEATURE:
<223> OTHER INFORMATION: Description of Artificial Sequence:oligo-
      nucleotide

<400> SEQUENCE: 52
tcgatggcaa acagctatta tgggtattat gggttcgaat taattaa                   47

<210> SEQ ID NO 53
<211> LENGTH: 47
<212> TYPE: DNA
<213> ORGANISM: Artificial Sequence
<220> FEATURE:
<223> OTHER INFORMATION: Description of Artificial Sequence:oligo-
      nucleotide

<400> SEQUENCE: 53
tcgattaatt aattcgaacc cataataccc ataatagctg tttgcca                   47

<210> SEQ ID NO 54
<211> LENGTH: 42
<212> TYPE: DNA
<213> ORGANISM: Artificial Sequence
<220> FEATURE:
<223> OTHER INFORMATION: Description of Artificial Sequence:primer

<400> SEQUENCE: 54
ccccaattgg tcgaccatca tcaataatat accttatttt gg                        42

<210> SEQ ID NO 55
<211> LENGTH: 37
<212> TYPE: DNA
<213> ORGANISM: Artificial Sequence
<220> FEATURE:
<223> OTHER INFORMATION: Description of Artificial Sequence:oligo-
      nucleotide

<400> SEQUENCE: 55
aattcggcgc gccgtcgacg atatcgatag cggccgc                              37

<210> SEQ ID NO 56
<211> LENGTH: 37
<212> TYPE: DNA
<213> ORGANISM: Artificial Sequence
<220> FEATURE:
<223> OTHER INFORMATION: Description of Artificial Sequence:oligo-
      nucleotide

<400> SEQUENCE: 56
aattgcggcc gctatcgata tcgtcgacgg cgcgccg                              37

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence:oligonucleotide

<400> SEQUENCE: 57
cgatcggacc gacgcgttcg cgagc                                            25

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence:oligo-
      nucleotide

<400> SEQUENCE: 58
ggccgctcgc gaacgcgtcg gtccgat                                          27

<210> SEQ ID NO 59
<211> LENGTH: 49
<212> TYPE: DNA
<213> ORGANISM: Artificial Sequence
<220> FEATURE:
<223> OTHER INFORMATION: Description of Artificial Sequence:oligo
      nucleotide

<400> SEQUENCE: 59
agctctagag gatccgttaa cgctagcgaa ttcaccggta ccaagctta                  49

<210> SEQ ID NO 60
<211> LENGTH: 49
<212> TYPE: DNA
<213> ORGANISM: Artificial Sequence
<220> FEATURE:
<223> OTHER INFORMATION: Description of Artificial Sequence:oligo-
      nucleotide

<400> SEQUENCE: 60
ctagtaagct tggtaccggt gaattcgcta gcgttaacgg atcctctag                  49

<210> SEQ ID NO 61
<211> LENGTH: 123
<212> TYPE: DNA
<213> ORGANISM: Artificial Sequence
<220> FEATURE:
<223> OTHER INFORMATION: Description of Artificial Sequence:single
      stranded sequence

<400> SEQUENCE: 61
agcttaacta taacggtcct aaggtagcga tagggataac aggtaatta attaatttaa       60 attaattaat ctatgtcggg tgcggagaaa gaggtaacta tgactctctt aagtagcca      120 aat                                                                  123

<210> SEQ ID NO 62
<211> LENGTH: 123
<212> TYPE: DNA
<213> ORGANISM: Artificial Sequence
<220> FEATURE:
<223> OTHER INFORMATION: Description of Artificial Sequence:single
      stranded sequence

<400> SEQUENCE: 62
ctagatttgg ctaccttaag agagtcatag ttacctcttt ctccgcaccc gacatagatt      60
aattaattta aattaattaa ttaccctgtt atccctatcg ctaccttagg accgttatag     120
tta                                                                  123

<210> SEQ ID NO 63
<211> LENGTH: 14
<212> TYPE: DNA
<213> ORGANISM: Artificial Sequence
<220> FEATURE:
<223> OTHER INFORMATION: Description of Artificial Sequence:oligo-
      nucleotide

<400> SEQUENCE: 63
taatacgtat taat                                                         14

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 64
ggcgtacgta gccctgtcga aag                                               23

<210> SEQ ID NO 65
<211> LENGTH: 35
<212> TYPE: DNA
<213> ORGANISM: Artificial Sequence
<220> FEATURE:
<223> OTHER INFORMATION: Description of Artificial Sequence:primer

<400> SEQUENCE: 65
ccaatgcatt cgaagtactt ccttctccta taggc                                  35

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 66
ccaatgcata cggcgcagac gg                                                22

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 67
gaggtggatc ccatggacga g                                                 21

<210> SEQ ID NO 68
<211> LENGTH: 39
<212> TYPE: DNA
<213> ORGANISM: Artificial Sequence
<220> FEATURE:
<223> OTHER INFORMATION: Description of Artificial Sequence:primer

<400> SEQUENCE: 68
cggaattctt aattaagtta acatcatcaa taatatacc                              39

<210> SEQ ID NO 69
<211> LENGTH: 20
<212> TYPE: DNA
<213> ORGANISM: Artificial Sequence
<220> FEATURE:

```
-continued

<223> OTHER INFORMATION: Description of Artificial Sequence:primer

<400> SEQUENCE: 69
tgattcacat cggtcagtgc                                          20
```